US006787643B2

(12) United States Patent
Dillon et al.

(10) Patent No.: US 6,787,643 B2
(45) Date of Patent: Sep. 7, 2004

(54) NUCLEOTIDE SEQUENCE OF *ESCHERICHIA COLI* PATHOGENICITY ISLANDS

(75) Inventors: Patrick J. Dillon, Carlsbad, CA (US); Gil H. Choi, Rockville, MD (US); Rodney A. Welch, Madison, WI (US)

(73) Assignees: Human Genome Sciences, Inc., Rockville, MD (US); Wisconsin Alumni Research Foundation, Madison, WI (US)

( * ) Notice: Subject to any disclaimer, the term of this patent is extended or adjusted under 35 U.S.C. 154(b) by 29 days.

(21) Appl. No.: 09/956,004

(22) Filed: Sep. 20, 2001

(65) Prior Publication Data

US 2002/0072595 A1 Jun. 13, 2002

Related U.S. Application Data

(62) Division of application No. 08/976,259, filed on Nov. 21, 1997, now Pat. No. 6,316,609.
(60) Provisional application No. 60/061,953, filed on Oct. 14, 1997, and provisional application No. 60/031,626, filed on Nov. 22, 1996.

(51) Int. Cl.[7] .................. C07H 21/04; C12N 15/85; C12N 15/86; C12N 1/21; C12N 15/63
(52) U.S. Cl. .................. 536/23.1; 435/252.3; 435/325; 435/320.1
(58) Field of Search .................. 536/23.1; 435/252.3, 435/325, 320.1

(56) References Cited

U.S. PATENT DOCUMENTS 5,814,478 A * 9/1998 Valenzuela et al. ........ 435/69.1

OTHER PUBLICATIONS

Lodish et al., Molecular Cell Biology, W H Freeman and Compnay, 4th Edition, 2000, pp. 1–7.*

US PN 5814478, SEQ ID NO 31, Issued Patents database, May 10, 1995.*
Lopez et al. Molecular Biology, 32:881–891,1999.*
Attwood, Science, 290:471–473, 2000.*
Gerhold et al. BioEssays, 18(12):973–981, 1996.*
Wells et al. Journal of Leukocyte Biology, 61(5):545–550, 1997.*
Russell et al. Journal of Molecular Biology, 244:332–350, 1994.*
GenBank Accession No. U59875, McDonough et al., "*Yersinia pestis* pesticin plasmid putative insertion sequence IS100" (Nov. 1996).
GenBank Accession No. Z32853, Podladchikova et al., "*Y.pestis* (106 Otten) insertion sequence IS100 DNA" (Jun. 1994).
McDonough et al., "Homology with a Repeated *Yersinia pestis* DNA Sequence IS100 Correlates with Pesticin Sensitivity in *Yersinia pseudotuberculosis,*" *J. Bacteriology*, 179(6):2081–2085 (Mar. 1997).
Podladchikova et al., "Nucleotide sequence and structural organization of *Yersinia pestis* insertion sequence IS100," *FEMS Microbiology Letters*, 121:269–274 (1994).

* cited by examiner

*Primary Examiner*—Ardin H. Marschel
*Assistant Examiner*—Cheyne D Ly
(74) *Attorney, Agent, or Firm*—Human Genome Sciences, Inc.

(57) ABSTRACT

The present invention relates to novel genes located in two chromosomal regions within uropathogenic *E. coli* that are associated with virulence. These chromosomal regions are known as pathogenicity islands (PAIs). In particular, the present application discloses 142 sequenced fragments (contigs) of DNA from two pools of cosmids covering pathogenicity islands PAI IV and PAI V located on the chromosome of the uropathogenic *Escherichia coli* J96. Further disclosed are 351 predicted protein-coding open reading frames within the sequenced fragments.

9 Claims, 2 Drawing Sheets

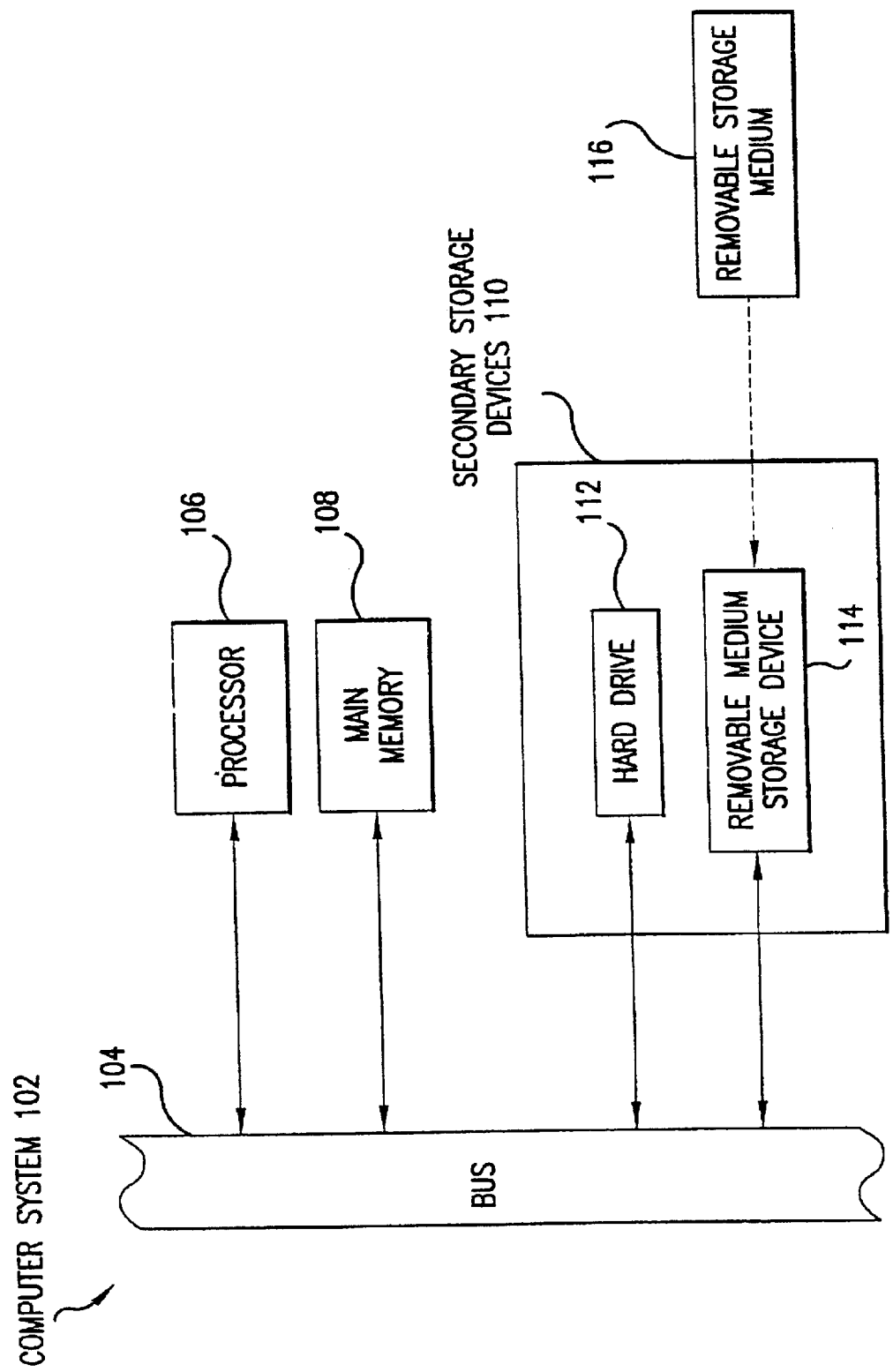

NUCLEOTIDE SEQUENCE OF *ESCHERICHIA COLI* PATHOGENICITY ISLANDS

CROSS-REFERENCE TO RELATED APPLICATIONS

This application is a divisional of, and claims benefit under 35 U.S.C. § 120 to U.S. patent application Ser. No. 08/976,259, filed Nov. 21, 1997, (U.S. Pat. No. 6,316,609) which in turn claims benefit under 35 U.S.C. § 119(e) to U.S. Provisional Application Nos. 60/061,953, filed on Oct. 14, 1997, and 60/031,626, filed on Nov. 22, 1996. Claimed priority documents are hereby incorporated by reference in its entirety.

STATEMENTS AS TO RIGHTS TO INVENTIONS MADE UNDER FEDERALLY-SPONSORED RESEARCH AND DEVELOPMENT

This invention was made with United States government support awarded by the following agencies:

NIH Grant # AI20323; AI25547.

The United States has certain rights to this invention.

BACKGROUND OF THE INVENTION

1. Field of the Invention

The present invention relates to novel genes located in two chromosomal regions within *E. coli* that are associated with virulence. These chromosomal regions are known as pathogenicity islands (PAIs).

2. Related Background Art

*Escherichia coli* (*E. coli*) is a normal inhabitant of the intestine of humans and various animals. Pathogenic *E. coli* strains are able to cause infections of the intestine (intestinal *E. coli* strains) and of other organs such as the urinary tract (uropathogenic *E. coli*) or the brain (extraintestinal *E. coli*). Intestinal pathogenic *E. coli* are a well established and leading cause of severe infantile diarrhea in the developing world. Additionally, cases of newborn meningitis and sepsis have been attributed to *E. coli* pathogens.

In contrast to non-pathogenic isolates, pathogenic *E. coli* produce pathogenicity factors which contribute to the ability of strains to cause infectious diseases (Mühldorfer, I. and Hacker, J., *Microb. Pathogen.* 16:171–181 1994). Adhesions facilitate binding of pathogenic bacteria to host tissues. Pathogenic *E. coli* strains also express toxins including haemolysins, which are involved in the destruction of host cells, and surface structures such as O-antigens, capsules or membrane proteins, which protect the bacteria from the action of phagocytes or the complement system (Ritter, et al., *Mol. Microbiol.* 17:109–212 1995).

The genes coding for pathogenicity factors of intestinal *E. coli* are located on large plasmids, phage genomes or on the chromosome. In contrast to intestinal *E. coli*, pathogenicity determinants of uropathogenic and other extraintestinal *E. coil* are, in most cases, located on the chromosome. Id.

Large chromosomal regions in pathogenic bacteria that encode adjacently located virulence genes have been termed pathogenicity islands ("PAIs"). PAIs are indicative of large fragments of DNA which comprise a group of virulence genes behaving as a distinct molecular and functional unit much like an island within the bacterial chromosome. For example, intact PAIs appear to transfer between organisms and confer complex virulence properties to the recipient bacteria.

Chromosomal PAIs in bacterial cells have been described in increasing detail over recent years. For example, J. Hacker and co-workers described two large, unstable regions in the chromosome of uropathogenic *Escherichia coli* strain 536 as PAI-I and PAI-II (Hacker J., et al., *Microbiol. Pathog.* 8:213–25 1990). Hacker found that PAI-I and PAI-II containing virulence regions can be lost by spontaneous deletion due to recombination events. Both of these PAIs were found to encode multiple virulence genes, and their loss resulted in reduced hemolytic activity, serum resistance, mannose-resistant hemagglutination, uroepithelial cell binding, and mouse virulence of the *E. coli*. (Knapp, S et al., *J. Bacteriol.* 168:22–30 1986). Therefore, pathogenicity islands are characterized by their ability to confer complex virulence phenotypes to bacterial cells.

In addition to *E. coli*, specific deletion of large virulence regions has been observed in other bacteria such as *Yersinia pestis*. For example, Fetherston and co-workers found that a 102-kb region of the *Y. pestis* chromosome lost by spontaneous deletion resulted in the loss of many *Y. pestis* virulence phenotypes. (Fetherston, J. D. and Perry, R. D., *Mol. Microbiol.* 13:697–708 1994, Fetherston, et al., *Mol. Microbiol.* 6:2693–704 1992). In this instance, the deletion appeared to be due to recombination within 2.2-kb repetitive elements at both ends of the 102-kb region.

It is possible that deletion of PAIs may benefit the organism by modulating bacterial virulence or genome size during infection. PAIs may also represent foreign DNA segments that were acquired during bacterial evolution that conferred important pathogenic properties to the bacteria. Observed flanking repeats, as observed in *Y. pestis* for example, may suggest a common mechanism by which these virulence genes were integrated into the bacterial chromosomes.

Integration of the virulence genes into bacterial chromosomes was further elucidated by the discovery and characterization of a locus of enterocyte effacement (the LEE locus) in enteropathogenic *E. coil* (McDaniel, et al., *Proc. Natl Acad. Sci.* (USA) 92:1664–8 1995). The LEE locus comprises 35-kb and encodes many genes required for these bacteria to "invade" and degrade the apical structure of enerocytes causing diarrhea. Although the LEE and PAI-I loci encode different virulence genes, these elements are located at the exact same site in the *E. coli* genome and contain the same DNA sequence within their right-hand ends, thus suggesting a common mechanism for their insertion.

Besides being found in enteropathogenic *E. coli*, the LEE element is also present in rabbit diarrheal *E. coli, Hafnia alvei*, and *Citrobacter freundii* biotype 4280, all of which induce attaching and effacing lesions on the apical face of enterocytes. The LEE locus appears to be inserted in the bacterial chromosome as a discrete molecular and functional virulence unit in the same fashion as PAI-I, PAI-II, and Yersinia PAI.

Along these same lines, a 40-kb *Salmonella typhimurium* PAI was characterized on the bacterial chromosome which encodes genes required for Salmonella entry into nonphagocytic epithelial cells of the intestine (Mills, D. M., et al., *Mol. Microbiol.* 15:749–59 1995). Like the LEE element, this PAI confers to Salmonella the ability to invade intestinal cells, and hence may likewise be characterized as an "invasion" PAI.

The pathogenicity islands described above all possess the common feature of conferring complex virulence properties to the recipient bacteria. However, they may be separated into two types by their respective contributions to virulence. PAI-I, PAI-II, and the *Y. pestis* PAI confer multiple virulence phenotypes, while the LEE and the *S. typhimurium* "invasion" PAI encode many genes specifying a single, complex virulence process.

It is advantageous to characterize closely-related bacteria that contain or do not contain the PAI by the isolation of a discrete molecular and functional unit on the bacterial chromosome. Since the presence versus the absence of essential virulence genes can often distinguish closely-related virulent versus avirulent bacterial strains or species, experiments have been conducted to identify virulence loci and potential PAIs by isolating DNA sequences that are unique to virulent bacteria (Bloch, C. A., et al., *J. Bacteriol.* 176:7121–5 1994, Groisman, E. A., *EMBO J.* 12:3779–87 1993).

At least two PAIs are present in *E. coli* J96. These PAIs, PAI IV and PAI V are linked to tRNA loci but at sites different from those occupied by other known *E. coli* PAIs. Swenson et al, *Infect. and Immun.* 64:3736–3743 (1996).

The era of true comparative genomics has been ushered in by high through-put genomic sequencing and analysis. The first two complete bacterial genome sequences, those of *Haemophilus influenzae* and *Mycoplasma genitalium* were recently described (Fleischmann, R. D., et al., *Science* 269:496 (1995); Fraser, C. M., et al., *Science* 270:397 (1995)). Large scale DNA sequencing efforts also have produced an extensive collection of sequence data from eukaryotes, including *Homo sapiens* (Adams, M. D., et al., *Nature* 377:3 (1995)) and *Saccharomyces cerevisiae* (Levy, J., *Yeast* 10:1689 (1994)).

The need continues to exist for the application of high through-put sequencing and analysis to study genomes and subgenomes of infectious organisms. Further, a need exists for genetic markers that can be employed to distinguish closely-related virulent and avirulent strains of a given bacteria.

SUMMARY OF THE INVENTION

The present invention is based on the high through-put, random sequencing of cosmid clones covering two pathogenic islands (PAIs) of uropathogenic *Escherichia coli* strain J96 (O4:K6; *E. coli* J96). PAIs are large fragments of DNA which comprise pathogenicity determinants. PAI IV is located approximately at 64 min (nearphe V) on the *E. coli* chromosome and is greater than 170 kilobases in size. PAI V is located at approximately 94 min (atpheR) on the *E. coli* chromosome and is approximately 106 kb in size. These PAIs differ in location to the PAIs described by Hacker and colleagues for uropathogenic strain 536 (PAI I, 82 minutes {selC} and PAI II, 97 minutes {leuX}).

The location of the PAIs relative to one another and the cosmid clones covering the J96 PAIs is shown in FIG. 1. The present invention relates to the nucleotide sequences of 142 fragments of DNA (contigs) covering the PAI IV and PAI V regions of the *E. coli* J96 chromosome. The nucleotide sequences shown in SEQ ID NOs: 1 through 142 were obtained by shotgun sequencing eleven *E. coli* J96 subclones, which were deposited in two pools on Sep. 23, 1996 at the American Type Culture Collection, 12301 Park Lawn Drive, Rockville, Md. 20852, and given accession numbers 97726 (includes 7 cosmid clones covering PAI (IV) and 97727 (includes 4 cosmid clones covering PAI V). The deposited sets or "pools" of clones are more fully described in Example 1. In addition, *E. coli* strain J96 was also deposited at the American Type Culture Collection on Sep. 23, 1996, and given accession number 98176.

Three hundred fifty-one open reading frames have been thus far identified in the 142 contigs described by SEQ ID NOs: 1 through 142. Thus, the present invention is directed to isolated nucleic acid molecules comprising open reading frames (ORFs) encoding *E. coli* proteins that are located in two pathogenic island regions of the chromosome of uropathogenic *E. coli* J96.

The present invention also relates to variants of the nucleic acid molecules of the present invention, which encode portions, analogs or derivatives of *E. coli* J96 PAI proteins. Further embodiments include isolated nucleic acid molecules comprising a polynucleotide having a nucleotide sequence at least 90% identical, and more preferably at least 95%, 96%, 97%, 98% or 99% identical, to the nucleotide sequence of an *E. coli* J96 PAI ORF described herein.

The present invention also relates to recombinant vectors, which include the isolated nucleic acid molecules of the present invention, host cells containing the recombinant vectors, as well as methods for making such vectors and host cells for *E. coli* J96 PAI protein production by recombinant techniques.

The invention further provides isolated polypeptides encoded by the *E. coli* J96 PAI ORFs. It will be recognized that some amino acid sequences of the polypeptides described herein can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

In another aspect, the invention provides a peptide or polypeptide comprising an epitope-bearing portion of a polypeptide of the invention. The epitope-bearing portion is an immunogenic or antigenic epitope useful for raising antibodies.

The invention further provides a vaccine comprising one or more *E. coli* J96 PAI antigens together with a pharmaceutically acceptable diluent, carrier, or excipient, wherein the one or more antigens are present in an amount effective to elicit protective antibodies in an animal to pathogenic *E. coli*, such as strain J96.

The invention also provides a method of eliciting a protective immune response in an animal comprising administering to the animal the above-described vaccine.

The invention further provides a method for identifying pathogenic *E. coli* in an animal comprising analyzing tissue or body fluid from the animal for one or more of:

(a) polynucleic acids encoding an open reading frame listed in Tables 1–4;

(b) polypeptides encoded for by an open reading frame listed in Tables 1–4; or (c) antibodies specific to polypeptides encoded for by an open reading frame listed in Tables 1–4.

The invention further provides a nucleic acid probe for the detection of the presence of one or more *E. coli* PAI nucleic acids (nucleic acids encoding one or more ORFs as listed in Tables 1–4) in a sample from an individual comprising one or more nucleic acid molecules sufficient to specifically detect under stringent hybridization conditions the presence of the above-described molecule in the sample.

The invention also provides a method of detecting *E. coli* PAI nucleic acids in a sample comprising:

a) contacting the sample with the above-described nucleic acid probe, under conditions such that hybridization occurs, and b) detecting the presence of the probe bound to an *E. coli* PAI nucleic acid.

The invention further provides a kit for detecting the presence of one or more *E. coli* PAI nucleic acids in a sample comprising at least one container means having disposed therein the above-described nucleic acid probe.

The invention also provides a diagnostic kit for detecting the presence of pathogenic *E. coli* in a sample comprising at least one container means having disposed therein one or more of the above-described antibodies.

The invention also provides a diagnostic kit for detecting the presence of antibodies to pathogenic *E. coli* in a sample comprising at least one container means having disposed therein one or more of the above-described antigens.

BRIEF DESCRIPTION OF THE FIGURES

FIG. 2 is a block diagram of a computer system 102 that can be used to implement the computer-based systems of present invention.

DETAILED DESCRIPTION OF THE INVENTION

Figure 1:
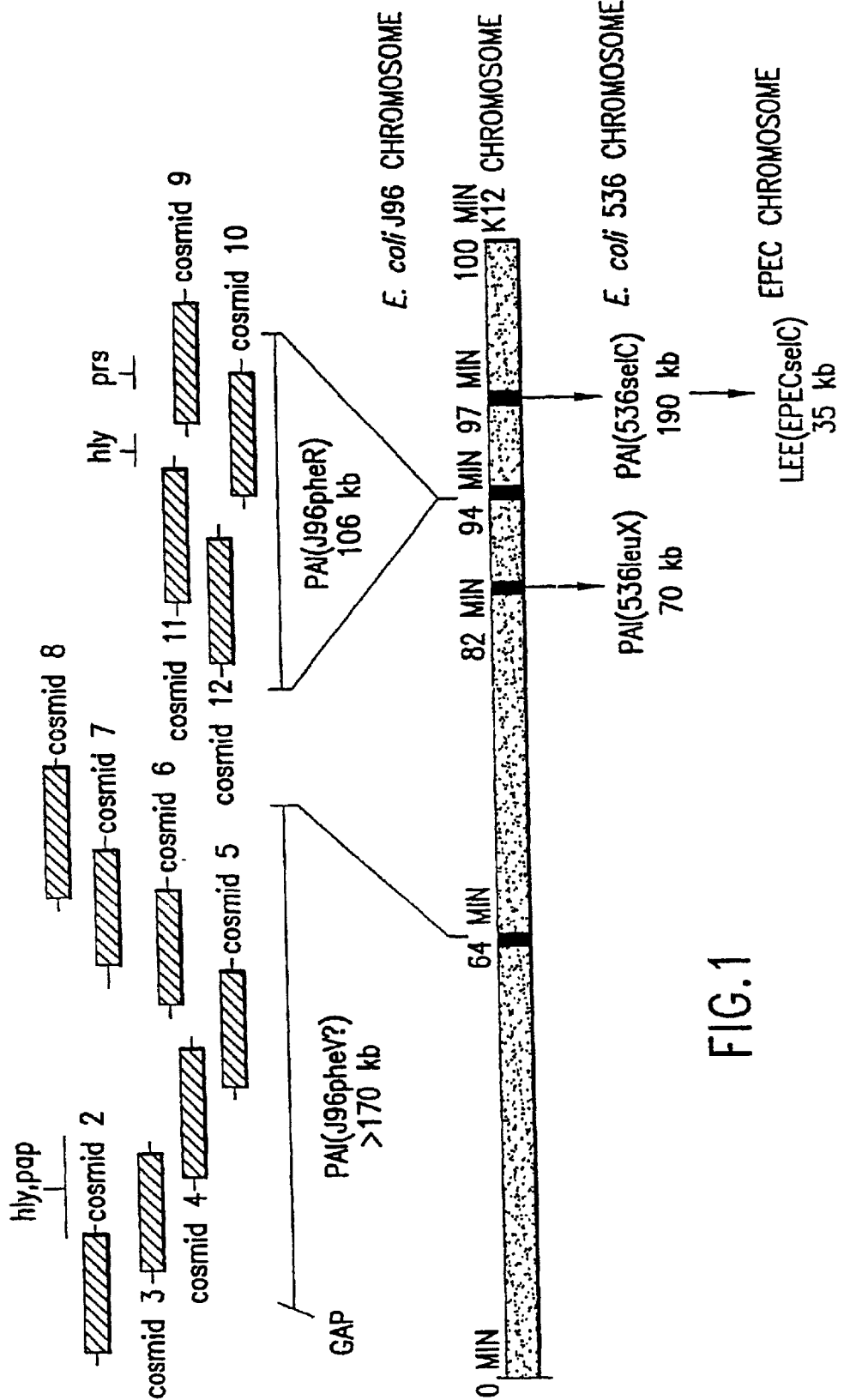
FIG. 1 is a schematic diagram of cosmid clones derived from *E. coli* J96 pathogenicity island and map positions of known *E. coli* PAIs (not drawn to scale). The gray bar represents the *E. coli* K-12 chromosome with minute demarcations of PAI junction points located above the bar. *E. coli* J96 overlapping cosmid clones are represented by hatched bars (overlap not drawn to scale) with positions of hly, pap, and prs operons indicated above bar. The PAIs and estimated sizes are shown above and below the K-12 chromosome map.

The present invention is based on high through-put, random sequencing of a uropathogenic strain of *Escherichia coli*. The DNA sequences of contiguous DNA fragments covering the pathogenicity islands, PAI IV (also referred to as $PAI_{J96(pheV)}$) and PAI V (also referred to as $PAI_{J96(pheU)}$) from the chromosome of the *E. coli* uropathogenic strain, J96 (O4:K6) were determined. The sequences were used for DNA and protein sequence similarity searches of the database.

The primary nucleotide sequences generated by shotgun sequencing cosmid clones of the PAI IV and PAI V regions of the *E. coli* chromosome are provided in SEQ ID NOs: 1 through 142. These sequences represent contiguous fragments of the PAI DNA. As used herein, the "primary sequence" refers to the nucleotide sequence represented by the IUPAC nomenclature system. The present invention provides the nucleotide sequences of SEQ ID NOs:1 through 142, or representative fragments thereof, in a form that can be readily used, analyzed, and interpreted by a skilled artisan. Within these 142 sequences, there have been thus far identified 351 open reading frames (ORFs) that are described in greater detail below.

As used herein, a "representative fragment" refers to *E. coli* J96 PAI protein-encoding regions (also referred to herein as open reading frames or ORFs), expression modulating fragments, and fragments that can be used to diagnose the presence of *E. coli* in a sample. A non-limiting identification of such representative fragments is provided in Tables 1 through 6. As described in detail below, representative fragments of the present invention further include nucleic acid molecules having a nucleotide sequence at least 95% identical, preferably at least 96%, 97%, 98%, or 99% identical, to an ORF identified in Tables 1 through 6.

As indicated above, the nucleotide sequence information provided in SEQ ID NOs:1 through 142 was obtained by sequencing cosmid clones covering the PAIs located on the chromosome of *E. coli* J96 using a megabase shotgun sequencing method. The sequences provided in SEQ ID NOs:1 through 142 are highly accurate, although not necessarily a 100% perfect, representation of the nucleotide sequences of contiguous stretches of DNA (contigs) which include the ORFs located on the two pathogenicity islands of *E. coli* J96. As discussed in detail below, using the information provided in SEQ ID NOs:1 through 142 and in Tables 1 through 6 together with routine cloning and sequencing methods, one of ordinary skill in the art would be able to clone and sequence all "representative fragments" of interest including open reading frames (ORFs) encoding a large variety of *E. coli* J96 PAI proteins. In rare instances, this may reveal a nucleotide sequence error present in the nucleotide sequences disclosed in SEQ ID NOs: 1 through 142. Thus, once the present invention is made available (i.e., once the information in SEQ ID NOs: 1 through 142 and in Tables 1 through 6 have been made available), resolving a rare sequencing error would be well within the skill of the art. Nucleotide sequence editing software is publicly available. For example, Applied Biosystem's (AB) AutoAssembler can be used as an aid during visual inspection of nucleotide sequences.

Even if all of the rare sequencing errors were corrected, it is predicted that the resulting nucleotide sequences would still be at least about 99.9% identical to the reference nucleotide sequences in SEQ ID NOs: 1 through 142. Thus, the present invention further provides nucleotide sequences that are at least 99.9% identical to the nucleotide sequence of SEQ ID NOs: 1 through 142 in a form which can be readily used, analyzed and interpreted by the skilled artisan. Methods for determining whether a nucleotide sequence is at least 99.9% identical to a reference nucleotide sequence of the present invention are described below.

Nucleic Acid Molecules

The present invention is directed to isolated nucleic acid fragments of the PAIs of *E. coli* J96. Such fragments include, but are not limited to, nucleic acid molecules encoding polypeptides (hereinafter open reading frames (ORFs)), nucleic acid molecules that modulate the expression of an operably linked ORF (hereinafter expression modulating fragments (EMFs)), and nucleic acid molecules that can be used to diagnose the presence of *E. coli* in a sample (hereinafter diagnostic fragments (DFs)).

By isolated nucleic acid molecule(s) is intended a nucleic acid molecule, DNA or RNA, that has been removed from its native environment. For example, recombinant DNA molecules contained in a vector are considered isolated for the purposes of the present invention. Further examples of isolated DNA molecules include recombinant DNA molecules maintained in heterologous host cells, purified (partially or substantially) DNA molecules in solution, and nucleic acid molecules produced synthetically. Isolated RNA molecules include in vitro RNA transcripts of the DNA molecules of the present invention.

In one embodiment, *E. coli* J96 PAI DNA can be mechanically sheared to produce fragments about 15–20 kb in length, which can be used to generate an *E. coil* J96 PAI DNA library by insertion into lambda clones as described in Example 1 below. Primers flanking an ORF described in Tables 1 through 6 can then be generated using the nucleotide sequence information provided in SEQ ID NOs: 1 through 142. The polymerase chain reaction (PCR) is then used to amplify and isolate the ORF from the lambda DNA library. PCR cloning is well known in the art. Thus, given SEQ ID NOs: 1 through 142, and Tables 1 through 6, it would be routine to isolate any ORF or other representative fragment of the *E. coli* J96 PAI subgenomes. Isolated nucleic acid molecules of the present invention include, but are not limited to, single stranded and double stranded DNA, and single stranded RNA, and complements thereof.

Tables 1 through 6 herein describe ORFs in the *E. coli* J96 PAI cosmid clone library.

Tables 1 and 3 list, for PAI IV and PAI V, respectively, a number of ORFs that putatively encode a recited protein based on homology matching with protein sequences from an organism listed in the Table. Tables 1 and 3 indicate the location of ORFs (i.e., the position) by reference to its position within the one of the 142 *E. coli* J96 contigs described in SEQ ID NOs: 1 through 142. Column 1 of Tables 1 and 3 provides the Sequence ID Number (SEQ ID NO) of the contig in which a particular open reading frame is located. Column 2 numerically identifies a particular ORF on a particular contig (SEQ ID NO) since many contigs comprise a plurality of ORFs. Columns 3 and 4 indicate an ORF s position in the nucleotide sequence (contig) provided in SEQ ID NOs: 1 through 142 by referring to start and stop positions in the contig sequence. One of ordinary skill in the art will appreciate that the ORFs may be oriented in opposite directions in the *E. coli* chromosome. This is reflected in columns 3 and 4. Column 5 provides a database accession number to a homologous protein identified by a similarity search of public sequence databases (see, infra). Column 6 describes the matching protein sequence and the source organism is identified in brackets. Column 7 of Tables 1 and 3 indicates the percent identity of the protein sequence encoded by an ORF to the corresponding protein sequence from the organism appearing in parentheses in the sixth column. Column 8 of Tables 1 and 3 indicates the percent similarity of the protein sequence encoded by an ORF to the corresponding protein sequence from the organism appearing in parentheses in the sixth column. The concepts of percent identity and percent similarity of two polypeptide sequences are well understood in the art and are described in more detail below. Identified genes can frequently be assigned a putative cellular role category adapted from Riley (see, Riley, M., *Microbiol. Rev.* 57:862 (1993)). Column 9 of Tables 1 and 3 provides the nucleotide length of the open reading frame.

Tables 2 and 4, below, provide ORFs of *E. coli* J96 PAI IV and PAI V, respectively, that did not elicit a homology match with a known sequence from either *E. coli* or another organism. As above, the first column in Tables 2 and 4 provides the contig in which the ORF is located and the second column numerically identifies a particular ORF in a particular contig. Columns 3 and 4 identify an ORF s position in one of SEQ ID NOs: 1 through 142 by reference to start and stop nucleotides.

Tables 5 and 6, below, provide the *E. coli* J96 PAI IV ORFs and PAI V ORFs, respectively, identified by the present inventors that provided a significant match to a previously published *E. coli* protein. The columns correspond to the columns appearing in Tables 1 and 3.

Further details concerning the algorithms and criteria used for homology searches are provided in the Examples below. A skilled artisan can readily identify ORFs in the *Escherichia coli* J96 cosmid library other than those listed in Tables 1 through 6, such as ORFs that are overlapping or encoded by the opposite strand of an identified ORF in addition to those ascertainable using the computer-based systems of the present invention.

Isolated nucleic acid molecules of the present invention include DNA molecules having a nucleotide sequence substantially different than the nucleotide sequence of an ORF described in Tables 1 through 4, but which, due to the degeneracy of the genetic code, still encode a *E. coli* J96 PAI protein. The genetic code is well known in the art. Thus, it would be routine to generate such degenerate variants.

The present invention further relates to variants of the nucleic acid molecules of the present invention, which encode portions, analogs or derivatives of an *E. coli* protein encoded by an ORF described in Table 1 through 4. Non-naturally occurring variants may be produced using art-known mutagenesis techniques and include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the *E. coli* protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical, to the nucleotide sequence of an ORF described in Tables 1 through 6, preferably 1 through 4. By a polynucleotide having a nucleotide sequence at least, for example, 95% identical to the reference *E. coli* ORF nucleotide sequence is intended that the nucleotide sequence of the polynucleotide is identical to the reference sequence except that the polynucleotide sequence may include up to five point mutations per each 100 nucleotides of the ORF sequence. In other words, to obtain a polynucleotide having a nucleotide sequence at least 95% identical to a reference ORF nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to the nucleotide sequence of an *E. coli* J96 PAI ORF can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Preferred are nucleic acid molecules having sequences at least 90%, 95%, 96%, 97%, 98% or 99% identical to the nucleic acid sequence of an E. coli J96 PAI ORF that encode a functional polypeptide. By a "functional polypeptide" is intended a polypeptide exhibiting activity similar, but not necessarily identical, to an activity of the protein encoded by the E. coli J96 PAI ORF. For example, the E. coli ORF [Contig ID 84, ORF ID 3 (84/3)] encodes a hemolysin. Thus, a functional polypeptide encoded by a nucleic acid molecule having a nucleotide sequence, for example, 95% identical to the nucleotide sequence of 84/3, will also possess hemolytic activity. As the skilled artisan will appreciate, assays for determining whether a particular polypeptide is functional will depend on which ORF is used as the reference sequence. Depending on the reference ORF, the assay chosen for measuring polypeptide activity will be readily apparent in light of the role categories provided in Tables 1, 3, 5 and 6.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of a reference ORF will encode a functional polypeptide. In fact, since degenerate variants all encode the same amino acid sequence, this will be clear to the skilled artisan even without performing a comparison assay for protein activity. It will be further recognized in the art that, for such nucleic acid molecules that are not degenerate variants, a reasonable number will also encode a functional polypeptide. This is because the skilled artisan is fully aware of amino acid substitutions that are either less likely or not likely to significantly affect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," Science 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

The present invention is further directed to fragments of the isolated nucleic acid molecules described herein. By a fragment of an isolated nucleic acid molecule having the nucleotide sequence of an E. coli J96 PAI ORF is intended fragments at least about 15 nt, and more preferably at least about 20 nt, still more preferably at least about 30 nt, and even more preferably, at least about 40 nt in length that are useful as diagnostic probes and primers as discussed herein. Of course, larger fragments 50–500 nt in length are also useful according to the present invention as are fragments corresponding to most, if not all, of the nucleotide sequence of an E. coli J96 PAI ORF. By a fragment at least 20 nt in length, for example, is intended fragments that include 20 or more contiguous bases from the nucleotide sequence of an E. coli J96 PAI ORF. Since E. coli ORFs are listed in Tables 1 through 6 and the sequences of the ORFs have been provided within the contig sequences of SEQ ID NOs: 1 through 142, generating such DNA fragments would be routine to the skilled artisan. For example, restriction endonuclease cleavage or shearing by sonication could easily be used to generate fragments of various sizes from the PAI DNA that is incorporated into the deposited pools of cosmid clones. Alternatively, such fragments could be generated synthetically.

Preferred nucleic acid fragments of the present invention include nucleic acid molecules encoding epitope-bearing portions of an E. coli J96 PAI protein. Methods for determining such epitope-bearing portions are described in detail below.

In another aspect, the invention provides an isolated nucleic acid molecule comprising a polynucleotide that hybridizes under stringent hybridization conditions to a portion of the polynucleotide in a nucleic acid molecule of the invention described above, for instance, an ORF described in Tables 1 through 6, preferably an ORF described in Tables 1, 2, 3 or 4. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide that hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., a E. coli ORF), for instance, a portion 50–500 nt in length, or even to the entire length of the reference polynucleotide, are also useful as probes according to the present invention, as are polynucleotides corresponding to most, if not all, of an E. coli J96 PAI ORF.

By "expression modulating fragment" (EMF), is intended a series of nucleotides that modulate the expression of an operably linked ORF or EMF. A sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments that induce the expression of an operably linked ORF in response to a specific regulatory factor or physiological event. EMF sequences can be identified within the E. coli genome by their proximity to the ORFs described in Tables 1 through 6. An intergenic segment, or a fragment of the intergenic segment, from about 10 to 200 nucleotides in length, taken 5' from any one of the ORFs of Tables 1 through 6 will modulate the expression of an operably linked 3' ORF in a fashion similar to that found with the naturally linked ORF sequence. As used herein, an "intergenic segment" refers to the fragments of the E. coli J96 PAI subgenome that are between two ORF(s) herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, an EMF will modulate the expression of an operably linked marker sequence. A more detailed discussion of various marker sequences is provided below.

A sequence that is suspected as being an EMF is cloned in all three reading frames in one or more restriction sites upstream from the marker sequence in the EMF trap vector. The vector is then transformed into an appropriate host using known procedures and the phenotype of the transformed host in examined under appropriate conditions. As described above, an EMF will modulate the expression of an operably linked marker sequence.

By a "diagnostic fragment" (DF), is intended a series of nucleotides that selectively hybridize to E. coli sequences. DFs can be readily identified by identifying unique sequences within the E. coli J96 PAI subgenome, or by generating and testing probes or amplification primers consisting of the DF sequence in an appropriate diagnostic format for amplification or hybridization selectivity.

Each of the ORFs of the E. coli J96 PAI subgenome disclosed in Tables 1 through 4, and the EMF found 5' to the ORF, can be used in numerous ways as polynucleotide reagents. The sequences can be used as diagnostic probes or diagnostic amplification primers to detect the presence of uropathogenic E. coli in a sample. This is especially the case with the fragments or ORFs of Table 2 and 4 which will be highly selective for uropathogenic E. coli J96, and perhaps other uropathogenic or extraintestinal strains that include one or more PAIs.

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the mRNA itself (antisense—Okano, *J. Neurochem.* 56:560 (1991); *Oligodeoxynucleotides as Antisense Inhibitors of Gene Expression*, CRC Press, Boca Raton, Fla. (1988)).

Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

Vectors and Host Cells

The present invention further provides recombinant constructs comprising one or more fragments of the E. coli J96 PAIs. The recombinant constructs of the present invention comprise a vector, such as a plasmid or viral vector, into which, for example, an E. coli J96 PAI ORF is inserted. The vector may further comprise regulatory sequences, including for example, a promoter, operably linked to the ORF. For vectors comprising the EMFs of the present invention, the vector may further comprise a marker sequence or heterologous ORF operably linked to the EMF. Large numbers of suitable vectors and promoters are known to those of skill in the art and are commercially available for generating the recombinant constructs of the present invention. The following vectors are provided by way of example. Bacterial: pBs, phagescript, PsiXI74, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

The present invention further provides host cells containing any one of the isolated fragments (preferably an ORF) of the E. coli J96 PAIs described herein. The host cell can be a higher eukaryotic host cell, such as a mammalian cell, a lower eukaryotic host cell, such as a yeast cell, or the host cell can be a procaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)). Host cells containing, for example, an E. coli J96 PAI ORF can be used conventionally to produce the encoded protein.

Polypeptides and Fragments

The invention further provides isolated polypeptides having the amino acid sequence encoded by an E. coli PAI ORF described in Tables 1 through 6, preferably Tables 1 through 4, or a peptide or polypeptide comprising a portion of the above polypeptides. The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of E. coli polypeptides can be varied without significant effect of the structure or function of the protein. If such differences in sequence are contemplated, it should be remembered that there will be critical areas on the protein which determine activity. In general, it is possible to replace residues that form the tertiary structure, provided that residues performing a similar function are used. In other instances, the type of residue may be completely unimportant if the alteration occurs at a non-critical region of the protein.

Thus, the invention further includes variations of polypeptides encoded for by ORFs listed in Tables 1 through 6 which show substantial pathogenic activity or which include regions of particular E. coli PAI proteins such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

Thus, the fragment, derivative or analog of a polypeptide encoded by an ORF described in one of Tables 1 through 6, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of said proteins. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-Â to only one of the two known types of TNF receptors. Thus, proteins encoded for by the ORFs listed in Tables 1, 2, 3, 4, 5, or 6, and that bind to a cell surface receptor, may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 7).

TABLE 7

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the proteins encoded by ORFs of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro; or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form, and preferably are substantially purified. A recombinantly produced version of the polypeptides can be substantially purified by the one-step method described in Smith and Johnson, *Gene* 67:31–40 (1988).

The polypeptides of the present invention include the polypeptide encoded by the ORFs listed in Tables 1–6, preferably Tables 1–4, as well as polypeptides which have at least 90% similarity, more preferably at least 95% similarity, and still more preferably at least 96%, 97%, 98% or 99% similarity to those described above, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482–489, 1981) to find the best segment of similarity between two sequences.

By a polypeptide having an amino acid sequence at least, for example, 95% "identical" to a reference amino acid sequence of a polypeptide is intended that the amino acid sequence of the polypeptide is identical to the reference sequence except that the polypeptide sequence may include up to five amino acid alterations per each 100 amino acids of the reference amino acid of said polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the aimnino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence encoded by the ORFs listed in Tables 1, 2, 3, 4, 5, or 6 can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting pathogenic protein expression as described below or as agonists and antagonists capable of enhancing or inhibiting protein function of important proteins encoded by the ORFs of the present invention. Further, such polypeptides can be used in the yeast two-hybrid system to "capture" protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. ULNA* 81.3998–4002 (1983), As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide, which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containering about 100 $\mu$g peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of antipeptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C—C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, E. coli PAI polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric E. coli J96 PAI proteins or protein fragments alone (Fountoulakis et al., J. Biochem 270:3958–3964 (1995)).

Vaccines

In another embodiment, the present invention relates to a vaccine, preferably in unit dosage form, comprising one or more E. coli J96 PAI antigens together with a pharmaceutically acceptable diluent, carrier, or excipient, wherein the one or more antigens are present in an amount effective to elicit a protective immune response in an animal to pathogenic E. coli. Antigens of E. coli J96 PAI IV and V may be obtained from polypeptides encoded for by the ORFs listed in Tables 1–6, particularly Tables 1–4, using methods well known in the art.

In a preferred embodiment, the antigens are E. coli J96 PAI IV or PAI V proteins that are present on the surface of pathogenic E. coli. In another preferred embodiment, the pathogenic E. coli J96 PAI IV or PAI V protein-antigen is conjugated to an E. coli capsular polysaccharide (CP), particularly to capsular polypeptides that are more prevalent in pathogenic strains, to produce a double vaccine. CPs, in general, may be prepared or synthesized as described in Schneerson et al J. Exp. Med. 152.361–376 (1980); Marburg et al. J. Am. Chem. Soc. 108:5282 (1986); Jennings et al., J. Immunol. 27:1011–1018 (1981); and Beuvery el al., Infect. Immunol. 40:39–45 (1983). In a further preferred embodiment, the present invention relates to a method of preparing a polysaccharide conjugate comprising: obtaining the above-described E. coli J96 PAI antigen; obtaining a CP or fragment from pathogenic E. coli; and conjugating the antigen to the CP or CP fragment.

In a preferred embodiment, the animal to be protected is selected from the group consisting of humans, horses, deer, cattle, pigs, sheep, dogs, and chickens. In a more preferred embodiment, the animal is a human or a dog.

In a further embodiment, the present invention relates to a prophylactic method whereby the incidence of pathogenic E. coli—induced symptoms are decreased in an animal, comprising administering to the animal the above-described vaccine, wherein the vaccine is administered in an amount effective to elicit protective antibodies in an animal to pathogenic E. coli. This vaccination method is contemplated to be useful in protecting against severe diarrhea (pathogenic intestinal E. coli strains), urinary tract infections (uropathogenic E. coli) and infections of the brain (extraintestinal E. coli). The vaccine of the invention is used in an effective amount depending on the route of administration. Although intra-nasal, subcutaneous or intramuscular routes of administration are preferred, the vaccine of the present invention can also be administered by an oral, intraperitoneal or intravenous route. One skilled in the art will appreciate that the amounts to be administered for any particular treatment protocol can be readily determined without undue experimentation. Suitable amounts are within the range of 2 micrograms of the protein per kg body weight to 100 micrograms per kg body weight.

The vaccine can be delivered through a vector such as BCG. The vaccine can also be delivered as naked DNA coding for target antigens.

The vaccine of the present invention may be employed in such dosage forms as capsules, liquid solutions, suspensions or elixirs for oral administration, or sterile liquid forms such as solutions or suspensions. Any inert carrier is preferably used, such as saline, phosphate-buffered saline, or any such carrier in which the vaccine has suitable solubility properties. The vaccines may be in the form of single dose preparations or in multi-dose flasks which can be used for mass vaccination programs. Reference is made to Remington's Pharmaceutical Sciences, Mack Publishing Co., Easton, Pa., Osol (ed.) (1980); and New Trends and Developments in Vaccines, Voller et al. (eds.), University Park Press, Baltimore, Md. (1978), for methods of preparing and using vaccines.

The vaccines of the present invention may further comprise adjuvants which enhance production of antibodies and immune cells. Such adjuvants include, but are not limited to, various oil formulations such as Freund's complete adjuvant (CFA), the dipeptide known as MDP, saponins (ex. Quillajasaponin fraction QA-21., U.S. Pat. No. 5;047,540), aluminum hydroxide, or lymphatic cytokines. Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Vaccine may be absorbed onto the aluminum hydroxide from which it is slowly released after injection. The vaccine may also be encapsulated within liposomes according to Fullerton, U.S. Pat. No. 4,235,877.

Protein Function

Each ORF described in Tables 1 and 3 possesses a biological role similar to the role associated with the identified homologous protein. This allows the skilled artisan to determine a function for each identified coding sequence. For example, a partial list of the *E. coli* protein functions provided in Tables 1 and 3 includes many of the functions associated with virulence of pathogenic bacterial strains. These include, but are not limited to adhesins, excretion pathway proteins, O-antigen/carbohydrate modification, cytotoxins and regulators. A more detailed description of several of these functions is provided in Example 1 below.

Diagnostic Assays

In another preferred embodiment, the present invention relates to a method of detecting pathogenic *E. coli* nucleic acid in a sample comprising:

(a) contacting the sample with the above-described nucleic acid probe, under conditions such that hybridization occurs, and (b) detecting the presence of the probe bound to pathogenic *E. coli* nucleic acid.

In another preferred embodiment, the present invention relates to a diagnostic kit for detecting the presence of pathogenic *E. coli* nucleic acid in a sample comprising at least one container means having disposed therein the above-described nucleic acid probe.

In another preferred embodiment, the present invention relates to a diagnostic kit for detecting the presence of pathogenic *E. coli* antigens in a sample comprising at least one container means having disposed therein the above-described antibodies.

In another preferred embodiment, the present invention relates to a diagnostic kit for detecting the presence of antibodies to pathogenic *E. coli* antigens in a sample comprising at least one container means having disposed therein the above-described antigens.

The present invention provides methods to identify the expression of an ORF of the present invention, or homolog thereof, in a test sample, using one of the antibodies of the present invention. Such methods involve incubating a test sample with one or more of the antibodies of the present invention and assaying for binding of the antibodies to components within the test sample.

In a further embodiment, the present invention relates to a method for identifying pathogenic *E. coli* in an animal comprising analyzing tissue or body fluid from the animal for a nucleic acid, protein, polypeptide-antigen or antibody specific to one of the ORFs described in Tables 1–4 herein from E. coli J96 PAI IV or V. Analysis of nucleic acid specific to pathogenic *E. coli* can be by PCR techniques or hybridization techniques (cf. *Molecular Cloning: A Laboratory Manual, second edition*, edited by Sambrook, Fritsch, & Maniatis, Cold Spring Harbor Laboratory, 1989; Eremeeva et al., *J. Clin. Microbiol.* 32:803–810 (1994) which describes differentiation among spotted fever group Rickettsiae species by analysis of restriction fragment length polymorphism of PCR-amplified DNA).

Proteins or antibodies specific to pathogenic *E. coli* may be identified as described in *Molecular Cloning: A Laboratory Manual, second edition*, Sambrook et al., eds., Cold Spring Harbor Laboratory (1989). More specifically, antibodies may be raised to *E. coli* J96 PAI proteins as generally described in *Antibodies: A Laboratory Manual*, Harlow and Lane, eds., Cold Spring Harbor Laboratory (1988). *E. coli* J96 PAI-specific antibodies can also be obtained from infected animals (Mather, T. et al., *JAMA* 205:186–188 (1994)).

In another embodiment, the present invention relates to an antibody having binding affinity specifically to an *E. coli* J96 PAI antigen as described above. The *E. coli* J96 PAI antigens of the present invention can be used to produce antibodies or hybridomas. One skilled in the art will recognize that if an antibody is desired, a peptide can be generated as described herein and used as an immunogen. The antibodies of the present invention include monoclonal and polyclonal antibodies, as well as fragments of these antibodies. The invention further includes single chain antibodies. Antibody fragments which contain the idiotype of the molecule can be generated by known techniques, for example, such fragments include but are not limited to: the F(ab) fragment; the Fab fragments, Fab fragments, and Fv fragments.

Of special interest to the present invention are antibodies to pathogenic *E. coli* antigens which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCTAUS86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al, *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al, *Nature* 314:446–449 (1985)); Shaw et al, *J. Natl. Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al, *Science* 239:1534 (1988); Beidler, C. B. et al, *J. Immunol.* 141:4053–4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1–21 (1980)).

In another embodiment, the present invention relates to a method of detecting a pathogenic *E. coli* antigen in a sample, comprising: a) contacting the sample with an above-described antibody, under conditions such that immunocomplexes form, and b) detecting the presence of said antibody bound to the antigen. In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to it Radioimmunoassay and Related Techniques*, Elsevier Science Publishers, Amsterdam, The Netherlands (1986); Bullock et al., *Techniques in Immunocytochemistry*, Academic Press. Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985); and *Antibodies. A Laboratory Manual*, Harlow and Lane, eds., Cold Spring Harbor Laboratory (1988).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

In another embodiment, the present invention relates to a method of detecting the presence of antibodies to pathogenic *E. coli* in a sample, comprising: a) contacting the sample with an above-described antigen, under conditions such that immunocomplexes form, and b) detecting the presence of said antigen bound to the antibody. In detail, the methods comprise incubating a test sample with one or more of the antigens of the present invention and assaying whether the antigen binds to the test sample.

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits.

One skilled in the art will readily recognize that the antibodies described in the present invention can readily be incorporated into one of the established kit formats which are well known in the art.

Screening Assay for Binding Agents

Using the isolated proteins described herein, the present invention further provides methods of obtaining and identifying agents that bind to a protein encoded by an *E. coli* J96 PAI ORF or to a fragment thereof.

The method involves:

(a) contacting an agent with an isolated protein encoded by a *E. coli* J96 PAI ORF, or an isolated fragment thereof; and (b) determining whether the agent binds to said protein or said fragment.

The agents screened in the above assay can be, but are not limited to, peptides, carbohydrates, vitamin derivatives, or other pharmaceutical agents. The agents can be selected and screened at random or rationally selected or designed using protein modeling techniques. For random screening, agents such as peptides, carbohydrates, pharmaceutical agents and the like are selected at random and are assayed for their ability to bind to the protein encoded by an ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide ligands, for example see Hurby et al., Application of Synthetic Peptides: Antisense Peptides, In *Synthetic Peptides, A User's Guide*, W. H. Freeman, NY (1992), pp. 289–307, and Kaspczak et al., *Biochemistry* 28:9230–8 (1989).

In addition to the foregoing, one class of agents of the present invention, can be used to control gene expression through binding to one of the ORFs or EMFs of the present invention. As described above, such agents can be randomly screened or rationally designed and selected. Targeting the ORF or EMF allows a skilled artisan to design sequence specific or element specific agents, modulating the expression of either a single ORF or multiple ORFs that rely on the same EMF for expression control.

One class of DNA binding agents are those that contain nucleotide base residues that hybridize or form a triple helix by binding to DNA or RNA. Such agents can be based on the classic phosphodiester, ribonucleic acid backbone, or can be a variety of sulfhydryl or polymeric derivatives having base attachment capacity.

Agents suitable for use in these methods usually contain 20 to 40 bases and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the niRNA itself (antisense—Okano, *J. Neurochem.* 56:560 (1991); *Oligodeoxynucleotides as Antisense Inhibitors of Gene Expression*, CRC Press, Boca Raton, Fla. (1988)). Triple helix-formation optimally results in a shut-off of RNA transcription from DNA, while antisense RNA hybridization blocks translation of an MRNA molecule into polypeptide. Both techniques have been demonstrated to be effective in model systems. Information contained in the sequences of the present invention is necessary for the design of an antisense or triple helix oligonucleotide and other DNA binding agents.

Computer Related Embodiments

The nucleotide sequence provided in SEQ ID NOs: 1 through 142, representative fragments thereof, or nucleotide sequences at least 99.9% identical to the sequences provided in SEQ ID NOs: 1 through 142, can be "provided" in a variety of media to facilitate use thereof. As used herein, "provided" refers to a manufacture, other than an isolated nucleic acid molecule, that contains a nucleotide sequence of the present invention, i.e., the nucleotide sequence provided in SEQ ID NOs: 1 through 142, a representative fragment thereof, or a nucleotide sequence at least 99.9% identical to SEQ ID NOs: 1 through 142. Such a manufacture provides the *E. coli* J96 PAI subgenomes or a subset thereof (e.g., one or more *E. coli* J96 PAI open reading frame (ORF)) in a form that allows a skilled artisan to examine the manufacture using means not directly applicable to examining the *E. coli* J96 PAI subgenome or a subset thereof as it exists in nature or in purified form.

In one application of this embodiment, one or more nucleotide sequences of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently know methods for recording information on computer readable medium to generate manufactures comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention.

By providing the nucleotide sequence of SEQ ID NOs: 1 through 142, representative fragments thereof, or nucleotide sequences at least 99.9% identical to SEQ ID NOs: 1 through 142, in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403–410 (1990)) and BLAZE (Brutlag et al., *Comp. Chem.* 17:203–207 (1993)) search algorithms on a Sybase system can be used to identify open reading frames (ORFs) within the *E. coli* J96 PAI subgenome that contain homology to ORFs or proteins from other organisms. Such ORFs are protein-encoding fragments within the *E. coli* J96 PAI subgenome and are useful in producing commercially important proteins such as enzymes used in modifying surface O-antigens of bacteria. A comprehensive list of ORFs encoding commercially important *E. coli* J96 PAI proteins is provided in Tables 1 through 6.

The present invention provides a DNA sequence-gene database of pathogenicity islands (PAIs) for *E. coli* involved in infectious diseases. This database is useful for identifying and characterizing the basic functions of new virulence genes for *E. coli* involved in uropathogenic and extraintestinal diseases. The database provides a number of novel open reading frames that can be selected for further study as described herein.

Selectable insertion mutations in plasmid subclones encoding PAI genes with potentially significant phenotypes for *E. coli* uropathogenesis and sepsis can be isolated. The mutations are then crossed back into wild type, uropathogenic *E. coli* by homologous recombination to create wild-type strains specifically altered in the targeted gene. The significance of the genes to *E. coli* pathogenesis is assessed by *in vitro* assays and *in vivo* murine models of sepsis/peritonitis and ascending urinary tract infection.

New virulence genes and PAI sites in uropathogenic *E. coli* may be identified by the transposon signature-tagged mutagenesis system and negative selection of *E. coli* mutants avirulent in murine models of ascending urinary tract infection or peritonitis.

Epidemiological investigations of new virulence genes and PAIs may be used to test for their occurrence in the genomes of other pathogenic and opportunistic members of the Enterobacteriaceae.

One can choose from the ORFs included in SEQ ID NOs: 1 through 142, using Tables 1 through 6 as a useful guidepost for selecting, as candidates for targeted mutagenesis, a limited number of candidate genes within the PAIs based on their homology to virulence, export or regulation genes in other pathogens. For the large number of apparent genes within the PAIs that do not share sequence similarity to any entries in the database, the transposon signature-tagged mutagenesis method developed by David Holden's laboratory can be employed as an independent means of virulence gene identification.

Allelic knock-outs are constructed using differentpir-dependent suicide vectors (Swihart, K. A. and R. A. Welch, *Infect. Immun.* 58:1853–1869 (1990)). In addition, two different animal model systems can be employed for assessment of pathogenic determinants. The initial identification of *E. coli* hemolysin as a virulence factor came from the construction of isogenic *E. coli* strains that were tested in a rat model of intra-abdominal sepsis (Welch, R. A. et al., *Nature* (London) 294:665–667 (1981)). The ascending UTI (Urinary Tract Infection) mouse model was also successfully performed with allelic knock-outs of the hpmA hemolysin of *Proteus mirabilis* (Swihart, K. A. and R. A. Welch, *Infect. Immun.* 58:1853–1869 (1990)).

The present invention further provides systems, particularly computer-based systems, which contain the sequence information described herein. Such systems are designed to identify commercially important fragments of the *E. coli* J96 PAI subgenome. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the *E. coli* genome that match a particular target sequence or target motif. A variety of known algorithms are disclosed publicly and a variety of commercially available software for conducting search means are available and can be used in the computer-based systems of the present invention. Examples of such software include, but are not limited to, MacPattern (EMBL), BLASTN and BLASTX (NCBIA). A skilled artisan can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that during searches for commercially important fragments of the E. coli J96 PAI subgenome, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzymic active sites and signal sequences. Nucleic acid target motifs include, but are not limited to, promoter sequences, hairpin structures and inducible expression elements (protein binding sequences).

Thus, the present invention further provides an input means for receiving a target sequence, a data storage means for storing the target sequence and the homologous E. coli J96 PAI sequence identified using a search means as described above, and an output means for outputting the identified homologous E. coli J96 PAI sequence. A variety of structural formats for the input and output means can be used to input and output information in the computer-based systems of the present invention. A preferred format for an output means ranks fragments of the E. coli J96 PAI subgenome possessing varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments of the E. coli J96 PAI subgenomes. For example, implementing software which implement the BLAST and BLAZE algorithms (Altschul et al., J. Mol. Biol. 215:403–410 (1990)) can be used to identify open reading frames within the E. coli J96 PAI subgenome A skilled artisan can readily recognize that any one of the publicly available homology search programs can be used as the search means for the computer-based systems of the present invention.

One application of this embodiment is provided in FIG. 2. FIG. 2 provides a block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage devices 110, such as a hard drive 112 and a removable medium storage device 114. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable medium storage device 114. The computer system 102 includes appropriate software for reading the control logic and/or the data from the removable medium storage device 114 once inserted in the removable medium storage device 114.

A nucleotide sequence of the present invention may be stored in a well known manner in the main memory 108, any of the secondary storage devices 110, and/or a removable storage medium 116. Software for accessing and processing the genomic sequence (such as search tools, comparing tools, etc.) reside in main memory 108 during execution.

Having generally described the invention, the same will be more readily understood by reference to the following examples, which are provided by way of illustration and are not intended as limiting.

EXPERIMENTAL

Example 1

High Through-Put Sequencing of Cosmid Clones Covering PAI IV and PAI V in E. coli J96

The complete DNA sequence of the pathogenicity islands, PAL IV and PAI V (respectively>170 kb and ~110 kb), from uropathogenic E. coli strain, J96 (O4:K6) was determined using a strategy, cloning and sequencing method, data collection and assembly software essentially identical to those used by the TIGR group for determining the sequence of the Haemophilus influenzae genome (Fleischmann, R. D., el al., Science 269:496 (1995)). The sequences were then used for DNA and protein sequence similarity searches of the databases as described in Fleischmann, Id.

The analysis of the genetic information found within the PAIs of E. coil J96 was facilitated by the use of overlapping cosmid clones possessing these unique segments of DNA. These cosmid clones were previously constructed and mapped (as further described below) as an overlapping set in the laboratory of Dr. Doug Berg (Washington University). A gap exists between the left portion of cosmid 2 and the end of the PAI IV that would represent the pheV junction to the E. coli K-12 genome.

Uropathogenic strain E. coli J96 (O4:K6) was used as a source of chromosomal DNA for construction of a cosmid library. E. coli K-12 DH5Â and DH12 (Gibco/BRL, Gaithersburg, Md.) were used as hosts for maintaining cosmid and plasmid clones. The cosmid library of E. coli J96 DNA was constructed essentially as described by Bukanow & Berg (Mol. Microbiol 11:509–523 (1994)). DNA was digested with Sau3AI under conditions that generated fragments with an average size of 40 to 50 kb and electrophoresed through 1% agarose gels. Fragments of 35 to 50 kb were isolated and cloned into Lorist 6 vector that had been linearized with BamIII and treated with bacterial alkaline phosphatase to block self-ligation. (Lorist 6 is a 5.2-kb moderate-copy-number cosmid vector with T7 and SP6 promoters close to the cloning site.) Cloned DNA was packaged in lambda phage particles in vitro by using a commercial kit (Amersham, Arlington Heights, Ill.) and cosmid-containing phage particles were used to transduce E. coli DH5a. Transductant colonies were transferred to 150 mL of Luria-Bertani broth supplemented with kanamycin in 96-well microtiter plates and grown overnight at 37° C. with shaking. Two sets of clones, one for each PAI were ultimately assembled, as previously described (Swenson et al, Infection and Immunity 64:3736–3743 (1996)), fully incorporated by reference herein).

The two sets of clones contain eleven sub-clones that were employed in the sequencing method described below. One set of four overlapping cosmid clones covers the prs-containing PAI V, ATCC Deposit No. 97727, deposited Sep. 23, 1996. A second set of seven subclones covers much of the pap-containing PAI V, ATCC Deposit No. 97726, deposited Sep. 23, 1996. See FIG. 1.

A high throughput, random sequencing method (Fleischmann et al., Science 269:496 (1995); Fraser et al., Science 270:397 (1995)) was used to obtain the sequences for 142 (contigs) fragments of E. coli J96 PAIs. All clones were sequenced from both ends to aid in the eventual ordering of contigs during the sequence assembly process. Briefly, random libraries of ~2 kb clones covering the two J96 PAIs were constructed, ~2,800 clones were subjected to automated sequencing (~450 nt/clone) and preliminary assemblies of the sequences accomplished which result in 142 contigs for each of the two PAIs that total 95 and 135 kb respectively. The estimated sizes of the PAI IV and PAI V based on the overlapping cosmid clones are $1.7 \times 10^5$ and $1.1 \times 10^5$ bp respectively. The 142 sequences were assembled by means of the TIGR Assembler (Fleischmann et al.; Fraser et al.); Sutton et al., Genome Sci. Tech. 1:9 (1995)). Sequence and physical gaps were closed using a combination of strategies (Fleischmann et al.; Fraser et aL). Presently the average depth of sequencing for each base assembled in the contigs is 6-fold. The tentative identity of many genes based on sequence homology is covered in Tables 1, 3, 5 and 6.

Open reading frames (ORFs) and predicted protein-coding regions were identified as described (Fleischmann et al.; Fraser et al.) with some modification. In particular, the statistical prediction of uropathogenic E. coli J96 pathogenicity island genes was performed with GeneMark (Borodovsky, M. & McIninch, J. Comput. Chem. 17:123 (1993)). Regular GeneMark uses nonhomogeneous Markov models derived from a training set of coding sequences and ordinary Markov models derived from a training set of noncoding sequences. The ORFs in Tables 1–6 were identified by GeneMark using a second-order Markov model trained from known E. coli coding regions and known E. coli non-coding regions. Among the important genes that are implicated in the virulence of E. coli J96 PAIs are adhesins, excretion pathway proteins, proteins that participate in alterations of the O-antigen in the PAIs, cytotoxins, and two-component (membrane sensor/DNA binding) proteins.

I. Adhesins

It is believed that the principal adhesin determinants involved in uropathogenicity that are present within PAIs of uropathogenic E. coli are the pili encoded by the pap-related operons (Hultgren et al., Infect. Immun. 50:370–377 (1993), Stromberg et al., EMBO J 9:2001–2010 (1990), High et al., Infect. Immun. 56:513–517 (1988)) and the distantly related afimbrial adhesins (Labigne-Roussel et al., Infect. Immun. 46:251–259 (1988)). The presence of two of these (pap, and prs) has been confirmed. In addition potential genes for five other adhesins including sla (described above), AIDA-I (diffuse adherence-DEAC), hra (heat resistant hemagglutinin-ETEC), jha (filamentous hemagglutinin-Bordetella pertussis) and the arg-gingipain proteinase of Porphyromonas gingivalis have been found.

II. Type II exoprotein secretion pathway

Highly significant statistics support the presence of multiple genes involved in the type II exoprotein pathway. Curiously, perhaps two different determinants appear to be present in PAI IV where one set of genes has the highest sequence similarity to eps-like genes (Vibrio cholerae Ctx export) and the other has greatest similarity to exe genes (Aeromonas hydophilia aerolysin and protease export). At present, the assembly of contigs involving these potential genes is incomplete. Thus, it is uncertain if two separate and complete determinants are present. However, it is clear that these genes are newly discovered and novel to pathogenic E. coli because the derived sequences do not have either the bfp or hop genes as the highest matches. The gene products that are the target of the type II export pathway are not evident at this time.

Within PAI IV there are sequences which suggest genes very similar to secD and secF. These two linked genes encode homologous products that are localized to the inner membrane and are hypothesized to play a late role in the translocation of leader-peptide containing proteins across the inner membrane of gram-negative bacteria. In addition, in each PAI, sequences are found that are reminiscent of the heat-shock htrA/degA gene that encodes a piroplasmic protease. They may perform endochaperone-like function as Pugsley et al. have hypothesized for different exoprotein pathways.

III. O-antigen/Capsule/Carbohydrate Modification (Nod Genes)

J96 has the O4. The O-antigen portion of lipopolysaccharide is encoded by rfb genes that are located at 45 min. on the E. coli chromosome. We have found in both PAIs a cumulative total of five possible rfb-like genes which could participate alterations of the O-antigen in the PAIs. Overall these data suggest that PAIs provide the genetic potential for greater change of the cell surface for uropathogenic E. coli strains than what was previously known.

The apparent capsule type for strain J96 is a non-sialic acid K6-type. Sequence similarity "hits" were made in PAI IV region to two region-1 capsule genes, kpsS and kpsE involved in the stabilization of polysaccharide synthesis and polysaccharide export across the inner membrane. This is not altogether surprising based on the genetic mapping of the kps locus to serA at 63 minutes on the genome of the K1 capsular type of E. coli. This suggests that these kps-like genes either are participating in the K6-biosynthesis or perhaps are involved in complex carbohydrate export for other purposes.

An intriguing discovery are the hits made on genes involved in bacteria-plant interactions by Rhizobium, Bradyrhizobium and Agrobacterium. Four potential genes identified thus far share significant sequence similarity to genes encoding products that modify lipo-oligosaccharides that influence nodule morphogenesis on legume roots. These are: ORF140, carbamyl phosphate synthetase; modulation protein 1265; phosphate-regulatory protein; and an ORF at a plant-inducible locus in Agrobacterium. To date there are no descriptions in the literature of such gene products being utilized by human or animal bacterial pathogens for the purposes of modification or secretion of extracellular carbohydrate. However, the sequence similarity to the capsular region-2 genes and to lipooligosaccharide biosynthetic genes in Rhizobium spp has been recently noted by Petit (1995).

IV. Cytotoxins

Besides the previously known hemolysin and CNF toxins in the PAIs, in each PAI sequences similar to the shiBA operon (cosmid 5 and 12) were found for a cytolytic toxin from Serratia marcescens and Proteus mirabilis. Ironically, the P. mirabilis hemolysin (HpmA) member of this family of toxins was discovered by Uphoff and Welch (1990), but not thought to exist in other members of the Enterobacteriaceae (Swihart (1990)). A shlB-like transporter does also appear to be involved in the export of the filamentous hemagglutinin of Bordetella pertussis which was described above and a cell surface adhesin of Haemophilus influenzae. It has been demonstrated that cosmid #5 of E. coli J96 encodes an extracellular protein that is ~1.80 kDa and cross-reactive to polyclonal antisera to the P. mirabilis HpmA hemolysin. Thus, there is evidence suggesting there is new member of this family of proteins in extraintestinal E. coli isolates. In addition, there is also a hit on the FhaC hemolysin-like gene within the PAI V although its statistical significance for the sequence thus far available is only 0.0043.

V. Regulators

A common regulatory motif in bacteria are the two-component (membrane sensor/DNA binding) proteins. In numerous instances in pathogenic bacteria, external signals in the environment cause membrane-bound protein kinases to phosphorylate a cytoplasmic protein which in turn acts as either a negative or positive effector of transcription of large sets of operons. On cosmid 11 representing PAI V were found, in two different PstI clones, sequences for two-component regulators (similar probabilities for OmpR/AIGB and separately RcsC, probabilities at the $10^{-22}$ level).

In addition, the phosphoglycerate transport system (pgta, pgtC, and pgtP) including the pgtB regulator is present in PAI IV. This transport system which was originally described in *S. typhimurium* is not appreciated as a component of any pathogenic *E. coli* genome. The operon had been previously mapped at 49 minutes near or within one of the *S. typhimurium* chromosome specific-loops not present in the K-12 genome. It should be noted that the *E. coli* K-12 glpT gene product is similar to pgtP gene product (37% identity), but the *E. coli* J96 genes are clearly homologs to the pgt genes and their linkage within the middle of PAI IV element (cosmid #4) is suspicious.

VI. Mobile Genetic Elements

There are numerous sequences that share similarity to genes found on insertion elements, plasmids and phages. The temperate bacteriophage P4 inserts within tRNA loci in the *E. coli* chromosome. The hypothesis was made that PAIs are the result of bacteriophage P4-virulence gene recombination events (Blum et al., *Infect. Immun.* 62:606–614 (1994). Data supporting this hypothesis was found during our sequencing with the identification of P4-like sequences in each of the PAIs (cosmids 7 and 9). This is a very important preliminary result which supports the hypothesis that PAIs can be identified by common sequence or genetic elements. However, there are indications that multiple mobile genetic elements involved in the evolution of the J96 PAIs. Conjugal plasmid-related sequences may also be present at two different locations (F factor and R1 plasmid). Sequences for multiple transposable elements are present that are likely to have originated from different bacterial genera (Tn1000, IS630, IS911, IS100, IS21, IS 1203, IS5376 (*B. stearothermophflu*) and RHS). Of particular interest is IS100, which was originally identified in *Yersinia pestis* (Fetherston et aL, *Mol. Microbiol.* 6:2693–2704 (1992)). The presence of IS106 is significant because it has been associated with the termini of a large chromosomal element encoding pigmentation and some aspect of virulence in *Y. pestis*. This element undergoes spontaneous deletions similar to the PAIs from *E. coli* 536 (Fetherston et al., *Mol. Microbiol.* 6:2693–2704 (1992)) and appears to participate in plasmid-chromosome rearrangements. This element was not previously known to be in genera outside of Yersinia.

The discovery of the apparent att site for bacteriophage P2 in the PAIs is interesting. P2 acts as a helper phage for the P4 satellite phage. The P2 att site is at 44 min in the K-12 genome. The significance of this hit is unknown at present, but may be explained as either a cloning artifact (some K-12 fragments in the Pst I library of cosmid 5) or evidence of some curious chromosomal-P4/P2 phage history. It may indicate that the J96 PAIs are composites of multiple smaller PAIs.

Example 2

Preparation of PCR Primers and Amplification of DNA

Various fragments of the sequenced *E. coli* J96 PAIs, such as those disclosed in Tables 1 through 6 can be used, in accordance with the present invention, to prepare PCR primers. The PCR primers are preferably at least 15 bases, and more preferably at least 18 bases in length. When selecting a primer sequence, it is preferred that the primer pairs have approximately the same G/C ratio, so that melting temperatures are approximately the same. The PCR primers are useful during PCR cloning of the ORFs described herein.

Example 3

Gene expression from DNA Sequences Corresponding to ORFs

A fragment of an *E. coli* J96 PAIs (preferably, a protein-encoding sequence provided in Tables 1 through 6) is introduced into an expression vector using conventional technology (techniques to transfer cloned sequences into expression vectors that direct protein translation in mammalian, yeast, insect or bacterial expression systems are well known in the art). Commercially available vectors and expression systems are available from a variety of suppliers including Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism, as explained by Hatfield et al., U.S. Pat. No. 5,082,767, which is hereby incorporated by reference.

The following is provided as one exemplary method to generate polypeptide(s) from a cloned ORF of an *E. coli* J96 PAI whose sequence is provided in SEQ ID NOs: 1 through 142. A poly A sequence can be added to the construct by, for example, splicing out the poly A sequence from pSG5 (Stratagene) using BglI and SalI restriction endonuclease enzymes and incorporating it into the mammalian expression vector pXT1 (Stratagene) for use in eukaryotic expression systems. pXT1 contains the LTRs and a portion of the gag gene from Moloney Murine Leukemia Virus. The position of the LTRs in the construct allow efficient stable transfection. The vector includes the Herpes Simplex thymidine kinase promoter and the selectable neomycin gene. The *E. coli* J96 PAI DNA is obtained by PCR from the bacterial vector using oligonucleotide primers complementary to the *E. coli* J96 PAI DNA and containing restriction endonuclease sequences for PstI incorporated into the 5 primer and BglII at the 5 end of the corresponding *E. coli* J96 PAI DNA 3 primer, taking care to ensure that the *E. coli* J96 PAI DNA is positioned such that its followed with the poly A sequence. The purified fragment obtained from the resulting PCR reaction is digested with PstI, blunt ended with an exonuclease, digested with BglII, purified and ligated to pXT1, now containing a poly A sequence and digested BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). The protein is preferably released into the supernatant. However if the protein has membrane binding domains, the protein may additionally be retained within the cell or expression may be restricted to the cell surface.

Since it may be necessary to purify and locate the transfected product, synthetic 15-mer peptides synthesized from the predicted *E. coli* J96 PAI DNA sequence are injected into mice to generate antibody to the polypeptide encoded by the *E. coli* J96 PAI DNA.

If antibody production is not possible, the *E. coli* J96 PAI DNA sequence is additionally incorporated into eukaryotic expression vectors and expressed as a chimeric with, for example, β-globin. Antibody to 13-globin is used to purify the chimeric. Corresponding protease cleavage sites engineered between the β-globin gene and the *E. coli* J96 PAI DNA are then used to separate the two polypeptide fragments from one another after translation. One useful expression vector for generating β-globin chimerics is pSG5 (Stratagene). This vector encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are available from the technical assistance representatives from Stratagene, Life Technologies, Inc., or Promega. Polypeptides may additionally be produced from either construct using in vitro translation systems such as In vitro Express™ Translation Kit (Stratagene).

Example 4

*E. coli* Expression of an *E. coli* J96 PAI ORF and Protein Purification

An *E. coli* J96 PAI ORF described in Tables 1 through 6 is selected and amplified using PCR oligonucleotide primers designed from the nucleotide sequences flanking the selected ORF and/or from portions of the ORF s NH- or COOH-terminus. Additional nucleotides containing restriction sites to facilitate cloning are added to the 5' and 3' sequences, respectively.

The restriction sites are selected to be convenient to restriction sites in the bacterial expression vector pQE60. The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6xHis tag") covalently linked to the carboxyl terminus of that polypeptide.

The DNA sequence encoding the desired portion of an *E. coli* J96 PAI is amplified from the deposited cDNA clone using PCR oligonucleotide primers which anneal to the amino terminal sequences of the desired portion of the *E. coli* protein and to sequences in the deposited construct 3' to the cDNA coding sequence. Additional nucleotides containing restriction sites to facilitate cloning in the pQE60 vector are added to the 5' and 3' sequences, respectively.

The amplified *E. coli* J96 PAI DNA fragments and the vector pQE60 are digested with one or more appropriate restriction enzymes, such as SalI and XbaI, and the digested DNAs are then ligated together. Insertion of the *E. coli* J96 PAI DNA into the restricted pQE60 vector places the *E. coli* J96 PAI protein coding region, including its associated stop codon, downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing an *E. coli* J96 PAI protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. isopropyl-β-D-thiogalactopyranoside ("IPTG") is then added to a final concentration of 1 mM to induce transcription from the lac repressor sensitive promoter, by inactivating the laci repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the *E. coli* J96 PAI protein is dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure *E. coli* J96 PAI protein. The purified protein is stored at 4° C. or frozen at −80° C.

Example 5

Cloning and Expression of an *E. coli* J96 PAI Protein in a Baculovirus Expression System An *E. coli* J96 PAI ORF described in Tables 1 through 6 is selected and amplified as above. The plasmid is digested with appropriate restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the *E. coli* J96 PAI gene by digesting DNA from individual colonies using appropriate restriction enzymes and then analyzing the digestion product by gel electrophoresis. The sequence of the cloned fragment is confirmed by DNA sequencing. This plasmid is designated herein pBac *E. coli* J96.

Five μg of the plasmid pBac *E. coli* J96 is co-transfected with 1.0 μg of a commercially available linearized baculovirus DNA ("BaculoGold baculovirus DNA", Pharmingen, San Diego, Calif.), using the lipofection method described by Felgner et al., *Proc. Natl. Acad. Sci. USA* 84:7413–7417 (1987). 1 μg of BaculoGold virus DNA and 5 μg of the plasmid pBac *E. coli* J96 are mixed in a sterile well of a microliter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-*E. coli* J96.

To verify the expression of the *E. coli* gene Sf9 cells are grown in Grace's medium supplemented with 10% heat inactivated FBS. The cells are infected with the recombinant baculovirus V-*E. coli* J96 at a multiplicity of infection ("MOI") of about 2. Six hours later the medium is removed and is replaced with SF900 II medium minus methionine and cysteine (available from Life Technologies Inc.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretary signal peptide.

Example 6

Cloning and Expression in Mammalian Cells

Most of the vectors used for the transient expression of an *E. coli* J96 PAI gene in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, 1HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV I, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molecular and Cellular Biology, 438447 (March, 1985)) plus a fragment of the CMV-enhancer (Boshart et al., *Cell* 41:521–530 (1985)). Multiple cloning sites, e.g., with the restriction enzyme cleavage sites BamHI, Xbal and Asp718, facilitate the cloning of the gene of interest. The vectors contain in addition the 3' intron, the polyadenylation and termination signal of the rat preproinsulin gene.

Example 6(a)

Cloning and Expression in COS Cells

The expression plasmid, p *E. coli* J96HA, is made by cloning a cDNA encoding *E. coli* J96 PAI protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the E. coli J96 PAI protein is cloned into the polylinker region of the vector so that recombinant protein expression is directed by the CMV promoter. The plasmid construction strategy is as follows. The E. coli cDNA of the deposited clone is amplified using primers that contain convenient restriction sites, much as described above for construction of vectors for expression of E. coil J96 PAI protein in E. coli.

The PCR amplified DNA fragment and the vector, pcDNAI/Amp, are digested with appropriate restriction enzymes for the chosen primer sequences and then ligated. The ligation mixture is transformed into E. coli strain SURE (available from Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the E. coli J96 PAI protein-encoding fragment.

For expression of recombinant E. coli J96 PAI protein, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of E. coli J96 PAI protein by the vector.

Expression of the E. coli J96 PAI-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 6(b)

Cloning and Expression in CHO Cells

The vector pC4 is used for the expression of an E. coli J96 PAI protein. Plasmid pC4 is a derivative of the plasmid pSV2-dhfr (ATCC Acc. No. 37146). The plasmid contains the mouse DHFR gene under control of the SV40 early promoter. Chinese hamster ovary or other cells lacking dihydrofolate activity that are transfected with these plasmids can be selected by growing the cells in a selective medium (alpha minus MEM, Life Technologies, Inc.) supplemented with the chemotherapeutic agent methotrexate. The amplification of the DHFR genes in cells resistant to methotrexate (MTX) has been well documented (see, e.g., Alt, F. W. et al., 1978, *J. Biol. Chem.* 253:1357–1370, Hamlin, J. L. and Ma, C. 1990, *Biochim. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, el al, *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter is BamHI restriction enzyme site that allows the integration of the gene. Behind these cloning sites the plasmid contains the 3' intron and polyadenylation site of the rat preproinsulin gene. Other high efficiency promoters can also be used for the expression, e.g., the human-actin promoter, the SV40 early or late promoters or the long terminal repeats from other retroviruses, e.g., HIV and HTLVI. Clontech's Tet-Off and Tet-On gene expression systems and similar systems can be used to express the E. coli protein in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with appropriate restriction enzymes and then dephosphorylated using calf intestinal phosphates by procedures known in the art. The vector is then isolated from a 1% agarose gel.

The DNA sequence encoding the complete E. coli J96 PAI protein including its leader sequence is amplified using PCR oligonucleotide primers corresponding to the 5' and 3' sequences of the gene.

The amplified fragment is digested with appropriate endonucleases for the chosen primers and then purified again on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 µg of the expression plasmid pC4 is cotransfected with 0.5 µg of the plasmid pSVneo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methothrexate plus 1 mgirnl GT418. After about 0–14 days single clones are trypsinized and then seeded in 6-well petri dishes or 10 ml flasks using different concentrations of methotrexate (50 nM, 100 nM, 200 nM, 400 nm, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reversed phase HPLC analysis.

Example 7

Production of an Antibody to an E. coli J96 Pathogenicity Island Protein

Substantially pure E. coli J96 PAI protein or polypeptide is isolated from the transfected or transformed cells described above using an art-known method. The protein can also be chemically synthesized. Concentration of protein in the final preparation is adjusted, for example, by concentration on an Amicon filter device, to the level of a few micrograms/ml. Monoclonal or polyclonal antibody to the protein can then be prepared as follows:

I. Monoclonal Antibody Production by Hybridoma Fusion

Monoclonal antibody to epitopes of any of the peptides identified and isolated as described can be prepared from murine hybridomas according to the classical method of Kohler and Milstein, Nature 256:495 (1975) or modifications of the methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., Meth. EnzymoL 70:419 (1980), and modified methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2 (1989).

II. Polyclonal Antibody Production by Immunization

Polyclonal antiserum containing antibodies to heterogenouis epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic than other molecules and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al., J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall (See Ouchterlony, O. et al., Chap. 19 in: Handbook of Experimental Immunology, Wier, D., ed, Blackwell (1973)). Plateau concentration of antibody is usually in the range of 0.1 to 0.2 mg/ml of serum (about 12 μM). Affinity of the antisera for the antigen is determined by preparing competitive binding curves, as described, for example, by Fisher, D., Chap. 42 in: Manual of Clinical Immunology, 2nd ed., Rose and Friedman, (eds.), Amer. Soc. For Microbio., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample.

While the present invention has been described in some detail for purposes of clarity and understanding, one skilled in the art will appreciate that various changes in form and detail can be made without departing from the true scope of the invention.

All patents, patent applications and publications recited herein are hereby incorporated by reference.

TABLE 1

(PAI IV)
Putative coding regions of novel E. coli PAI IV proteins similar to known proteins

| Contig ID | ORF ID | Start (nt) | Stop (nt) | match acession | match gene name | % sim | % ident | length (nt) |
|---|---|---|---|---|---|---|---|---|
| 65 | 2 | 1902 | 1042 | gl\|1655838 | ORFB, putative transposase [Yersinia paetia] | 100 | 100 | 861 |
| 65 | 3 | 2096 | 1821 | gl\|467612 | ORF1 [Yersinia paetia] | 100 | 100 | 276 |
| 63 | 11 | 7856 | 9238 | gl\|154262 | transporter protein pgtP [Salmonella typhimurium] | 98 | 93 | 1383 |
| 65 | 4 | 2889 | 1915 | gl\|1655837 | ORFA, putative transposase [Yersinia paetia] | 97 | 96 | 975 |
| 138 | 1 | 2 | 172 | gl\|1208992 | unknown [Escherichia coli] | 97 | 78 | 171 |
| 64 | 6 | 4075 | 4338 | gl\|1143207 | Description: IS630 insertion element; ORF5 protein; Method: conceptual translation supplied by author [Shigella sonnei] | 92 | 92 | 264 |
| 67 | 1 | 1 | 273 | gl\|809648 | ExeP gene product [Aeromonas hydrophila] | 92 | 71 | 273 |
| 73 | 4 | 3029 | 2511 | gl\|799234 | glucose-1-phosphate thymidylyltransferase [Escherichia coli] | 92 | 86 | 519 |
| 73 | 5 | 3139 | 2996 | gl\|454900 | rfbC gene product [Shigella flexneri] | 92 | 92 | 144 |
| 64 | 5 | 3741 | 4088 | gl\|47542 | ORF (343 AA) [Shigella sonnei] | 91 | 85 | 348 |
| 73 | 3 | 2613 | 2242 | gl\|46985 | glucose-1-phosphate thymidylyltransferase [Salmonella enterica] | 91 | 82 | 372 |
| 90 | 1 | 1 | 366 | gl\|38826 | ExeE gene product [Aeromonas hydrophila] | 91 | 77 | 366 |
| 91 | 2 | 604 | 248 | gl\|609625 | putative [Vibrio cholerae] | 91 | 67 | 357 |

TABLE 1-continued (PAI IV)
Putative coding regions of novel *E. coli* PAI IV proteins similar to known proteins

| Contig ID | ORF ID | Start (nt) | Stop (nt) | match acession | match gene name | % sim | % ident | length (nt) |
|---|---|---|---|---|---|---|---|---|
| 63 | 9 | 6301 | 5234 | gl\|858753 | regulatory protein pgtB [*Salmonella typhimurium*] | 89 | 84 | 1068 |
| 73 | 2 | 2179 | 1811 | gl\|294899 | dTDP-6-deoxy-L-mannose-dehydrogenase [*Shigella flexneri*] | 89 | 84 | 369 |
| 90 | 2 | 201 | 689 | gl\|38826 | ExeE gene product [*Aeromonas hydrophila*] | 89 | 80 | 489 |
| 95 | 2 | 1519 | 413 | gl\|581654 | dTDP-glucose 4,6-dehydratase [*Salmonella enterica*] | 88 | 81 | 1107 |
| 96 | 1 | 729 | 457 | PIR\|543483\|S434 | Orf104 homolog - *Escherichia coli* | 88 | 72 | 273 |
| 63 | 6 | 4281 | 3019 | gl\|154255 | phosphoglycerate transport system activator protein [*Salmonella typhimurium*] | 87 | 79 | 1263 |
| 67 | 2 | 251 | 745 | gl\|609628 | putative [*Vibrio cholerae*] | 87 | 72 | 495 |
| 82 | 12 | 5254 | 4406 | gl\|1208992 | unknown [*Escherichia coli*] | 87 | 74 | 849 |
| 60 | 1 | 693 | 4 | gl\|609625 | putative [*Vibrio cholerae*] | 86 | 57 | 690 |
| 95 | 1 | 428 | 3 | gl\|508238 | dTDP-6-deoxy-L-mannose-dehydrogenase [*Escherichia coli*] | 85 | 74 | 426 |
| 64 | 7 | 4336 | 4731 | gl\|47542 | ORF (343 AA) [*Shigella sonnei*] | 84 | 81 | 396 |
| 80 | 8 | 2800 | 2582 | gl\|38832 | ExeE gene product [*Aeromonas hydrophila*] | 84 | 53 | 219 |
| 82 | 10 | 4380 | 3829 | gl\|1033137 | ORF_o152 *Escherichia coli* | 84 | 72 | 552 |
| 63 | 8 | 5399 | 4830 | sp\|P37433\|PGTB_ | PHOSPHOGLYCERATE TRANSPORT SYSTEM SENSOR PROTEIN PGTB [EC 2.7.3.-], | 83 | 75 | 570 |
| 63 | 10 | 7572 | 6259 | gl\|154258 | regulatory protein pgtC [*Salmonella typhimurium*] | 83 | 78 | 1314 |
| 65 | 7 | 3351 | 3100 | gl\|1196999 | unknown protein [Transposon Tn3411] | 82 | 80 | 252 |
| 100 | 1 | 337 | 2 | gl\|41004 | ORF 2 [*Escherichia coli*] | 82 | 64 | 336 |
| 138 | 2 | 109 | 429 | gl\|1033128 | ORF_o273 [*Escherichia coli*] | 80 | 62 | 321 |
| 74 | 4 | 1331 | 831 | gl\|38826 | ExeE gene product [*Aeromonas hydrophilia*] | 79 | 62 | 501 |
| 63 | 7 | 4873 | 4256 | sp\|P37433\|PGTB_ | PHOSPHOGLYCERATE TRANSPORT SYSTEM SENSOR PROTEIN PGTB [EC 2.7.3.-], | 78 | 72 | 618 |
| 70 | 13 | 5759 | 5529 | gl\|1773143 | Hha protein [*Escherichia coli*] | 78 | 58 | 201 |
| 91 | 3 | 1154 | 534 | gl\|609625 | putative [*Vibrio cholerae*] | 77 | 65 | 621 |
| 75 | 5 | 3524 | 3255 | gl\|463911 | heat resistant agglutinin 1 [*Escherichia coli*] | 76 | 62 | 270 |
| 63 | 1 | 2 | 667 | gl\|1574313 | *H. influenzae* predicted coding region HT1472 [*Haemophilus influenzae*] | 75 | 56 | 666 |
| 104 | 2 | 485 | 315 | gl\|530438 | arabinose transport protein [*Hycoplasma capricolum*] | 72 | 41 | 171 |
| 63 | 3 | 2180 | 1629 | gl\|622948 | transposase [*Escherichia coli*] | 71 | 60 | 552 |
| 63 | 12 | 9688 | 10005 | sp\|P39213\|YI91_ | INSERTION ELEMENT I6911 HYPOTHETICAL 12.7 KD PROTEIN, | 71 | 57 | 310 |
| 61 | 3 | 1283 | 876 | gl\|581535 | ORF140 gene product [Rhizobium sp.] | 70 | 54 | 408 |
| 84 | 3 | 2361 | 3437 | gl\|1772623 | Hecλ [*Erwinia chysanthemi*] | 70 | 60 | 1071 |
| 91 | 1 | 300 | 4 | gl\|295430 | spaE [*Vibrio cholerae*] | 70 | 49 | 297 |
| 74 | 1 | 541 | 2 | gl\|609627 | putative [*Vibrio cholerae*] | 69 | 54 | 540 |
| 67 | 0 | 1297 | 1581 | gl\|151469 | PlID-dependent protein [*Pseudomonas aeruginosa*] | 68 | 50 | 285 |
| 84 | 1 | 578 | 1741 | gl\|1772622 | HacB [*Erwinia chysanthemi*] | 68 | 54 | 1164 |
| 84 | 2 | 1698 | 2363 | gl\|1772622 | HacB [*Erwinia chysanthemi*] | 67 | 48 | 666 |
| 63 | 2 | 1734 | 1393 | gl\|1323798 | transposase [Plasmid pRL1063a] | 65 | 46 | 342 |
| 71 | 1 | 1234 | 4 | gl\|397405 | kpaB gene product[*Escherichia coli*] | 65 | 36 | 1131 |
| 64 | 2 | 2828 | 1839 | gl\|310632 | hydrophobic membrane protein [*Streptococcus gordonii*] | 64 | 38 | 990 |
| 74 | 2 | 861 | 355 | gl\|148436 | secretory component [*Erwinia chrysanthemi*] | 64 | 54 | 507 |
| 66 | 1 | 556 | 2 | gl\|1235662 | RfbC [*Hyxococcus xanthus*] | 62 | 39 | 555 |
| 70 | 6 | 3017 | 2814 | gl\|1657478 | similar to *E. coli* ORF_o208 *Escherichia coli*] | 62 | 41 | 204 |
| 85 | 1 | 278 | 66 | plr\|λ15253\|λ452 | activator 1 37 K chain - human | 62 | 56 | 213 |
| 126 | 1 | 3 | 323 | gl\|1778562 | hypothetical protein [*Escherichia coli*] | 62 | 45 | 321 |
| 73 | 1 | 773 | 3 | pir\|λS32879\|S328 | lipλ protein - *Neisseria meningitidia* | 61 | 46 | 771 |
| 96 | 2 | 796 | 644 | gnl\|PID\|o276217 | T03F6.t [*Caenorhabditis elegans*] | 61 | 46 | 153 |
| 67 | 3 | 743 | 1312 | gl\|609629 | putative [*Vibrio cholerae*] | 60 | 43 | 570 |
| 70 | 10 | 4666 | 4292 | gl\|1657478 | similar to *E. coli* ORF_o208 [*Escherichia coli*] | 60 | 45 | 375 |
| 81 | 1 | 1 | 1179 | gl\|1591717 | spore coat polysaccharide biosynthesis protein E [*Hethanococcus jannaschii*] | 60 | 44 | 1179 |
| 80 | 5 | 2563 | 1790 | gl\|609632 | putative [*Vibrio cholerae*] | 59 | 41 | 771 |
| 237 | 1 | 73 | 528 | gl\|1736670 | Adhesin AIDA-I precursor. [*Escherichia coli*] | 59 | 45 | 456 |
| 61 | 1 | 773 | 3 | gl\|1196968 | unknown protein [Insertion sequence /IS66] | 58 | 41 | 771 |
| 63 | 5 | 2831 | 2178 | gl\|622948 | transposase [*Escherichia coli*] | 58 | 41 | 654 |
| 64 | 3 | 3568 | 2690 | gl\|1335913 | unknown [*Erysipalothrix rhusiopathiaa*] | 57 | 36 | 879 |
| 64 | 1 | 1819 | 917 | gl\|153826 | adhesin 8 [*Streptococcus sanguia*] | 55 | 30 | 903 |
| 64 | 9 | 7008 | 6685 | gl\|155259 | icrB gene product [Rhizobium sp.] | 55 | 42 | 321 |
| 70 | 14 | 6481 | 6753 | pir\|G42465\|G124 | hypothetical protein 88 - phage phi-R73 | 53 | 30 | 271 |
| 85 | 5 | 9317 | 1530 | gl\|144048 | filamentous hemagglutinin [*Bordatella pertussis*] | 52 | 37 | 273 |
| 64 | 8 | 5063 | 4806 | gnl\|PID\|o264304 | P53C11.6 [*Caenorhabditis elegans*] | 51 | 27 | 258 |
| 80 | 9 | 3411 | 2761 | gl\|149309 | pulJ [*Klebsiella pneumoniae*] | 50 | 40 | 651 |
| 88 | 1 | 98 | 388 | gl\|156087 | (*Brugia malayi* myosin heavy chain gene, complete cds.), gene product [*Brugia malayi*] | 50 | 32 | 291 |
| 96 | 3 | 1127 | 687 | gl\|1196964 | unknown protein [Plasmid Ti] | 50 | 38 | 441 |
| 89 | 1 | 981 | 4 | gl\|57633 | neuronal myosin heavy chain [*Rattus rattus*] | 48 | 22 | 978 |
| 113 | 1 | 657 | 199 | gl\|147899 | extragenic suppressor [*Escherichia coli*] | 48 | 25 | 459 |
| 118 | 1 | 654 | 145 | pir\|S27564\|S275 | polysaccharide translocation-related protein - *Escherichia coli* | 48 | 25 | 510 |
| 58 | 2 | 2101 | 4245 | gl\|1235662 | RfbC [*Hyxococcus xanthus*] | 47 | 35 | 2145 |
| 87 | 1 | 595 | 134 | gl\|1235662 | RfbC [*Hyxococcus xanthus*] | 42 | 20 | 462 |

TABLE 1-continued (PAI IV)
Putative coding regions of novel *E. coli* PAI IV proteins similar to known proteins

| Contig ID | ORF ID | Start (nt) | Stop (nt) | match acession | match gene name | % sim | % ident | length (nt) |
|---|---|---|---|---|---|---|---|---|
| 85 | 2 | 1018 | 515 | bba\|117606 | glycine-rich protein, atGRP (clone atGRP-1) [*Arabidopsis thaliana*, C24, Peptide Partial, 210 nn] [*Arabidopsis thaliana*] | 36 | 36 | 504 |
| 85 | 3 | 1779 | 973 | bba\|157676 | silk fibroin heavy chain (C-terminal) [*Bombyx mori*-silkworm, Peptide Partial, 633 nn] [*Bombyx mori*] | 34 | 29 | 807 |

TABLE 2

(PAI IV)
Putative coding regions of novel *E. coli*
PAI IV proteins not similar to known proteins

| Contig ID | ORF ID | Start (nt) | Stop (nt) |
|---|---|---|---|
| 58 | 1 | 1176 | 2120 |
| 61 | 2 | 54 | 560 |
| 63 | 4 | 1875 | 2639 |
| 64 | 4 | 3911 | 3627 |
| 65 | 6 | 3009 | 3239 |
| 65 | 12 | 6027 | 6683 |
| 66 | 2 | 1289 | 978 |
| 70 | 2 | 1418 | 861 |
| 70 | 3 | 1886 | 1476 |
| 70 | 4 | 2124 | 1900 |
| 70 | 5 | 2795 | 2220 |
| 70 | 7 | 3645 | 3259 |
| 70 | 8 | 4078 | 3680 |
| 70 | 9 | 4220 | 4513 |
| 70 | 11 | 4950 | 4498 |
| 70 | 12 | 4594 | 4866 |
| 70 | 15 | 6805 | 7449 |
| 70 | 16 | 9520 | 10806 |
| 73 | 7 | 3247 | 3666 |
| 74 | 3 | 720 | 1301 |
| 75 | 1 | 1 | 165 |
| 79 | 1 | 719 | 354 |
| 80 | 6 | 2108 | 2575 |
| 80 | 7 | 2831 | 2469 |
| 80 | 10 | 3223 | 3387 |
| 80 | 11 | 3541 | 3362 |
| 82 | 8 | 3313 | 4260 |
| 82 | 11 | 4340 | 5218 |
| 82 | 13 | 6090 | 5614 |
| 84 | 4 | 3487 | 3281 |
| 85 | 4 | 1485 | 2285 |
| 85 | 6 | 8373 | 9320 |
| 104 | 1 | 358 | 2 |
| 112 | 1 | 677 | 105 |
| 142 | 1 | 3 | 143 |
| 142 | 2 | 119 | 328 |

TABLE 3

(PAI V)
Putative coding regions of novel *E. coli* PAI V proteins similar to known proteins

| Contig ID | ORF ID | Start (nt) | Stop (nt) | match acession | match gene name | % sim | % ident | length (nt) |
|---|---|---|---|---|---|---|---|---|
| 14 | 3 | 2826 | 3686 | gl\|1655838 | ORFB, putative transposase [*Yersinia pestis*] | 100 | 100 | 861 |
| 14 | 2 | 1837 | 2907 | gl\|1655837 | ORFA, putative transposase [*Yersinia pestis*] | 99 | 99 | 1071 |
| 3 | 9 | 7927 | 7595 | gl\|1657499 | putative transposase for insertion sequence IS3 [*Escherichia coli*] | 89 | 85 | 333 |
| 20 | 6 | 3462 | 4304 | gl\|1208992 | unknown [*Escherichia coli*] | 87 | 73 | 843 |
| 6 | 6 | 3541 | 3263 | pir\|S43483\|S434 | Orf104 homolog - *Escherichia coli* | 81 | 62 | 279 |
| 20 | 3 | 1616 | 2332 | gl\|1033129 | ORF_o233 [*Escherichia coli*] | 80 | 61 | 717 |
| 9 | 1 | 1 | 681 | gl\|537112 | ORF_o396 [*Escherichia coli*] | 77 | 55 | 681 |
| 15 | 3 | 1899 | 1672 | pir\|S43483\|S434 | Orf104 homolog - *Escherichia coli* | 75 | 55 | 228 |
| 20 | 9 | 4302 | 4880 | gl\|1552816 | similar to *E. coli* ORF_o152 [*Escherichia coli*] | 74 | 60 | 579 |
| 14 | 13 | 12972 | 15359 | gl\|1772623 | Hacλ [*Erwinia chrysanthemi*] | 70 | 60 | 2388 |
| 5 | 3 | 4112 | 1570 | gl\|1001737 | regulatory components of sensory transduction system [*Synachocystis sp.*] | 68 | 45 | 459 |
| 3 | 1 | 2572 | 1373 | gl\|849022 | Lactate oxidase [*Aereococcus viridans*] | 66 | 46 | 1200 |
| 3 | 8 | 6869 | 6498 | gl\|581535 | ORF140 gene product [*Rhizobium sp.*] | 66 | 45 | 172 |
| 6 | 5 | 3265 | 2951 | gl\|642184 | F19C6.1 [*Caenorhabditis elegans*] | 66 | 44 | 315 |
| 14 | 12 | 11775 | 12974 | gl\|1772622 | HacB [*Erwinia chrysanthemi*] | 66 | 50 | 1200 |
| 20 | 1 | 545 | 1450 | gl\|1033127 | ORF_o289 [*Escherichia coli*] | 66 | 45 | 906 |
| 57 | 1 | 696 | 124 | gl\|1772622 | HacB [*Erwinia chrysanthemi*] | 66 | 47 | 573 |
| 3 | 3 | 3320 | 3700 | gl\|431950 | similar to a *B. subtilis* gene (GB: BACHENEHY_5) [*Clostridium pasteurianum*] | 65 | 34 | 381 |
| 5 | 7 | 4565 | 4239 | sp\|P39213\|YI91_ | INSERTION ELEMENT I5911 HYPOTHETICAL 12.7 KD PROTEIN. | 65 | 38 | 327 |

TABLE 3-continued (PAI V)
Putative coding regions of novel *E. coli* PAI V proteins similar to known proteins

| Contig ID | ORF ID | Start (nt) | Stop (nt) | match acession | match gene name | % sim | % ident | length (nt) |
|---|---|---|---|---|---|---|---|---|
| 22 | 2 | 1651 | 557 | gl\|290430 | adhesin [*Escherichia coli*] | 64 | 48 | 1095 |
| 5 | 4 | 1455 | 1841 | gl\|1575577 | DNA-binding response regulator [*Thermotoga maritima*] | 61 | 47 | 387 |
| 14 | 11 | 11161 | 11937 | gl\|1772622 | HacB [*Erwinia chrysanthemi*] | 60 | 39 | 777 |
| 14 | 1 | 930 | 1700 | gl\|1657478 | similar to *E. coli* ORF_o208 [*Escherichia coli*] | 58 | 47 | 771 |
| 5 | 6 | 3834 | 3391 | gl\|155032 | ORF B [Plasmid pEa34] | 56 | 36 | 444 |
| 3 | 5 | 6500 | 5982 | gl\|1633572 | Herpesvirus salmiri ORF73 homolog [Kaposi's sarcoma-associated herpes-like virus] | 54 | 25 | 519 |
| 14 | 7 | 8429 | 8809 | gl\|1196729 | unknown protein [Bacteriophage P4] | 54 | 41 | 381 |
| 14 | 14 | 15191 | 21793 | gl\|144048 | filamentous hemagglutinin [*Bortadella pertussis*] | 52 | 37 | 6603 |
| 14 | 16 | 21427 | 22671 | bba\|117613 | glycine-rich protein, atGRP (clone atGRP-4) [*Arabidopsis thaliana*, C24, Peptide Partial 112, nn] [*Arabidopsis thaliana*] | 52 | 39 | 1245 |
| 5 | 2 | 1004 | 381 | gl\|48518 | HydC [*Holinella succinogenea*] | 51 | 34 | 624 |
| 5 | 5 | 1941 | 3311 | gl\|143331 | alkaline phosphatase regulatory protein [*Bacillus subtilis*] | 51 | 21 | 1171 |
| 14 | 4 | 3968 | 5431 | gl\|1033120 | ORF_o469 [*Escherichia coli*] | 51 | 29 | 1464 |
| 32 | 1 | 481 | 227 | gl\|1673731 | (AE000010) Hycoplasma pneumoniae, fructose-permease IIBC component; similar to Swiss-Prot Accession Number P20966, from *E. coli* [*Hycoplasma pneumoniae*] | 50 | 41 | 255 |
| 20 | 17 | 7039 | 7284 | gl\|1123054 | coded for by *C. elegans* cDNA CEESN53P, similar to protein kinases including CDC15 in yeast [*Caenorhabditis elegans*] | 48 | 28 | 246 |

TABLE 4

(PAI V)
Putative coding regions of novel *E. coli* PAI V proteins not similar to known proteins

| Contig ID | ORF ID | Start (nt) | Stop (nt) |
|---|---|---|---|
| 1 | 1 | 809 | 1165 |
| 3 | 2 | 3275 | 2640 |
| 3 | 6 | 6006 | 6425 |
| 3 | 7 | 5423 | 6833 |
| 4 | 1 | 3 | 455 |
| 5 | 1 | 501 | 4 |
| 6 | 1 | 2168 | 1749 |
| 6 | 2 | 2577 | 2114 |
| 6 | 3 | 2618 | 2331 |
| 6 | 4 | 3099 | 2626 |
| 14 | 5 | 7112 | 7699 |
| 14 | 6 | 7800 | 8507 |
| 14 | 8 | 9040 | 9624 |
| 14 | 10 | 10586 | 10846 |
| 14 | 15 | 21721 | 20921 |
| 15 | 1 | 575 | 826 |
| 15 | 2 | 850 | 1365 |
| 20 | 2 | 904 | 605 |
| 20 | 4 | 2330 | 3157 |
| 20 | 5 | 3139 | 3396 |
| 20 | 7 | 3812 | 3492 |
| 20 | 8 | 4373 | 3828 |
| 20 | 18 | 7282 | 7950 |
| 22 | 1 | 356 | 3 |
| 24 | 1 | 492 | 4 |

TABLE 5

(PAI IV)
Putative coding regions of novel *E. coli* PAI IV containing known *E. coli* sequences

| Contig ID | ORF ID | Start (nt) | Stop (nt) | match accession | match gene name | % sim | % ident | length (nt) |
|---|---|---|---|---|---|---|---|---|
| 59 | 1 | 968 | 54 | emb\|X61239\|ECPA | *E. coli* papABCDEFGHIJK genes for F13 P-pili proteins | 99 | 790 | 915 |
| 59 | 2 | 1551 | 805 | emb\|Y00529\|ECPA | *E. coli* papC gene involved in formation of pap pili | 99 | 518 | 747 |
| 59 | 3 | 1742 | 1494 | emb\|Y00529\|ECPA | *E. coli* papC gene involved in formation of pap pili | 99 | 182 | 249 |
| 61 | 4 | 1975 | 1220 | emb\|X61239\|ECPA | *E. coli* papABCDEFGHIJK genes for F13 P-pili proteins | 100 | 69 | 756 |
| 63 | 13 | 10097 | 10480 | gb\|AW000133\| | *Escherichia coli* from bases 263572 to 274477 (section 23 of 400) of the complete genome | 91 | 216 | 384 |
| 65 | 1 | 886 | 671 | gb\|006468\| | *Escherichia coli* O111:H- insertion sequence IS1203 12.7 kDa protein and putative transposase genes, complete cds | 93 | 264 | 216 |
| 65 | 5 | 3218 | 2868 | gb\|006468\| | *Escherichia coli* O111:H- insertion sequence IS1203 12.7 kDa protein and putative transposase genes, complete cds | 85 | 285 | 351 |
| 65 | 8 | 4064 | 3216 | gb\|006468\| | *Escherichia coli* O111:H- insertion sequence IS1203 12.7 kDa protein and putative transposase genes, complete cds | 86 | 145 | 849 |
| 65 | 9 | 4939 | 4337 | emb\|Y00976\|ECHN | *E. coli* hns gene for DNA-binding protein H-IIS (5'-region) | 96 | 53 | 603 |
| 65 | 10 | 4919 | 5266 | emb\|Y00976\|ECHN | *E. coli* hns gene for DNA-binding protein H-IIS (5'-region) | 98 | 310 | 348 |
| 65 | 11 | 5206 | 5781 | gb\|AE000133\| | *Escherichia coli* from bases 263572 to 274477 (section 23 of 400) of the complete genome | 89 | 431 | 576 |
| 68 | 1 | 1575 | 1315 | emb\|X61329\|ECPA | *E. coli* papABCDEFGHIJK genes for F13 P-pili proteins | 100 | 186 | 261 |
| 68 | 2 | 2468 | 1848 | emb\|X51704\|ECPA | *E. coli* papJ gene for PapJ protein | 99 | 621 | 621 |
| 68 | 3 | 2232 | 2594 | emb\|X61239\|ECPA | *E. coli* papABCDEFGHIJK genes for F13 P-pili proteins | 99 | 363 | 363 |
| 68 | 4 | 3212 | 2466 | emb\|X61239\|ECPA | *E. coli* papABCDEFGHIJK genes for F13 P-pili proteins | 100 | 747 | 747 |
| 69 | 1 | 300 | 4 | gb\|H14040\| | *E. coli* apt gene encoding adenine phosphoribosyl-transferase (APRT), complete cds | 98 | 225 | 297 |
| 69 | 2 | 383 | 117 | gb\|H14040\| | *E. coli* apt gene encoding adenine phosphoribosyl-transferase (APRT), complete cds | 95 | 162 | 267 |
| 70 | 1 | 832 | 149 | gb\|009857\| | *Escherichia coli* 4787 o115,v165:f165 fimbrial regulatory f16521, f16528 and f1652 λ genes, complete cds | 89 | 225 | 684 |
| 70 | 17 | 10799 | 11767 | gb\|AE000291\| | *Escherichia coli* Abrv, arfk, cobf, cob9, cobU, yl52_6, yl22_3, yl21_3 genes from bases 2060089 to 2072765 (section 181 of 400) of the complete genome | 95 | 553 | 969 |
| 70 | 18 | 11809 | 11045 | gb\|AE000291\| | *Escherichia coli* Abrv, arfk, cobf, cob9, cobU, yl52_6, yl22_3, yl21_3 genes from bases 2060089 to 2072765 (section 181 of 400) of the complete genome | 94 | 595 | 765 |
| 70 | 19 | 12022 | 15222 | dbj\|090838\|0908 | *E. coli* genomic DNA, Kohara elong 4348 (44.5–44.9 min.) | 89 | 2667 | 3201 |
| 70 | 20 | 15316 | 16836 | gb\|AE000292\| | *Escherichia coli* yeaλ, abmC, yeaC, abcB, yeaD, yeaE genes from bases 2072708 to 2083664 (section 182 of 400) of the complete genome | 96 | 1488 | 1521 |
| 70 | 21 | 16722 | 17711 | gb\|AE000292\| | *Escherichia coli* yeaλ, abmC, yeaC, abcB, yeaD, yeaE genes from bases 2072708 to 2083664 (section 182 of 400) of the complete genome | 96 | 82 | 990 |
| 70 | 22 | 17426 | 16776 | gb\|AE000292\| | *Escherichia coli* yeaλ, abmC, yeaC, abcB, yeaD, yeaE genes from bases 2072708 to 2083664 (section 182 of 400) of the complete genome | 96 | 63 | 651 |
| 72 | 1 | 12 | 1061 | gb\|H10133\| | *E. coli* (J96) hlyC, hlyA, hlyB and hlyD genes coding for chromosomal hemolysins C, λ, B and D | 99 | 1024 | 1050 |
| 72 | 2 | 947 | 1285 | gb\|H10133\| | *E. coli* (J96) hlyC, hlyA, hlyB and hlyD genes coding for chromosomal hemolysins C, λ, B and D | 96 | 261 | 339 |
| 73 | 6 | 4437 | 3205 | gb\|AE000379\| | *Escherichia coli* from bases 3102169 to 3112339 (section 269 of 400) of the complete genome | 95 | 392 | 1233 |

TABLE 5-continued

Putative coding regions of novel *E. coli* PAI IV containing known *E. coli* sequences (PAI IV)

| Contig ID | ORF ID | Start (nt) | Stop (nt) | match acession | match gene name | % sim | % ident | length (nt) |
|---|---|---|---|---|---|---|---|---|
| 73 | 8 | 6177 | 4555 | gb\|U28377\| | *Escherichia coli* K-12 genome; approximately 65 to 68 minutes | 90 | 1133 | 1623 |
| 73 | 9 | 6835 | 6128 | gb\|AE000380\| | *Escherichia coli*, glcB, glcO, glcD genes from bases 3112500 to 3126185 (section 270 of 400) of the complete genome | 93 | 703 | 708 |
| 75 | 2 | 1553 | 1059 | gb\|AE000498\| | *Escherichia coli* from bases 4493507 to 4503769 (section 388 of 400 of the complete genome | 90 | 385 | 495 |
| 75 | 3 | 2579 | 1566 | gb\|AE000498\| | *Escherichia coli* from bases 4493507 to 4503769 (section 388 of 400 of the complete genome | 92 | 464 | 1014 |
| 75 | 4 | 1297 | 2743 | gb\|007174\| | *Escherichia coli* 09:H10:K99 heat resistant agglutinin 1 gene, complete cds | 81 | 283 | 555 |
| 76 | 1 | 698 | 3 | gb\|M10133\| | *E. coli* (J96) hylC, hylA, hylB and hylD genes coding for chromosomal hemolysine C, λ, B and D | 99 | 693 | 696 |
| 78 | 1 | 382 | 59 | gb\|AE000360\| | *Escherichia coli* from bases 2885166 to 297277 (section 250 of 400 of the complete genome | 99 | 315 | 324 |
| 79 | 2 | 2620 | 1529 | gb\|H10133\| | *E. coli* (J96) hylC, hylA, hylB and hylD genes coding for chromosomal hemolysine C, λ, B and D | 99 | 1084 | 1092 |
| 79 | 3 | 2925 | 2587 | gb\|H10133\| | *E. coli* (J96) hylC, hylA, hylB and hylD genes coding for chromosomal hemolysine C, λ, B and D | 97 | 322 | 339 |
| 79 | 4 | 3576 | 2923 | gb\|H10133\| | *E. coli* (J96) hylC, hylA, hylB and hylD genes coding for chromosomal hemolysine C, λ, B and D | 99 | 654 | 654 |
| 80 | 1 | 376 | 83 | gb\|005251\| | *Escherichia coli* polysialic acid gene cluster region J, promoter region | 93 | 210 | 294 |
| 80 | 2 | 638 | 210 | gb\|AE000379\| | *Escherichia coli* from bases 3102169 to 3112339 (section 269 of 400 of the complete genome | 95 | 347 | 429 |
| 80 | 3 | 1246 | 710 | gb\|AE000379\| | *Escherichia coli* from bases 3102169 to 3112339 (section 269 of 400 of the complete genome | 96 | 388 | 537 |
| 80 | 4 | 1796 | 1182 | gb\|AE000379\| | *Escherichia coli* from bases 3102169 to 3112339 (section 269 of 400 of the complete genome | 94 | 397 | 615 |
| 82 | 1 | 1 | 567 | amb\|X74567\|ECKP | *E. coli* K5 antigen gene cluster region 1 kpaE, kpaD, kpaU, kpaC and kpaS genes | 87 | 551 | 567 |
| 82 | 2 | 549 | 1157 | amb\|X74567\|ECKP | *E. coli* K5 antigen gene cluster region 1 kpaE, kpaD, kpaU, kpaC and kpaS genes | 88 | 554 | 609 |
| 82 | 3 | 1500 | 1180 | gb\|AE000292\| | *Escherichia coli* yeaA, abmC, yeaC, abcB, yeaD, yeaE genes from bases 2072708 to 2083664 (section 182 of 400) of the complete genome | 90 | 62 | 321 |
| 82 | 4 | 2163 | 1519 | gb\|AE000292\| | *Escherichia coli* yeaA, abmC, yeaC, abcB, yeaD, yeaE genes from bases 2072708 to 2083664 (section 182 of 400) of the complete genome | 89 | 143 | 645 |
| 82 | 5 | 2594 | 2139 | gb\|AE000292\| | *Escherichia coli* yeaA, abmC, yeaC, abcB, yeaD, yeaE genes from bases 2072708 to 2083664 (section 182 of 400) of the complete genome | 97 | 456 | 456 |
| 82 | 6 | 3000 | 2605 | gb\|AE000292\| | *Escherichia coli* yeaA, abmC, yeaC, abcB, yeaD, yeaE genes from bases 2072708 to 2083664 (section 182 of 400) of the complete genome | 98 | 396 | 396 |
| 82 | 7 | 3463 | 3047 | gb\|AE000292\| | *Escherichia coli* yeaA, abmC, yeaC, abcB, yeaD, yeaE genes from bases 2072708 to 2083664 (section 182 of 400) of the complete genome | 96 | 283 | 417 |
| 82 | 9 | 3831 | 3337 | gb\|AE000292\| | *Escherichia coli* yeaA, abmC, yeaC, abcB, yeaD, yeaE genes from bases 2072708 to 2083664 (section 182 of 400) of the complete genome | 96 | 453 | 495 |
| 83 | 1 | 3 | 311 | gb\|AE000151\| | *Escherichia coli* ybaE, cof, mdlA, mdlB, ginK, amtB, taaB, ffa genes from bases 464774 to 475868 (section 41 of 400) of the complete genome | 99 | 207 | 309 |
| 86 | 1 | 529 | 2 | gb\|AE00379\| | *Escherichia coli* from bases 3102169 to 3112339 (section 269 of 400) of the complete genome | 93 | 398 | 528 |

TABLE 5-continued

Putative coding regions of novel E. coli PAI IV containing known E. coli sequences
(PAI IV)

| Contig ID | ORF ID | Start (nt) | Stop (nt) | match acession | match gene name | % sim | % ident | length (nt) |
|---|---|---|---|---|---|---|---|---|
| 93 | 1 | 440 | 3 | gb|M10133| | E. coli (396) klyC, hlyA, hlyB and hlyD genes coding for chromosomal hemolysine C, λ, B and D | 95 | 351 | 438 |
| 94 | 1 | 368 | 72 | amb|X14180|ECOL | Escherichia coli glutamine permease glnHPQ operan | 100 | 229 | 297 |
| 99 | 1 | 161 | 586 | gb|AE000379| | Escherichia coli from bases 3102169 to 3112339 (section 269 of 400) of the complete genome | 98 | 426 | 426 |
| 99 | 2 | 643 | 476 | gb|AE000379| | Escherichia coli from bases 3102169 to 3112339 (section 269 of 400) of the complete genome | 99 | 168 | 168 |
| 99 | 3 | 532 | 1092 | gb|AE000379| | Escherichia coli from bases 3102169 to 3112339 (section 269 of 400) of the complete genome | 95 | 537 | 561 |
| 99 | 4 | 1094 | 1396 | gb|AE000379| | Escherichia coli from bases 3102169 to 3112339 (section 269 of 400) of the complete genome | 94 | 274 | 303 |
| 102 | 1 | 527 | 3 | amb|Y00529|ECPA | E. coli papC gene involved in formation of pap pili | 100 | 427 | 525 |
| 102 | 2 | 762 | 373 | amb|Y00529|ECPA | E. coli papC gene involved in formation of pap pili | 99 | 333 | 390 |
| 105 | 1 | 377 | 3 | gb|AE000480| | Escherichia coli from bases 4277211 to 4288813 (section 370 of 400) of the complete genome | 100 | 343 | 375 |
| 107 | 1 | 2 | 397 | gb|H10133| | E. coli (96) hlyC, hlyλ, hlyB and hlyD genes coding for chromosomal hemolysine C, λ, B and D | 99 | 390 | 396 |
| 107 | 2 | 406 | 966 | gb|H10133| | E. coli (96) hlyC, hlyλ, hlyB and hlyD genes coding for chromosomal hemolysine C, λ, B and D | 99 | 549 | 561 |
| 110 | 1 | 148 | 2 | amb|X56175|ECSE | Escherichia coli sacD and sacF genes for membrane proteins involved in protein export | 99 | 143 | 147 |
| 110 | 2 | 312 | 40 | gb|H63939| | E. coli tRNA-guanine-transglycosylase (tgt) gene, complete cds | 100 | 125 | 273 |
| 115 | 1 | 501 | 325 | gb|AE000459| | Escherichia coli from bases 3102169 to 3112339 (section 269 of 400) of the complete genome | 98 | 177 | 177 |
| 117 | 1 | 3 | 302 | gb|AE000506| | Escherichia coli from bases 4584059 to 4024654 (section 196 of 400) of the complete genome | 100 | 263 | 300 |
| 121 | 1 | 2 | 250 | gb|H16202| | E. coli papil gene encoding a pilin-like protein | 98 | 148 | 249 |
| 123 | 1 | 361 | 2 | gb|AE000379| | Escherichia coli from bases 3102169 to 3112339 (section 269 of 400) of the complete genome | 99 | 113 | 360 |
| 127 | 1 | 2 | 229 | gb|AE000233| | Escherichia coli , racC, ydaD, alaB, trkG genes from bases 1415432 to 1425731 (section 123 of 400) of the complete genome | 100 | 200 | 228 |
| 127 | 2 | 227 | 382 | gb|AE000233| | Escherichia coli , racC, ydaD, alaB, trkG genes from bases 1415432 to 1425731 (section 123 of 400) of the complete genome | 97 | 113 | 156 |
| 130 | 1 | 337 | 2 | amb|X60200|ECTM | E. coli and transposase | 99 | 335 | 336 |
| 131 | 1 | 510 | 79 | gb|M30198| | E. coli racQ gene complete cds, and pldλ gene, 3′ and | 98 | 304 | 432 |
| 131 | 2 | 743 | 270 | gb|M30198| | E. coli racQ gene complete cds, and pldλ gene, 3′ and | 99 | 314 | 474 |
| 133 | 1 | 1 | 258 | gb|AE000115| | Escherichia coli , yabF, kefC, folλ, apaH, apaG, ksgλ, pdxλ, surA, imp genes from bases 47163 to 57264 (section 5 of 400) of the complete genome | 98 | 237 | 258 |
| 133 | 2 | 192 | 350 | gb|AE000115| | Escherichia coli , yabF, kefC, folλ, apaH, apaG, ksgλ, pdxλ, surA, imp genes from bases 47163 to 57264 (section 5 of 400) of the complete genome | 99 | 115 | 159 |
| 135 | 1 | 103 | 327 | amb|X02143|ECPL | Escherichia coli K-12 pldλ gene for DR-phospholipase A | 97 | 178 | 225 |
| 135 | 2 | 152 | 409 | amb|X02143|ECPL | Escherichia coli K-12 pldλ gene for DR-phospholipase A | 98 | 157 | 258 |
| 136 | 1 | 122 | 532 | gb|AE000459| | Escherichia coli from bases 4013123 to 4024654 (section 349 of 400) of the complete genome | 97 | 237 | 411 |

TABLE 5-continued

Putative coding regions of novel *E. coli* PAI IV containing known *E. coli* sequences
(PAI IV)

| Contig ID | ORF ID | Start (nt) | Stop (nt) | match acession | match gene name | % sim | % ident | length (nt) |
|---|---|---|---|---|---|---|---|---|
| 140 | 1 | 576 | 244 | gb|AE000291| | *Escherichia coli* asnV, arkK, cobT, cobS, cobU, y152_6, y122_3, y121_3 genes from bases 2060089 to 2072765 (section 181 of 400) of the complete genome | 89 | 329 | 333 |
| 141 | 1 | 445 | 2 | gb|AE000291| | *Escherichia coli* asnV, arkK, cobT, cobS, cobU, y152_6, y122_3, y121_3 genes from bases 2060089 to 2072765 (section 181 of 400) of the complete genome | 77 | 432 | 444 |

TABLE 6

Putative coding regions of novel *E. coli* PAI V containing known *E. coli* sequences (PAI V)

| Contig ID | ORF ID | Start (nt) | Stop (nt) | match accession | match gene name | percent ident | HSP nt length | ORF nt length |
|---|---|---|---|---|---|---|---|---|
| 3 | 4 | 6150 | 4855 | gb|AE000292| | *Escherichia coli* yeaλ, abmC, yeaC, abcB, yeaD, yaaE genes from bases 2072708 to 2083664 (section 182 of 40) of the complete genome | 91 | 129 | 1296 |
| 3 | 10 | 8214 | 7723 | emb|X02311|ECTS | *E. coli* insertion sequence IS3 | 76 | 274 | 492 |
| 3 | 11 | 7867 | 8319 | emb|X02311|ECTS | *E. coli* DNA for insertion sequence IS3 | 80 | 378 | 453 |
| 3 | 12 | 8462 | 8157 | emb|X02311|ECTS | *E. coli* DNA for insertion sequence IS3 | 90 | 267 | 306 |
| 3 | 13 | 8487 | 8663 | gb|L19084| | *Escherichia coli* RhsD genetic element; core protein (rhsD) gene, complete cds; complete ORF-D2; completee ORF-D3 | 96 | 112 | 177 |
| 4 | 2 | 1441 | 815 | gb|AE000498| | *Escherichia coli* from bases 4493507 to 4503769 (section 388 of 400) of the complete genome | 91 | 577 | 627 |
| 4 | 3 | 923 | 1372 | gb|AE000498| | *Escherichia coli* from bases 4493507 to 4503769 (section 388 of 400) of the complete genome | 92 | 448 | 450 |
| 4 | 4 | 2343 | 1324 | gb|AE000498| | *Escherichia coli* from bases 4493507 to 4503769 (section 388 of 400) of the complete genome | 92 | 244 | 1020 |
| 7 | 1 | 3 | 743 | amb|X61239|ECPA | *E. coli* papaABCDEFGHIJK genes for F13 P-pili proteins | 100 | 741 | 743 |
| 7 | 2 | 977 | 615 | amb|X61239|ECPA | *E. coli* papaABCDEFGHIJK genes for F13 P-pili proteins | 99 | 363 | 363 |
| 7 | 3 | 741 | 1214 | amb|X51704|ECPA | *E. coli* papJ gene for PapJ protein | 98 | 459 | 474 |
| 8 | 1 | 438 | 4 | amb|X60200|ECTN | *E. coli* transposon Tn1000 (gamma delta) tnkR and tnpλ genes for resolvase and transposase | 99 | 435 | 435 |
| 10 | 1 | 1932 | 2426 | amb|X61238|ECPR | *E. coli* prsEFG genes for F13 pili tip proteins | 97 | 462 | 495 |
| 11 | 1 | 903 | 1550 | gb|H10133| | *E. coli* (196) hlyC, hlyλ, hlyB and hlyD genes coding for chromosomal hemolysine C, λ, B and D | 99 | 452 | 648 |
| 12 | 1 | 2559 | 1531 | gb|U82598| | *Escherichia coli* genomic sequence of minutes 9 to 12 | 100 | 1029 | 1029 |
| 12 | 2 | 1594 | 1860 | amb|X13668|ECIS | *E. coli* insertion element 5 (IS5) DNA | 100 | 267 | 267 |
| 12 | 3 | 1858 | 2235 | gb|095365| | *Escherichia coli* transposon IS5, transposase (is58) gene, complete cds | 99 | 354 | 378 |
| 13 | 1 | 93 | 1424 | amb|X61239|ECPA | *E. coli* papaABCDEFGHIJK genes for F13 P-puli proteins | 99 | 885 | 1332 |
| 14 | 9 | 9832 | 10515 | gb|U09857| | *Escherichia coli* 4787 o115,v165,f165 fimbrial regulatory f16528 and f1652 λ genes, complete cds | 92 | 225 | 684 |
| 16 | 1 | 1 | 375 | gb|U07174| | *Escherichia coli* 09:H10:K99 heat resistant agglutinin 1 gene, complete cds | 94 | 320 | 375 |
| 16 | 2 | 263 | 616 | gb|U07174| | *Escherichia coli* 09:H10:K99 heat resistant agglutinin 1 gene, complete cds | 98 | 283 | 354 |
| 17 | 1 | 282 | 4 | amb|Y00529|ECPA | *E. coli* papC gene involved in formation of pap pili | 98 | 240 | 279 |
| 17 | 2 | 410 | 174 | amb|Y00529|ECPA | *E. coli* papC gene involved in formation of pap pili | 100 | 168 | 237 |
| 19 | 1 | 1 | 369 | gb|AE000418| | *Escherichia coli* from bases 3550279 to 3561054 (section 308 of 400) of the complete genome | 99 | 347 | 369 |
| 20 | 10 | 5401 | 4829 | gb|AE000292| | *Escherichia coli* yeaλ, abmC, yeaC, abcB, yeaD, yeaE genes from bases 2072708 to 2083664 (section 182 of 400) of the complete genome | 96 | 468 | 573 |
| 20 | 11 | 4874 | 5371 | gb|AE000292| | *Escherichia coli* yeaλ, abmC, yeaC, abcB, yeaD, yeaE genes from bases 2072708 to 2083664 (section 182 of 400) of the complete genome | 96 | 453 | 498 |
| 20 | 12 | 5245 | 5679 | gb|AE000292| | *Escherichia coli* yeaλ, abmC, yeaC, abcB, yeaD, yeaE genes from bases 2072708 to 2083664 (section 182 of 400) of the complete genome | 89 | 235 | 435 |
| 20 | 13 | 5732 | 6139 | gb|AE000292| | *Escherichia coli* yeaλ, abmC, yeaC, abcB, yeaD, yeaE genes from bases 2072708 to 2083664 (section 182 of 400) of the complete genome | 93 | 329 | 408 |
| 20 | 14 | 6316 | 5822 | gb|AE000292| | *Escherichia coli* yeaλ, abmC, yeaC, abcB, yeaD, yeaE genes from bases 2072708 to 2083664 (section 182 of 400) of the complete genome | 95 | 239 | 495 |
| 20 | 15 | 6048 | 6590 | gb|AE000292| | *Escherichia coli* yeaλ, abmC, yeaC, abcB, yeaD, yeaE genes from bases 2072708 to 2083664 (section 182 of 400) of the complete genome | 87 | 406 | 543 |

TABLE 6-continued

Putative coding regions of novel E. coli PAI V containing known E. coli sequences
(PAI V)

| Contig ID | ORF ID | Start (nt) | Stop (nt) | match accession | match gene name | percent ident | HSP nt length | ORF nt length |
|---|---|---|---|---|---|---|---|---|
| 20 | 16 | 6569 | 7075 | gb|AE000292| | Escherichia coli yeaλ, abmC, yeaC, abcB, yeaD, yeaE genes from bases 2072708 to 2083664 (section 182 of 400) of the complete genome | 87 | 136 | 507 |
| 20 | 19 | 8686 | 9915 | gb|M67452| | Escherichia coli lysine decarboxylase (cadB, and cadC, complete cds, and cadA, 5' and) genes | 98 | 1205 | 1230 |
| 20 | 20 | 10604 | 11938 | gb|U14003| | Escherichia coli K-12 chromomosal region from 92.8 to 00.1 minutes | 98 | 1308 | 1335 |
| 20 | 21 | 12940 | 12368 | gb|H76431| | E. coli cadA, gene, 5' cds and cadB and cadC genes, complete cds | 100 | 363 | 429 |
| 21 | 1 | 369 | 4 | amb|X03391|ECPA | E. coli major pilu subunit genes papI, papB, papA and papH 5'-region | 98 | 201 | 366 |
| 23 | 1 | 1 | 879 | gb|U14003| | Escherichia coli K-12 chromomosal region from 92.8 to 00.1 minutes | 98 | 879 | 879 |
| 23 | 2 | 900 | 16 | gb|U14003| | Escherichia coli K-12 chromomosal region from 92.8 to 00.1 minutes | 100 | 885 | 885 |
| 23 | 3 | 953 | 1186 | amb|X77707|ECCY | E. coli ORF112, DIPZ and ORF191 genes | 99 | 225 | 234 |
| 23 | 4 | 1223 | 2677 | amb|X77707|ECCY | E. coli ORF112, DIPZ and ORF191 genes | 97 | 1454 | 1455 |
| 25 | 1 | 536 | 171 | amb|X60200|ECTN | E. coli transposon Tn1000 (gamma delta) tnpR and tnpA genes for resolvase and transposase | 100 | 164 | 366 |
| 25 | 2 | 1128 | 562 | amb|X60200|ECTN | E. coli transposon Tn1000 (gamma delta) tnpR and tnpA genes for resolvase and transposase | 99 | 459 | 567 |
| 27 | 1 | 708 | 436 | amb|X61239|ECPA | E. coli papaABCDEFGHIJK genes for F13 P-pili proteins | 100 | 252 | 273 |
| 28 | 1 | 309 | 4 | amb|X77707|ECPA | E. coli ORF112, DIPZ and ORF191 genes | 98 | 278 | 306 |
| 28 | 2 | 431 | 213 | amb|X77707|ECPA | E. coli ORF112, DIPZ and ORF191 genes | 96 | 150 | 219 |
| 30 | 1 | 399 | 4 | gb|H26893| | E. coli amidophosphoribosyltransferase (purF) gene, complete cds | 98 | 295 | 396 |
| 31 | 1 | 706 | 170 | amb|X56780|ECRR | E. coli terminator sequence of RNA G operon gene | 99 | 511 | 537 |
| 37 | 1 | 2 | 400 | gb|H63703| | E. coli pyruvate kinase type II (pykA) gene, complete cds | 98 | 399 | 399 |
| 38 | 1 | 463 | 2 | amb|X13463|ECGU | Escherichia coli gutH gene and gutR gene for activator and repressor proteins | 99 | 363 | 462 |
| 42 | 1 | 413 | 3 | gb|H64367| | Escherichia coli DNA recombinase (racG) gene, complete cds, apoU gene, 3' end, and gltS gene, 3' and | 97 | 316 | 411 |
| 42 | 2 | 115 | 591 | gb|H64367| | Escherichia coli DNA recombinase (racG) gene, complete cds, apoU gene, 3' end, and gltS gene, 3' and | 98 | 266 | 477 |
| 46 | 1 | 2 | 277 | amb|X77707|ECCY | E. coli ORF112, DIPZ and ORF151 genes | 98 | 187 | 276 |
| 48 | 1 | 1 | 171 | gb|AE000491| | Escherichia coli from bases 4413548 to 4424699 (section 381 of 400) of the complete genome | 98 | 162 | 171 |
| 48 | 2 | 105 | 464 | gb|AE000491| | Escherichia coli from bases 4413548 to 4424699 (section 381 of 400) of the complete genome | 98 | 144 | 360 |
| 49 | 1 | 2 | 172 | gb|000800| | Escherichia coli cloning vector Pk184, complete sequence, kanamycin phosphotransferase (kan) and (lacZalpha) genes, complete cds | 98 | 167 | 171 |
| 50 | 1 | 414 | 4 | gb|AE000341| | Escherichia coli , glyλ, hmpA, ginB, yfhA, yfhG genes from bases 2677406 to 2687636 (section 231 of 400) of the complete genome | 99 | 411 | 411 |
| 52 | 1 | 2 | 307 | amb|X60200|ECTH | E. coli transposon Tn1000 (gamma delta) tnpR and tnpA genes for resolvase and transposase | 100 | 284 | 306 |
| 53 | 1 | 280 | 41 | gb|H36536| | E. coli htrA gene, complete cds | 100 | 131 | 240 |
| 53 | 2 | 558 | 214 | gb|H36536| | E. coli htrA gene, complete cds | 99 | 315 | 345 |
| 54 | 1 | 9 | 263 | gb|AE000381| | Escherichia coli from bases 3125914 to 3136425 (section 271 of 400) of the complete genome | 94 | 111 | 255 |
| 55 | 1 | 1 | 675 | gb|AE000179| | Escherichia coli modA, modB, modC, ybhA, ybhE, yhhE, yhhD genes from bases 794199 to 805132 (section 69 of 400) of the complete genome | 98 | 332 | 675 |

What is claimed is:

1. An isolated polynucleotide comprising the nucleic acid sequence of ORF ID 4 of Contig ID 65, consisting of nucleotides 2889–1915 at SEQ ID NO:65.

2. The isolated polynucleotide of claim 1, wherein said polynucleotide further comprises a heterologous polynucleotide sequence.

3. The isolated polynucleotide of claim 2, wherein said heterologous polynucleotide sequence encodes a heterologous polypeptide.

4. A method for making a recombinant vector comprising inserting the isolated polynucleotide of claim 1, into a vector.

5. A nucleic acid sequence fully complementary to the entirety of the nucleotide sequence of claim 1.

6. A recombinant vector comprising the isolated polynucleotide of claim 1.

7. The recombinant vector of claim 6, wherein said polynucleotide is covalently linked to a heterologous regulatory sequence that controls expression of the polypeptide encoded by ORF ID 4 of Contig ID 65.

8. A recombinant host cell comprising the isolated polynucleotide of claim 1.

9. The recombinant host cell of claim 8, wherein said polynucleotide is covalently linked to heterologous regulatory sequence that controls expression of the polypeptide encoded by ORF ID 4 of Contig ID 65.

* * * * *

SEQUENCE LISTING

<160> NUMBER OF SEQ ID NOS: 142

<210> SEQ ID NO 1
<211> LENGTH: 1178
<212> TYPE: DNA
<213> ORGANISM: Escherichia coli
<220> FEATURE:
<221> NAME/KEY: misc_feature
<222> LOCATION: (2)..(2)
<223> OTHER INFORMATION: n equals a, t, g, or c
<221> NAME/KEY: misc_feature
<222> LOCATION: (5)..(5)
<223> OTHER INFORMATION: n equals a, t, g, or c
<221> NAME/KEY: misc_feature
<222> LOCATION: (18)..(18)
<223> OTHER INFORMATION: n equals a, t, g, or c

<400> SEQUENCE: 1

```
cntanattag gcctgctnaa tgtatttata tctaaaaaaa ttcgcatcca aaaggaatcc      60
aatctgtact gttttttctt gtgctgacat cttcttttcc ctggctggta tggcaagtga    120
cggagacaag agaaacgttt taagctcagt tatctccgcc atcactttcc acgaatgaca    180
agtaattttg cctatttaa aaccatgcaa aaggcagggt aaaaggagaa aattcgatcg    240
aatcgatcga caaaatcgat catacatgat gaagatttct tatcgaatcc ataaaaatag    300
tgacagctaa ccggcgttgc aggaacagtc agaaatgggc gtttgggaaa gagccatagc    360
atacgtcgtc gctgacatag aggaactgtg ctttgttgat aagatccttt atacggcaac    420
caatccactg gacaaaagat gaactacgta atcaccgggt tctcactgac gaaatacaga    480
agttaatgac acaactgtgc catgcacctt gtacaacagc ggtggaaagc tctcagaaca    540
atggaattgc agaaaggtgt taaaacgatg aaagccttca tacccaaatc gaatgtaaga    600
acggcagtaa agactgaatt gcgtaacctt gcagtagctc gagtattaca ctgcatagtg    660
tgcagggtta tctcccatcg agaaaatatc ggcgccagcg aataacgtca ccttagatgt    720
agcagttgcc aaatagtgac tcaagggcgg gcttaccgca tacactgaca cttagcggat    780
cgacagaata ttattagcag atcatcactg aacgctacgt aattatcgta ataaaggctt    840
tttctggcta ccaggaagac ctgacatggc tctgctctgg aaccaggccg caggaagcat    900
caatctggag tttatcagct actggaattc cggtgtattg gcagccctg ataatcacct    960
gacccacgaa gagcgctctg ctttgcagaa actctggggc ggtttggaga caggagatgt   1020
aacgattata ggacgttctg atgaagtcca tgattttacc tccgccttaa ttaactgttt   1080
tctttctgaa gagaaattg tctggtggca atcaggtggc attttcccgg atccttggcc   1140
cgctaatata tcccggctga actgacgatt aacgcgat                           1178
```

<210> SEQ ID NO 2
<211> LENGTH: 414
<212> TYPE: DNA
<213> ORGANISM: Escherichia coli

<400> SEQUENCE: 2

```
atcctattca ttttgccatg acgggcgaac tccagataaa ggttttgaaa gtaatgagaa      60
attattaatt catccatgtt actggcttgg tttgaatcta aatcgtaatg cacttgctcc     120
agaggaagca gaggagataa atgacgaata tgatattaat attatttcag ataattcagc     180
cattagaaat aaaacaatag gtcaaataac tactcatcta gatcagatac cgataggaaa     240
tgaaggtgcc actgaatttg aacaatggtg tttagacgca ctaagaatag tatttgcatc     300
```

| | |
|---|---|
| ccacctaaca gacatcaagt cccatccaaa tggtaacgca gttcagagac gagatattat | 360 |
| aggcaccaat ggtggcaaat ctgawttttg graacgagta ttggaggact ataa | 414 |

<210> SEQ ID NO 3
<211> LENGTH: 8752
<212> TYPE: DNA
<213> ORGANISM: Escherichia coli
<220> FEATURE:
<221> NAME/KEY: misc_feature
<222> LOCATION: (16)..(16)
<223> OTHER INFORMATION: n equals a, t, g, or c
<221> NAME/KEY: misc_feature
<222> LOCATION: (37)..(37)
<223> OTHER INFORMATION: n equals a, t, g, or c
<221> NAME/KEY: misc_feature
<222> LOCATION: (119)..(119)
<223> OTHER INFORMATION: n equals a, t, g, or c
<221> NAME/KEY: misc_feature
<222> LOCATION: (2309)..(2309)
<223> OTHER INFORMATION: n equals a, t, g, or c
<221> NAME/KEY: misc_feature
<222> LOCATION: (3498)..(3498)
<223> OTHER INFORMATION: n equals a, t, g, or c
<221> NAME/KEY: misc_feature
<222> LOCATION: (3645)..(3645)
<223> OTHER INFORMATION: n equals a, t, g, or c
<221> NAME/KEY: misc_feature
<222> LOCATION: (6614)..(6614)
<223> OTHER INFORMATION: n equals a, t, g, or c

<400> SEQUENCE: 3

| | |
|---|---|
| ttgggatctg gtacantcca cccagcggca ttatccngaa ggcaatattt ttaaggatta | 60 |
| ttcgtccaca aaatcagtac tggaaccagg ctcaaaaaag ctttaacgt gacctgctnc | 120 |
| catctacagt agatgtacaa cctgttaagt taattgaaaa tggtgttaat ccggttgttt | 180 |
| ctccaggggt agcaagggcc ttattcgata cagtgggtaa tgttactgta aaattaccat | 240 |
| cattccctgt ggtcacattg caggtctgag ctacaacttt gcctgtaaac gtaattgttc | 300 |
| cgtcataggc catagctgaa ccaacaaaca cagcagaaac aaatgtagcc aatgctataa | 360 |
| cttttatttt cataaaatga attcctgttt aattccggta ttgatcattt gttcagcaat | 420 |
| catccccaac aaaacaatca ttttcaaaat gttttaccg atcgataacc agcacatgat | 480 |
| agattgcacc tatcatgatt gctaaaacga tcgggaaaag cgatcaaaaa ccatatttat | 540 |
| tgtgttggta atgacaaaag atatgcttta ccctgaaatg agcgacctat tcatgaaaat | 600 |
| atgtaggtct gtatttgatt actatcattg ctatatttcc actatccaat ttatatttca | 660 |
| tgattaaaat atacctttt acactattat ttatttgttg cagcttgcct ggctttatct | 720 |
| tattccgact attttatggt agatacgaaa tacaattaat taaacttatt taagattttt | 780 |
| ataaatacca tattggagtt gaccgataga tacctactaa caagagcaat caccaccacc | 840 |
| ccatgaggtg tttaggaata caatcaataa acaacatcca tgcccggcga cgtacatacc | 900 |
| tgtttgctat gatatctgtt acgctacgct tgctaattta ctgaaactca gcatctgtcg | 960 |
| acggagattc gtccgggccc tgatacaaca agggcaagaa accacccga aatacagata | 1020 |
| ttcttataaa aatggatcat atttccatgt gcaagttcag ctggcatcgt ccagaatgcg | 1080 |
| tgtccaagaa atgaagcaaa cacggtatac aggcacagaa taatgctcac tggccgggtg | 1140 |
| aaaaagccra aaacaatcat taatgctcca acgatttcga caaggaccac tattgctgca | 1200 |
| gtaatcgccg gaaatataag cccaagagag gccatttttat cgatagtgcc agtgaatgat | 1260 |
| agcagcttgg gaacgccgga tatcatataa aggcatgcca gcatcagacg ggcaaggagc | 1320 |

```
aacaatgccg acgtgtaatt tcccatatta aaatacctga ttttatccac tatcaatgct    1380
cagtctcctt gtttctgata aagccctgag ccaaatcctt aagtgtacga gcaccactca    1440
gtaacattgc cgtcctcagc tccgtcttca ggtgctcaat gacactggca acgcccccga    1500
caccacctgc tgcgatgcca taaagaacag gacgtccgac cgcaacagcc gttgcccaa     1560 gagagatagc ccttacaaca tcaaccccc  tgcgaatacc gctgtcaaaa atgaccggaa    1620
ctttgtgccc gactcttgca gcaacttcct gcaactggct gatggcagaa ggaacaccat    1680
caatctggcg accaccatga ttagacacct ggatggcatc tgctcctgca tcaatggcga    1740
ccactgcatc ctcacctctg aggatgccct tgacaatgac tggcagcccg gtgatttttt    1800
ttacaaactc aatatcagcc ggggtcagct caactttttg gttaaaaaaa tcacctttgc    1860
caccgtaacg ggggtcatga ttaccgaacg tcgctcctgc agggaaaggc gagctcatgc    1920
tgagaaaagc atcacttgtc ccgggaccaa gcgcatccgc tgtgataata atggctgaat    1980
agcctgccgc ttttgcacgc tccagtaaac ttcgggtcac accagcatcc gcgttaaaat    2040
acagctggaa ccatttaggt cctttactgg cttttgcaat atcctccaga gagcggttgg    2100
atgcccctga tgattcataa agtgcccgg  ccttttctgc acccgctgca gcaatcacct    2160 cccttccgg  atggacgaac atatgcgcgc ccataggtgc tatcagcagg ggatgttcca    2220
gatgatggcc caaaggtca  gtccggatat caatgctgtg ggcagcaact ccactgagtc    2280
ggtgaggtaa caaggataa  tcactgaant gcctgcggtt ctcatgatac gtccactcat    2340
ctccagcacc atgagcaata tatgcatacg cagcttccgt catcacatct tttgctgaag    2400
tctycagtct gtccagactg atgatatgaa gagatttgct ggtcgatgta tcagcatgtc    2460
cagacgtttt actgatgata tgtgccgttg aagatgagat attttttggca agggccggcg    2520 cagttgacag cctgcggcag atattcctaa acggcattc  tgaataaaat tacgtcggga    2580
aagaggcata ataagctcca tatattataa ataagccagg tctccctggc ttataatgat    2640
catgccacgc cctgaagcgg gttggtgttg aaggtataaa ggaaaatttt ccattcacca    2700 ttaatttttac tgaggacaaa aacttcacgg ttcaggtcaa taatggttttt ctgctctttta   2760 aagttcgtta caacagaacc cacatggtgg tgagtgcgga caaccgcggt atctccgttg    2820
atccagatag agtcaaacgc aaaatcggtc tcaaactttt cacgcttgaa cagatcatcg    2880
tactgcccct ggcgttttttc tgtattgtca gccgtcaact tatcattcca ctgggaataa    2940
ctttcatcag caaacaggcc caggatggtt tttgtatccc cggcattcag tgcgttctga    3000
tacttgatta tcgtgtcata cacgttcttc tgctcagtag caatcttact gtctgtggag    3060
tatttgaatg taccgccgga ttgttcaggt gagctttcct tctgtgctgt cgacgatgag    3120
gcagccagag cattagagcc gaaaagaagg gatgatgcca tgactgctgt tgctataaaa    3180
tgtttcatat attctccatc agttcttctg gggatctgtg ggcagcatat agcgctcata    3240
ctatgctgct gtttcaatat tagcggcaga cgtcagcctt accgcactac ttattggata    3300
agaatatcaa aagtgaccgt gaagtcaatt ttatcacaac acagaaggcc actatttatg    3360
cccagaaaat atgaatcgtc ctcatcatgc acgaaagact cgtagttgca gcccggaaaa    3420
aactgccagg acacgacagc agatagcccg ggcagcactt gaggagttct ctgcacaagg    3480
gttcgctcgc gccacatnca gcaatatcag caagcgcgca ggagtagcta aaggcacggt    3540
atataactac ttcccaacaa aggaattatt gtttgaagcg gttctgaagg agttcattgc    3600
taccgtccgt actgaactgg aatcttcccc ccgccgcaac ggggnaaacc gtaaaagcct    3660
atctgttgag agtgatgtta cctgccgtca ggaaaattga cgacgcatca acaggcagag    3720
```

-continued

```
ccagaatagc ccacctggtt atgacagaag ggagccggtt cccggtaatc gctcaggctt      3780
atttacggga aatacatcag ccactacagc aagccatgac ccaactgatt caggaagcag      3840
catcagccgg agagttaaaa gcagagcaac tgctctgckt cccctgttta ttgctggctc      3900
caaactggtt tggcatggtg tataacgaat tctgaacccg gcagcaccgg tcagtacagg      3960
cgatcttttt gaagccggaa ttggtgcttt tttccgatag acacataact gtcagtatta      4020
tgaccatgcc gtcaggagga ggtataccag tgatacgctg ccatgacccg gtaacgtctc      4080
ctggctgcct taaacctgaa agacctggcc ccaccacact gccggttacg catcaagatg      4140
cagcaaccct gcataaggc tgttttgtgc agagggctac cggaaagata taacgtcac      4200 agcccgtatg catcagataa aacagtgtat tttatctgtc agcagtcact ggagcggatt      4260
gtggggcgag attcaggtgc tgatactgta acgactctgc gccgctgctg cggtaaaagc      4320
ggctgccacc aggcacggtt atcagaggag gatgaccgtg tccgcccctg gtggtgatga      4380
actctccatc acaatcaata atgccgccgg gtggatgaag cagacaggga tggcaagtcc      4440
cactatcccg gataaaatgg gctctgggcg ctcagaagac ctgtgtgtca ggcaggggtg      4500
agaacggtga tgttttttgt tgtctgaaag tccagctcca gcattgcctg ccagcctcaa      4560
gacttccgct ttctgccctt tccggcattt tcttccgtta ccatcattct gttaattcag      4620
aggcgtagta gtagtaaacg taatacatat ccgggaggat gaagtcatct aatcctgctc      4680
cccgaatatc atacagccat tcctgagtgt gactgcacca tttccaatta tgcagtctgt      4740
cctcatcaca aaaatgttgc aagcagtgcg gagtcacgtt ccgtattcat gccctctgcc      4800
agatattgag cggggggagaa atgtgtaagc gtcaacagag cgccgtattg acacttattt      4860
atcggtgaaa actacgttcc atggcagcag ttcgtcaaca cggttggagg gccattccgg      4920
cagtacgctc aggatatggc gcagatacgc ttctggatcg ataccgttca accgacagct      4980
cccgattagt ccgtacagca gagctccgcg ctcgcctcca tgatcgttgc cgaagaacat      5040
gtaattcttt ttcccgagac agacggcacg aagcgctctt tctgctgtgt tattgtccgc      5100
ctccgccaga ccgtcatcac tgtaataaca gagggcgtcc cactgattca ggacatagct      5160
gaacgcttsr cccagtctgg attttttcga caacgtgcca ttcttctcca ccatccattc      5220
atgcagcgac gtcagtaacg ctttgcttcg ctgctgcctg gctgcaagac gttcagactc      5280
cggtaagccc cgtatttcat cmtcaatggc gtacagttca ctgatgcgct tcagagcttc      5340
ttctgccgtc gtacttttgc tgctgatgta tacatcgtgg attttcgcc gggcatgggc      5400 ccagcacgca acttctgtca gtgcaccacc ttcacgttcg gcactgaaca gccgatcgta      5460
accgctgaat gcatccgcct gcaggatacc ccggaaggga cgaaggtgtt gtaccggatg      5520
ttttccctgc ctgtctggtg agtaggcgaa ccagaccscc ggtggctctg atgagcccgc      5580
attccggtca tcccsgacat acgtccagat gcgtcctgtt tttgcctttt ttctgcccgg      5640
tgccagcact tttactggta tgtcgtcagt gtgaaccttg cgggtgttca tcacgtaacg      5700
gtacagggca tcattcagcg gagtcattaa ctggcagcac gcgtcaaccc agttggagag      5760
taatgcacgg ctcagttcgg caccctgtcg ggcaaagatt tcactctgac gatacagtgg      5820
caggtgttcg cagtattttc ccgttaacac gcgggcaagt aatccggagc cgcgatgcc      5880 gcgctctatc gggcgggacg gcgctggcgc ttcaactata cagtcacatt ttgtacaggc      5940 ttttttttacc cgaacagtgc ggatcacttt cagggcgcta ctcaccagtt ccagctgctc      6000
agcactaact tcacccagat aatccagctc actgccacac tccgggcaac aactttcttc      6060
```

```
aggctccagg cggtgtattt cacggggaag atgtgctggt aacggacgac gatgacgtga    6120
ttgtcgcaac tggcgggaa ctgcgggtca tcctcacgcc cactgtaacg atcgctttcc    6180
tgttcgcgtt gtttcagttg ggcctcagcc tgttcaacct cacgctgcag tttttcagaa    6240
cgggtaccga acagcatccg gcgcagtttt tctatctggg ccctcagatg ttctatttcc    6300
cgctcctcct cttcgatctt ttcttcggca cgtgccartg cagagcgcag gaaggcctcc    6360
gtctcttcaa ccagactcag ttgctgatct ttctgacgga gggcttcagc ctgctcagag    6420
agtagccttt ccagctcagt gatacgaatg aggtatttcc gactcatgac cgtttttata    6480
atccggccat gacatttta caacattgtc agtgcattaa ggcgggatgt tttgggttga    6540
cgccagtcca gtttatcgag gagcattgcc agctgcgagc gggtaatgga taccttaccg    6600
tcacgcaccg cagnccagat aaactggcct tcctccagac gtttggtgaa caggcacaga    6660
ccatcagcat cagcccacag gattttaatc gtgtcacccc gtcggccgcg aaagataaac    6720
aggtgaccgg agaaggggtt ctcatccagc acatgttgta cctgttcacc cagaccgttg    6780
aaggatttac gcatatcagt aacgccggca accagccaga ttcgagtgtc tgatgggagc    6840
gagatcatcg tcctctcccg gtcagttcac ggatcaacac cgtgagcagc tctggtgaag    6900
gattttccag cgtcatgtta ccgtggcgga actcaacttt acaggaactg cactgactg     6960 tgctttgtga aggagtggat aaaagcggag taagagccgc cataggctct ttctgctcat    7020
caggcgttat ctcaacaggt aataattcaa cgccagcgcc agaagaggtt gttaccggaa    7080
gacgccgcga tatacgccct tcgttctgcc agagcctgag ccatttgaac aggaggttat    7140
cattgatatc gtgttccctg gcaatacggg caacagaggc tcctggttgt gaagccagtt    7200
taaccatttg aagtttaaac tcatttgaaa atgttctgca gggttctgcg gataatattt    7260
tctgttccat aacaggtgtc cactagttga aaaagtgggc acctacgtta ccaatactgg    7320
cttaatggct acatacggcg gtcagtttac gcttacagaa atgtaatgaa cacgtcctac    7380
cattaactga agagcatggt gacggatgaa ggaaaaagca ggagtgtgtg gtgcctcaca    7440
gatttccgac atcatagctg tcaacgacgg atgaaaagcg gctcttccgc aacttgggtg    7500
gaagaaaatg gatgaaactt tctggtgtga gaaccttaag gaaacaacat gttgggtgga    7560
gcggacaatc caaatggtga attaccgtct tatatcactg gcgctgacat tccgggcgtc    7620
ttctccgcca caacgccatt tgcagtgcat cacaggccag ttgtgctgtc attcgcggtg    7680
acatcgacca gccaataacg gcgcgtgacc acaggtcgat gactactgcg agatacaacc    7740
agccctcatc ggtacgcaag tamgtgatgt cacccgccca mttctggttc ggagcctggc    7800
gctgaagttc ctgctccagc agattctcca atacgggcag gccatgtgca cggtagctga    7860
ccgggctgaa cttccggctg ctttcgcccg cagcccctga cgacgcaggc tggcggcaat    7920
ggttttaata ttgaactccg gcatttcgtc agcaaggcgg ggagcaccgt atcgctgctt    7980
tgcctcaatg aatgccttat ggacagcggc atcgcaggtg agccgaaact gttggcgcag    8040
gctcatctgg tgacgacgcc tgagccagac ataccagccg ctgcgggcaa cccgaagtac    8100
acgacacatc gctttgatgc tgaactctgc ccgatgattt tcgatgaaga catacttcat    8160
ttcaggcgct tcgcgaagta tgtcgcggcc ttttggagga tggccagttc ctcagcctgc    8220
tccgccagtt gtcgtttaag gcggacattt tcagcggcca gttcgctttc gcgctctgac    8280
gaactcattt gttgctgctg tttactgcgc caggcataaa gctgagattc atacaggctg    8340
agttcacggg ctgcggcggc cacaccgatg cgttcagcga gtttcagggc ttcgttacga    8400
aattcaggcg tatgttgttt acggggcttc ttgctgattg atactggttt tgtcatgagt    8460
```

-continued

```
cacctctggt tgagagttta ctcacttagt cctgtgtcca ctattggtgg gtaagatcac    8520
tcagcaacgt atcaaaagtc tgtaaaatca tgggcgtttc gcgtgataca ttttatcgtt    8580
accgcgaact ggtcgatgaa ggcggtgtgg atgcgctgat taatcgtagt gccgcgctcc    8640
taaccttaag aacgtaccga tgaggcaact gaacaggctg ttgttgatta cgccgtcgct    8700
ttcccggcac acggtcagca ccggaccagc aaacaagctg cgtaaacagg gc            8752
```

<210> SEQ ID NO 4
<211> LENGTH: 2417
<212> TYPE: DNA
<213> ORGANISM: Escherichia coli
<220> FEATURE:
<221> NAME/KEY: misc_feature
<222> LOCATION: (1170)..(1170)
<223> OTHER INFORMATION: n equals a, t, g, or c
<221> NAME/KEY: misc_feature
<222> LOCATION: (2400)..(2400)
<223> OTHER INFORMATION: n equals a, t, g, or c
<221> NAME/KEY: misc_feature
<222> LOCATION: (2402)..(2402)
<223> OTHER INFORMATION: n equals a, t, g, or c

<400> SEQUENCE: 4

```
tggtcaaaga tgcaactgca tttcgtcgcg gctttgcggc aaatacttac atcgcagaaa      60
tactgtgcgg aaatctgcat ccatttccac ttgctgtatg cataactttt tcaggcggtc     120
cggatactgc cgaagattat tatgccacat accaccggtt atgggggcaa tatccggaag     180
cattgctgtt tgtaaactgg ctctataatc attcctctgt gctgcatgaa cgggcagaaa     240
tcattaaatg cgccgaaatg ctgatgcagg aagatgattt cgaaatatgc gaaagtattt     300
taagacagca ggagaagttg cgtgaaagaa ttgatgagcg ctttctgag aaaattgtac      360 agaaatgcag aaatatgaat ggtgaatatg tctggccctg gatattgccg ttttcagcgg     420
caggcatgaa acatactggc atacagtatc agtagatatt gcattagtgt atcctgcaca     480
caagtaataa tttatccacc aataataaca ctgttaatgt ccccttcccc tggttgtcag     540 ccagggggtta tcttctgaat atttcttttg aaaaggataa cacaataaat tattttatg     600 aattatccca tggactcatt aacacccttt cataatgttt tattgtcaaa cacgttatgg     660
ctgacatcaa aaaaaaccgg atttcctctg ccagcgggta atcacctccc cggtgttttc     720
ggttggtctg gttactcctg tctggttatt agcaagataa ttgctataaa cagtggaaaa     780
ctcatcgtac ataatctggt gatgaacatt acgcttattt tcccttgacc ggaagaatca     840
gaggctgcgg tttcagactg tctgccggta cattcctctc tccgttaaaa accataatgg     900
gttcattatc ttcgtctgtc agtagattga atggcggtat attttcagta cgaatgccgg     960
tcagccactg aaaaatacct gcgaaatgac gggcactgat ttttctgctg acggactgat    1020
gagacgtgat gtcactggcg gtaataatca ggggaacgct gtagcctccc tgcacatgac    1080
catcatgatg aacaggatta gcactgtcgc tgaccgacag cccatggtca gaaaagtaaa    1140
gcatgacgaa atgacgggaa tgccggcgan ggataccatc aagctgaccg agaaagttat    1200
ccagtttact gatgctggcg aggtaacagg caaccttcg gggatactgc tccaggtaat    1260
gattcggcca ggagtgaagc cggtcacacg ggttcggatg agaccccatc atgtgcagga    1320
atatcacctt cggagaggat ttatccgcca gcgcacgttc tgtttcctgt aacaacaaca    1380
tgtcatccgt tttacgggaa gcgaatgcsc tttcttgagg aaaacggtat gctccgcatc    1440
agaagcaata acagagatgc gtgtgtcatg ctctcccagt tttccctgat tggatatcca    1500
```

-continued

```
ccatgtgctg tatcctgctt ttgctgccag cgccaccacg ttgttgcggg aatcagggtt      1560
ctgctcatag tcataaatca gtgtccsgct cagggaaggt acggtactgg ctgctgccga      1620
tgtatagccg tcaataaata aaccgggagc tgtcattcca gccacggcgt ggttggccac      1680
gggataacca tataccgaca tataatccct gcgcacactc tcaccagtga caatcacaat      1740
cgtgtcatat aacggtgttc cccggccagg attttcccag ttgtcagccc cgtgctgact      1800
cagttgttta taatgctgca tttcacgcaa tgtgtcagtt gtccccacaa cagttccttt      1860
aaccatccgc aacggccagc tgtttactga gcataatacg aacagcagca gtgccagcca      1920
gttacggtga ccacggcggt gtgttcgcca gaaaatcacc atgaatacct gaatcgcggc      1980
actgaccaga aaatgataaa caggaatcat cccggtaaac tccgctgcct catcagttgt      2040
ggtctgcagc aacgcgacaa taaaactgtt gttgatttta ccgtacgtca taccggcagg      2100
cgcatacagt gcacaacaga acagaaataa cagcgctgta atggatgtga gggtatttct      2160
gtgtgcaagg agcagaagga gaaacagaag cagcacattt cctgttgcat tcctctcagt      2220
gtatccgcat gcaattgtgg ttattgcaga cacaacaaaa aagaataaaa acaataaaat      2280
ccgggggggg ttgcccggac aaaacagttt tctgatattc atcggagtat atcgacaaca      2340
ttattatgaa gagaacagga taataaaaat cagaaattat tgtaaaacag ataaaagcan      2400
cnatgcagta atagact                                                     2417
```

<210> SEQ ID NO 5
<211> LENGTH: 6294
<212> TYPE: DNA
<213> ORGANISM: Escherichia coli
<220> FEATURE:
<221> NAME/KEY: misc_feature
<222> LOCATION: (1066)..(1066)
<223> OTHER INFORMATION: n equals a, t, g, or c
<221> NAME/KEY: misc_feature
<222> LOCATION: (1461)..(1461)
<223> OTHER INFORMATION: n equals a, t, g, or c

<400> SEQUENCE: 5

```
agacaaaaac cagttacggt tatcacgtac cagcccccgt atttccaatt tataatcctg        60
gccatcaatt actgggatct cttcttctcc atagaaggca ttaaaaggga atggagtggt       120
aatgtcctct ggaagatatt ctggtgccac actgtttttg ctgaacagaa aactttgaat       180
ccggtcatta aatctggata tacggaacaa tgcttttttca atatcatcat tattgcttat      240
atcacagcca gtcagcatca taattccccc aagcgtcagt ccctgttgga gtaaacgacg       300
tctgtccggc gcaaggattt tttctgcatc tttcaccacg taatgggcat cactgtcaga       360
caaaaaacgt tttttcttca ttagtgaccc cgtatcatag ataacaatgc acgcggaacc       420
aataacacca taaccaggtg aataataatg aacagtacca taatgttcat gcacagaaag       480
tggatataac gcgctgtatc ataaccaccg ratagtatag tcagaaggga aaactgaacg       540
ggtttccata aaaccagacc agacaataga agagcagcgc catctaaaat aatcagaata       600
taggcgactt tttgcaccat attgtattcc tgcatattcg tatgatgcag ctttccatac       660
agtgcctgcg taagggattt tttcagtgag gtccatgaca gcgggaaaaa cttgctccgg       720
aaacgtccgc tacaaattcc cagagtaaga tagatcgtgg cattaatcag cagaatccac       780
atcagggcga agtgccacag taacgcaccg ccaagccagc caccgagagt taatgctgcc       840
ggatagttaa agaaaacaa aggagaagca ttataaatgc gccatccact acatatcatg       900
cctgcgacag taacagcatt aatccagtgg caacagcgta accacagagg rtgtatttgt       960
```

```
tttaacggta atggctgcat tatgtgatct ctgtctgtaa actaagtata ttatggaaag    1020
gaatgttcat cacatcctca caagagttta aaaaaaatgt gacaantcat cgtcaaatgc    1080
tggggtaaaa ttcagataaa gaatatgtgg ataacttttg atgaataacg taaaaaaaat    1140
actgctgatg gaagatgatt atgatattgc agctctgttg cggcttaatc tgcaggatga    1200
agggtatcag atagttcatg aagcggatgg cgccagagct cgtttattac tagacaagca    1260
gacctgggat gccgtaatac ttgatcttat gctgcctaat gttaatgggc tggagatttg    1320
ccgttatatc cgtcagatga cccgttatct gcctgtgatt atcatcagtg cccgtaccag    1380
cgaaacccac cgcgtcctgg gactggaaat ggggctgat gactatctac cgaaaccctt     1440
ttccattcct gagctgattg ncccgcatca aagcgttgtt tcgtcgtcag gaagccatgg    1500
ggcaaaatat tctcctggca ggtggactga tttgctgtca cggtctgtgc atcaatccat    1560
tttcacgtga agttcatttg cataataaac aggttgatct taccccacgc gagtttgatc    1620
tgctgctctg gtttgcacgt catcctggcg aagttttttc ccgtctttca ctgctggata    1680
atgtctgggg gtatcagcat gaaggatatg agcatacagt caacacgcat atcaaccgtc    1740
ttcgtgccaa aattgaacag gatgcagcag agccaaagat gatccagacc gtctggggaa    1800
aagggtatag gttttcagtt gacaatgcag gaatgcgata aatgaattgt agcctgacat    1860 taagccagg gttaagccta gtatttacag tcgttttgct gttttgcgcc gtggacatgt     1920
ggcgttcata tttacagcag taatctgtat ggcaatgcaa tggtacagcg tttatctgca    1980
ggctggcgca acagattgtc atcacggagt ctctgctgga taatcgtggg caggtgaatc    2040
accggacatt aaagagtctg tttgagcgtc tgatgacgct taatcccagt gtggagctgt    2100
atattgtctc gccggaaggt cggctgcttt tggaggccgc ccctccaggt catatcaaac    2160
gtcggtatat caatatagcg cccttgaaaa aatttctctc cggtgctgtc tggcccgtat    2220
atggtgatga tccccgaagt gtaaataaga aaaagttttt cagtaccgca ccgctttacc    2280
tgagggatga tctgaaagga tatctgtata ttattttaca gggagaggaa cttaatgctc    2340
ttactgatgc agcctggaca aaggcactat ggaatgcact gtactggtcg ctgtttctgg    2400
tagtgatatg tggtctgctg tcgggtatgc tggtctggta ctgggtaacc cgtcccatac    2460
agcaactaac tgaaaatgtc agcgggatag agcaggacag tattagtgcc attaaacaac    2520
tggcaattca gcgccctgcc accccccta gcaacgaggt cgagatatta cacaatgcct     2580
tcattgaact ggcccgtaaa atatcctgtc agtgggatca actttcagaa agtgatcaac    2640
agcgccgtga atttattgcc aatatctccc atgatttacg gacgccatta acatcacttc    2700
tgggatatct ggaaaccctg tcaatgaagt cggattcgct atcatcagag gactgtcata    2760
aatatctgac aacagctctc cggcagggac acaaggtgag gcatctgtcc tgtcagcttt    2820
ttgagctggc acgtcttgag catggtgcta taaaacctca actggagcaa ttttctgtct    2880
gtgaacttat tcaggatgta gctcaaaaat ttgagctcag catagaaacc cgtcgattgc    2940
aactaagaat tatgatgtca cattccctgc ctcttatcag ggcagatatt tcaatgatag    3000
agcgtgtgat aacaaattta ctggataatg ctgtacgcca cacacctccg gaaggctcga    3060
tcaggctgaa agtctggcag gaagataatc ggttgcacgt cgaagtggct gacagcggcc    3120
ctggactaac tgaagatatg cgaactcatc ttttccggcg ggcatcagtg ttatgtcatg    3180
aaccgtcaga agagccccgg ggaggactgg gattgctgat tgtacgcagg atgctggtac    3240
tacacggtgg tgatatcagg ttgactgatt caacgactgg agcctgcttt cgttttttc     3300 ttccattata acatcaggcg gcatattttg gggtggttat gtgtatctgc ctttgtaaaa    3360
```

-continued

```
gggatacaag ttctgtagtg gagcacaaaa tcaggacacc ggaataacct gtttccactt    3420
ttcttcatgt aagcaaggcg gtaaaccatc gttgttcgtg tgaggtcgat aaacgttgta    3480
ataaccatta atccactggt ttatatcacg taccgcatgg ataaaatcac cataaccacc    3540
tttcggaagc cattcatttt taaggctgcg aaagactctt ccatcggcg aattatccag     3600 gccattccct ctgcaactca tactttgcat taccccataa cgccagagta actttctgta    3660
tttattgctt ttatactgaa caccttgatc tgaatgaaac agcaggcggc catcacgcgg    3720
tcgagtttcc agtccgttac gcaaagccct acacaccaac tcagcatcag cggttaatga    3780
gagggctgaa ccgataatcc gccgtgaata taaatcaaca acgagcgcga gctaacacca    3840
tttgtcctgc aggcgaataa aactgatgtc gcgcaccaga cgcagtttgg tgcggcgggg    3900
tgaaattgcc ggttcagtaa atttggcaat ggcggacttt tgtcttcgtt tacccggttg    3960
tgatgtttaa ccggctgtcg acttgtcagc cctcattccc gcatcagtcg tcatgccagc    4020
caccggcctg catcaacgcc actctggcgc aacatctgac tgattgcccg gctacccggc    4080
tgcgccacga ctgagagcat ggaaagccct cacccggctt cgtaattcaa ttcttttgcac   4140 attaacagga cgcttcacct gcgcgtaata aacgctacgg ttaataccga ataaatgaca    4200
aataacccac actggccact ttgctttcag ctgtgtgatt agcgcgacag cttcccgggg    4260
atttcgctca tcagcacggc agcctgcttt agtatttctt tttccatctc aacgcgcttt    4320
atctgcgctt taagctgctg aatttcgcgt tgttcagggg taatagcatt accagctggc    4380 tcaatacccct gaagttcctg cttatacaac cgtatccatt tacgcaaatg gtcagggttg    4440
agctcgagtg cctgcgcgac ttctctgaca tcacgctggt atttaaccac cacctgctcg    4500
aaagcttcaa gcttgaactc cggggaaaag gtacgtttag tccgacgagt tttgatcatg    4560
catcacctca ttttcactgt tttaacatta acaggatttc gaggtgtcct gaattaccga    4620
tccactacaa agtacgacag gtactgtgga ggtactcccg taaagacggc catcaagctc    4680
ccgctccgac atacctgcgg gcagaggcca tgaaaagcca gctttgcgaa agcgcacgaa    4740
cataccacaa gctgttgatt ttggtacgcc caggcgacgc ccgaccacaa cctggggtaa    4800
atgttcttca agtgaagac gtaaagcttc agtgatccaa gtccggtgtt tcatacgata     4860
gtgtccatta aaaatgatgg acattatttt tgtaaaaccg gaggaaacag accagacggt    4920
ttaaatgagc cggttacatg taatccatac tcatccaagg tttaattctg acacaataag    4980
aaaatatgga aagtctcgct ctagagatgg ggagagggat attgaagtgt atgatattcc    5040
aagaactgcc ggagatatcc tcgtaaatgg attttccagt gcaaactgat aacaaattcg    5100
aagtcattat ctgcaacaag attgattgat gtagggata tgttagagca ttataatgct     5160
caaggatttg gcgtgatgac atctgcgcca attgatgcga cactatatga taaactggat    5220
gctatttgca gtaagtgtaa aatagaacaa ataaatttttt cagtattaga gtcagaacgc    5280
gcactatatt atgacgatat attaagatgc cgttactttg gtaaatamca taaaattaat    5340
caatatggta atatatcagt tgtaattgat cgaaacaaag cacataaatg ccatcttata    5400
aagatggtgt ttkttaagca tataaaatat attttctata agatataggg caaactaaat    5460
ttcttgactt ctatgatgga ctaactagat atacatgccg ccagttttta taaaacgacg    5520
gcatatataa tcatttatat atcttttgat tttattcgta accactcatg ttgatctaaa    5580
cctattcttg acagattagc aacaatatca gttgttattt tttgcgcgta cgttgttttt    5640
atttccccga tccatttcaa tacttttgga gtagatattt tttcaacgag taaaggaacg    5700
```

-continued

| | |
|---|---|
| aatgagatat agtcagtatt aactagattg ttcttttttcc ctatgatgac accgtttcca | 5760 |
| ttttcgactc caaatgaaaa tgaaataata ttagaagctt ttgccggcat tttaatttta | 5820 |
| taaaaaccgc catattcatc ttcgattaac aaattgtaat tattatcgtc cagtgttccc | 5880 |
| ctgaggaata aaaaatcggc tttttcatgc aatctgacgc tatcacataa tggttgtatg | 5940 |
| catagataga caaattata tgcatctaaa agtaaagttc cttgttttaa ggacacatta | 6000 |
| tctatatgag aatgatatct taaactcctg cgcgtgattt ccagagagca taattgcatt | 6060 |
| aacttttat cttcttcacc atcttggctt aagtattcct ttttacctaa agatgcgtgt | 6120 |
| tcaatagcgt gttgaatttc ttctaaagaa tcagcagaga gtatattcct tagatgttct | 6180 |
| actgataagt cttttgttt ttttccagtt aatagaaaat tcttacaacc atttttttgca | 6240 |
| tagtgaaaaa taggccaatg ggataaggag ttttgctta gagatttctg ggga | 6294 |

<210> SEQ ID NO 6
<211> LENGTH: 4519
<212> TYPE: DNA
<213> ORGANISM: Escherichia coli
<220> FEATURE:
<221> NAME/KEY: misc_feature
<222> LOCATION: (3483)..(3483)
<223> OTHER INFORMATION: n equals a, t, g, or c
<221> NAME/KEY: misc_feature
<222> LOCATION: (3487)..(3487)
<223> OTHER INFORMATION: n equals a, t, g, or c
<221> NAME/KEY: misc_feature
<222> LOCATION: (4292)..(4292)
<223> OTHER INFORMATION: n equals a, t, g, or c
<221> NAME/KEY: misc_feature
<222> LOCATION: (4318)..(4318)
<223> OTHER INFORMATION: n equals a, t, g, or c
<221> NAME/KEY: misc_feature
<222> LOCATION: (4329)..(4329)
<223> OTHER INFORMATION: n equals a, t, g, or c

<400> SEQUENCE: 6

| | |
|---|---|
| tattcctttc tctcccatga tagggcgaaa ggctttatta ctatccactg ctggtttatt | 60 |
| aattgcatca tcgtcgatta atttgctgga ggttccaata gtcaaccacc tctcttcaaa | 120 |
| ttcatcggtt gtcataccta atccatcatc tctcaagata agaagatttt ctttcctaaa | 180 |
| aaaatcaact tcgacattat cagcataggc atcatgagca ttttttaaata actcactcaa | 240 |
| ggcagtaggt atacctgcaa tttgttgtct gccaagcatg tccaaagctc gagcctttgt | 300 |
| tcttatttta gccatatatc tatgaatcct tattagtaca attttctatg agatgtagcc | 360 |
| caaatagtct agcgagttcg caaggtacag cattgccgat ttgctttgcc attgaattca | 420 |
| gcgaaccttt aaaaacatag cttaaaggaa atgtttgtaa tcttgatgct tcttcttatgc | 480 |
| taattgctct atgttgagtg gggtcaggat gcccaaaacg accattggag taactattac | 540 |
| atttcgtcgt aagtgtaggc gcaggcttat cccaactcat tcttccataa gtatctgtgt | 600 |
| ggccatcata attttatgg catttattaa ctaactcttc tggccaattt cttctatccc | 660 |
| ctccttctgg agtgtgcata aktcttttta ggttaagagg gctcagtgtt ccagccctat | 720 |
| gtaaaggatc tttggggtcg gtttctcctg aacataactt tgtgaagtcc tggatataat | 780 |
| ctcgtacagt tttgaatggg atttttatttt taccatgggt tatctctggt agggtaactt | 840 |
| tacctactcg actagctaag agcacgagtc ttttttcttct ttggggaatc ccatagttct | 900 |
| cagcattggc tataaaagat atatagttat actctaactc tttaagtagc ttaataaact | 960 |
| cctgaaatgg gccttctttt tcttcatcaa ttttttttgcat tccaggaaca ttttcaagca | 1020 |
| taatatattc aggaagaagt tctctaataa aacgatgagt ttcatttagt agatttctcc | 1080 |

```
ttgagtcgtc actagtttta tttttattct gttgcgaaaa tggttgacat ggtgcacatg    1140
cactcagtaa caaaggccgt ttagctttaa tatcaatgat gtcggagata tcttgaggtt    1200
cgattttcct aatatcatct tggatgaatt ttgcatcagg gaaattagct ttaaatgttt    1260
ctgatgcttg ttggtcaata tctaatccaa gctcgatatc aaagccagcc tgacgtagcc    1320
cttcactggc tccaccacag ccacaaaaaa aatctataac tatcaatttg ataccttctt    1380
tgaactaaat aaaacaactc gaataagttg atatttaaa taaaaataat tggtatggat     1440
atgaactttg gtcacgctac cgccctgagk tcatggccat ccccagacct tttaaaggga    1500
ttatgaacaa cacccagccg acgttcaacg tgttaccca tacatatcac aaagttagtt     1560
aattggttgg tcgtaaattg acctaaaatg gattgagggc aatgcaaaaa tcattgggaa    1620
atccaggcga cacagatgtt cggaagagac tgaatgttaa aaatatagaa tgtatattct    1680 caaaaagag atatttcatt acattttata tgtgtatagg aaagtgagat tggcgaatca     1740
cctcccaatc atcccgccag cgctccattc agcgccacgc caaccctcac tccagcccac    1800
gtcatcgccc ccagccagaa tgtcggcaac accagaaaca tcaacctcat caccagattg    1860
ataatcacgt catcctgcgt attctggatc ccggctaaat tccagctact gtgggtatcg    1920
ctgttgtaga gcacatccag cagccagcta tcaagccacc gtgccagttc ccaccaaaag    1980
gtgaggaaaa atagtgcaaa ctgcacaaac gtcagcgtca tcactacttt cacatcccac    2040
gccgaacaga gcgttatcag cggaatacag atcaccagcg ctatttgcag tgcgcctgta    2100
ccatcggtag tgcctaacgc acgctgtcga atgccgtaca tgccgctatg ctgccgagga    2160
tatttctagc gccggatgcc aaccgggtgg cggcattggc gacggtgcca tcaacgttac    2220
cgccatagct tggataaacg cgcccattct gcgatacctg catatttcgt tcactgaccc    2280
gcgagcgcag cacggcctct tcatacacta cctgcgactg gtcgattttt ttaaacgccg    2340
tccagatatc tagggcagga agttgcagta gacgggcttt cagcccaagc ggtgtcgtcg    2400
gcccaccgct gtttacaagt gggatagccg cccgcgcccg tatcggccag cccggcatcg    2460
cgcgatgcac tgtacggcca agcactgtgt ggtgaaagcg catggtcgga aaaggcctgt    2520
tcagctaacc aagcacatcc caccatcaca agaatcgcca gaaaccaaa ctcagtcaga     2580 ataactcttc ctgattcagg cttgctcct gcattatggc taccactatt gtttgcctgc     2640
acgtatcatc tgataacggt taattaactg atttagcgcc atttcagcct gttttttgctg   2700 ctgttcactg ccattctggt tacgacttc accgtagcga cgtaactgct cttccgccgg    2760
gatatgccgg ttaaaagcct gcatgatgcc aaacacctcc gttttcagtt cactgaccgt    2820
catgtatttt cccgctgtt catcctgacg gttcaggcgc tcagccaact gctgtaagcg    2880
gatcatgcct tcgttccagc ccgtcatcgc ctcttccggg agcgcacgac tccttacact    2940
cttctgccag ttatccacca tttcctgaac acggggattg ccggggacaa gaaccctcag    3000
ttgctgcagc agctgcgcac tgcaccgcag gttgtatgct ggaggtaatt ctgccagtcg    3060
cgttatctgc tgaccggaaa gggttatcca gtgcactcag gcagataccg ggattcaggt    3120
taattttttc aaacagggaa gcatatacgc tgtcgccggt atgcgtttca gataccacac    3180
tctctgcgac gttcttttct ttctgtacag acatcagcat tttctgtaag cgtacagcga    3240
gggccgtatt gacggggatg tgttattcag ctggcagtgc tatgcgccac ggaagcagtt    3300
cgctgacccg gttgaccggc cagtctgcta tgacggcaag cacatggcga aggtagcttt    3360
ctggatccac gtcattcagt ttgcacgtcc cgatcaggct gtacagtagc gctccccgct    3420
```

-continued

```
caccaccatg gtcagagccg aagaacagga agtttttacg acccagactg accgcccgca   3480
ggncatnttt cagcgatgtt gttgtcgatt tccacccagc catcgttcgc atagtacgtc   3540
atgccggcca ctggttaagt gcgtacgcga acgccttcgc caccatcagg ctggacaggg   3600
gactttcacc cccaagctgc tgaacatgcc cggcacacaa agaagatctc ggctcagtgg   3660
ccgggattag ttatacaatt atctgattga tttttaatat atcttttctt aaatcatcgt   3720
taatatctga cggttctagc tggtttataa gttgccttat ttgggtaaag gtacttttct   3780
gatcttttag atcttctcct tttatcgttg ataaagctgc aattagttca ccatcgtaat   3840
attcacccgc taacggctct ttagttagaa cttccaacac tcttggcatc aactgatcaa   3900
tacataaatt ttgtcggata gcgcggcaaa gatcttccac tgttaacttt tcaagaggca   3960
catctatgat acgttcgaac cagagttcaa gcggtgattg ttgctcaggc tcttttgtca   4020
tattgatgtt tccaatcaat ttacgtaagg taatcatatt ccatatcctt tcaaggctga   4080
ttctatttta ttaatagcat ctgttgctct gccatacgca gcctgagctt caggattgtt   4140 gacgttttc aacgtatccg catgatttct taatcctctg agcgtatttt gcatttcctg   4200
catatgatcc caatatcctc cattctcttt aggaactggc ttaccatcca tatccttgag   4260
agttccaatt aatatcatga atcttttcag ancatttttt taatagtggt taatcgantc   4320
ttctttaant cggcaacttt tcttggcctt cctggaatta aaggctttaa tcctaacaag   4380 ttttttttctc aattttggc tggctttagg gaatcaattt ttcccggatt gggtgggtgg   4440
gtggtaaccc gggtttccct tgaagcccgg gaaacccggc cccaagttct tacttttttt   4500
cccgcaatcg ggtcaagat                                                 4519
```

<210> SEQ ID NO 7
<211> LENGTH: 1213
<212> TYPE: DNA
<213> ORGANISM: Escherichia coli

<400> SEQUENCE: 7

```
attacagaat gtggaaatta agtatgattc gaaaaaagat tctgatggct gccatccccc     60
tgtttgttat atccggggca gacgctgctg tttcgctgga cagaacccgc gcggtgtttg    120
acgggagtga aagtcaatg acgcttgata tctccaatga taacaaacaa ctgccctatc    180
ttgctcaggc atggatagaa aatgaaaatc aggaaaaaat tattacaggg ccggttattg    240 ccaccccctcc ggttcagcgc cttgagccgg gtgcgaaaag catggtcagg ctgagtacca    300
caccggatat cagtaaactt cctcaggaca gggaatcact gttttatttt aatctcaggg    360
aaataccgcc gaggagtgaa aaggccaatg tactgcagat agccttacag accaaaataa    420 agcttttta tcgcccggca gcaattaaaa ccagaccaaa tgaagtatgg caggaccagt    480
taattctgaa caaagtcagc ggtgggtatc gtattgaaaa cccaacgccc tattatgtca    540
ctgttattgg tctgggagga agtgaaaagc aggcagagga aggtgagttt gaaaccgtga    600
tgctgtctcc ccgttcagag cagacagtaa aatcggcaaa ttataatacc ccttatctgt    660
cttatattaa tgactatggt ggtcgcccgg tactgtcgtt tatctgtaat ggtagccgtt    720
gctctgtgaa aaagagaaa taatgtaccg caataacggt taaatgcggg tgggatatta    780
tggttgtgaa taaacaaca gcagtactgt atcttattgc actgtcgctg agtggtttca    840
tccatacttt cctgcgggct gaagagcggg tatatacga tgacgtcttt actgcagatg    900
agttgcgtca ttaccggata aatgaacggg gggacgcac cggaagcctg accgtcagtg    960
gtgcactgct gtcctcaccc tgcacgctgg tgagtaatga ggtgccgtta arcctccggc   1020
```

```
cggaaaatca ctctgcggca gccggagcac ctctgatgct gaggctggca ggatgtgggg    1080
acggtggtgc acttcagccc ggaaaacggg gcgttgcgat gacagtctcc ggctcactgg    1140
taaccggtcc cggaagcgga agtgctttac ttcctgaccg taasctatcc ggctgtgaca    1200
tcttgttata cac                                                       1213
```

<210> SEQ ID NO 8
<211> LENGTH: 451
<212> TYPE: DNA
<213> ORGANISM: Escherichia coli
<220> FEATURE:
<221> NAME/KEY: misc_feature
<222> LOCATION: (437)..(437)
<223> OTHER INFORMATION: n equals a, t, g, or c
<221> NAME/KEY: misc_feature
<222> LOCATION: (449)..(449)
<223> OTHER INFORMATION: n equals a, t, g, or c

<400> SEQUENCE: 8

```
acgctctagt attctctgtc gttctgcctg ggccactgca gatagaatag tgacaaccat     60
tttacccatc tccccatcgg tactgattcc gtcatcaata aaccgaatgg atacaccttg    120
ggcgtcaaac tcttttatta actggatcat gtcagcagta tcgcgcccaa ggggttcaag    180
tttcttcacc aagatgacgt caccttcctc caccttcatc ctcagcaagt ccagcccttt    240
ccgatcgctt gaactgcccg atgccttgtc agtaaagatg cgatttgctt tcacgcctgc    300
gtctttgagt gcccgaacct gaatatcgag agattgctgg ctggttgata cccgtgcgta    360
accaaaaagt cgcataaaaa tgtatccyaa atcaaatatc ggacaagcag tgtctgttat    420
aacaaaaaat cgatttnaat tagacaccnt t                                   451
```

<210> SEQ ID NO 9
<211> LENGTH: 720
<212> TYPE: DNA
<213> ORGANISM: Escherichia coli
<220> FEATURE:
<221> NAME/KEY: misc_feature
<222> LOCATION: (621)..(621)
<223> OTHER INFORMATION: n equals a, t, g, or c

<400> SEQUENCE: 9

```
gacaaggctt ataaactcac tgacggggct ggcatgttcc tgctggtaca tcctaatggt     60
tcccgttact ggcgtctccg ttatcgtatt ctgggtaagg agaagactct ggcacttggt    120
gtgtatccag aagtttctct ctccgaagct cgtacaaaac gggatgaggc ccgaaaactg    180
atttcggagg ggattgaccc ttgcgaacag aaaagagcta aaaagtagt ccctgattta    240 cagctctctt tgaacatat tgcacgacgc tggcatgcca gtaataaaca atgggcacaa    300
tcacacagcg ataaagtact caaaagcctc gaaacacacg ttttcccctt tatcggcaac    360
cgggatatca caacactcaa taccccggat ctgcttatcc ctgttcgtgc tgcagaagct    420
aaacaaattt atgaaatcgc cagtcgtctg cagcaaagaa tatctgccgt aatgcgttat    480
gccgtacagt ctggcatcat cagatataat cctgctctgg atatggctgg cgcattgact    540
acggtaaaac gccagcatcg ccccgctctt gatctttcac gtctgcctga acttctgtcg    600
cgtattaaca gttataaagg ncagcctgtc accggcttg cgttgatgct gaatttactg    660 ggttttatt cgttccagtg aactcagata cgcccgctgg ttctgaaaat tgatattgga    720
```

<210> SEQ ID NO 10
<211> LENGTH: 2920

```
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n equals a, t, g, or c
<221> NAME/KEY: misc_feature
<222> LOCATION: (3)..(3)
<223> OTHER INFORMATION: n equals a, t, g, or c
<221> NAME/KEY: misc_feature
<222> LOCATION: (1250)..(1250)
<223> OTHER INFORMATION: n equals a, t, g, or c

<400> SEQUENCE: 10
```

| | | | | | |
|---|---|---|---|---|---|
| ncnttaattt | tatatctcgt | aaaataaaat | gttttctgta | ccgctctccg | gagggggaa | 60 |
| tgattcgttt | atcattattt | atatcgttgc | ttctgacatc | ggtcgctgta | ctggctgatg | 120 |
| tgcagattaa | catcaggga | aatgtttata | tcccccatg | caccattaat | aacgggcaga | 180 |
| atattgttgt | tgattttggg | aatattaatc | ctgagcatgt | ggacaactca | cgtggtgaag | 240 |
| tcacaaaaac | cataagcata | tcctgtccgt | ataagagtgg | ctctctctgg | ataaaagtta | 300 |
| cgggaaatac | tatgggagga | ggtcagaata | atgtactggc | aacaaatata | actcattttg | 360 |
| gtatagcgct | gtatcaggga | aaggaatgt | caacacctct | tacattaggt | aatggttcag | 420 |
| gaaatggtta | cagagttaca | gcaggtctgg | acacagcacg | ttcaacgttc | acctttactt | 480 |
| cagtgcccctt | tcgtaatggc | agcgggatac | tgaatggcgg | ggatttccgg | accacggcca | 540 |
| gtatgagcat | gatttataac | tgagtcatac | ccaaatgaat | aactgtaatt | acggaagtga | 600 |
| tttctgatga | aaaaatggck | ccctgcttt | ttattttat | ccctgtcagg | ctgtaatgat | 660 |
| gctctggctg | caaaccagag | tacaatgttt | tactcgttta | atgataacat | ttatcgtcst | 720 |
| caacttagtg | ttaaagtaac | cgatattgtt | caattcatag | tggatataaa | ctccgcatca | 780 |
| agtacggcaa | ctttaagcta | tgtggcctgc | aatggattta | cctggactca | tgrtctttac | 840 |
| tggtctgagt | attttgcatg | gctggttgtt | cctaaacatg | tttcctataa | tggatataat | 900 |
| atatatcttg | aacttcagtc | cagaggaagt | ttttcacttg | atgcagaaga | taatgataat | 960 |
| tactatctta | ccaagggatt | tgcatgggat | gaagcaaaca | catctggaca | gacatgtttc | 1020 |
| aatatcggag | aaaaagaag | tctggcatgg | tcatttggtg | gtgttacccct | gaacgccaga | 1080 |
| ttgcctgttg | accttcctaa | gggggattat | acgtttccag | ttaagttctt | acgtggcatt | 1140 |
| cagcgtaata | attatgatta | tattggtgga | cgctacaaaa | tcccttcttc | gttaatgaaa | 1200 |
| acatttcctt | ttaatggtac | attgaatttc | tcaattaaaa | ataccggagn | atgccgtcct | 1260 |
| tctgcacagt | ctctggaaat | aaatcatggt | gatctgtcga | ttaatagcgc | taataatcat | 1320 |
| tatgcggctc | agactctttc | tgtgtcttgc | gatgtgccta | caaatattcg | ttttttcctg | 1380 |
| ttaagcaata | caaatccggc | atacagccat | ggtcagcaat | tttcggttgg | tctgggtcat | 1440 |
| ggctgggact | ccattatttc | gattaatggc | gtggacacag | gagagacaac | gatgagatgg | 1500 |
| tacagagcag | gtacacaaaa | cctgaccatc | gcagtcgcct | ctatggtgaa | tcttcaaaga | 1560 |
| tacaaccagg | agtactatct | ggttcagcaa | cgctgctcat | gatattgcca | taaatggttt | 1620 |
| atccggagcc | ggatagtgtg | ttgtggatat | ctggcatgcc | ccgggaagtc | accttttcaga | 1680 |
| cgggcgagg | gctggtgaat | tatccgcgat | tactgagcag | tatggataat | ccttttttcac | 1740 |
| agacttgtca | gcagccagca | tttatgttct | tttatctgag | ggaatttatc | tgtacgctgt | 1800 |
| gccgggatat | ctcagttata | cagaaatcag | gcaggaataa | attgtagtgg | aaagtcgatg | 1860 |
| tttaccggat | gactgatgcg | cgcttgtaca | cagacagtgt | gtttcagtaa | tatggagaat | 1920 |

```
aatgaaatga ataacacaga cacattagaa aaaataatca gacaccaaaa aaacaaagac     1980
cccgcatatc ctttcgggaa catttgttga tgcagctctg tattcgcaca ataaaagaa     2040 tgcaggataa tatatctgaa tttctggggg cgtatggaat aaatcactca gcatatatgg    2100
tcctcaccac attattcgca gcggagaacc attgtctgtc accttcagag ataagccaga    2160
aacttcagtt taccagaact aatattaccc gcattacaga ttttttagaa aaagccggat    2220
atgtaaaaag gacggatagc agggaggatc gccgtgctaa aaaatcagt ctgacatctg    2280 aaggtatgtt ttttattcag aggctcactc ttgcacaaag catgtatctg aaagaaatct    2340
gggattatct gacccatgat gaacaggaac tgtttgaagt cattaataaa aaattactgg    2400 cacattttc tgatgccagc tcataaagtg cgaaatatct gaggatgccg gatagcttca    2460
ggcaaaataa taatgattct gcagatgtg tttttccgga tacaaaaaca aatgataaaa     2520
attgcagcgc caggcaccct tcaaagcagg gagacctgta ccgcgtcgaa aatttcagcc    2580
agttaatatc attgtctgaa ccaggcactt tgcccgggca ggagaaggag ttgtggcggt    2640
ctcagcccgg aacaatttga aaaccataat ctcgcttagg gccgtgtcca cattacgtgg    2700
gtaggatcac tcctggattt tctcttttg gacattgacg tctccattgg tttaaacacg     2760
gcaatggaga ctgcggtgaa aagagttaat tcccggagtg actggctgga tgccaatcaa    2820
tgatcggaag catgccaaac tgtgaacgga atggatgcc gccaaatcat gatcgattca     2880
gatgccatat ttgcaatatc gcgttaatcg tcagttcagc                          2920

<210> SEQ ID NO 11
<211> LENGTH: 1678
<212> TYPE: DNA
<213> ORGANISM: Escherichia coli
<220> FEATURE:
<221> NAME/KEY: misc_feature
<222> LOCATION: (1666)..(1666)
<223> OTHER INFORMATION: n equals a, t, g, or c
<221> NAME/KEY: misc_feature
<222> LOCATION: (1677)..(1677)
<223> OTHER INFORMATION: n equals a, t, g, or c

<400> SEQUENCE: 11
ggtaaggaag ttatatatat gagcaactat acatcttaga tgtatgataa agaaaaagat     60
aacagttctt tagaatatgt atattgaaga gaatgcaata gcatggttta tataaattac    120
gcataaaaat aagcatatgt aagcattttg gtttgctttt tttaacctgc caccgcaatg    180
aatgcttttt ttatgttaat gtgcgttatg aaactaaatg caagaaacat atttaaagga    240
ttaatatcgt tctctcacag actccgttta cttattcaag aatataattt aatttatagt    300
gagcttatta tgaatatgaa caatccatta gaggktcttg gcatgtatc ctggctckgg     360 ggccagttcc ccattacaca gaaacyggcc agtttctttg tttgcaataa atgtattacc    420
tgcaatacgg ggctaaccaa tatgctttat taacccgggg ataattaccc tgttgcatat    480
tgtagttggg gctaattta gtttagaaaa tgaaattaaa tatcctaatg atgttaccctc    540 attagtcgca gaagactgga cttcaggtga tcgtaaakgg tycattgact ggattgctcc    600
tttcggggat aacggtgccc tgtacaaata tatgggaaaa aaattccctg atgaactatt    660
ccgagccatc agggtggaty ccaaaactca tgttggtaaa gtatcagaat ttcacggagg    720
taaaattgat aaacagttag cgaataaaat ttttaaacaa tatcaccacg agttaataac    780
tgaagtaaaa aacaagacag atttcaattt tcattaaca ggttaagagg taattaaatg     840
ccaacaataa ccactgcaca aattaaaagc acactacagt ctgcaaagca atccgctgca    900
```

-continued

```
aataaattgc actcagcagg acaaagcacg aaagatgcat taaaaaaagc agcagagcaa        960
acccgcaatg ggggaaaaca gactcatttt tacttatccc taaagattat aaaggacagg       1020
gttcaagcct taatgacctt gtcaggacgg cagatgaact gggaattgaa gtccagtatg       1080
atgaaaagaa tggcacggcg attactaaac aggtattcgg cacagcagag aaactcattg       1140
gcctcaccga acgggagtg actatctttg caccacaatt agacaaatta ctgcaaaagt        1200
atcaaaaagc gggtaataaa ttaggcggca gtgctgaaaa tataggtgat aacttaggaa       1260
aggcaggcag tgtactgtca acgtttcaaa attttctggg tactgcactt tcctcaatga       1320
aaatagacga actgataaag aaacaaaaat ctggtagcaa tgtcagttct tctgaactgg       1380
caaaagcgag tattgagcta atcaaccaac tcgtggacac agctgccagc attaataata       1440
atgttaactc attttctcaa caactcaata agctgggaag tgtattatcc aatacaaagc       1500
acctgaacgg tgttggtaat aagttacaga atttacctaa ccttggataa tatcggtgca       1560
gggttagata ctgtatcggg katttatct gcgrtttcag caagcttcat tctgagscat        1620
gcagatgcag ataccggrac taaagctgcc agcaggtgtt ggattnacca acggaant        1678
```

<210> SEQ ID NO 12
<211> LENGTH: 2676
<212> TYPE: DNA
<213> ORGANISM: Escherichia coli
<220> FEATURE:
<221> NAME/KEY: misc_feature
<222> LOCATION: (128)..(128)
<223> OTHER INFORMATION: n equals a, t, g, or c
<221> NAME/KEY: misc_feature
<222> LOCATION: (447)..(447)
<223> OTHER INFORMATION: n equals a, t, g, or c
<221> NAME/KEY: misc_feature
<222> LOCATION: (1100)..(1100)
<223> OTHER INFORMATION: n equals a, t, g, or c
<221> NAME/KEY: misc_feature
<222> LOCATION: (2660)..(2660)
<223> OTHER INFORMATION: n equals a, t, g, or c

<400> SEQUENCE: 12

```
aaggattact ttggaatctg acaacaaagt tactatgaaa aagaactaac aaagttatat         60
aatgacgcta aaaatgcttt gaaagatgtg caatctaaag caaataggtt aatttctgat        120
aataaganaa aacataagag tgaactaaaa aacatttctt atgaattcca atcaactaat        180
ctcaatggca aagatactgc gtatatattg gatgtaraaa gaaatctaga agtaaaatt         240 gagaatactc caaacgaatg agtgtaatga ataagaaaa ctaaccgacc agattgcaat        300
aattagtgat agtaccactt ctgaaaattt atcatcggct caagtaactg aagcaatcga       360
aactgaactt gaacatttac gagaccaaca agcaaataac gcagagttaa tactacttgg      420
catggctctt tctgtagtac atcatgnatt taatggtaat attagggcaa ttagaagtgc       480
gctaagggaa ttaaaagcat gggctgacag aaatcctaag cttgatatta tataccaaaa      540
aatcagaact agttttgatc acttagatgg ttatttaaaa acctttacac cattgacaag     600
acgtttaagt cgctctcmaaa ccaatataac tggaactgcc attttagaat ttatcagaga     660
tgtattcgat gatcgtcttg agaaagaagg aattgaatta ttcactacct caaagtttgt      720
taatcaagaa attgtaactt acacatcaac catttaccct gtctttataa atctaattga      780
taacgcaata tactggcttg ggaaaacaac tggagaaaaa agacttatac ttgatgckac      840
tgaaacagga tttgttattg gtgatactgg tcccggtgtt tcaactagag atcgagatat      900
aatatttgat atgggattta cacgaaaaac aggagggcgt ggaatgggat tattcatttc     960
```

```
caaagagtgt ttatctcgag atggatttac tataagattg gatgattaca ctcctgaaca    1020
gggtgctttc tttattattg agccatcaga agaaacaagt gaatagcgga tataaataaa    1080
tgacaagctc tactgattn cataaacttt ctgaagactg cgttcgccgt ttttacatt    1140 ctgtagttgc tgtagatgac aatatgtctt ttggagctgg tagtgatact ttccctacag    1200
acgaagatat taatgcttta gttgatcccg acgatgatcc tacaccaata ataacagcat    1260
cagcatcccc aaggatagaa tcaactaaat caaaagcaaa ggtaaaaaac catccttttg    1320
attaccaagc tctagcagaa gctttcgcca aagatggtat tgcttgttgc ggattattag    1380
ctaaggaagg tgcgaataag cggggaaatt cttctcggct gactcagtca tttcatttct    1440
tcatgtttga gccgattttt tctcccgtaa atgccttgaa tcagcctatt tagaccgttt    1500
cttcgccatt taaggcgtta tccccagttt ttagtgagat ctctcccact gacgtatcat    1560
ttggtccgcc cgaaacaggt tggccagcgt gaataacatc gccagttggt tatcgtttt    1620 cagcaacccc ttgtatctgg cttcacgaa gccgaactgt cgcttgatga tgcgaaatgg    1680
gtgctccacc ctggcccgga tgctggcttt catgtattcg atgttgatgg ccgttttgtt    1740
cttgcgtgga tgctgtttca aggttcttac cttgccgggg cgctcggcga tcagccagtc    1800
cacatccacc tcggccagct cctcgcgctg tggcgcccct tggtagccgg catcggctga    1860
gacaaattgc tcctctccat gcagcagatt acccagctga ttgaggtcat gctcgttggc    1920
cgcggtggtg accaggctgt gggtcaggcc actcttggca tcgacaccaa tgtgggcctt    1980
catgccaaag tgccactgat tgcctttctt ggtctgatgc atctccggat cgcgttgctg    2040
ctctttgttc ttggtcgagc tgggtgcctc aatgatggtg gcatcgacca aggtgccttg    2100
agtcatcatg acgcctgctt cggccagcca gcgattgatg gtcttgaaca attggcgggc    2160
cagttgatgc tgctccagca ggtggcggaa attcatgatg gtggtgcggt ccggcaaggc    2220
gctatccagg gataaccggg caaacagacg catggaggcg atttcgtaca gagcatcttc    2280
catcgcgcca tcgctcaggt tgtaccaatg ctgcatgcag tgaatgcgta gcatggtttc    2340
cagcggataa ggtcgccggc cattaccagc cttggggtaa aacggctcga tgacttccac    2400
catgttttgc catggcagaa tctgctccat gcgggacaag aaaatctctt ttctggtctg    2460
acggcgctta ctgctgaatt cactgtcggc gaaggtaagt tgatgactca tgatgaaccc    2520
tgttctatgg ctccagatga caaacatgat ctcatatcag ggacttgttc gcaccttccc    2580
taagagtttt aatgtttgaa gaaagagata taattacagc atcatcccac aaagcagata    2640
ttacaatacc ttgactgggn tattgccaag cggata    2676
```

<210> SEQ ID NO 13
<211> LENGTH: 1485
<212> TYPE: DNA
<213> ORGANISM: Escherichia coli
<220> FEATURE:
<221> NAME/KEY: misc_feature
<222> LOCATION: (16)..(16)
<223> OTHER INFORMATION: n equals a, t, g, or c
<221> NAME/KEY: misc_feature
<222> LOCATION: (144)..(144)
<223> OTHER INFORMATION: n equals a, t, g, or c

<400> SEQUENCE: 13

```
aaatttgtcc tccggntctt ttcccgtgga tacgggcatt gagacccgaa aggscctgta     60
tttgcgaccg gagaggcatc ctgggggctc agtaaaccag tggtcgctgt atggcgggc    120 tgtgcttgcc ggtgattata atgncactgg sagccggtgc cggctgggac ctgggtgtgc    180
```

| cggggaccct | ttccgctgat | atcacgcagt | cagtagcccg | tattgaggga | gagagaacgt | 240 |
| tcagggaaa | atcctggcgt | ctgagctact | ccaaacggtt | tgataatgcg | gatgccgaca | 300 |
| ttacgttcgc | cgggtatcgt | ttctcagagc | gaaactatat | gaccatggag | cagtacctga | 360 |
| acgcccgcta | ccgtaatgat | tacagcagtc | gggaaaaaga | gatgtatacc | gttacgctga | 420 |
| ataaaaacgt | ggcggactgg | aacacctctt | taacctgca | gtacagccgt | cagacatact | 480 |
| gggacatacg | gaaaacggac | tattatacgg | tgagcgtcaa | ccgctacttt | aatgttttcg | 540 |
| gactgcaggg | tgtggcggtt | ggattgtcag | cctcaaggtc | taaatatctg | ggcgtgata | 600 |
| acrrttctgc | ttacctgcgt | atatccgtgc | cgctggggac | ggggacagcg | agctacagtg | 660 |
| gcagtatgag | taatgaccgt | tatgtgaata | tggccggcta | cactgacacg | ttcaatgacg | 720 |
| gtctggacag | ctacagcctg | aacgccggcc | ttaacagtgg | cggtggactg | acatcgcaac | 780 |
| gtcagattaa | tgcctattac | agtcatcgta | gtccgctggc | aaatttgtcc | gcgaatattg | 840 |
| catccctgca | gaaaggatat | acgtctttcg | gcgtcagtgc | ttccggtggg | gcaacaatta | 900 |
| ccggaaaagg | tgcggcgtta | catgcagggg | gaatgtccgg | tggaacacgt | cttcttgttg | 960 |
| acacggatgg | tgtgggaggt | gtaccggttg | atggcgggca | ggtggtgaca | aatcgctggg | 1020 |
| gaacgggcgt | ggtgactgac | atcagcagtt | attaccggaa | tacaacctct | gttgacctga | 1080 |
| agcgcttacc | ggatgatgtg | gaagcaaccc | gttctgttgt | ggaatcggcg | ctgacagaag | 1140 |
| gtgccattgg | ttaccggaaa | ttcagcgtgc | ttaaagggaa | acgtctgttt | gcaatactgc | 1200 |
| gtcttgctga | tggctctcag | ccccccgtttg | gtgccagtgt | aaccagtgaa | aaaggccggg | 1260 |
| aactgggcat | ggtggccgac | gaaggccttg | cctggctgag | tggcgtgacg | ccgggggaaa | 1320 |
| ccctgtcggt | aaactgggat | ggaaaaatac | agtgtcaggt | aaatgtaccg | gagacagcaa | 1380 |
| tatctgacca | gcagttattg | cttccctgta | cgcctcagaa | ataaatgaaa | gtccggaata | 1440 |
| ttaacggctg | attgaattgc | ggtttatgcc | attttcccgg | accaa | | 1485 |

```
<210> SEQ ID NO 14
<211> LENGTH: 22671
<212> TYPE: DNA
<213> ORGANISM: Escherichia coli
<220> FEATURE:
<221> NAME/KEY: misc_feature
<222> LOCATION: (19750)..(19750)
<223> OTHER INFORMATION: n equals a, t, g, or c
<221> NAME/KEY: misc_feature
<222> LOCATION: (20174)..(20174)
<223> OTHER INFORMATION: n equals a, t, g, or c

<400> SEQUENCE: 14
```

| ttaccaattt | catcgtccgg | tacatcctcc | agaacatctc | gcaataaact | ctcgtctgcc | 60 |
| tcattccatg | ccacaccagc | atttgggaaa | cgaggatcga | tctctctttc | cttcttctcc | 120 |
| ttcttacttt | gctctttcg | ggatgataca | gatacgacag | aacgttcttt | taccgctgta | 180 |
| attgccataa | ctgcattgag | cagagatctg | cgctccacat | cgttcagcat | ttttccttca | 240 |
| cagatcaaat | cattcaggat | gtcaatgact | agattcagac | tttcttctgt | tagcttcata | 300 |
| tttcagacct | tgaagtatgt | agataatcag | cacaattact | aatgtgataa | atatcagaag | 360 |
| ataatttaca | ggtaaaccgg | aaaatacatc | tgaagaataa | aggcctcagc | ttaacgtttc | 420 |
| agccagtttg | tgagctgatt | gaggtacggc | gatgacatta | acgggaatta | ctcccctata | 480 |
| gctctgagct | tattttcac | cctggcaaca | tatggtggct | actgcgcatg | gttttggagt | 540 |
| agatatctta | ctactcgtag | aattgtgctt | actggtcagg | ccagcgcaca | ggcattccgt | 600 |

```
gcaatcaata gaacactggt tttttagtct tccgttaccc atcaggatgt tagtgcagat    660
tccggtgtat tcgatcagtt gttcggcgaa tcagcgatcg atcacgatgc gatttcgtat    720
gttagggatg ctggtatgat tactcgctga aaaataatgt gaaaaggcag tttttcttta    780
gacatttagc tcattcatgc tgttgtttta cgttttgctg tcgtgtgcag gattatcttt    840
tcgttacggg acgattcatt ccgtttaat caggagctat tggcgttgct cattggtggg    900
atgccgtaaa gttttaccgc ggcgattaat gatgtgaagt caatccaaat caacggagat    960
ctctcatcat gaatcaacca atacacaatg attactggtt atcccgtttt gaaagtattc   1020
tcaacagtgc cctggtgcaa caccgtgccg tctcgttaat ctgggtggat ttacgtttcc   1080
ctgagcatat gcctgtcacc atcatggatc ccgatccgga ttcagcggtg atttctcgtt   1140
ttttcgaatc cctgaaagcc aaaattcagg cttaccagcg gaaaaaacga cgtaccaaca   1200
agcgtgtgcg tgcaaccacc ctgcattatt tctggtgtcg ggagtttggc aaggaaaaag   1260
gcaggaaaca ttatcacgtg atattactgc tcaacaaaga tacctggtgc tcgccagggg   1320
atttcaccgt tccttcttcg ctggcgacgc tgatccaact ggcatggtgt agcgctctgc   1380
atcttgagcc ctggcagggt aatggactgg ttcattttc caggcggacg cytttccgta   1440
aaccggtatc atctgatgct cgcccttctt ccgatgatac gcctttgtcg ggtggatgtt   1500
ctgaaaccag gaaggcttca gacaaaaagc gggtgaagc cgctgttctc tggatcaagc   1560
gtggtgatgt ggaagcgatg cagaaagcca tggagagagc ccgttatctc gtgaagtatg   1620
agacgaagca gcatgacggt tctggtcaac gtaattatgg ttgcagccgt ggagcggggc   1680
gtctactgga tggcaggtga accctgtaaa acggcatccg gtgccagagt atatgtcaca   1740
gtaagggcgt ggttgatgcc cttagctcgt tttctgaaaa agtcgtcctg aagtcatgtg   1800
tcacgaacgg tgcaatagtg atccacaccc aacgcctgaa atcagatcca gggggtaatc   1860
tgctctcctg attcaggaga gyttatggtc acttttgaga cagttatgga aattaaaatc   1920
ctgcacaagc agggaatgag tagccgggcg attgccagag aactggggat ctcccgcaat   1980
acggttaaac gttatttgca ggcaaaatct gagccgccaa aatatacgcc gcgacctgct   2040
gttgcttcac tcctggatga ataccgggat tatattcgtc aacgcatcgc cgatgctcat   2100
ccttacaaaa tcccggcaac ggtaatcgct cgagagatca gagaccaggg atatcgtggc   2160
ggaatgacca ttctcagggc attcattcgt tctctctcgg ttcctcagga gcaggagcct   2220
gccgttcggt tcgaaactga acccggacga cagatgcagg ttgactgggg cactatgcgt   2280
aatggtcgct caccgcttca cgtgttcgtt gctgttctcg gatacagccg aatgctgtac   2340
atcgaattca ctgacaatat gcgttatgac acgctggaga cctgccatcg taatgcgttc   2400
cgcttctttg gtggtgtgcc gcgcgaagtg ttgtatgaca atatgaaaac tgtggttctg   2460
caacgtgacg catatcagac cggtcagcac cggttccatc cttcgttgtg gcagttcggc   2520
aaggagatgg gcttctctcc ccgactgtgt cgccccttca gggcacagac taaaggtaag   2580
gtggaacgga tggtgcagta cacccgtaac agtttttaca tcccactaat gactcgcctg   2640
cgaccgatgg ggatcactgt cgatgttgaa acagccagcc gccacggtct gcgctggctg   2700
cacgatgtcg ctaaccaacg aaagcatgaa acaatccagg cccgtccctg cgatcgctgg   2760
ctcgaagagc agcagtccat gctggcactg cctccggaga aaaagagta tgacgtgcat   2820 cctggtgaaa atctggtgaa cttcgacaaa cacccctgc atcatccact ctccatttac   2880
gactcattct gcagaggagt ggcgtgatga tggaactgca acatcaacga ctgatggcgc   2940
tcgccgggca gttgcaactg gaaagcctta taagcgcagc gcctgcgctg tcacaacagg   3000
```

```
cagtagacca ggaatggagt tatatggact tcctggagca tctgcttcat gaagaaaaac  3060
tggcacgtca tcaacgtaaa caggcgatgt atacccgaat ggcagccttc ccggcggtga  3120
aaacgttcga agagtatgac ttcacattcg ccaccggagc accgcagaag caactccagt  3180
cgttacgctc actcagcttc atagaacgta atgaaaatat cgtattactg ggaccatcag  3240
gtgtggggaa aacccatctg gcaatagcga tgggctatga agcagtccgt gcaggtatca  3300
aagttcgctt cacaacagca gcagatctgt tacttcagtt atctacggca caacgtcagg  3360
gccgttataa aacgacgctt cagcgtggag taatggcccc ccgcctgctc atcattgatg  3420
aaataggcta tctgccgttc agtcaggaag aagcaaaact gttcttccag gtcattgcta  3480
aacgttacga aaagagcgca atgatcctga catccaatct gccgttcggg cagtgggatc  3540
aaacgttcgc cggtgatgca gccctgacct cagcgatgct ggaccgtatc ttacaccact  3600
cacatgtcgt tcaaatcaaa ggagaaagct atcgactcag acagaaacga aaggccgggg  3660
ttatagcaga agctaatcct gagtaaaacg gtggatcaat attgggccgt tggtggagat  3720
ataagtggat cacttttcat ccgtcgttga catcatgcaa tgtttcctgg ttttcatgca  3780
tccatcattt gtcgctgcga tgccagactt ctggatgcac acatgttgtt ttacttttgt  3840
cagcatcata aatgcgccgg gactggtgaa tggagataag ccattttatt atcgacgtca  3900
gcgaacatac tcaccatgcc ggtatgttcc tgaactgaac aataagtttt gcgctgatta  3960
cagtatgtga aggaggtccg ttacaatgaa ttccgcttat atgcaatcct tgcagacatc  4020
ccaccacttc ccagctgatt taacctacag attatttcct agtgagcttg catatctcat  4080
tgacgactta tatgaaagta cccaacttcc gctggagctc attttaata ctgtactggc  4140
aacgctctca ctctcctgtc agtcactggt tgacgttgtt catcctcaca ccaacatgcc  4200
ggaaccctgc tcactttatc tgttggcaat cgcagagcca ggcgcgggaa aaacaacgat  4260
aaacagactg gtgatgaacc cctgttacga atttgccgat cgactcattc aacaatacga  4320
agagagaaac aaagattata agactgaact acagatctgg aatacccggc agaaagcgct  4380
tgctgccaat ttaagaaagg ctgttaaccg ggggtatccg ggggaacagg aagaagaggc  4440
gctgcgtaat cacgaaagaa ataaaccgac acgtccggtt cgaccgaatt ttatctatga  4500
agatgtttcg cttaaagcgc ttgtggaagg gctcaatgaa catcctgagg caggggttat  4560
ttctgacgag gcggtcactt ttttcagaag ctatctgaaa aattatccgg gcctgttgaa  4620
taaagcatga agtggacaac cgtttgattt tggacgggct gacgagaaat accatatcac  4680
gccacgtctg acattttcgt taatgtccca gccggatgtc tttacgaatt atataaataa  4740
aaatgacgta ctggcgtggg gaagcggatt tctttcccgg tttctgttca gtcagaccgg  4800
aagtccttcc cgggtacggg attatacgag aggcgagttc agaacaaaac caaccctgga  4860
gaagtttcat aaaaagatta acggatttct gttaagccat aacattaatt cccccggtat  4920
gagcaccgaa aggaaaacat taaaacttgc aaagaaagcg ttgggggagt ggcaggaaaa  4980
ccagattaag attgaaagaa aagcgcttgc aggaggggag tgggaacaca tcagagatat  5040
tgttctgaaa gcaggttcta atatactgag gatagctgga atattcacct gctattgcta  5100
taaagatgct gaggaaattg aatcaattgc gcttttaaa gctatgcatc tcatgggctg  5160
gtatctggag gaggcgagca caatatttta tcccatgtct gcacgatgcc agtttgaaca  5220
ggatgcctgt gaactgtatg catggattat gacccgaata aggcagaata attggcgtgc  5280
tatcaggaaa acagacattg aaagatatgg tcccaatcgt ctgagaagag cagaaaaact  5340
```

```
tacacctgta ctcaatcagt taatcgytca gaattatttc cgtatcatcm aagatgcgat   5400
cgcatcaggc actttatgtt tctgctcttg ataataatgg ttacatcctt cctttcggcg   5460
caatgtctta cgaaccgttt gatattgttc caccccagta taaccataat gcgaaaacat   5520
attccgttgt tattccaccg gcattaattc agtcatttac acctgattcc tcagcttaca   5580
ccttatttta aaacaatttt gtgagtagaa acgaaaatc ataatccttc gaatgaaggt    5640
taatgataag gtgtgttgca tatcctgcac ctgtgcaaat attcaccaat cattgggtgt   5700
gaatgaaaat ttctctgaaa aaatcgctat ggtagcaaca gtagcagcac atacactaca   5760
tctgtgattt ggttttgttt tcataatgac ctgctgtcag agctgattga atgctgggat   5820
gtgcgcactg gtggaagagt ggttttcgtt tcagatataa cgaaggtaa tcgaaagatt    5880 gttttaaaca tggattaaag ctaataatta accatattgt gtgagttttt atatataagt   5940
ttgtttgatt cttgccgtga tgagtgctgg ggtatatgac gatgtcgctc tctttctgaa   6000
taacaaatta ttattcgtct gttactgata agggatgcga ttcatgtttt aatagagggt   6060
tgaagaaaat taatttgata ttttttttgta agggaatgga actgtccgga atatgttcag  6120
aacggcggat ttctcatttc cattcattaa acatggataa ttttaattta ggtttattac   6180
tattattata ctcactccct ttttcataca atctctattg ttatttactt cctgtcttta   6240
ctcactctct atctttacga ttatattcac tctatcgtta cattccat tagtattact     6300 cttgttatcg tattcattcc atccctcaat catatttact gtaactcata tgatgttcag   6360
gtaagttatt ctctaccatt ctactgatga tatccatctg ttctcatttt cagtgaaaca   6420
gcaattgatt ttaatcttat ccatcatgaa ctgtatttgc ttaacaatga ttgtttatct   6480
gaagtgtttt aactattctg gttggaaaca atttctctgt catcacagat taactgaatg   6540
tttactcttt gataaggtat ccatgattcc gtcatgttta acagcgcagg ataaacaaca   6600
gaattaacag agtgaatttc tgattatatt tgttgccggt tgtattgttt aaggtactgg   6660
gtgaaaatta ttcatccatg gtatgttgtc ttatgctatc gtgtgtcgtt aacgttcata   6720
tcctggagaa cagattgaat gagcgcatat aagtttattg cattggcctt gtacacggtt   6780
tttacaacca ctgagagcaa gtttgtagtt tatgatgtga ttggtcgcaa tatgtttctt   6840
aaccttctgg tcgtggtgtt ttatcgcgta ttttgcagta tttcgtgatg ttttattgag   6900
tctgtatttt ctttactcct cgtttatctc atctctttag ctaataccat cagataatcc   6960
atttctttct gcataatgct gcgtatcgtt aataacccgt cgtatccatt ctgctacagc   7020
atgcctgata aataccatct gtaagttatt accgttttag atctgattat gagcgaaagc   7080
attaattcgt tcacagagct taaaacatca ttaactttca ggagtcatca acatgcctaa   7140
atcttacaca ccaaactggt tttttaccgc tttacttgac aatcacatca atcaaatgat   7200
ggcacgctat tcctgcctgc gggccttacg catggatttc ttctacagga agatacgcc    7260 cgatttctta caacctgatc atcgctggct gaattgcag ttgcgtatga tgctggagca    7320
ggtggaacaa tttgaaaata tcgttggctt cttctgggtg attgaatgga cggctgatca   7380
tggttttcat gcgcatgcgg ttttctggat cgatcgtcag agggttaaaa aaatatatcc   7440
ctttgcggag cggattacgg aatgctggcg gtctattacg cataacagcg gttcggcaca   7500
ccgctgcaca tatcagccgc attatacata caacatcaac attcctgtgc gccacaacga   7560
tcctgaaagc atcgataata ttcgcggtgc cctgcattat ctggcgaaag aagagcaaaa   7620
agacgggctg tgtgcttacg gctgcaatga agttcctgaa cgtcctgctg cagggcgtcc   7680
tcgtaagcct cacttctgaa gcttaaggcc tgagccttcg ctcctggaaa cactccgtcg   7740
```

```
gtaaaaactt accgccttga ttaatgatgt gaactgaagt caacggagat cattcatcct    7800
gaacctgcat ccggtgtttt gttccttgtc ttcccgttct gcttcggttc ttacttatt    7860 ccatcaatct cattccgcaa gccataacac gtcagctcat tcacgggcag gacgcattgt    7920
gggctgcgca taacggaaca tatcttatga atgctattcc ttatttcgac tatagcctgg    7980 caccettctg gccatcttat cagaacaaag tcatcggcgt ccttgagcgt gcgctgcgtg    8040
agcagtccgg ctcacggata cggcggatcc tgcttcgtct gccgtgggaa catgacaacg    8100
ccttcagcag cagaaagatc tggttcggta tggactttat cgaaaccgtc agtgcgctga    8160
tgaatgcgaa acccggacgc gacctttgct ggctcctgac ccgtcatccg gaaaagccgg    8220
aataccacgt ggtgctgtgc gtcagacagg agtatttcga cggccccgaa ctggatcggt    8280
tgatactgga tgcctggagt aatgtgctgg gtttcgcgtc accaggtgaa gcaaagccgt    8340
accagaagca gatcacccgg gatgtggtac tggatcgccg gtcaccggac tgcgaagccc    8400
tgtttaagga ccttatctgg gcgttcagtg atttcgcccg cgatcgccgt ggagtgtgcg    8460
atccggaagc ccgttgcctt gccggcaatc ccggttggca gtgctgaaag cagcacgcca    8520
tcccatcccc cgtattaccc cattcttcat aaatctcact gaggacattc tgaccatgtt    8580
gaccacaaca agccacgaca gcgtattgct gcgtgccgac gatcccctga tcgacatgaa    8640
ctacatcacc agtttcaccg gcatgaccga taaatggttt tacaggctga tcagtgaagg    8700
gcattttcct aaacccatca aactggggcg cagcagccgc tggtacaaaa gtgaagtgga    8760
gcagtggatg caacaacgaa ttgaggaatc acgaggagca gcagcatgaa acgtgttgtg    8820
atgccagtac gttggcaatg tgcaaaatgc cagcgctggt attgtggaaa tcagccctgt    8880
ccctggtgct ggcgacattc ccgcttatct ttccgctgac ccctccggt cagccaactg    8940 ttagtcatca tttcctgact gattcgtcat tccattctta ttgattataa ctggcattac    9000
accggtgctg gcgtgctttc ctgcgtgtct gcaccggttt gacaaaattc aacagggttt    9060
gaaaaggaac atttcgtgca ataaccgaa gccttaattt cagagccggg agacatccgg    9120
cgttttattc aacatgctgt tgaccactgg ccgcgtctgc tggcagtcca cttcatactc    9180
cattcgacag aaggaaacat ctacgggcaa cagattcatg cattctgcac ttcctttat    9240 cgacaactgc atgaacgtat tactgagagc aatcacactg ccagtccatc atcgtcggtg    9300
gtattacgct ggttgcggga acaacatgga ggagcaacaa ttcgatgcct gttgctgctc    9360
agccagacga gtatttgtca cccgcgagcc agtgtcacag ttgatgaaca atgttcgcaa    9420
gtggtggatt tactgcaaca tagctggcag gtgataagtg ctggcggaca atgccgggtg    9480
gaaaggtgtt tcggggttgc ccggggtgat acatccggtc agtatgttgc gttaaaaaca    9540
gtcgcattgt ctctggggtt accggttgtg accgccatta cccatcgtcc ggtacagcgc    9600
tgtacattga ttacagctca gtgaatcagc gctttctggc ttttcgtcgg tcattctgtc    9660
aacgccacga tgtttgaccg ttatggggat gcggacgatt ccctgcacag cgttgtttca    9720
cggtggtgga tgacgcaaca ccgctgttaa aaacagtcgt tcagtccttt gtgttaccgg    9780
ttgtgacaac aatcagttgg taatggacgt gtgaaccatc tgcgcttccg ttgatttta    9840 tggactgata aagttttgcc agctgaatct ttatacggaa tgctcttcag tatgcgtaca    9900
cgaattgact atctggcgga taaatactct tttaccgaac ggaatgaatc tccacgcctt    9960
cgccggcagt ggcaggatgt tctggaggag tgtcggctga cagaggccgg accagaagaa    10020
cggctgcgta ttgccctgct gaatgtggat tacgtcacca gttttgaact gccttttcgc    10080
```

```
ttgttgctta ctcgtacacc acaactgatt gccgcgcttc gggaagaatg gggcctcagc    10140
cagaaaaatg tggtgttcaa cgataaacgg tttggctgcg tgtacagcct gaaggccagt    10200
ctttctggtg taccggatac attccggtat catctgtctc atcgtattcg ccggatggtt    10260
gggaatgaaa atacatcatc gccatatcag cagattgccc gggaagtgaa agtgccccgt    10320
gaacggctga gtatgcgct ggaagccggt ttactggtga ctgcactgga cgggctgttc     10380
tggtctggta gtcagcgcat tgcggctgat atcctgagac tgagaaagag cggaatgccg    10440
gtggtgacaa cgtccgtgga agcgagcgat aacctgacgg gaacaacccg caaaataccg    10500
gcataccatc tctgacattg cgatgaaggg cagatttcac cttgacaggg gcagagtgcc    10560
gctttttata ctttattccc gtgtctgaaa aaatgtgca aaggaaacgg gaatggcaag    10620
gtccgattac gattttatca atctgtctct gggacatgaa ctgaatgagt ggctggcaga    10680
gagaggttat gccggacagg cggataaccg gaaccgactg gcagaggtgg ttacccgcaa    10740
attgcgggac agtttttatg cggacgtctc ctgggatgcg ctgaatgtgg catacagtga    10800
acaccctgag tggttttcag agcttgcctc cggggatgag gattaacagg caaattatgc    10860
tgctatcggg cagagtgatt acctgcaggg atttccattt ataagaatac gccgcttcgg    10920
gaaagctccg gttctccgga gagttacgat tattttact caaattcaca acacctgaac    10980
tggaacttgc gttgtgtccc ggattgttac tccgcagaag catcctttt accatacgga     11040 tgtttgtttt ccatttcccc tccgaaaaat acaactccga tcacatttct gatattttcc    11100
ccggatttta cataacagga ttgtttctgt atgttttta tctggtgtaa atttcagcac     11160
tgacattccg cttacgttaa tttacactgg ataccccacg aggagaatat gcagcaccgg    11220
caggataact tactggcgaa cagaaatttg ttgcctggta tggtttccgg tcagtacgca    11280
ttcaggatcc gtaccttatc tcaggtggta cgctattttt ccctcctccc ctgcctttgc    11340
attctttcat tttcgtctcc ggcagccatg ctgtctccgg gtgaccgcag tgcaattcag    11400
cagcaacagc agcagttgtt ggatgaaaac cagcgccagc gtgatgcgct ggagcgcagt    11460
gcgccgctga ccatcacgcc gtctccggaa acgtctgccg gtactgaagg tccctgcttt    11520
acggtgtcac gcattgttgt cagtggggcc acccgactga cgtctgcaga aaccgacaga    11580
ctggtggcac cgtgggtgaa tcagtgtctg aatatcacgg gactgaccgc ggtcacggat    11640
gccgtgacgg acggctatat acgccgggga tatatccacca gccggccctt tctgacagag    11700
caggaccttt caggggggcgt actgcacata acggtcatgg aaggcaggct gcagcaaatc    11760
cgggcggaag gcgctgacct tcctgcccgc accctgaaga tggttttccc gggaatggag    11820
gggaaggttc tgaactgcgg gatattgagc aggggatgga gcagattaat cgtctgcgta    11880
cggagccggt acagattgaa atatcgcccg gtgaccgtga gggatggtcg gtggtgacac    11940
tgacggcatt gccggaatgg cctgtcacag ggagcgtggg catcgacaac agcgggcaga    12000
agaataccgg tacggggcag ttaaatggtg tcctttcctt taataatcct ctggggctgg    12060
ctgacaactg gtttgtcagc gggggacgga gcagtgactt ttcggtgtca catgatgcga    12120
ggaattttgc cgccggtgtc agtctgccgt atggctatac cctggtggat tacacgtatt    12180
catggagtga ctacctcagc accattgata accggggctg gcggtggcgt tccacgggag    12240
acctgcagac tcaccggctg ggactgtcgc atgtcctgtt ccgtaacggg gacatgaaga    12300
cagcactgac cggaggtctg cagcaccgca ttattcacaa ttatctggat gatgttctgc    12360
ttcagggcag cagcctgtaaa ctcacttcat tttctgtcgg gctgaatcac acacacaagt    12420
ttctgggtgg tgtcggaaca ctgaatccgg tattcacacg ggggatgccc tggttcggcg    12480
```

```
cagaaagcga ccacgggaaa aggggagacc tgcccgtaaa tcagttccgg aaatggtcgg    12540
tgagtgccag ttttcagcgc cccgtcacgg acagggtgtg gtggctgacc agcgcttatg    12600
cccagtggtc accggaccgt cttcatggtg tggaacaact gagcctcggg ggtgagagtt    12660
cagtgcgtgg cttaaggag cagtatatct ccggtaataa cggcggttat ctgcgaaatg    12720
agctgtcctg gtctctgttc tccctgccat atgtggggac agtccgtgca gtgactgcac    12780
tggacggcgg ctggctgcac tctgacagag atgacccgta ctcgtccggc acgctgtggg    12840
gtgctgctgc cgggctcagc accaccagtg gtcatgtttc cggttcgttc actgccggac    12900
tgcctctggt ttacccggac tggcttgccc ctgaccatct cacggtttac tggcgcgttg    12960
ccgtcgcgtt ttaagggatt attaccatgc atcagcctcc cgttcgcttc acttaccgcc    13020
tgctgagtta ccttatcagt acgattatcg ccgggcagcc gttgttaccg gctgtggggg    13080
ccgtcatcac cccacaaaac ggggctggaa tggataaagc ggcaaatggt gtgccggtcg    13140
tgaacattgc cacgccgaac ggggccggga tttcgcataa ccggtttacg gattacaacg    13200
tcgggaagga agggctgatt ctcaataatg ccaccggtaa gcttaatccg acgcagcttg    13260
gtggactgat acagaataac ccgaacctga agcgggcgg ggaagcgaag ggtatcatca    13320
acgaagtgac cggcggtaac cgttcactgt tgcagggcta tacggaagtg gccggcaaag    13380
cggcgaatgt gatggttgcc aacccgtatg gtatcacctg tgacggctgt ggttttatca    13440
acacgccgca cgcgacgctc accacaggca aacctgtgat gaatgccgac ggcagcctgc    13500
aggcgctgga ggtgactgaa ggcagtatca ccatcaatgg cgcgggcctg gacggcaccc    13560
ggagcgatgc cgtatccatt attgcccgtg caacggaagt gaatgccgcg cttcatgcga    13620
aggatttaac tgtcactgca ggcgctaacc ggataactgc agatggtcgc gtcagtgccc    13680
tgaagggcga aggtgatgtg ccgaaagttg ccgttgatac cggcgcgctc ggtggaatgt    13740
acgccaggcg tattcatctg acctccactg aaagtggtgt cggggttaat ctgggtaacc    13800
tttatgcccg cgagggcgat atcatactga gcagtgccgg aaaactggtc ctgaagaaca    13860
gccttgccgg cggcaatacc accgtaaccg gaacggatgc tcactttca ggggataaca    13920 aagccggagg aaatctcagc gttaccggga caacgggact gacactgaat cagccccgtc    13980
tggtgacgga taaaatctg gtgctgtctt catccgggca gattgtacag aacggtggtg    14040
aactgactgc cggacagaac gccatgctca gtgcacagca cctgaaccag acttccggga    14100
ccgtgaatgc agctgaaaat gtcacccta ccaccaccaa tgataccaca ctgaaaggcc    14160
gcagcgttgc cgggaaaaca ctcactgtca gttccggcag cctgaacaac ggtgggacac    14220
tggttgccgg gcgcgatgcc acggtgaaaa ccgggacatt cagtaatacc ggtaccgtcc    14280
aggggaatgg cctgaaagtt accgccactg acctgaccag caccggcagt attaaaagtg    14340
gcagcacact cgatatcagc gcccgcaatg ccacactgtc cggtgatgcc ggtgcaaaag    14400
acagtgcccg cgttaccgtc agcggtacac tcgaaaaccg cggcagactt gtcagcgatg    14460
acgtgctgac gctcagtgcc acgcagataa acaacagcgg tacctctcc ggggcaaagg    14520 aacttgtggc ttctgcagac acactgacca ccacagaaaa atcggtcaca aacagtgacg    14580
gtaacctcat gctggacagc gcgtcttcca cactggcggg tgaaaccagt gcgggtggca    14640
cggtgtctgt aaaaggcaac agtctgaaga ccacgaccac tgcgcagacg cagggcaaca    14700
gtgtcagcgt ggatgtgcag aacgcacagc ttgacggaac acaggctgcc agagacatcc    14760
ttaccctgaa cgccagtgaa aagctcaccc acagcgggaa aagcagtgcc ccgtcgctca    14820
```

```
gcctcagtgc gccggaactg accagcagcg gcgtacttgt tggttccgcc ctgaatacac    14880
agtcacagac cctgaccaac agcggtctgt tgcaggggga ggcctcactc accgttaaca    14940
cacagaggct tgataatcag cagaacggca cgctgtacag tgctgcagac ctgacgctgg    15000
atataccgga catccgcaac agcgggctta tcaccggtga taatggttta atgttaaatg    15060
ctgtctccct cagcaatccg ggaaaaatca tcgctgacac gctgagcgtc agggcgacca    15120
cgctggatgg tgacggcctg ttgcagggcg ccggtgcact ggcgcttgct ggcgacaccc    15180
tctcacaggg tagtcacgga cgctggctga cggcggacga cctctccctc cggggcaaaa    15240
cactgaatac cgcaggacca cgcagggaca gaatatcacc gtgcaggcgg acagatgggc    15300
gaacagtggt tccgtgctgg caaccggtaa ccttactgct tcggcaaccg gtcagttgac    15360
cagtaccggc gatatcatga gccagggtga caccacgctg aaagcagcca ccacggacaa    15420
ccggggcagt ctgctttcgg ccggcacgct ctcccttgat ggaaactcac tggataacag    15480
cggcactgtc caggctgacc atgtcacgat tcgccagaac agtgtcacca acagtggcac    15540
gctcaccggg atcgccgcgc tgacgcttgc cgcccgtatg gtatcccctc aacctgcgct    15600
gatgaataac ggaggttcat tgctgaccag cggcgatctg acaatcaccg caggcagtct    15660
ggtaaacagc ggggcgatcc aggcggctga cagcctgact gcacgtctga cgggtgagct    15720
cgtcagcaca gcgggcagca aagtcacctc gaacggtgaa atggcgctca gtgcactgaa    15780
tttaagcaac agcggacaat ggattgcaaa aaatctgacc ctgaaggcga actcactgac    15840
cagtgcgggt gacatcaccg gtgtggatac tctcacgctc acggtgaatc agacgctgaa    15900
caatcaggcg aacggaaaac tgctcagtgc aggtgtgctg acgctgaagg cagacagtgt    15960
cacaaacgac gggcaattac agggaaatgc caccaccatc acggcaggac aactcacaaa    16020
cggcgggcat ctgcagggcg aaacgctgac gctggccgcc tccggtggcg tgaacaaccg    16080
ttccggtggt gttctgatga gccggaatgc actgaatgtc agtactgcga ccctgagtaa    16140
ccagggcacg atacaggggtg gtggcggggt ttccctgaac gccactgacc gtctgcagaa    16200
cgacggcaaa atcctctccg gcagtaacct cacgctgacg gcgcaggtgc tggcgaacac    16260
cggcagcgga ctggtacagg ctgccaccct gctgctggat gtggtgaata ctgtcaacgg    16320
cggacgcgta cttgccaccg gcagtgccga cgttaaagga accacgctga ataataccgg    16380
tacgcttcag ggtgcggacc tgctggtgaa ttaccacaca ttcagcaaca gcggtaccct    16440
gctgggaacc tccgggcttg gcgtcaaggg cagttcactg ctgcaaaatg gtacagggcg    16500
gctgtacagt gcaggcaacc tgctgcttga cgctcaggac ttcagtggtc aggggcaggt    16560
ggtggccacc ggtgatgtca cactgaaact gattgctgcc ctcacgaatt acggtaccct    16620
ggccgcaggg aaaaccctt ccgtcacgtc gcaaaatgcc atcaccaacg gcggtgtcat    16680
gcagggtgat gccatggtgc tcggtgccgg agaggcattc accaacaatg gaacgctgac    16740
tgccggtaaa ggcaacagtg ttttcagcgc acagcgtctt ttccttaacg caccgggttc    16800
acttcaggcc ggtggcgatg tgagtctgaa cagccggagt gatatcacca tcagtggttt    16860
taccggcacg gcaggcagtc tgacaatgaa tgtggccggt accctgctga acagtgcgct    16920
gatttatgcg gggaataacc tgaagctgtt tacagaccgt ctgcataacc agcatggtga    16980
tatcctggcc ggcaacagtc tgtgggtaca gaaggatgct tccggcggtg caaacacaga    17040
gattatcaat acttccggga atattgagac gcatcagggc gatattgttg taagaaccgg    17100
gcatcttctg aaccagcggg agggattttc tgccacaaca caacccggac taacccctc    17160
atccattcag ggaatgggaa atgctctggt tgatattccc cttttccctt ttcctgacgg    17220
```

```
cagctatggc tatttcaccc gtgaagttga aaatcagcac ggtacgccct gcaacgggca    17280
cggggcatgc aatatcacaa tggatacgct ttattattac gctccgtttg ctgacagtgc    17340
cacacagcgc tttctcagca gccagaacat cacaacagta accggtgctg ataatccggc    17400
aggccgcatt gcgtcagggc gtaatctttc tgctgaggct gaacgactgg aaaaccgggc    17460
gtcatttatc ctggcgaatg gggatatcgc actctcgggc agagagttaa gcaatcagag    17520
ctggcagacg gggacagaga atgaatatct ggtataccgc tacgacccga aaacgtttta    17580
cggtagctat gcaacaggct ctctggataa actgcccctg ctgtcaccgg aatttgaaaa    17640
caataccatc agattttcac tggatggccg ggaaaaagat tacacgcccg gtaagacgta    17700
ttattccgtt attcaggcgg gcggggatgt taagacccgt tttaccagca gtatcaataa    17760
cggaacaacc actgcacatg caggtagtgt cagtccggtg gtctctgcac ctgtactgaa    17820
tacgttaagt cagcagaccg gcggagacag tctgacacag acagcgctgc agcagtatga    17880
gccggtggtg gttggctctc cgcaatggca cgatgaactg gcaggtgccc tgaaaaatat    17940
tgccggaggt tcgccactga ccggtcagac cggtatcagt gatgactggc cactgccttc    18000
cggcaacaat ggatacctgg ttccgtccac ggacccggac agtccgtatc tgattacggt    18060
gaacccgaaa ctggatggtc tcggacaggt ggacagccat ttgtttgccg gactgtatga    18120
gcttcttgga gcgaaaccgg gtcaggcgcc acgtgaaacg gctccgtcgt ataccgatga    18180
aaaacagttt ctgggctcat cgtattttct tgaccgcctc gggctgaaac cggaaaaaga    18240
ttatcgtttc ctgggggatg cggtctttga tacccggtat gtcagtaacg cggtgctgag    18300
ccggacgggt tcacgttatc tcaacggact gggttcagac acggaacaga tgcggtatct    18360
gatggataac gcggccagac aacagaaagg actgggatta gagtttggtg tggcgctgac    18420
agctgaacag attgctcagc ttgacggcag catgctgtgg tgggagtcag tcaccatcaa    18480
cggacagaca gtcatggtcc cgaaactgta tctgtcgccg gaagatatca ccctgcataa    18540
cggcagcgtt atcagcggga caacgtgca gcttgcggac ggcaatatca ccaacagcgg    18600
cggcagcatc aacgcacaga acgacctttc gctcgacagt accggctata tcgacaacct    18660
gaatgcaggg ctgataagcg cgggcggtag cctggacctg agcgccatcg ggatatcag    18720 caatatcagc tcagtcatca gcggtaaaac cgtacaactg gaaagcgtga gtggcaacat    18780
cagcaatatc acccggcgtc agcaatggaa tgcgggcagt gacagccgat atggtggtgt    18840
gcatctcagc ggtacggaca ccggtccggt tgcgaccatt aaaggcactg attcactttc    18900
actggatgca gggaaaaaca ttgatattac cggggcaacg gtctcgtccg gtggagacct    18960
tggaatgtct gcgggtaatg acatcaacat tgccgtaaac ctgataagcg ggagcaaaag    19020
tcagtccggt ttctggcaca ctgatgacaa cagttcatca tccaccacct cacagggcag    19080
cagcatcagc gccggcggta acctggcgat ggctgcaggc cataatctgg atgtcacagc    19140
atcctctgtt tctgccgggc acagcgccct gctttctgca ggtaacgacc tgagtctgaa    19200
tgcagtcagg gaaagcaaaa acagtcgcaa cggcaggtca gaaagtcatg aaagccacgc    19260
agctgtgtcc acggtgacgg cgggcgataa cctcctcctt gttgccggtc gtgatattgc    19320
cagtcaggct gccggtatgg ctgcggaaaa taacgtggtc atccggggcg acgtgatgt    19380 gaacctggtg gcagagtctg ccggcgcagg cgacagctat acgtcgaaga aaagaaaga    19440 gattaacgag acagtccgtc agcagggaac ggaaatcgcc agcggtggtg acaccaccgt    19500
caccgcagga cgggatatca ccgctgttgc gtcatccgtt accgcaaccg gcaatatcag    19560
```

```
cgtgaatgcc ggtcgtgatg ttgccctgac cacggcgaca gaaagtgact atcactatct    19620
ggaaacgaag aaaaaaagcg gaggttttct cagtaagaaa accacccaca ccatcagtga    19680
ggacagtgcc tcccgtgaag caggttccct gctgtcgggg aaccgcgtga ccgttaacgc    19740
cggtgataan ctgacggtag agggttcgga tgtggtggct gaccgggatg tgtcactggc    19800
ggcgggtaac catgttgatg ttcttgctgc caccagtaca gatacgtcct ggcgctttaa    19860
ggaaacgaag aaatccggtc tgatgggtac cggcggtatt ggtttcacca ttggcagcag    19920
taagacaacg cacgaccgcc gcgaggcsgg gacaacgcag agtcagagtg ccagtaccat    19980
cggctccact gccggtaatg tcagtattac cgcgggcaaa caggctcata tcagcggttc    20040
ggatgtgatt gcgaaccggg atatcagcat taccggtgac agtgtggtgg ttgacccggg    20100
gcatgatcgt cgtactgtgg acgaaaaatt tgagcagaag aaaagcgggc tgacggttgc    20160
cctttccggc acgntgggca gtgccatcaa taatgcggtc accagtgcac aggagacgaa    20220
ggagagcagt gacagccgtc tgaaagccct gcaggccaca agacagcgc tgtctggtgt    20280 gcaggccgga caggctgcgg caatggccac cgcaaccggt gacccgaatg cgacgggagt    20340
cagcctgtcg cttaccaccc agaaatcgaa atcacaacaa cattctgaaa gtgacacagt    20400
atccggcagt acgctgaatg ccgggaataa tctgtctgtt gtcgcaaccg gcaaaaacag    20460
gggagataac cgcggagata ttgtgattgc aggaagccag cttaaggccg gtggtaacac    20520
aagcctggat gccgcgaatg atgttctgtt gagtggcgct gcaaacacac aaaaaacaac    20580
gggcaggaac agcagcagtg gcggtggcgt gggtgtcagt atcggtgccg gtggtaacgg    20640
tgccggtatc agcgtctttg ccagcgttaa tgcggcaaaa ggcagcgaga aggtaacgg    20700 tactgagtgg actgaaacca caacagacag cggtaaaacc gtcaccatca acagtggtcg    20760
ggatacggta ctgaacggtg ctcaggtcaa cggcaacagg attatcgccg atgtgggcca    20820
cgacctgctg ataagcagcc agcaggacac cagtaagtac gacagtaaac agaccagcgt    20880
ggctgccggc ggcagttta ccttttggctc catgaccggc tcaggttaca tcgctgcctc    20940
ccgggataag atgaagagcc gctttgactc cgttgctgaa caaaccggga tgttttccgg    21000
agatggcggc ttcgatatca cggtcggcaa ccacacccag ctcgatggtg cggttatcgc    21060
ttccacggcg acggcagata aaaacagcct cgataccggg acgctcggct tcagcgatat    21120
tcacaacgaa gcggattata agtcagtca cagtggaatc agtctgagcg gtggtggcag    21180
cttcggggat aaatttcagg gtaacatgcc gggtggcatg atatccgccg gaggtcacag    21240
cggacatgcg gaaggaacga ctcaggccgc agtggcagat ggcacaatca ccatccggga    21300
cagggacaat cagaagcaga atctggcgaa cctgagccgt gaccctgcgc acgctaatga    21360
cagtatcagc ccgatattg acaaggagaa agagcagagg cgtctgcaga cagtggggct    21420
tatcagtgac attggcagtc aggtggcgga tatcgcgcgg acgcagggg aactgaatgc    21480 gttgaagctg cgcaggataa atatgggcct gttccggcgg atgcgacgga gaacagcgg    21540 caggcatatc tggcaaaact gcgtgatacg ccggaataca aaaggaaca ggaaaagtat    21600 ggtaccggca gcgatatgca gcgcggtatc caggctgcaa cggctgcact tcagggcctg    21660
gtgggcggca atatggcagg cgcgctggca ggtgcttcag cgccggagct ggcgaacatc    21720
atcggtcatc acgcgggtat tgatgacaat acagcggcaa aagccattgc ccatgccatt    21780
ctcggtggtg tgacagcagc ccttcagggc aacagtgcgg cagcaggcgc aattggtgcg    21840
ggtactggtg aagtgatcgc gtcagccatt gcgaaaagcc tctacccggg cgtagatccg    21900
tcgaaactga cagaagatca gaagcaaact gtaagcacgc tggcaacgct gtcagcgggt    21960
```

```
atggccggcg gcattgccag tggcgatgtg gctggcgcgg ctgctggagc tggtgccggg    22020
aagaacgttg ttgagaataa tgcgctgagt ctggttgcca gaggctgtgc ggtcgcagca    22080
ccttgcagga ctaaagttgc agagcagttg ctagaaatcg gggcgaaagc gggcatggcc    22140
gggcttgccg gggcggcagt caaggatatg gccgacagga tgacctccga tgaactggag    22200
catctgatta ccctgcaaat gatgggtaat gatgagatca ctactaagta tctcagttcg    22260
ttgcatgata agtacggttc cggggctgcc tcgaatccga atatcggtaa agatctgacc    22320
gatgcggaaa aagtagaact gggcggttcc ggctcaggaa ccggtacacc accaccatcg    22380
gaaaatgatc ctaagcagca aaatgaaaaa actgtagata agcttaatca gaagcaagaa    22440
agtgcgatta agaagatcga taacactata aaaaatgctc tgaaagatca tgatattatt    22500
ggaactctca aggatatgga tggtaagcca gttcctaaag agaatggagg atattgggat    22560
catatgcagg aaatgcaaaa tacgctcaga ggattaagaa atcatgcgga tacgttgaaa    22620
aacgtcaaca atcctgaagc tcaggctgcg tatggcagag caacagatgc t            22671
```

<210> SEQ ID NO 15
<211> LENGTH: 2385
<212> TYPE: DNA
<213> ORGANISM: Escherichia coli
<220> FEATURE:
<221> NAME/KEY: misc_feature
<222> LOCATION: (131)..(131)
<223> OTHER INFORMATION: n equals a, t, g, or c
<221> NAME/KEY: misc_feature
<222> LOCATION: (133)..(133)
<223> OTHER INFORMATION: n equals a, t, g, or c

<400> SEQUENCE: 15

```
gggcgacacg gaaatgttga atactcatac tcttcctttt tcaatattat tgaagcattt      60
atcagggtta ttgtctcatg agcggataca tatttgaatg tatttaggca actgaaaccc     120
gctgacggat nangtgtaca gtggcatcag tggacggmtt acagcataag tgcttaaggc     180
gcgtgaccat acagmtacgg tcgctgcaga gaacagggag aatatcatcc ggaacacggt     240
ggccataaac cgtaacacca ggggctgct ttccccggga gaggtgctgg agatgcatgc      300
ggacgtctga acagtcagca gggctgatta atgagaatca cgaggaaatg aagcgggagc     360
cgtacagtga ggataaattt aacgccatag cggctgtggg cgggtatagt gccaagcaga     420
ctgcttaaag gcaggtacta ctttcagtgg cggctatgtt tcctggaatg tgggtgtcaa     480
ctggtagttc tgaacccggg cctgagtcac cggggaggca gttttcggta tgaagtaatg     540
attcgctgcc tgttttttctc cccgatggca taactgactg ttcccgggta ttcctgaaga    600
tctgagagga agagtgtata tgctgaacta tcgcataagg tcagtgcagc tatttattgt     660
aaacggtcgg gctgacaggg cgcaggtgcg tctggaatgc gacgatgaag ccgttttttga   720 atgttatctt cttgctgaag gggaagggga actgaaagaa ctgagcctgt cagagctgga     780
agagcgggcg ctgatgtatg cggcagacag tttccgttat gaatgataag tcagttatac    840
cggtaatggt aaacggagcc ggtatccggg atacaagggg cagagagtat gctgattatt    900
attatgaccc gggacagata tctggaatat ggcctgatgc gtatactgag cggatatcag    960
gtcacgacag gcagagagct gtttaatgcc ggaaagcaac gtcagtcact tcccgaagac    1020
agttatgtga ttctctgtga ccgtaatctg gaaaggctta catactctat gttctgtggg    1080
cgtcggtttc ttgtcattcc tgtttcctct gtgagatgcc tgacagatat caggcaaacc    1140
atccgccgtg gagcgtggct gttcggacat acggcaaggc cactgacccg gacagagatg   1200
```

```
gtggtggtct tcggggttgt tttccatgac tacgggttta cctttctggc agaccggctg   1260
gggataacca tgaagacggt atgtgcgcat ctttacaatg cgatggagaa aaatggtatg   1320
cgcggcgtca gtattaaata tctctgcaac accatagacc ggtaaaaaga tggttttctg   1380
ataaaggctg ttgcgacggg gatttctgtg catgctgtgt cacgggcatc ccagctctcc   1440
ggataattaa tgttatgtag tcaggcgtga taaatttcat atggaacagg tatgcgtttt   1500
atttgtgata acagttaatg aggtgtttcc atacacactg aagttacctg taatattagc   1560
gggggatttg aatgatgttg cgtgtctgcg accactcgtt tattcatgca aataagtgga   1620
ctgctggatc cacggtaaga gtacagcgag ggccgtattg acgggatgt gttattcagc    1680 gggcagtgct atgcgccacg gaagcagttc gctgacacgg ttgaccggcc agtcagctat   1740
gacgccaaac acatggcgaa ggtagttttc tggatcctcg tcgttcagtt tgcacgtccc   1800
gatcaggctg tacagtagca ctccccgctc accaccatgc tcagagctgc gtattaccgt   1860
gaaggagatc ggtgagtaac cctctgtgtc ggcacattat agccgtcaca tcggataact   1920
gttatccttc tgttctgatg tattctggga gtgatgtttt cactcctgat aagagcatta   1980
ctaattacag ctgcttttcg gataacattc gggcagtttt ctttaattct gaagtctgaa   2040
agagatatca gtaattgtat tgcttttaaa cattgtcagt atttatttgt ccaaatcgtt   2100
cacgtttctc ataatcttcc cgacagtcac catcacaaaa caatccagtc ttaacaggtt   2160
ctccgcagtt atagcagaat cctgtttcag ggagtctatt ccggatacga ttttttagtc   2220
tgatgctcat gctgaattgt tcattttcat aagcaatatc tgcactatct gccataaacg   2280
atcctctgag gagaccacat ctttataacc caccaccgaa atattacaaa gtaatactca   2340
ttgtataatc tttaaccrgg ggcaggataa ttgtatcctg ccccct                  2385
```

<210> SEQ ID NO 16
<211> LENGTH: 746
<212> TYPE: DNA
<213> ORGANISM: Escherichia coli
<220> FEATURE:
<221> NAME/KEY: misc_feature
<222> LOCATION: (718)..(718)
<223> OTHER INFORMATION: n equals a, t, g, or c
<221> NAME/KEY: misc_feature
<222> LOCATION: (741)..(741)
<223> OTHER INFORMATION: n equals a, t, g, or c

<400> SEQUENCE: 16

```
ctttcagacc agcgtttcct gtcaggagat gaggaagaaa catcaaagta taaaggcggc    60
gatgaccatg atacggtatt cagtggcggt attgcggccg gttatgattt ttatccgcag   120
ttcagtattc cggttcgtac agaactggag ttttacgctc gtggaaaagc tgattcgaag   180
tataacgtag ataagacag ctggtcaggt ggttactggc gtgatgacct gaagaatgag    240
gtgtcagtca acacactaat gctgaatgcg tactatgact tccggaatga cagcgcattc   300
acaccatggg tatccgcagg attggctacg cagaattcac cagaaaacaa ccggtatcag   360
tacctgggat tatgagtacg gaagcagtgg tcgcgaatcg ttgtcacgtt caggctctgc   420
tgacaacttc gcatggagcc ttggcgcggg tgtccgctat gacgtaaccc cggatatcgc   480
tctggacctc agctatcgct atcttgatgc aggtgacagc agtgtgagtt acaaggacga   540
gtggggcgat aaatataagt cagaagttga tgttaaaagt catgacatca tgcttggtat   600
gacttataac ttctgacgac actgctcctg aacgataatt gcgtatattc tgtaattaag   660
ataattgcat atckctctgca attaarcaga aatacccctgc agtctattac tgcagggntg  720
```

| | |
|---|---|
| tcttttatct gttttacaga naattt | 746 |

<210> SEQ ID NO 17
<211> LENGTH: 411
<212> TYPE: DNA
<213> ORGANISM: Escherichia coli

<400> SEQUENCE: 17

| | |
|---|---|
| tctgtttgtc gtttttccc cgttgtagcg gytctgctcc tggcttccct gatagtcagc | 60 |
| ccgcaggcgc cagggcccca gattcccccc cacagtcccg ttataactga actgatgaga | 120 |
| gtctcctccc tgataattac gggaaaccgt cccgttgagg ttataatcca gcatcagtcc | 180 |
| gggaatgccg tcgtcccagc gtgagggagg cagccaggtg gcatcagaat actcaagccc | 240 |
| agctgcggca tattgatgcg taatacgccc gctccggtat caggacgaat atccactccc | 300 |
| ggcaacccat gaaaatccgc acactgacca tcatgccagt aaacaacttt atccagagat | 360 |
| tctgctgtta accccatcag tctgaccata tctgatgtca gacaggcctg c | 411 |

<210> SEQ ID NO 18
<211> LENGTH: 977
<212> TYPE: DNA
<213> ORGANISM: Escherichia coli
<220> FEATURE:
<221> NAME/KEY: misc_feature
<222> LOCATION: (956)..(956)
<223> OTHER INFORMATION: n equals a, t, g, or c

<400> SEQUENCE: 18

| | |
|---|---|
| tattatcgcg cgcgcgctgc acaggggtta tctacatctg ctgctgctgc cggtttaatt | 60 |
| gcttctgtag tgacattagc aattagtccc ctctcattcc tgtccattgc cgataagttt | 120 |
| aaacgtgcaa ataaaataga ggagtattca caacgattca aaaaacttgg atacgatggt | 180 |
| gacagtttac ttgctgcttt ccacaaagaa acaggagcta ttgatgcatc attaacaacg | 240 |
| ataagcactg tactggcttc agtatcttca ggtattagtg ctgckgcaac gacatctctt | 300 |
| gttggtgcac cggtaagcgc actggtaggt gctgttacgg ggataatttc aggtatcctt | 360 |
| gaggcttcaa agcaggcaat gtttgaacat gttgccagta aaatggctga tgttattgct | 420 |
| gaatgggaga aaaacacgg taaaaattac tttgaaaatg gatatgatgc ccgccatgct | 480 |
| gcatttttag aagataactt taaaatatta tctcagtata taaagagta ttctgttgaa | 540 |
| agatcagtcc tcattactca acaacattgg gatatgctga taggtgagtt agctagtgtc | 600 |
| accagaaatg gagacaagac actcagtggt aaaagttata ttgactatta tgaagaggga | 660 |
| aagcggctgg aaagaaggcc aaaagagttc cagcaacaaa tctttgatcc attaaaagga | 720 |
| aatattgacc tttctgacag caaatcttct acgttattga aatttgttac gccattgtta | 780 |
| actcccggtg aggaaattcg tgaaggaggg cagtccggaa aatatgaata tattaccgag | 840 |
| ttattagtca agggtgttga taaatggacg gtgaagggg ttcaggacaa ggggtctgta | 900 |
| tatgattact ctaacctgat tcagcatgca tcagtcggta ataaccagta tcgggnaatt | 960 |
| cgtattgagt cacacct | 977 |

<210> SEQ ID NO 19
<211> LENGTH: 400
<212> TYPE: DNA
<213> ORGANISM: Escherichia coli

<400> SEQUENCE: 19

-continued

| | |
|---|---|
| tttcttaagt ccggcattgc cacgcgtaac ccccacttca accgcatgat tgagcagatc | 60 |
| gaaaaagtgg cgatcaaatc ccgcgcgccg attctgctta acggtccaac cggcgcgggc | 120 |
| aagtcatttc tggcgcgacg catcttagag ttaaaacagg cgcggcatca gtttagcggc | 180 |
| gcktttgtgg aagtgaactg cgccaccctg cgcggcgata ccgccatgtc gacgctgttt | 240 |
| ggtcatgtaa aaggcgcgtt taccggggcg cgggaatctc gtgaaggttt attacgcagc | 300 |
| gccaacgggg aaatgttgtt tcttgatgag attggcgaac tggcgcgac gaacaggcaa | 360 |
| tgctgctgaa acccattgaa grggaaaacc ttttacccgt | 400 |

<210> SEQ ID NO 20
<211> LENGTH: 12368
<212> TYPE: DNA
<213> ORGANISM: Escherichia coli
<220> FEATURE:
<221> NAME/KEY: misc_feature
<222> LOCATION: (6059)..(6059)
<223> OTHER INFORMATION: n equals a, t, g, or c
<221> NAME/KEY: misc_feature
<222> LOCATION: (10634)..(10634)
<223> OTHER INFORMATION: n equals a, t, g, or c

<400> SEQUENCE: 20

| | |
|---|---|
| gtatgcgttt tcattaagat attctctgct gtagagaaac ttatagcaat ataatctgat | 60 |
| aatatctttt atgtaaaatt taaatagttc acctgtgaca gatatatgtt ttctgctcag | 120 |
| taactcctgt gtattaagcc attcccgtga ccgaagcaca cccttgtgaa aacttttttct | 180 |
| tacttgcttt gaggcacggc attgatgtaa tattttttgcg tcctcaataa ttctctttcc | 240 |
| cgttttattt tttgcagcat ctcttactcc ataaaatatc tcccggtcca gacttttgtc | 300 |
| atatttactg attatacgac aaatattcct gacccgacga ttctctttat ttcgcttcca | 360 |
| tagcttataa tgatcatcgc ataaccttaa ggcatttgcc tcatcaaatt ctgaaacagg | 420 |
| attactgcat ttttttattcc gacaaatacc tttgttttta gccatactct tcttcccgtc | 480 |
| aatggaaaaa ttttcacacc catattacct gaatgataaa ccggattagt gtgatccggt | 540 |
| tcagtgaaat caacaggata ccggtatgcc attcagcaat tcttccctct ccgcgcaagt | 600 |
| gaaatcatat ctgacgtttc ttcctgaaga aatacgccag aaaatccttg aacatctcca | 660 |
| cggtgttatt cattacgagc ccgtgattgg cattatgggt aaatccggca ccggcaagag | 720 |
| cagcctgtgt aatgccattt ttcagtcccg tatctgcgcc acgcatcccc tgaacggctg | 780 |
| cacccgccag gctcatcgtc ttaccctgca gctcggtgaa cgcagaatga cgctggtcga | 840 |
| tctgcccggc attggtgaaa caccgcagca tgatcaggaa taccgagcgc tttatcgtca | 900 |
| gttactgccg gaactggatc tgattatctg gatcctgcgg agtgatgaac gtgcgtatgc | 960 |
| tgccgatatt gccatgcatc agttttttact gaatgagggc gcagatccct cgcgctttct | 1020 |
| gtttgttctc agccatgccg atcgcatgtt tcctgctgaa gaatggaatg ccacagaaaa | 1080 |
| atgcccgtcc cgtcaccagg aactctcact ggcgacagta atagcccggg tggccaccct | 1140 |
| gttcccttca tcatttccgg tactcccgt agccgcacct gcaggctgga accttccagc | 1200 |
| gctggtgtca ctgatgatcc acgcgctgcc accacaggca accagcgcag tttattcaca | 1260 |
| tatcaggggg gaaaaccgct ctgaacaggc ccggaaacac gcacaacaga cttttggtga | 1320 |
| tgccatcggg aaaagttttg acgacgccgt tgcccggttc agttttccgg cctggatgtt | 1380 |
| acagcttctg cgtaaagccc gggaccgcat tatccacctg ctgatcacac tgtgggagcg | 1440 |
| tctgttctga cacactcacg ccgacagatg tgtcgctgga ttaacgagca ttcttctttt | 1500 |

```
tatgaaatca tgcttaaaaa tcagataatt araagaatat tttttctgct gcattttatt      1560
cctgattatc cggatgcgac acatcctttc aacatcatga tgcataataa catcatgaaa      1620
taaaagatgt tttcttacgg agtgcacatc tatgtctgat aatcgttccc ggcatgatcg      1680
cctggcggtt cgcttatcac tcattatcag ccgactgatg gccggagaat ctctgtcact      1740
aaaaacactg tcagatgaat ttggcgttac agaacgtact ttacagcgcg attttcatca      1800
gcgtctggtt cacctagatt tagagtacag aaatggcagg tacagcctca gacgacagag      1860
cagcccaggt gcgatccctg aaatgctttc ttttatacag aataccggga tcgcacggat      1920
acttccgctc cggaacggac gactgataac ctgtcttacc gacaaccagg agccctctcc      1980
ctgccttatc tggctaccgg cgccggatat cactgcaacg ttccccgagt gtttctcgca      2040
actcatcctg gcaataagac agtgtatcca catctctctg atgactgagc gatggtatcc      2100
gtcactggag ccctgccggc tcatttatta cagcggtagc tggtatctga tcgcgttaca      2160
gaagggaaaa ctgcaggtct ttcctctggc agatatcaaa tcagtcagcc tgacatcaga      2220
acggtttgaa cggagaggcc acatccacag tctggtcgct gaagagcgtt ttatctccgc      2280
cctgccacat ttctctttca tccataaact tatcaacacc tttaacctgt gatcgccggc      2340
ctgccaaagc cgtcccgaca ggtatggaga caatatgttg aacagaaaac taaatatacg      2400
gctacgtcat tccctgaaca gtcactgcat accttccatc attatcaata acaccgtacg      2460
ttcatttcag aggtcagtca tgaataccag agctcttttt cccctgctgt tcactgtggc      2520
atcattctcc gcctccgccg gcaactgggc tgtcaaaaac ggctggtgtc agaccatgac      2580
ggaagatggt caggcgctgg taatgctgaa aaatggcacg attggtatta ccggcctgat      2640
gcagggatgc ccgaatggtg tacagacgct cctgggcagc cgtatcagta ttaacggtaa      2700
cctgatcccc acatcacaaa tgtgtaatca gcagacggga ttcagggctg ttgaggtgga      2760
aatcggacag cgccggaaa tggtcaaaaa agccgttcac tccatagcag agcgtgatgt      2820
gtccgtttta caggcatttg gtgtacgaat ggaattcacc cgcggtgata tgctgaaggt      2880
ctgtccgaaa tttgtcacat cacttgccgg ttttccccg aaacagacga ccactattaa      2940
taaagattcc gtcctgcagg ctgcccggca ggcatacgcc cgggaatatg acgaggaaac      3000
aacagaaacc gctgattttg gctcttacga agtaaaaggc aataaggttg agtttgaagt      3060
attcaatcct gaagaccgtg cgtacgacaa agtgaccgtc acggttggtg ctgacggtaa      3120
tgccaccggc gccagcgttg aatttatcgg aaaatagccg gtatgtcgga ctgccaccct      3180
gttttattgc ccgaaggccc tttctcacgc gaacaggcga tggctgtcac aacagcttac      3240
cgcaatgtgc ttattgaaga tgaccaggga acgcatttcc ggctggttat ccgcaatgcc      3300
gaagggcagc tacgctggcg gtgctggaat tttgaacctg atgccggaaa acagctaaat      3360
tcgtatctcg ccagtgaggg aattctcagg caataaacgt cttcatttca tccatcaggc      3420
cgcgtcttct ccgggagacg cggcctttc gtttataccg ctaattcatt cataaggagc      3480
aaagtatgca attagccagt cgttttggtc atgtaaatca gatccgtcgg gagcgcccac      3540
tgacacgcga agaactgatg taccacgtcc gagtatttt tggagaagac cggcacacct      3600
cccgcagtga acgtatgcg tacattccca ccatcaccgt cctggaaaat ctgcagcggg      3660
aaggctttca gccgtkcttc gcctgccaga cccgtgtgcg cgaccagagc cgccgggaat      3720
ataccaaaca tatgctgcgt ctgcggcggg ccggacagat aaccggtcag catgtgcctg      3780
aaattattct gctcaactcc catgacggtt catccagcta ccagatgtta cccggatatt      3840
ttcgtgccat ttgtaccaat ggcctggtct gcggtcagtc gctgggagaa gtccgggtgc      3900
```

```
cacaccgggg aaacgtggtg gacagggtca tagaaggtgc ttacgaagtg gtgggcgtgt   3960
ttgacctgat tgaggaaaag cgtgatgcca tgcagtcgct ggtcctgccg ccaccggcac   4020
gccaggcgct ggcacaggcg gcgctgactt accgttatgg tgatgaacat cagcccgtca   4080
ccactaccga cattctgacg ccacgacgcc gggaggatta cggtaaggac ctgtggagtg   4140
cttatcagac catccaggag aatatgctga aaggcgggat ttccggtcgc agtgccagag   4200
gaaaacgtat ccatacccgg gccattcaca gcatcgatac cgacattaag ctcaaccggg   4260
cgttgtgggt gatggcagaa acgctgctgg agagcctgcg ctgataccgt ttccctgaaa   4320
gcgcagtcct gttcacggct gtcccttccc ccagacattc caccattcat ttacttttta   4380
taaggaataa tctcatgaca acctcttcgc ataattccac cacaccttct gtttccgtgg   4440
ccgctgcatc agggaataac cagtctcagt tggttgccac tcccgtccct gatgaacagc   4500
gcatcagctt ctggccgcag cattttggcc tcattccaca gtgggtcacc ctggagcccc   4560
gtgtcttcgg ctggatggac cgtctgtgcg aaaactactg cgggggtatc tggaatctgt   4620
acaccctgaa caacggtggc gcatttatag cacctgaacc ggatgaagat gatggagaaa   4680
cctggatact gttcaatgcc atgaacgtta accgcgctga atgagcccg gaagctgccg    4740
gcattgccgc ctgtctgatg acgtacagcc atcatgcctg tcgtacggag aattatgcca   4800
tgacggtcca ttattaccgg ttgcgggatt acgccctgca gcatccggaa tgcagcgcca   4860
ttatgcgcat cattgactga aaggggccgg aataatgcaa cagatttcct ttctgcccgg   4920
agaaatgacg cccggcgagc gcagtcacat tctgcgggcc ctgaaaaccc tggaccgcca   4980
tcttcatgaa cccggtgtgg ccttcacctc cacccgtgcg gcacgggaat ggctgattct   5040
gaacatggcg ggactggagc gtgaagagtt ccgggtgctg tatctgaata accagaatca   5100
gctgattgcc ggtgaaaccc tcttcaccgg caccatcaac cgcacggaag tccatccccg   5160
ggaagtgatt aaacgcgccc tgtaccacaa tgccgctgcc gtggtgctgg cgcacaatca   5220
cccgtccggt gaagtcacac ccagtaaggc agaccggctt atcaccgaac gtctggtaca   5280
ggcactgggc ctggtggata tccgggtgcc ggaccatctg atagtcggtg gcagccaggt   5340
tttctccttt gcggaacacg gtctgcttta acccgtcacc gtcacaatca ccttcatatc   5400
acttcagttt ctctttctca gctgtttctt actttcacat tcaggaggac tattctcatg   5460
aaaatcatca cccgtggtga agccatgcgt attcaccgtc agcatcctgc atccgtcttt   5520
tttccgttct gtaccggtaa ataccgctgg cacggtagca cggatacata taccggccgt   5580
gaagtacagg atattcccgg tgtgctggct gtgtttgctg aacgccgtaa ggacagtttt   5640
ggcccgtatg tccggctgat gagcgtcacc ctgaactgaa tcaggacggg cattcagaag   5700
agcagaatta tcgccaccac cggaccattc ttaaccaatt ttctgtgagg attttatcgt   5760
gtcagacact ctccccggga caacgcatcc cgacgataac aacgaccgcc cctggtgggg   5820
gctaccctgc accgtgacgc cctgttttgg ggcacgtctg gtgcaggagg gtaaccggtt   5880
gcattacctt gcagaccgcg ccggtatcag aggccggttc agcgacgcgg atgcgtacca   5940
tctggaccag gcctttccgc tgctgatgaa acaactggaa ctcatgctca ccagcggtra   6000
actgaatccc cgccatcagc ataccgtcac gctgtatgca aaaaggctga cctgcgaanc   6060
gacaccctcg gcagttgtgg ctacgtttat atggctgttt atccgacgcc cgaaacgaaa   6120
aagtaactct ccagaataac cttctgcccc ggcctggtgc tttccaccac cccactttcc   6180
attttcatc tctgcatatc aggaaaatct tcagtatgaa cacattaccc gatacacaca   6240
```

```
tacgggaggc atcgcattgc cagtctcccg tcaccatctg gcagacactg ctcacccgac    6300
tgctggacca gcattacggc ctcacactga atgacacacc gttcgctgat gaacgtgtga    6360
ttgagcagca tattgaggca ggcatttcac tgtgtgatgc ggtgaacttt ctcgttgaaa    6420
aatacgcact ggtgcgtacc gaccagccgg gattcagcgc ctgtactcgt tctcagttaa    6480
taaacagtat tgatatcctc cgggcccgcc gggcaaccgg cctgatggcc cgcgacaatt    6540
acagaacggt aaataacatt accctgggta agcatccgga gaaacgatga aactttccct    6600
gatgctggaa gccgacagaa ttaatgtgca ggcactgaac atgggcgaa ttgtcgttga     6660
cgtcgatggt gttaatctca ctgaactgat taacaaggtc gctgaaaacg gttattcact    6720
ccgcgtggtg gaggaatccg accaacagtc aacctgcaca ctaccaccgt ttgcaaccct    6780
tgccggcata cgctgcagta ccgcacatat cacggaaaag gataacgcct ggctgtactc    6840
gctgtcacac cagaccagtg acttcggtga atcagaatgg attcatttca caggtagcgg    6900
atatctgtta cgtaccgatg cgtggtcata tccggttctg cggcttaaac gcctggggct    6960
gtcaaaaacg ttccgtcgtc tggttatcac acttacccga cgttatggcg tcagtctcat    7020
tcatctggat gccagcgctg aatgcctgcc gggtttaccc actttcaact ggtaaccagg    7080
aacaacatga atcattaac cacggaaacc gcactggata ttctgattgc gtggctgcag     7140
gacaatatcg actgcgaatc gggaattatc tttgacaaca atgaggataa aacggattca    7200
gcagcactgt tgccctgtat cgaacaggcc agagaggata tccgtaccct gcgccaactg    7260
cagcttcagc accagaaccg gtgagtctca ctcatcatct cactcaccag acttcattcc    7320
actsacgcca gcctgaacac ggctggcgtt ttcatttatc tgcaaaaagg aatatcgatt    7380
atgtctgaaa tcacagtctc ccgtccggaa gtggtcaacg agaatacgga cgttatctgc    7440
tccacctcag tcaggtacag gtcactggaa tatgataatt ttccggaaat cagcgaagcg    7500
aacattctga gcacatttga acaactgcac cagaacaaag atgaagtgtt tgaacgggga    7560
gtgatcaacg tcttcaaagg gctgagctgg gattacaaaa ccaactcacc ctgtaaattt    7620
ggcagtaaaa ttatcgtcaa caatctggtg agatgggacc agtggggatt tcatcttatc    7680
agtggaatgc aggcagatcg cctggctgac ctggaaagaa tgttgcatct gctcagcggt    7740
aaaccgatcc ccgacaaccg agggaatatc accattaatc tggatgacca catacagtcc    7800
gttcagggta aggacgcta tgaagatgag atgttcatca ttaaatactt taagaaggga    7860
tctgcacaca tcactttcaa aaggctggag ctgattgaca gaattaacga tataatagcc    7920
aggcactttc cttctgtgct ctcagcctga ccccgagttt gattcccttt cgatatcaaa    7980
agggactgcg ggtacaaaag agggtacatc tttcaccaaa ccaaacaaaa taaactaata    8040
tcaacatgat agaagcattc ttcgattccg agtccggcac caaattcata taaacggacc    8100
tccacggagg tccgtttttc gtttcaggac gccacgattt aagcgtcctg ccgccaaatc    8160
aattctaccg aactcaacca gattctcccc acatcaccag caatttgcgg gcatatccca    8220
attcgggaaa atttgtttct gagctatagc gctgactgac gtgaaatgtc gtgcggcccc    8280
gtgatgctgt tgaamgtcaa atgacgtcat caggagcgta acgcacccat aaagcacaac    8340
atcgggcaga acgccaactg atgagatttt ctgaatgaga acaaagagaa atgtatcagt    8400
ccgtttgctc atgcaaagac taacaatcca ttaaaatagt aagcgctccg gacaattttc    8460
catggattat tttctgaaca ttttttctttg gcaaagatga tgaattttga tggtaaggaa    8520
aattacttct ggttctcagt aaaatccttt cgtaatacta tgtaatcaag aagtttatgg    8580
ctagtaaaaa taacgtcttg cattcaccaa taatatgtaa ataaacccat ctatagatgg    8640
```

```
aaaaaatagg ttatggaatt atcattgcat cattccctttt tcgaatgagt ttctattatg   8700
caacaacctg tagttcgcgt tggcgaatgg cttgttactc cgtccataaa ccaaattagc   8760
cgcaatgggc gtcaacttac ccttgagccg agattaatcg atcttctggt tttctttgct   8820
caacacagtg gcgaagtact tagcagggat gaacttatcg ataatgtctg gaagagaagt   8880
attgtcacca atcacgttgt gacgcagagt atctcagaac tacgtaagtc attaaaagat   8940
aatgatgaag atagtcctgt ctatatcgct actgtaccaa agcgcggcta taaattaatg   9000
gtgccggtta tctggtacag cgaagaagag ggagaggaaa taatgctatc ttcgcctccc   9060
cctataccag aggcggttcc tgccacagat tctccctccc acagtcttaa cattcaaaac   9120
accacaacgc cacctgaaca atccccagtt aaaagcaaac gattcactac cttttgggta   9180
tggttttttt tcctgttgtc gttaggtatc tgtgtagcac tggtagcgtt ttcaagtctt   9240
gaaacacgtc ttcctatgag taaatcgcgc attttgctca atccacgcga tattgacatt   9300
aatatggtta ataagagttg taacagctgg agttctccgt atcagctctc ttacgcgata   9360
ggcgtgggtg atttggtggc gacatcactt aacaccttct ccacctttat ggtgcatgac   9420
aaaatcaact acaacattga tgaaccgagc agttccggta aaacattatc tattgcgttt   9480
gttaatcagc gccaataccg tgctcaacaa tgctttatgt cggtaaaatt ggtagacaat   9540
gcagatggtt caaccatgct ggataaacgt tatgtcatca ctaacggtaa tcagctggcg   9600
attcaaaatg atttgctcca gagtttatca aaagcgttaa accaaccgtg gccacaacga   9660
atgcaggaga tgctccagca aattttgccg catcgtggtg cgttattaac taattttttat   9720
caggcacatg attatttact gcatggtgat gataaatcat tggatcgtgc cagtgaatta   9780
ttaggtgaga ttgttcaatc atccccagaa tttacctacg cgagagcaga aaargcattr   9840
gttgrtatcg tgcgccattc tcaacatcct ttagacgraa aacaattagc cagcactgaa   9900
cacagaaata gataacattg ttacactgcc ggaattgaac aacctgtcca ttatatatca   9960
aataaaagcg gtcagtgccc tggtaaaagg taaaacagat gagtcttatc aggcgataaa  10020
taccggcatt gatcttgaaa tgtcctggct aaattatgtg ttgcttggca aggttttatga  10080
aatgaagggg atgaaccggg aagcagctga tgcatatctc accgccttta atttacgccc  10140
aggggcaaac acccttttact ggattgaaaa tggtatattc cagacttctg ttccttatgt  10200
tgtaccttat ctcgacaaat ttckcgcttc agaataagta actcccgggt tgattcatgc  10260
tcggaatat ttgttgttga gttttttgtat gttcccgttg gtataatatg gttcggcaat  10320
ttatttgccg cataattttt attacataaa tttaaccaga gaatgtcacg caatgcattg  10380
taaacattga atgtttatct tttcatgata tcaacttgcg atcctgatgt gttaataaaa  10440
aacctcaagt tctcacttac agaaactttt gtgttatttc acctaatctt taggattaat  10500
cctttttttcg tgagtaatct tagcgccagt ttggtctggt caggaaatag ttatacatca  10560
tgacccggac tccaaattca aaaatgaaat taggagaaga gcatgagttc tgccaagaag  10620
atcgggctat ttgncctgta ccggtgttgt tgccggtaat atgatgggga gcggtattgc  10680
attattacct gcgaacctag caagtatcgg tggtattgct atctggggtt ggattatctc  10740
tattattggt gcaatgtcgc tggcatatgt atatgcccga ctggcaacaa aaaacccgca  10800
acaaggtggc ccaattgcgt atgccggaga aatttcccct gcatttggtt ttcagacagg  10860
tgttctttat taccatgcta actgattggg taacctggca attggtatta ccgctgtatc  10920
ttatctttcc accttcttcc cagtattaaa tgatcctgtt ccggcgggta tcgctgttat  10980
```

-continued

```
tgctatcgtc tgggtattta cctttgtgaa tatgctcggc ggtacctggg taagccgttt     11040
aaccacgatt ggtctggtgc tggttcttrk tcctgtggtg atgactgcta ttgttggctg     11100
gcattggttt gatgcagcaa cttatgcagc taactggaat actgcggata ccactgatgg     11160
tcatgcgatc attaaaagta ttctgctctg cctgtgggcc ttcgtgggtg ttgaatccgc     11220
agcagtaagt actggtatgg ttaaaaaccc gaaacgtacc gttccgctgg caaccatgct     11280
gggtactggt ttagcaggta ttgtttacat cgctgcgact caggtgcttt ccggtatgta     11340
tccgtcttct gtaatggcgg cttccggtgc tccgtttgca atcagtgctt caactatcct     11400
cggtaactgg gctgcaccac tggtttctgc attcaccgcc tttgcgtgtc tgacttctct     11460
gggctcctgg atgatgttgg taggccaggc aggtgtacgt gccgctaacg acggtaactt     11520
cccgaaagtt tatggtgaag tcgacagcaa cggtattccg aaaaaaggtc tgctgctggc     11580
tgcagtgaaa atgactgccc tgatgatcct catcactctg atgaactctg ccggtggtaa     11640
agcctctgac ctgttcggtg aactgaccgg tatcgcagta ctgctgacta tgctgccgta     11700
cttctactct tgcgttgacc tgattcgttt tgaaggcgtt aacatccgca actttgtcag     11760
cctgatctgt tctgtactgg gttgcgtgtt ctgcttcatc gcgctgatgg gcgcaagctc     11820
cttcgagctg gcaggtacct tcatcgtcag cctgattatc ctgatgttct atgctcgcaa     11880
aatgcacgag cgcccagagcc actcaatgga taaccacaca cgtctaacg cacattaatt     11940 aaaagtattt tccgaggctc ctcctttcat tttgtcccat gtgttgggag gggcctttt     12000 tacctggaga tatgactatg aacgttattg caatattgaa tcacatgggg gtttatttta     12060
aagaagaacc catccgtgaa cttcatcgcg cgcttgaacg tctgaacttc cagattgttt     12120
acccgaacga ccgtgacgac ttattaaaac tgatcgaaaa caatgcgcgt ctgtgcggcg     12180
ttatttttga ctgggataaa tataatctcg agctgtgcga agaaattagc aaaatgaacg     12240
agaacctgcc gttgtacgcg ttcgctaata cgtattccac tctcgatgta agcctgaatg     12300
actgcgttta cagattagct tctttgaata tgcgctgggt gctgctgatg atattgctaa     12360
caagatcc                                                              12368
```

<210> SEQ ID NO 21
<211> LENGTH: 833
<212> TYPE: DNA
<213> ORGANISM: Escherichia coli
<220> FEATURE:
<221> NAME/KEY: misc_feature
<222> LOCATION: (19)..(19)
<223> OTHER INFORMATION: n equals a, t, g, or c
<221> NAME/KEY: misc_feature
<222> LOCATION: (111)..(111)
<223> OTHER INFORMATION: n equals a, t, g, or c
<221> NAME/KEY: misc_feature
<222> LOCATION: (430)..(430)
<223> OTHER INFORMATION: n equals a, t, g, or c

<400> SEQUENCE: 21

```
gcacggcact ctgatgtanc ttttatctgt tcccagtgga agcatgcccc acaactgagt        60
cattaagtgt ggaagaacag ttttgtcccc gcctgcaatc tctccctttc naaaaaccag       120
tatgtcgcca tgcctcgcct taatggagag cgctgaacca taccttcttt ttcccagtaa       180
taacaggtaa tagcgtgcct ggtaatccgt taccgccagc gcctccgcaa tttctgcggt       240
tttccctcca ttatgcctgt tcagaaatyc cagtatttca ttcttcatat attcactcat       300
ctcactgtaa caaagttyct ycgaataata aaaatcatgc tttctgttat caacggaaag       360
gtatttttat tctctgtgtt tgctttattt gtgaaattta gtgaatttgc tttttgttgg       420
```

-continued

```
ctttatttgn atgtgtgtca cattttgtgt gttattttc tgtgaaaaga aagtccgtaa      480
aaatgcattt agacgatctt ttatgctgta aattcaattc accatgatgt ttttatctga      540
gtgcattctt tttgttggtg ttttattcta gtttgatttt gttttgtggg ttaaaagatc      600
gtttaaatca atatttacaa cataaaaaac taaatttaac ttattgcgtg aagagtattt      660
ccgggccgga agcatatatc caggggcccg acagaagggg gaaacatggc gcatcatgaa      720
gtcatcagtc ggtcaggaaa tgcgtttttg ctgaatatac gcgagagcgt aytgttgccc      780
ggctmtatgt ctgaaatgca ttttttttta ctgataggta tttcttctca ttc             833
```

<210> SEQ ID NO 22
<211> LENGTH: 2916
<212> TYPE: DNA
<213> ORGANISM: Escherichia coli
<220> FEATURE:
<221> NAME/KEY: misc_feature
<222> LOCATION: (2453)..(2453)
<223> OTHER INFORMATION: n equals a, t, g, or c
<221> NAME/KEY: misc_feature
<222> LOCATION: (2864)..(2864)
<223> OTHER INFORMATION: n equals a, t, g, or c
<221> NAME/KEY: misc_feature
<222> LOCATION: (2908)..(2908)
<223> OTHER INFORMATION: n equals a, t, g, or c

<400> SEQUENCE: 22

```
tgcaccatca ctgataccac cgggacccg gattttatcc ggtccccgcg gactgacagg       60
gtttgtgaca cctgagtcat atccgatgta aacttcattt tcacgggttg tacaggaaaa     120
ctcccctgtg ccattgagtt ctgatgtgtg cccttcgcca caactcccac cgtcacggca     180
ccagttgcat ctgacgccga ccaactgctg agagccatgc cgtttccggc tttgtcgaca     240
acgcatgctg cagttcccag cgatgcgaac tggtctggca tgcattcacg aaccaacagc     300
agtggtgcta cgtccggatg caattcgcat gagctccaac cgcggttgta agttcagcag     360
cccgggcctc tgccccggc acagtcgcat aagtattcga taccgtgcga caccattacc     420
ttcaggatac gccacggacc cgtcacccta cgaaaacgcc ggagcaccgg caatcagcaa     480
aggcagcagt gataaaagac tgatatattt cctgtcatta ttttttcatat taatttaact     540 cctgattaac cggtttttat tgatatgaga agtaatagt tgcaatagcc ttcacacttc      600
caggtgtagt tgcatcagca attttttatat aattggctct taaattgata tgtggattta    660
cctctcccct gtaatcggag aagtgccatt gactgccatt tcctttcaca ggggagtctt     720
caccatagct gatggcagtt acatcactgt ctttatatag cctgatgcca aatccttttg     780
cagtggattc actgcttaag gtcaatatat ctgttctgtt cactggctgt gatgcatctg     840
tcaatgtagc ataaacatca attccatccg ggcattgtag gtgtatgtca attttacctc     900
cctgtatttc tttatacaaa gatgtgaact gtgattgata tacggtattt aatggcacca     960
catagttttt ttgccccatg gtacatgtct gactctgtac ctgaatgcgc ccaccattta    1020
acataacagg tgctgtcagt cctttattat ttaaacttgt acgttttgct tccaacaaaa    1080
tagtaccaag ctgcctggtg ggtattgtta tatatccatt gggtaatctt cccgttgcga    1140
caaaagcaac aaacaaacga gctccgaagc ttgctgtcgc accgttataa gtattggggt    1200
ttgtattggc acctacaggg tcaatatata tacctgagct atttatgggg accagaggcg    1260
ttgcgggcca atagcccgcc atgccaataa taatacccag tccggataca ccaatatcat    1320
agatatcaaa atcagatgaa tcacggctgt ttccttgatg gaaagtatac gtaatacttc    1380
```

```
caattttagg cagtgcgggt gtaaactttc cacgcatcag agcgatggca ccgccattaa    1440
aaacatactg gttacttgtt cccgccagct ctcctatcac ccggggatag gtatgggcat    1500
cagcaggacc aatcacaaca cctggcaatg tggatgtatt aaccgctatc tgcgaaggca    1560
cataatcatc cggacccgct accgccagct tagggagtaa aattaaaaac aatggtatga    1620
aaaagattct tttcatgttt tttcctgatt agggtgctgt atacacagaa caggaacgag    1680
ctgagattgc atatcatctt tattgtgtgc aacatgatat acaaatgaac atctgtcttt    1740
attatctggt ccccatacaa cgctgagatg acctttttca gggagtcccc tggtaaatac    1800
cttcccggcc tgagcgacat atccggccaa ctgtccatgt tcatccagaa cttcagaagc    1860
cattggaggg ggattgccag tagacatacg aatatcaaat aacagacttc ttcctgtttt    1920
agtgtcaaat ttyactaacg tggcgctatt agcacgagga atgatttcct gctccgtcgc    1980
cgataattca acattcaaat ctaaattgga gggatcgatg ctaatttgat ttttctcata    2040
gggtgtaaca taaggaacaa taccatttcc ccaaaaatcc agacgactac cagaggcatt    2100
attgatggca gccccctgag ctccttcagc atggataatg gcaaaagtat cactcaggtc    2160
attactcaat gtcactccat aggggtgtgc gaccaccgct cccgacgcac caaatgacct    2220
ttgattatta ttctgagtat catgcccgac tgttgtggtt atatttacat aaggtgaacg    2280
ataaccccca ttcattgcat aaccggaagg cccgttttcc tggctgtttc ctgaaagacc    2340
ataagagaac tgattatcct ccccgccagt accactaatt gatgtctgaa tactattttt    2400
ctcttctttg ctataattta aaacagtgga aaacaccggg ctttgaacac ttncctccca    2460
gagggagagt aaaattaata taaaatctgt catcacggcg ttgttgctca ttatctcttg    2520
actgagacaa tccaatttga tagccgagtt gtttccagaa gttgctgtac cccatctggt    2580
attcattacg acttccttta tgtccccagt aattataggt tgttcctgtt aaatacatcc    2640 cacccccattt ttcacctaat tcctggttga ttgaaatctg gaattgattc ctgggacgat    2700
aaaacgctgt acttttttaca gaaacatcat caataaacgc gttgtgatta gctgatagcg    2760
catccttcag atgataaaaa tcttttgatg aataacgata agccgccaga gttatatttg    2820
tgttttgagg gctgggaata ttggatggct aataacttgg agtngcagga ctaataaacc    2880
ttttacggcg gttacaccgg gaataccngg aaatgc                              2916
```

<210> SEQ ID NO 23
<211> LENGTH: 2677
<212> TYPE: DNA
<213> ORGANISM: Escherichia coli
<220> FEATURE:
<221> NAME/KEY: misc_feature
<222> LOCATION: (2522)..(2522)
<223> OTHER INFORMATION: n equals a, t, g, or c

<400> SEQUENCE: 23

```
accgcatcgc caatctcagc ggcagtggtt tacatgtctt ccgtgatgga aggtcatggc      60
atcagctacc tccatctgct ctccgtggtc atcccgtcca ccctgctggc ggttctggtg     120
atgtccttcc tggtcactat gctgttcaac tccaaactct ctgacgatcc gatttatcgc     180
aagcgtctgg aagagggcct ggttgaactg cgcggtgaaa agcagattga aatcaaatcc     240
ggtgcaaaaa cgtccgtctg gctgttcctg ctgggcgtag ttggcgtggt tatctatgca     300
atcatcaaca gcccaagcat gggtctggtt gaaaaaccac tgatgaacac caccaacgca     360
atcctgrtca tcatgctcag cgttgcaact ctgaccaccg ttatctgtra artcgatacc     420
gacaacattc tcaaytccag caccttcaaa gcaggtatga gcgcctgtat ttgtatcctg     480
```

```
ggtgttgcgt ggctgggcga tactttcgtt tccaacaaca tcgactggat caaagatacc      540
gctggtgaag tgattcaggg tcatccgtgg ctgctggccg tcatcttctt ctttgcttct      600
gctctgctgt actctcaggc tgcaaccgca aaagcaytga tgccgatggc tctggcactg      660
aacgtttctc cgctgaccgc tgttgcttct tttgctgcgg tgtctggtct gttcattctg      720
ccgacctacc cgacactggt tgctgcgtta cagatggatg cacgggtac  tacccgtatc      780
ggtaaattcg tcttcaacca tccgttcttc atcccgggta ctctgggtgt tgccctggcc      840
gtttgcttcg gcttcgtgct gggtagcttc atgctgtaat gacccatygc ggggcgttca      900
cgccccgctt tctttcccgc cgactaacat cctttccccg tccgttgtat agtgacctct      960
ctcttgcggt tccatctgtt cttgcgaggt gtttatgctt gatgaaaaaa gttcgaatac     1020
cacgtctgtc gtggtgctat gtacggcacc ggatgaagcg acagcccagg atttagccgc     1080
caaagtgctg gcggaaaaac tggcggcctg cgcgaccttg atccccggcg ctacctctct     1140
ctattactgg gaaggtaagc tggagcaaga atacgaatgc agatgatttt aaaaactacc     1200
gtatctcacc agcaggcact gmtgaatgcc tgaagtctca tcatccatat caaaccccgg     1260
aacttctggt tttacctgtt acacacggag acacagatta cctctcatgg ctcaacgcat     1320
ctttacgctg atcctgctac tttgcagcac ttccgttttt gccggattat tcgacgcgcc     1380
gggacgttca caatttgtcc ccgcggatca agcctttgct tttgattttc agcaaaacca     1440
acatgacctg aatctgacct ggcagatcaa agacggttac tacctctacc gtaaacagat     1500
ccgcattacg ccggaacacg cgaaaattgc cgacgtgcag ctgccgcaag gcgtctggca     1560
tgaagatgag ttttacggca aaagcgagat ttaccgcgat cggctgacgc ttcccgtaac     1620
catcaaccag gcgagtgcgg gagcaacgtt aactgtcacc taccagggct gtgctgatgc     1680
cggtttctgt tatccgccag aaaccaaaac cgttccgtta agcgaagtgg tcgccaacaa     1740
cgaagcgtca cagcctgtgt ctgttccgca gcaagagcag cccaccgcgc aattgcccc     1800
ttccgcgctc tgggcgttgt tgatcggtat tggtatcgcc tttacgccat gcgtgctgcc     1860
aatgtaccca ctgatttctg gcatcgtgct gggcggtaaa cagcggcttt ccactgccag     1920
agcattgttg ctgaccttta tttatgtgca ggggatggcg ctgacttaca cggcgctggg     1980
tctggtggtt gccgccgcag gkttacagtt ccaggcggcg ctacagmacc catacgtgct     2040
cattggcctc gccatcgtct ttacyttgct ggcgatgtca atgtttggct tktttactct     2100
gcaactcccc tcttcgctgc aaacacgtct cacgctgatg agcaatcgcc aacagggcgg     2160
ctcacctggc ggtgtgttta ttatgggggc gattgccgga ctgatctgtt caccytgcac     2220
caccgcaccg cttagcgcga ttctgctgta tatcgcccaa agcgggaaca tgtggctggg     2280
cagcggcacg ctttatcttt atgcgctggg catgggcctg ccgctgatgc taattaccgt     2340
ctttggtaac cgcttgctgc cgaaaagcgg cccgtggatg gaacaagtca aaaccgcgtt     2400
tggttttgtg atcctcgcac tgccggtctt cctgctggag cgagtgattg tgatatatg     2460
gggattacgc ttgtggtcgg cgcttggtgt cgcattcttt ggctgggcct ttatcaccag     2520
cntacaggcc aaacgcggct ggatgcgcgt ggtgcaaata atcctgctgg cagcggcatt     2580
ggttagcgtg cgcccacttc aggattgggc atttggtgca acacataccg cgcaaactca     2640
gacgcatctc aactttacac aaatcaaaac agtagat                              2677
```

<210> SEQ ID NO 24
<211> LENGTH: 537
<212> TYPE: DNA

```
<213> ORGANISM: Escherichia coli
<220> FEATURE:
<221> NAME/KEY: misc_feature
<222> LOCATION: (521)..(521)
<223> OTHER INFORMATION: n equals a, t, g, or c

<400> SEQUENCE: 24
atcctgatga cgccgtaaat gtgcatttgc caggattgcc gcatagaggg cacgaagaaa      60
aggtcggttg tcaggatgta tccagatgat tctgccactg aaaccttcag ggataagacg     120
attgccaact gccagtcctt taagggcagc attcagcgcc ttacgcgggg cattctgctc     180
cagaaatacg tatgccaagt gagcgtgtac atcaataaag tcattctcct gtcgggcaag     240
gcgcctgagt ttgttgatgt aacttgtttc gctgatttca ccgcatcgt atgcatcaat      300
cagttcttca aactcatcca gcaacgagcc aaaccaggtt ccggaaata tgaaacagcc      360
ctggttatcg ttcacttcaa agcgtaattt gccagtcata ttctgaacct gtaaaaaagg     420
atagaccata atctgcaggc tataaaaatt gtggatgcct ggcatcgggt gtccttttat     480
tgtccgggat taacgttgcc catgataata cagtgaatcc ngttctgtgg taagacg        537

<210> SEQ ID NO 25
<211> LENGTH: 1128
<212> TYPE: DNA
<213> ORGANISM: Escherichia coli
<220> FEATURE:
<221> NAME/KEY: misc_feature
<222> LOCATION: (1074)..(1074)
<223> OTHER INFORMATION: n equals a, t, g, or c
<221> NAME/KEY: misc_feature
<222> LOCATION: (1079)..(1079)
<223> OTHER INFORMATION: n equals a, t, g, or c
<221> NAME/KEY: misc_feature
<222> LOCATION: (1115)..(1115)
<223> OTHER INFORMATION: n equals a, t, g, or c

<400> SEQUENCE: 25
cgctcgagca ccagattcac tgacatgcgc aaactcatgt gtaaatcctg tctgggcatc      60
tatctcaagt aacagttccg ttaaatctac cggtgggagt agctgtttga tccgattatt     120
tagacgaagc aatgatggtg ctcttcctg tttctccaga caactgatag tcagggatgg      180
atatttacct tcattacaga tatgaacttc cgcattcttt tcaaatcgtg atgccaggct     240
ttccaggtct catccagctg aatagccagt tgttcacac ctttacgtcc atcgacagga     300
tgtcccagtg cccgacagac aggaatacgc tgagtctgcc actcttcacc ttgcaacaac     360
ttctcgcgag gatctcccca gcgatcactg ttttcaagcc cagatgtccc cggcggcgca     420
rtgcatcctg aaggcgttcc agcaaacata gtgaataacc tgcacgctgt atcccgtccc     480
tccgcatcgt atacgaggcg tttccaggga ccggtgataa tatgttcagc gcatcatcaa     540
ggatgcgctt tttcgaacca ttcagttctg ccagataatg aatcgcagcc agtacatgtc     600
acctgccggt gccgcacgga aatgcaggtc ccgcaacacc gccggaagaa acgtttaac     660
ccgaccgtac tgctcaacca tttcgtcatg gaaattattg ttctgtggac gagcaagttc     720
attaaccttg cttacagatt ctgccagtct gtttttgggt acgcacttga agataacctg     780
cctgagatct gggacatctg tattatcatc cagcaacaat gcacatgccc gcgccagtaa     840
caatgcggcc tgatcaagat ctttcagtgt cctgagtctt ttttttgcc cggttttctt     900
tgcttcgcgg ataatgtcca gaattagcat atcaagcaca tcaacggcat cgtctaatgc     960
cgttatttcc tgtgctttaa cgaatgcagt aagtacagca agctttctct gctgtggcat    1020
tcgagcgata tattttaccg acgccatgcc agcatgaacg agccagatta cgcnttggna    1080
```

```
atggtcaggc agaccgggaa aagttccagt cgggnaaaac tccaagaa            1128
```

<210> SEQ ID NO 26
<211> LENGTH: 2311
<212> TYPE: DNA
<213> ORGANISM: Escherichia coli
<220> FEATURE:
<221> NAME/KEY: misc_feature
<222> LOCATION: (3)..(3)
<223> OTHER INFORMATION: n equals a, t, g, or c
<221> NAME/KEY: misc_feature
<222> LOCATION: (2008)..(2008)
<223> OTHER INFORMATION: n equals a, t, g, or c

<400> SEQUENCE: 26

```
ggntgataaa aatcytttga tgaataacga taagccgccc agagttatat ttgtgtttga    60
ggctggaata ttgatgctat aacttgagtg cagactataa cctttacgcg ttacaccgga   120
atacctgaat gctgttctgg acaatgtaat gtcagatgct atagcaccca gatgggtatt   180
aaaggccagg ccagctaacc ccgctgtata tcctgaagct gtggtaagac cactgtttaa   240
agtaatatca ttcgtcaggc cgtattgata ggtgccttgt gctattaaat cattatatgt   300
tttattcgca taacgatact ttcccactga catttgccag cgactaaatc cgggacgaat   360
gagttgagca acgccgcaa aaggaaccgt gaacattcgt gtctggccat tagactctgt    420
tatcttaacg agaaggtcac cagcatatcc actgggatat aaatcattga tgacaaatgg   480
tccggctggc accgtcgttt catagaggat atgagcattt tgataaatgg ttactttagc   540
attactgtta gctattcccc ggacagcagg rgcatagcca cgtaaagaac cgggtaacat   600
tcgttcatcc gatgctaacc tgactccccg caaactgagg ctatccatta gctcaccatt   660
cgtataaaaa tccccctaatg tgaattgtgc tctcaatggg gcaaggtcat gcattatact   720
tgtttctata ttctgatatc cggcaggata gctattattc cagctctcac tgccacggtg   780
gcgcaaagcc atccccacaa attgaatcca gcttttaatc ccagataagt ctgttcgtta   840
ctcgtcccgg aagagctata ctggtaatag ttagcatcat agtttataaa tgctgcagga   900
acaccacttt gccactgaga aggggaaata tatcctcttg gacgtgtatt cagcagtgct   960
gcgggatttc gatattcaac cttaaagtcg ataagtcaaa attaattctg ctgaagaaaa  1020
gccctgttga cgccggaaag caggaggtgt ttcccgacat agtatctttg actaaatcaa  1080
tcaatgaaag cagctcaggc gtcaggcata acgtcggagc accggtattg gcagtacgta  1140
aatactgcaa atcagccttc cccttccata cattattaac ataaatatca gaataatacc  1200
tgccctcagg cacagggtta ccatgactaa agcggcggat atcaatagca tttatccctt  1260
tatccaaatg caaaaactca gaatcaaact cagcctcttc agcagcaaat gaatggtttg  1320
ttactgttaa ccctaatgca gcaaaaagca gaagagaaca acgacagtaa atcaggcatg  1380
acagattatt agcgttcatt attaccttac tccagaacag attctccttg ctgatatcct  1440
ccgtaatcat taacaataac ccaggaaact tgctggtgg cgcagttctg ccttttaagtg  1500
caaatactgt tgaagagaaa gggggaatca ttccaccatg ttcaacaggc gttaagtgct  1560
tattctggtc aactgcaatt ttgttgtagg ttatgtaata aggtgttgga ttaactgctt  1620
taattcggcc ttcctcctgg tgccaggtaa ctttcagata agcatcattt ggtgttaact  1680
tcaggtgagc aggacgaaag aaaaatttta tgcgactacg aacagctagt tgcaaataat  1740
tattattccg ctgctctgag ttatcggagt ctttttttgc cctggctttt gctggaatat  1800
ccagaacatt tagatagaaa agagattctc ggtctttcgg tagtgactcg cctgtatata  1860
```

```
caattctgac tgtttgtcct gatttagagt ccatacgaaa tattggcgga gtaatgataa    1920
aaggacgtgg actgactcag ggggagctgc tgcatctcca tcgycaacca ggactggact    1980
aatgccgaga tttcattgtc attatttnaa cgtatgctaa tactcttttg agtcgccgga    2040
taaacaacac gggttcccat gataactaca ctaccctgaa caactgcaga tacagataga    2100
gtaaaaaaaa acagcacaaa ccttagcatg gtatctccag aagaaagcag ggcagtattt    2160
cctgccccaa aatacaaaac cgtttgttat tcgtaggcga tggtataatt gactgttgtt    2220
tttacattgc ctggagttga tgtcccggtc gcataatatt gagccatata acgtaatgtg    2280
gcattaccat ccccaccaat agtttcagaa t                                   2311
```

<210> SEQ ID NO 27
<211> LENGTH: 1118
<212> TYPE: DNA
<213> ORGANISM: Escherichia coli
<220> FEATURE:
<221> NAME/KEY: misc_feature
<222> LOCATION: (142)..(142)
<223> OTHER INFORMATION: n equals a, t, g, or c
<221> NAME/KEY: misc_feature
<222> LOCATION: (228)..(228)
<223> OTHER INFORMATION: n equals a, t, g, or c
<221> NAME/KEY: misc_feature
<222> LOCATION: (261)..(261)
<223> OTHER INFORMATION: n equals a, t, g, or c
<221> NAME/KEY: misc_feature
<222> LOCATION: (693)..(693)
<223> OTHER INFORMATION: n equals a, t, g, or c

<400> SEQUENCE: 27

```
tattacctgt gattttccg ggcgtaaatg gagtccctaa agttatcgca gtcccaatat      60
ttcctgcatt actgttataa agataaacga gtaacccatc agaagatgtg tttgatgtat    120
tctgaactaa aatagcattg tnataagtgt ttgttgccgt tatcgtaacc ttcattgttc    180
ccagattata gggacaccgc atattcacag taaactcttt ttcgtgantt ccattttgac    240
tcagggtctg aatctctaca ncctgccagt caacagttgt gttgcttaca gtacaggcag    300
gaataatcag ttttcctctg aaggtcagat tatcaactgc atgtacatgc tgagacatta    360
acactgcccc cagcattacc ggaagacaca aacctcttat cttttttcatc tgaaatatcc    420 tgtacaaaaa ttttgctaac gatatgtcaa ttcaaacgtg gctgttgctt cataatcacc    480
gggtaccaca ctcttcgtcc gcagggcttc cggcgttgcc acaacatacg cgccgaaagg    540
aagctcaaga ctgtttccgg taaccttttc cccctgcct tgttatggg aggtgccggg    600 tttcagcaga ctgctgccat cggtgtccag cagtgcaatg cctaaccggc cagcattcac    660
tccggttacc ttcagatggc ccgggagrcg cyntcttccg tccccttaaa ggtcagggtc    720
acaattttgc caactgctgt tgcatggcag ttttccagcc tgatgacaaa cgactctgtc    780
ggcgaacgtc cggcggata ccagaaatcc ctggacgccc gggttttgaa gacgacatgt    840
ttattcagac tgtcaccgga cacatggcag ggtctgtcaa gcagattacc cctgaatgcc    900
acatctgagg ctattgcctg tccggcagac agtgcggcaa acagtaaaag agcgcctgtg    960 cttttttatca tcacattccc ttactcatat tttatgctca gacgcagcat ggccggattg   1020
ctcctggcat cagaatactc aacctcctgt ggcggccttt tcctccaggc gggcaagcat   1080
ctcctcctgg cggcgggtaa ggcggggaca gtaaaaaa                          1118
```

<210> SEQ ID NO 28
<211> LENGTH: 562

<212> TYPE: DNA
<213> ORGANISM: Escherichia coli

<400> SEQUENCE: 28

```
ttcgtgggtg aaatcgtagg ccgcgctttt ttgctgatcg gccagttgat gaatagggtg     60
gccakgatcg ggataaaacg tacaggcagc gataaacaga cagcccggat agcggttgtt    120
tttaacgcac tccgataacg cctgataacg tgccagcaac ttttgttcgg cggtttgcgt    180
ttcgtccagc atcagctgac gacgccagac atctatctgt tggctaagat aacgcagcgc    240
atcgtagagg attgcctctt tgtctggcca gaagcggcgt actcgtccag tggataatcc    300
acacgttcag caaccatctc cagcgtggtg ttggcaatcc cttgtaattc taataatttc    360
agggcttctc ccagtacatc ttcacgttgc acgctatttt cctccgkctt tcccactgca    420
atgttcgktc acggttggcg atcgcgcaaa tgtgcgctgg aaggtttcag catccataaa    480
gcccgtgacg cgtgcttgtg gatgctcctg gccttggtcc ggtcaaaaaa gagaatttgt    540
ccggtagggc caaggatatt aa                                             562
```

<210> SEQ ID NO 29
<211> LENGTH: 745
<212> TYPE: DNA
<213> ORGANISM: Escherichia coli

<400> SEQUENCE: 29

```
ccatcgcttt accccagaaa agttaagcca tataatgtga gggatataag tcgtcgtatc     60
cggtaagtac agataaccac aacataagct cattcagtaa attttatctc tgaacaaacg    120
actatggcat gctcatttat actattcata agaaagtgtg attatctgta agcattaacc    180
atcaaatcat ataaccatac taaactggcg gatcatcagc accattagca ggtaacttat    240
tgaaattta ttatgtgttt tttgttgata attaatatgc aatatgaatt tgctatttta    300
gaatcatgaa caccatttaa aattaccatc attaacatca tataaaaata tatttttact    360
aaaacatgaa ttgtatatat ttattagctc aggaaaatta tcagggttca ccttcaaatt    420
aacctgaatg ttatgcttaa tttcacccag tagttcttca tgtgtagatt ttattatccc    480
attattataa tcgataaatg cacacatgtt ttttatgaat tcaaaacctt ttcctgtata    540
cagtttaatg aatgccacca gagcaaacat ttcaagatgt agccataatg ctacgttagt    600
ttttgcaaa gtataaaaaa ttgaattcgc cacttttta cttattgctc ttttatactg    660
tgatcgagca agattcagta gcggaagtcc tcgttcaata atgaatgtg aaaagactgg    720
ataaattgat gtcggaaacc tttca                                          745
```

<210> SEQ ID NO 30
<211> LENGTH: 400
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n equals a, t, g, or c

<400> SEQUENCE: 30

```
gcgttnatgc atttcgasat tttccacttc gttctgacgt tgcactgctt tggcgtcatc     60
attacgtaac gtatcgagga aatcgaggta gccctgatca acatctttgg tgacgtagac    120
gccgttgaac accgagcatt caaactgctg gatatccgga ttttcagcgc gaacggcgtc    180
gatcagatcg ttcagatcct ggaaaatcaa cccgtcagca ccgatgatct ggcgaatttc    240
```

```
atcaacttcg cgaccgtgag cgatcagttc cgtggcgctc ggcatatcaa taccataaaa    300
cgttcgggaa agcgaatttc cggtgccgca gaagcgaggt acactttctt cgctccggct    360
tcgcgtgcca tctcgataat ctgtcagaag tggtgccacg                           400

<210> SEQ ID NO 31
<211> LENGTH: 824
<212> TYPE: DNA
<213> ORGANISM: Escherichia coli

<400> SEQUENCE: 31
tgtcgacgat gaggcagcca gagcattaga gccgaaaaga agggatgatg ccatgactgc     60
tgttgctata aaatgtttca tatattctcc atcagttctt ctggggatct gtgggcagca    120
tatagcgctc atactagggg tttgagggcc aatggaacga aaacgtacgt taaggagata    180
attcgttgtt tatatttaaa tttagagctc tcagttcccc ttttaaaata tcctctggca    240
acgtgaatgt ataatggccc aacatattga tatgcccgtg catcagggga gatagccgag    300
cgatatcttc atctataatt tcttcgccat tacggcgcat ccagctcaac gcttcctcca    360
tatagagcgt gttccacaga accactgcat tagtaaccag gcccagcgcc cccagttgat    420
cttcctgccc ttcacgataa cgctttctga tctctccgcg ttgtccgtaa caaatcgcac    480
gagccacagc gtgcgktcct tctcctcgat taagctgcgt caggatccgc cgacgataat    540
cttcatcatc aatataattg aggagatata gcgttttgtt tacacgccct acttccataa    600
ttgcctgtgc cagtcctgat gggcgcgagc ttttcagtaa agagcgaatg agttctgacg    660
catgaattgt acccaacttc aggaaccagc ggttcgcatc atctcatccc actgactctc    720
cgcttttgac agatctgcat atcctcgggc caacttatcc agtactccgt agtttgccga    780
tttattcacc cgccagaaca ccgcctcacc tgcatcggca agcc                    824

<210> SEQ ID NO 32
<211> LENGTH: 911
<212> TYPE: DNA
<213> ORGANISM: Escherichia coli
<220> FEATURE:
<221> NAME/KEY: misc_feature
<222> LOCATION: (841)..(841)
<223> OTHER INFORMATION: n equals a, t, g, or c

<400> SEQUENCE: 32
acaaatcaga ccagttaacc agtcagtcgg ttttatgatt tcactcacta tactttgttt     60
cataaggatt tcaggatctg ccagactgcg cagaaatgat gcttacgaat acacagtaaa    120
ggcaatgtca tttccgatac agagcctgac attgccataa tgagctattt atctgaaaaa    180
cgacagaata tgatgtttta tcgtaacgta atttttaagtt ctcaacttat tgagacatat    240 tgtcttttt acccatgtgg tcatttttca tcccatccgt tttgctcatg tgttctttct    300
ccattttctc tttatccatt gcattttttgc acataccatc cttgcacatt ttatcatgcg    360
cgctggacat gctgcctttt acttcatgtg ttttatccat tgtgtctgct gcctgagcat    420
tgaacatgaa cagcgcggat agtacagttg cagaaaataat atttttcatg gttcttcctc    480
atttttaaca attgtatcaa caaccaccaa accagttata accctggtct tcccagtacc    540
cccccggaaa atgattagtg acctctataa cctgaacatg cttggggttt ttatatccca    600
gcttagtagg gatacgtatc tttatgggat agccatattc ttttggcaat accctgttat    660
tccatgtcaa tgtcagcaat gttttgtgaat gtagtgctgt cgccatatca atactggtgt    720
agtaaccatc gacgcaacga aaactgacgt attttgcccg catatcggca ccaatcagcg    780
```

```
tcaggaaatg ccggaatggt atccctcccc attttcctat tgcactccat ccttcaacac      840
ngatatgacg ggttatctga ctcacatgct gcatgttata caattcagac caaaaaccag      900
ttacgggtta t                                                           911
```

<210> SEQ ID NO 33
<211> LENGTH: 463
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n equals a, t, g, or c
<221> NAME/KEY: misc_feature
<222> LOCATION: (27)..(27)
<223> OTHER INFORMATION: n equals a, t, g, or c

<400> SEQUENCE: 33

```
ngggcagga taattgtatc ctgcccngta tataattctc agcacaggtg ttgactaaag       60
agcgtgaaac tttgctatta tgtcttcgta agattcacgg acggttatac ttgagcctga     120
ttctgtgaag taaacaacag cagaagcatc gttgccttt tcaatgtatg aaacattcca      180
gtcatggata gccactgcgg gctgaccatt atcccgacgg tgcgtcttaa tgaatcgcgg     240
aagtaattct gcaatatcgt taaaaacacc atttacggta tgagtgatac caccaacgca     300
atgtagatga gttgactccg gggtatcatt gtctgcttct gcaaagagta tagctgtctt     360
gctaattgta acaggcgcct gtgarcggga taattcgaga gaaataaacc cggattctgc     420
cataaaaact ccagtttgtg atgttatatc atttcatatg ttt                       463
```

<210> SEQ ID NO 34
<211> LENGTH: 565
<212> TYPE: DNA
<213> ORGANISM: Escherichia coli

<400> SEQUENCE: 34

```
ttctaacctc tgaccaaaaa cagaattacg gttgttatgc tgcagaacct aatgacgtgc      60
aactggcgcg ctattttcat cttgatgaac gggatctggc cttcattaac caacgacggg     120
gcaaacataa taggctgggc attgcgcttc agctcaccac agcccgtttt ctggaaacat     180
ttctgacgga tttaactcag gttctgcctg gtgttcaaca ttttgtcgcg gtacagctta     240
atatccaccg tccagaagtt ctctcccgct atgctgaacg ggacactacc cttagagaac     300
atactgcatt aattaaggaa tattacggct atcatgaatt tggtgatttt ccatggtctt     360
tccgcctgaa gcgtctgcta tatcccgggg cgtggctcag taatgacgac cgggtctgat     420
gtttgatttt gccactgcat ggttgcttca aaataaggta ttactgcccg gagcaaccac     480
actagtacgt ctcatcagtg aaattcgtga agggcaaat cagcggctgt ggaaaaagct      540
ggccgcactg ccgaacaaat ggcag                                           565
```

<210> SEQ ID NO 35
<211> LENGTH: 512
<212> TYPE: DNA
<213> ORGANISM: Escherichia coli

<400> SEQUENCE: 35

```
cgatggcgtc cggggtgaac gccggataag tttaatttat ccggtcaggc aaaaggcatt      60
aatctgcaga tagctgatgt caggggaaat attgcccggg caggaaaagt aatgcctgca     120
ataccattga cgggtaatga agaagcgctg gattacaccc tcagaattgt gagaaacgga     180
```

```
aaaaaacttg aagccggaaa ttattttgct gtgctgggat tccgggtcga ttatgagtga    240
gtcactccgg tgagatgtcc ggttatttat cttttttgtg aatctggtga tgcgtggaat    300
gaaagacaga ataccttttg cagtcaacaa tattacctgt gtgatattgt tgtctctgtt    360
ttgtaacgca gccagtgccg ttgagtttaa tacagatgta cttgacgcag cggacaagaa    420
aaatattgac ttcacccgtt tttcagaagc cggctatgtt ctgccggggg caatatcttc    480
tgggatgtgg aattgttaac ggggccaaag ta                                  512
```

<210> SEQ ID NO 36
<211> LENGTH: 827
<212> TYPE: DNA
<213> ORGANISM: Escherichia coli
<220> FEATURE:
<221> NAME/KEY: misc_feature
<222> LOCATION: (16)..(16)
<223> OTHER INFORMATION: n equals a, t, g, or c
<221> NAME/KEY: misc_feature
<222> LOCATION: (361)..(361)
<223> OTHER INFORMATION: n equals a, t, g, or c

<400> SEQUENCE: 36

```
ttgccggtgc ggttantagt ggcagtggtg tcttttggtg taaatgctgc tccaactatt     60
ccacaggggc agggtaaagt aacttttaac ggaactgttg ttgatgctcc atgcagcatt    120
tctcagaaat cagctgatca gtctattgat tttggacagc tttcaaaaag cttccttgag    180
gcaggaggtg tatccaaacc aatggactta gatattgaat tggttaattg tgatattact    240
gcctttaaag gtggtaatgg cgccaaaaaa gggactgtta agctggcttt tactggcccg    300
atagttaatg gacattctga tgagctagat acaaatggtg gtacgggcac agctatcgta    360
nttcaggggg caggtaaaaa cgttgtcttc gatggctccg aagtgatgct aatacctga    420 aagatggtga aaacgtgctg cattatactg ctgttgttaa gaagtcgtca gccgttggtg    480
ccgctgttac tgaaggtgcc ttctcagcag ttgcgaattt caacctgact tatcagtaat    540
actgataatc cggtcggtaa acagcggaaa tattccgctg tttatttctc agggtattta    600
tcatgagact gcgattctct gttccacttt tctttttttgg ctgtgtgttt gttcatggtg    660
tttttgccgg tccgtttcct ccgcccggca tgtcccttcc tgaatactgg ggagaagagc    720
acgtatggtg ggacggcagg gctgcttttc atggtgaggt tgtcagacct gcctgtactc    780
tggcgatgga agacgcctgg cagattattg atatgggga ataccc                    827
```

<210> SEQ ID NO 37
<211> LENGTH: 400
<212> TYPE: DNA
<213> ORGANISM: Escherichia coli
<220> FEATURE:
<221> NAME/KEY: misc_feature
<222> LOCATION: (238)..(238)
<223> OTHER INFORMATION: n equals a, t, g, or c
<221> NAME/KEY: misc_feature
<222> LOCATION: (364)..(364)
<223> OTHER INFORMATION: n equals a, t, g, or c
<221> NAME/KEY: misc_feature
<222> LOCATION: (384)..(384)
<223> OTHER INFORMATION: n equals a, t, g, or c
<221> NAME/KEY: misc_feature
<222> LOCATION: (398)..(398)
<223> OTHER INFORMATION: n equals a, t, g, or c

<400> SEQUENCE: 37

```
ccaggggccc aaaatccgtg tatccacctt taaagaaggc aaagtttttcc tcaatattgg    60
```

```
ggataaattc ctgctcgacg ccaacctggg taaaggtgaa ggcgacaaag aaaaagtcgg    120
tatcgactac aaaggcctgc ctgctgacgt cgtgcctggt gacatcctgc tgctggacga    180
tggtcgcgtc cagttaaaag tactggaagt tcagggcatg aaagtgttca ccgaagtnac    240
cgtcggtggt ccctctcca acaataaagg tatcaacaaa cttggcggcg gtttgtcggc    300
tgaagcgctg accgaaaaag acaaagcaga cattaagact gcggcgttga ttggcgtaga    360
ttanctggct gtctccttcc cacnctgtgg cgaagatntg                          400
```

<210> SEQ ID NO 38
<211> LENGTH: 578
<212> TYPE: DNA
<213> ORGANISM: Escherichia coli
<220> FEATURE:
<221> NAME/KEY: misc_feature
<222> LOCATION: (106)..(106)
<223> OTHER INFORMATION: n equals a, t, g, or c
<221> NAME/KEY: misc_feature
<222> LOCATION: (501)..(501)
<223> OTHER INFORMATION: n equals a, t, g, or c
<221> NAME/KEY: misc_feature
<222> LOCATION: (549)..(549)
<223> OTHER INFORMATION: n equals a, t, g, or c
<221> NAME/KEY: misc_feature
<222> LOCATION: (556)..(556)
<223> OTHER INFORMATION: n equals a, t, g, or c

<400> SEQUENCE: 38

```
ccgattttt gcgaaacgtt ccgcctggca tcaggatagt ttgttcgtta tccagttcgg     60
atagcgcatt gacgatatgc aggctgttgg tcatcaccgt gatgtnatta aagcgcgaga   120 gcagggaac catctgcaaa acggtactgc cagcatcaag aatgatcgaa tcgccatcat    180
ggataaaact aacggcagct tctgcaatca gctctttctt gtgggtgttg atgagtgttt   240
tatgatcgat aggcggatcg gattcctctt tattcaacac cactccgcca taagtacgaa   300
tgacggttcc ggcatgttcc agaatgacca gatctttgcg aatggktgtg cctgtggtgt    360
caaatattgc gccattcttc aaccgagcat ttaccctgct ttgcagatac tccagaatgg    420
cggcctgacg ctgacgagtt tcatgggcgt gatacctgat ttaggttcaa atgataactc    480
gcaagcagta acatcacacg naatatccac gttcagttaa gcgccatgat agagcatccg    540
tgatagggnc agggnagtc acacggcgta atcaccgc                             578
```

<210> SEQ ID NO 39
<211> LENGTH: 399
<212> TYPE: DNA
<213> ORGANISM: Escherichia coli
<220> FEATURE:
<221> NAME/KEY: misc_feature
<222> LOCATION: (380)..(380)
<223> OTHER INFORMATION: n equals a, t, g, or c

<400> SEQUENCE: 39

```
tgttaggtca gggcccacag tcaagcttag gttttactga atatacctca aatgttaaca     60
gtgcasatgc agcaagcaga cgacactttc tggtagttat aaaagtgcrc gtaaaatata   120
tcaccaataa taatgtttca tatgttaatc attgggcaat tcctgatgaa gccccggttg   180
aagtactggc tgtggttgac aggmgattta attttcctga gccatcaacg cctcctgata   240
tatcaaccat acgtaaattg ttatctctac gatatttta agaaagtatc gaaagcacct    300
ccaaatctaa ctttcagaaa ttaagtcgcg gtaaatattg gatgtgctta aaggacgggg   360
aagatttcat cgacacgtcn gcgtgcaatc tatccgtat                           399
```

-continued

<210> SEQ ID NO 40
<211> LENGTH: 327
<212> TYPE: DNA
<213> ORGANISM: Escherichia coli

<400> SEQUENCE: 40

| | |
|---|---|
| cagcctccgt taccggacag caaggaggct gaatggagtt tacaggattt gcttttttat | 60 |
| aatgtctggc catgcagtma aaccggacag gttttattat catgtgaggt attctgacat | 120 |
| aaaatgctgg atttttattt tgtgacgaat gctgcaaaat tgcatctgca ctctgatgta | 180 |
| gcttttatct gtttcagtga agcatgccca caaactgagt tattaagttg tggaagaaca | 240 |
| gttttgtccc gcctgcatat ctcctttcaa aaaccagtat gtcgccatgc ctcgccttaa | 300 |
| tggagagcgc tgaaccatac cttcttt | 327 |

<210> SEQ ID NO 41
<211> LENGTH: 314
<212> TYPE: DNA
<213> ORGANISM: Escherichia coli
<220> FEATURE:
<221> NAME/KEY: misc_feature
<222> LOCATION: (72)..(72)
<223> OTHER INFORMATION: n equals a, t, g, or c

<400> SEQUENCE: 41

| | |
|---|---|
| ggagatgggc atggaactca cttcataata atgcctaccg aagaaatatt aatagatgac | 60 |
| atttccacga gngatagcaa taaaacatca gagcagtctt ctcgcttaga aaaagcttta | 120 |
| ttaggtttta caaacacaat gtacagtgat tcaaaccctc ctattatagc tcgttttaga | 180 |
| gactatctgg aagatggtga gtgcattgac agaattagcg aatcaatttt ttttacaccg | 240 |
| caagaattca atcttgcaga tcaccacatt gaaggatggt tcaatgaatt tggtcaattc | 300 |
| agtggaactg tttc | 314 |

<210> SEQ ID NO 42
<211> LENGTH: 590
<212> TYPE: DNA
<213> ORGANISM: Escherichia coli
<220> FEATURE:
<221> NAME/KEY: misc_feature
<222> LOCATION: (44)..(44)
<223> OTHER INFORMATION: n equals a, t, g, or c
<221> NAME/KEY: misc_feature
<222> LOCATION: (58)..(58)
<223> OTHER INFORMATION: n equals a, t, g, or c
<221> NAME/KEY: misc_feature
<222> LOCATION: (142)..(142)
<223> OTHER INFORMATION: n equals a, t, g, or c
<221> NAME/KEY: misc_feature
<222> LOCATION: (145)..(145)
<223> OTHER INFORMATION: n equals a, t, g, or c
<221> NAME/KEY: misc_feature
<222> LOCATION: (491)..(492)
<223> OTHER INFORMATION: n equals a, t, g, or c
<221> NAME/KEY: misc_feature
<222> LOCATION: (584)..(584)
<223> OTHER INFORMATION: n equals a, t, g, or c

<400> SEQUENCE: 42

| | |
|---|---|
| tcccaagatc tttttggccg caaatccaca aaacccgtcg ttantgtcgc gcagccantt | 60 |
| gcaggccgaa tttgcaccgt tttagaaagc ggcgttttgt agagcagcac gcagtgagaa | 120 |
| gccaccgcgc cacgacctac gngcncgcgc agctggtgta attgcgccag acccagacgc | 180 |
| tccgggtttt cgataatcat cagactggcg ttaggcacat caacgccgac ttcaataacg | 240 |

```
gttgtggcaa ccagcaggtg tagctcacct tgtttaaacg acgccatcac cgcctgtttc      300
tcggcaggtt tcatccgccc gtgtaccagg ccaacgttca actctggtag cgccagtttc      360
aactcttccc aggtagttcc gmcgcctgcg cttccagcaa ttccgactct tcaatcaacg      420
tacaaaccca gtatgcctga cgaccttcag ttatgcaggc gtggtgcacc gggtgcaatg      480
gatgtcggta nngcgggtat caggaatagc gaccgtagtc actgggcgtg cggcctgggc      540
ggcactccat ctatcaccga gggtatcgag atcgggcata cgcntgcatt                 590

<210> SEQ ID NO 43
<211> LENGTH: 400
<212> TYPE: DNA
<213> ORGANISM: Escherichia coli

<400> SEQUENCE: 43
gacgaaaggg cctcgtgata cgcctatttt tataggttaa tgtcatgata ataatggttt       60
cttagacgtc aggtggcact tttcggggaa atgtgcgcgg aacccctatt tgtttatttt      120
tctaaataca ttcaaatatg tatccgctca tgagacaata accctggata aatgcttcaa      180
taatattgaa aaaggaagag tatgagtatt caacatttcc gtgtcgccct tattccctt      240 tttgcggcat tttgccttgc ctgttttgc tcacccagaa acgctggtga agtaaaaga       300 tgctgaagat cagttgggtg cacgagtggg ttacatcgaa ctgggatctg caacagcggt      360
aagatccttg agagttttc gccccgaagg aacgttttc                              400

<210> SEQ ID NO 44
<211> LENGTH: 400
<212> TYPE: DNA
<213> ORGANISM: Escherichia coli
<220> FEATURE:
<221> NAME/KEY: misc_feature
<222> LOCATION: (20)..(20)
<223> OTHER INFORMATION: n equals a, t, g, or c

<400> SEQUENCE: 44
attcggaaag atgcttctan ttttttttaag cacgtataaa ctgttaattc aggttcaatg       60
ctacgaaatg cactagttat aacctgtatt gaaggaaaga tcttctgata ctctttccag      120
agatcttcaa gtctggccat ggaaattgac ttggctgcat attctaggtc agtgtttatg      180
atagtttctc tattctctct gaatgcggaa aaaaaagctt cattcaacaa tgatagtaaa      240
tccctgggcc ggtaaagggt aaattgcaaa catcgcttaa aaccattcct ccctttaaga      300
tcatccgctg tgcatctatc ccaaactcgt tgatctttct caatatctag cttaaatgct      360
actttcattc ttttagctga cagcattagg agttgtgccc                            400

<210> SEQ ID NO 45
<211> LENGTH: 585
<212> TYPE: DNA
<213> ORGANISM: Escherichia coli
<220> FEATURE:
<221> NAME/KEY: misc_feature
<222> LOCATION: (25)..(25)
<223> OTHER INFORMATION: n equals a, t, g, or c
<221> NAME/KEY: misc_feature
<222> LOCATION: (178)..(178)
<223> OTHER INFORMATION: n equals a, t, g, or c

<400> SEQUENCE: 45
taatgttgaa gacagagata taatntacag catcatccca caaggcagat ataacaatac       60
ttgactggga tatgcaaagc gatagtgggc aatttgctat tgaaataata aaatcgataa      120
```

```
tcgtttcaga tataaattct ggaggacgtt tacgtcttct ttctatttat actggtgnac      180
atgttactgc tgttataact aagttgaaca atgagttaaa gaaaacatac cgtagcgtaa      240
taaaaaatga tgatagtatt tttattgaag ataactatgc actcgaacaa tggtgtatag      300
ttgttattag taaagacgtt tatgaaaaag atcttccaaa tgtgttaata aaaaaattca      360
ctaaccttac agctggggttg ctatccaacg ccgcactctc ttgcatttct gaaataagag      420
awaaaaccca tgggatatta acaaaatata ataataaatt agacactgca tatgtttccc      480
acatcttaaa tttaataaaa tccaaggrgt caagggcata tgcttatgaa aatgctcatg      540
attatgcagt agatttaatt tctgaagaaa taagatcaat attgc                     585
```

<210> SEQ ID NO 46
<211> LENGTH: 390
<212> TYPE: DNA
<213> ORGANISM: Escherichia coli
<220> FEATURE:
<221> NAME/KEY: misc_feature
<222> LOCATION: (2)..(2)
<223> OTHER INFORMATION: n equals a, t, g, or c
<221> NAME/KEY: misc_feature
<222> LOCATION: (195)..(195)
<223> OTHER INFORMATION: n equals a, t, g, or c
<221> NAME/KEY: misc_feature
<222> LOCATION: (198)..(198)
<223> OTHER INFORMATION: n equals a, t, g, or c

<400> SEQUENCE: 46

```
antcatccaa ctggccgatc agcaaaaaag cgcggcctac gatttcaccc acgaactgtt       60
aaccacgctg gaagttgacg atccggcgat ggtagcaaag cagatggaac tggtgctgga      120
aggctgttta agccgaatgc tggtgaatcg tagccaggcg gatgtcgaca ccgcacatcg      180
gctggcggaa gatantcntt gcgttcgccc gctgccgtca gggtggtgca ctgacctgac      240
agaaacacag aaaagaagcg atttgccgca atcttaagca gttgaatcgc ttttactgaa      300
attaggttga cgagatgtgc agattacggt ttaatgcgcc ccgttgcccg datagctcag      360
tcgtagagca ggggattgaa aatccgttgt                                        390
```

<210> SEQ ID NO 47
<211> LENGTH: 473
<212> TYPE: DNA
<213> ORGANISM: Escherichia coli
<220> FEATURE:
<221> NAME/KEY: misc_feature
<222> LOCATION: (437)..(437)
<223> OTHER INFORMATION: n equals a, t, g, or c
<221> NAME/KEY: misc_feature
<222> LOCATION: (465)..(465)
<223> OTHER INFORMATION: n equals a, t, g, or c
<221> NAME/KEY: misc_feature
<222> LOCATION: (468)..(468)
<223> OTHER INFORMATION: n equals a, t, g, or c

<400> SEQUENCE: 47

```
ggatgccagt gtcagcgact ggttaaagtg gtcgatatcg atgagcaaat ttacgcgcgc       60
ctgcgcaata acagtcggga aaaattagtc ggtgtaagaa agacgccgcg tattcctgcc      120
gttccgctca cggaacttaa ccgcgagcag aagtggcaga tgatgttgtc aaagagtatg      180
cgtcgttaat tttatctcgt tgataccggg cgtcctgctt gccagatgcg atgttgtagc      240
atcttatcca gcaaccaggt cgcatccggc aagatcaccg tttaggcgtc acatccgtcg      300
tcccctggca aacgggggcg atttttcctcc atttgcctca gtggctggcg tttcatgtaa      360
cgatacatga cagcgcccga caagatcctg atactctttg ggtattcaac cgtttccagt      420
```

```
gtaattcgtc gttcacnaac attggcgtta caggcggggc tggcngtnac cca            473
```

<210> SEQ ID NO 48
<211> LENGTH: 482
<212> TYPE: DNA
<213> ORGANISM: Escherichia coli
<220> FEATURE:
<221> NAME/KEY: misc_feature
<222> LOCATION: (48)..(48)
<223> OTHER INFORMATION: n equals a, t, g, or c
<221> NAME/KEY: misc_feature
<222> LOCATION: (87)..(87)
<223> OTHER INFORMATION: n equals a, t, g, or c

<400> SEQUENCE: 48

```
gaagtgacgg atggctgtgg tttctccatc ggtcaccagc agcagttngc atcatggatt     60
gcctataaag tcgcgccgtt cctcggnaaa aagaggaga gcgttgaaga cctcaaattg     120
ccgggctggc tgaacatttt ccacgacaac atcgtctcca cgcgattgtg atgaccatct   180
tctttggtgc cattctgctc tcttcggtat cgacaccgtg cagcgatggc aggcaaagtg   240
cactggacgg tgtacatcct gcaaactggt tctcctttgc ggtggcgatc ttcatcatca   300
cgcagggtgt gcgcatgttt gtggcggaac tctctgaagc atttaacggc atttcccagc   360
gcctgatccc aggtgcggtt ctggcgattg actgtcagc tatctatagt tcgcgccgaa     420
cgccgtggtc tggggcttta tgtggggcac catcggtcag ctgattgcgg ttggcatcct   480
ag                                                                   482
```

<210> SEQ ID NO 49
<211> LENGTH: 185
<212> TYPE: DNA
<213> ORGANISM: Escherichia coli
<220> FEATURE:
<221> NAME/KEY: misc_feature
<222> LOCATION: (168)..(168)
<223> OTHER INFORMATION: n equals a, t, g, or c

<400> SEQUENCE: 49

```
gacgacctgc aggcatgcaa gcttggcact ggccgtcgtt ttacaacgtc gtgactggga     60
aaaccctggc gttacccaac ttaatcgsct tgcagcacat cccccttcg ccagctggcg    120
taatagcgaa gaggcccgca ccgatcgccc ttcccaacag ttgcgcanct gaatggcgaa   180
tggcg                                                                185
```

<210> SEQ ID NO 50
<211> LENGTH: 491
<212> TYPE: DNA
<213> ORGANISM: Escherichia coli
<220> FEATURE:
<221> NAME/KEY: misc_feature
<222> LOCATION: (472)..(472)
<223> OTHER INFORMATION: n equals a, t, g, or c

<400> SEQUENCE: 50

```
taacgcttca atacgcgcga ccagctggcg gcgctcatac ggcgtaattt tggcgtcggc     60
gagcaaaatc ccttgtttaa aggtattttg ccagctgccg tcgtcatatt ggcgagcttg   120
ctgacgcgac tgcgcaggca ttaaacgatc agcacaatcc atcgcccgca gccagtaaag   180
cggattggtt tcggttgatt taccttgcag cgcccagatg tcgctacatt cagtagaaag   240
atagtcagcc agttgataaa ccggaatttt tccttctgct ggcgtatcaa tggctggctt   300
attgtgattc tgcacgcaac ccagcaatgc cagacatgga gaccctgcca gccacagccg   360
```

```
tcggggcaat aatcgttgaa aaatgtgtcg catattcacc agacttaaag cctatcccag    420
tgggcgtaat tgttgcagac agtctggaca tggacagcgc ggagaaaccg gnagcgtaca    480
tatcgtacgt g                                                         491
```

<210> SEQ ID NO 51
<211> LENGTH: 106
<212> TYPE: DNA
<213> ORGANISM: Escherichia coli
<220> FEATURE:
<221> NAME/KEY: misc_feature
<222> LOCATION: (105)..(105)
<223> OTHER INFORMATION: n equals a, t, g, or c

<400> SEQUENCE: 51

```
acttgaacgg caattattat ttatccatgc aacttcaagt tgcagtatcg gaacattaac     60
ttttctgggg tgaatatcac tctgatatcg tttttgtat gcgtnt                    106
```

<210> SEQ ID NO 52
<211> LENGTH: 481
<212> TYPE: DNA
<213> ORGANISM: Escherichia coli
<220> FEATURE:
<221> NAME/KEY: misc_feature
<222> LOCATION: (439)..(439)
<223> OTHER INFORMATION: n equals a, t, g, or c

<400> SEQUENCE: 52

```
tttatgtgcg gtattgatgg ctgaagcctg taatatcgga ctggaaccgc tgataaagca     60
caatatacca gcactgaccc gccatcggct cagttgggtg aaacagaatt accttcgtgc    120
agaaacgctg gtcagcgcca atgcccgcct ggttgatttt cagtccacac tggagcttgc    180
tggtcgttgg ggaggtggag aagtggcatc agctgacggc atgcgctttg tcacaccagt    240
gaagaccatc aactcaggat ctaacagaaa atattttggt tctgggacga ggcatcacct    300
ggtataactt cgtatctgga tcagtactct gggttccatg gcattgtggt acccggtaca    360
ttacgggrct cgatttttgta ctggaaggac ttcttgagca gcagacaggg ctgaatccag    420
ttgaaatcat gacagacant gcgggtagca gcgatattat tttcggtctg ttctggctac    480
t                                                                    481
```

<210> SEQ ID NO 53
<211> LENGTH: 558
<212> TYPE: DNA
<213> ORGANISM: Escherichia coli
<220> FEATURE:
<221> NAME/KEY: misc_feature
<222> LOCATION: (4)..(4)
<223> OTHER INFORMATION: n equals a, t, g, or c
<221> NAME/KEY: misc_feature
<222> LOCATION: (36)..(36)
<223> OTHER INFORMATION: n equals a, t, g, or c
<221> NAME/KEY: misc_feature
<222> LOCATION: (69)..(69)
<223> OTHER INFORMATION: n equals a, t, g, or c
<221> NAME/KEY: misc_feature
<222> LOCATION: (456)..(456)
<223> OTHER INFORMATION: n equals a, t, g, or c
<221> NAME/KEY: misc_feature
<222> LOCATION: (462)..(462)
<223> OTHER INFORMATION: n equals a, t, g, or c

<400> SEQUENCE: 53

```
tggnccgtaa ttcccaacca tttgccgagg tccagntttt tcaccatgtt actcgggata     60
```

| | |
|---|---|
| gccaaaacng ataccgatgt tgccgccgtc ccggtgcgag gatcgcggtg ttgataccga | 120 |
| tcagttcgcc gttcaggtta accagcgcac caccggagtt accacggttg atcgctgcat | 180 |
| cggtctggat gaagttttcg tagttttcgg cattcaggcc gtacgcccca gcgcagagac | 240 |
| aatcccggaa gttaccgtct cgcccagacc aaacgggtta ccaatcgcta cggtgtaatc | 300 |
| acccacgcgc agtgcatcag aatccgccat cttaattgcg gtcaggtttt tcgggttctg | 360 |
| gatttggatc agcgcgatat cagagcgcgg atctttgcca accatcttcg cgtcgaactt | 420 |
| acggccatcg ctcagttgaa ctttaatgac cgtcgngtta tnaacaacgt ggttgttggt | 480 |
| gacgacatag cctttatcgg catcaatgat gacgccggaa cccagcgcca tgaattctgt | 540 |
| tgctggccgc caccatta | 558 |

<210> SEQ ID NO 54
<211> LENGTH: 263
<212> TYPE: DNA
<213> ORGANISM: Escherichia coli
<220> FEATURE:
<221> NAME/KEY: misc_feature
<222> LOCATION: (37)..(37)
<223> OTHER INFORMATION: n equals a, t, g, or c
<221> NAME/KEY: misc_feature
<222> LOCATION: (180)..(180)
<223> OTHER INFORMATION: n equals a, t, g, or c

<400> SEQUENCE: 54

| | |
|---|---|
| cacctgcgtg acgtgaccga ccttttctcc tcgctgnttg tttcccctat cgtcggcctg | 60 |
| gtcattgcgg gaggcctgat attcctgctg cgacgctact ggcgcgggac gaaaaaagcg | 120 |
| tgaccgtatt cgccgcattc cggaagatcg caaaagaaa aaacggcaaa cgtcaaccgn | 180 |
| cattctggac gcgtattgcg ctgattgttt ccgctgcggg cgtggcgttt tcgcacggcg | 240 |
| cgaacgacgg accaaagggg atc | 263 |

<210> SEQ ID NO 55
<211> LENGTH: 683
<212> TYPE: DNA
<213> ORGANISM: Escherichia coli
<220> FEATURE:
<221> NAME/KEY: misc_feature
<222> LOCATION: (517)..(517)
<223> OTHER INFORMATION: n equals a, t, g, or c
<221> NAME/KEY: misc_feature
<222> LOCATION: (600)..(600)
<223> OTHER INFORMATION: n equals a, t, g, or c

<400> SEQUENCE: 55

| | |
|---|---|
| gtaacgcgtc tggaagatgg cctgccagtg ggcgtcgtcg atgtggtcga ggggctggac | 60 |
| ggttgccatt ccgccaatat ctcaccggac aaccgtacgc tgtgggttcc ggcattaaag | 120 |
| caggatcgca tttgcctgtt tacggtcagc gatgatggtc atctcgtggc gcaggaccct | 180 |
| gcggaagtga ccaccgttga gggggccggc ccgcgtcata tggtattcca tccaaacgaa | 240 |
| caatatgcgt attgcgtcaa tgagttaaac agctcagtgg atgtctggga actgaaagat | 300 |
| ccgcacggta taatcgaat gtgtccgagc gctggatatg atgccggaaa attctccgac | 360 |
| acccgttggg cggckgatat tcatatcacc ccggatggtc gccatttata cgcctgcgac | 420 |
| cgtaccgcca gcctgattac cgttttcagc gtttcggaag atggcagcgt gttgagtaaa | 480 |
| gaaggcttcc agccaacgga aacccagccg cgcggcntca atgttgatca cagcggcaag | 540 |
| tatctgattg ccgccgggca aaaatctcac cacatctcgg tatacgaaat tgttggcgan | 600 |
| caggggctac tgcatgaaaa aggccgctat gcggtcgggc aggaccaat gtgggtggtg | 660 |

```
gttaacgcac actaaccgct gat                                          683

<210> SEQ ID NO 56
<211> LENGTH: 282
<212> TYPE: DNA
<213> ORGANISM: Escherichia coli
<220> FEATURE:
<221> NAME/KEY: misc_feature
<222> LOCATION: (231)..(231)
<223> OTHER INFORMATION: n equals a, t, g, or c

<400> SEQUENCE: 56
tggatgcagg gaaaaacatt gatattaccg gggcaacgtg ctcgtccggt ggagaccttg     60
gaatgtctgc gggtaatrac atcaacattg ccgtaaacct gataagcggg acaaaagtca    120
gtccggtttc tggcacactg atgacaacag ttcatcatcc accacctcac agggcagcag    180
catcagcgcc ggcgataacc tgggcgatgg ctgcaggcag agatkctggg ntgtcacagc    240
atcctctgtt tctgccgggc acagcgccct gctttctgca gt                      282

<210> SEQ ID NO 57
<211> LENGTH: 697
<212> TYPE: DNA
<213> ORGANISM: Escherichia coli
<220> FEATURE:
<221> NAME/KEY: misc_feature
<222> LOCATION: (36)..(36)
<223> OTHER INFORMATION: n equals a, t, g, or c
<221> NAME/KEY: misc_feature
<222> LOCATION: (696)..(696)
<223> OTHER INFORMATION: n equals a, t, g, or c

<400> SEQUENCE: 57
atgaacggcc ccccccacag cccgttaaca aacggntgcc ccggcgataa tcgtactgat     60
aagttaactc cagcaggcgg ttaattgaaa gcgaacggga ggctgatgca tggtaataat    120
cccttaaaac gcgacggcaa cgcgccagta accgtgaga tggtcagggg caagccagtc     180
cgggtaaacc agaggcagtc cggcagtgaa cgaaccggaa acatgaccac tggtggtgct    240
gagcccggca gcagcacccc acagcgtgcc ggacgagtac gggtcatctc tgtcagagtg    300
cagccagccg ccgtccagtg cagtcactgc acggactgtc cccacatatg cagggagaa     360 cagagaccag gacagctcat ttcgcagata accgccgtta ttaccggaga tatactgctc    420
cttaaagcca cgcactgaac tctcaccccc gaggctcagt tgttccacac catgaagacg    480
gtccggtgac cactgggcat aagcgctggt cagccaccac accctgtccg tgacggggcg    540
ctgaaaactg gcactcaccg accatttccg gaactgattt acgggcaggt ctcccctttt    600
cccgtggtcg ctttctgcgc cgaaccaggg catcccccgt gtgaataccg gattcagtgt    660
tccgacacca cccagaaact tgtgtgtgtg attcanc                             697

<210> SEQ ID NO 58
<211> LENGTH: 4835
<212> TYPE: DNA
<213> ORGANISM: Escherichia coli

<400> SEQUENCE: 58
ttcgactgag caccacaaat actgggtatc tccccagata gttcattgcg gtacaagcaa     60
tataggtgca gaaagtcaac ctgctgcacc ctattggata attatatatg gccttcaata    120
aagtttgcgg ttgtcgacgt tggctatatc agccatttcc aatgcatagt tctttggttt    180
agcaccatca agtyatagat ttgggaatag tttcaactgg tattgattga attgggtttc    240
```

-continued

```
atcgtcgatg attaatacta tttgtaaaga ctttattgtt gatttcttat tataccacaa    300
acccaaactg gtctaggtca tcatttggtg ttgataacgg gctctgataa tttctgctct    360
tctgctatac tggggattat gaagaatatt aaggctgagt gtattgaggt agtgttcttt    420
gaaccgacca ttcatgacaa tatattcttc aattcgtgag tgatccagca actggttgaa    480
tttaaaacac tgagtgatgt tatcctctgt aatcgtatgg ttgctgaact agttgatgta    540
gccgataagg tttataccag atatcttttg ggggattag ataacgtagc cgcggatagc     600
aaacgagata gttgaatttt attaccgtaa tttcttccat tgagaaaagc ttattttttct   660
tggtggtatt cgcagttatg tatcttccat aaagacttgg gaatatcttg cttgaaargc    720
tatctggaga tagccttagt tatttgataa atatttcaaa taggaggagc cgtatggctg    780
tcatttatac cctcactaaa tcgtcacttg tcaagtctgg tggtcaatta cattggaata    840
ttgattcgcc atcagaacaa cagccacaaa agatcgtcaa tggtcgggtt gcgcttcggg    900
gatggttact ggcagatgtg gaaaaagatc tccgtgttgc ggttaaaatt gaacatttga    960
catacagttt tcccttcaat ataaagcgcc ctgatgttat ttcagctata ctgaaacagc   1020
cacctgaaaa acatcaaaga cttcattgtg gatttgatat caatgtccca ttttctacta   1080
aaataattat tggccttgag tctgatgggt tgattacctg gttggaagag ttattatttc   1140
tcctgcctga taattgaatt aagtatctat accgatagta tcgcgataga tatattttt    1200
tacaggatga taatttgaga atctatatag ccgctattat caaggatgag tattcaagtt   1260
tacttgaatg gattgcctac catcgagtat taggtgttga tgggttakt attgcagata    1320
atggcagtcg tgawggtagc cgagaattac tattttccct cgctcgccta ggtattgtga   1380
cgatgttcga acaaccgact ttggtgaatc aaaagccaca attacctgca tatgaacata   1440
ttttacgtag ctgtcccaga gacatagacc tgcttgcatt tatagatgct gatgaatttt   1500
tattgccact tgaatcggat accaatttgt cagattttt ttctgaaaag tttcaggatg    1560
agagtgtcag cgctattgca ttgaattggg caaattttgg ttctagtggt gaatggtttg   1620
ctgaagaggg gttggttatt gaacgttta cctatcgtgc cccgcaatcc tttaacgttc    1680
atcataactt caaaagcgtg gtcaaacccg aacgagttaa ccgctttcat aatccgcatt   1740
atgctgattt gcgttatggt cgatatatcg atgcattggg tcgtgatttg attctgcacc   1800
cgaggcatgg taatggggtt agtgctgaag tgacttggag cggtgtcagg gtaaatcact   1860
atgcagttaa atcacttgag gaattcttgt tgggcaagca tctgcgtggt agtgctgcca   1920
ctgctaatcg agtaaagcat aaagattatt tcaaggcaca tgatcgtaat gatgaagagt   1980
gccttctcgc tgccgcattc tcagaacaag taaaagctga aatggaacga ttaagtgtga   2040
agttgactga gttaccagca gttgaaccta ttcctactgg ttcttggttc aaaaaaaaaa   2100
tgaagaaatg gatggtttga atatattgag caagcacttt ggtatttatt tctgctctta   2160
tctacaggtc tgctaataag gatctgtatc ccccaggtgt taccttggac tgtaagttat   2220
attatgtgta gctattgcga ttggcagcct ctgacattgc cagactcgtt ttctcttcat   2280
tctggttggc ttctgattcg ggggcgcgtg ttgacgactc aaactcgagg tgaaactcgt   2340
ctgcgctggc aatgcggaca aggaatatgg catgaacaga agttgccggt cactcgtcga   2400
ggcacgttgc tggagctggt ttatctaccy tcgggagcta gtcattkgtc tttgctggca   2460
agtaataagg gcgctgagtg taatgttgaa attactcagc tttgttgtgt atcccgtgcc   2520
gagagtctct ggcgtcgatt gcgccgggtt gtaccttttt accgacgctt aacgaagtcc   2580
```

-continued

```
agacgcaaaa ggttaggcct ttcatggcat ttgtggctca cggacttgca gcaagcttac    2640
caacttgtca gcagagttcg cgatgataaa ccactcaata gctatgatga gtggctagca    2700
gacttcgaca cccttgaacc cgccgaatac aagctgatta agcgccagct ggctcgctgg    2760
ggcacattac cacgtttctg tttgcatctt gttggcgttg gggatgaaca gagccgccac    2820
aagaccctgg agagtattca ggcactctgt tatccggcaa gcaatataaa cctgcaggag    2880
catggtgcat atccagaaat ctccagtcag tcaagcggcg aatggcagtg ggtgttgcct    2940 gtagggggcag tggtttcgcc aagcgcctta ttttggttg cccaccagtt acgccagaat    3000
cctgattgtt tatggatata cggtgatcac gatctgcttg acgagagagg tgaacgtcac    3060
tctcccaact caaacctga ttggaatgaa acgctgctac agagccaaaa ctatattagt    3120
tggtgtggtt tgtggcgtga acaaggtgct ggccgtgttc cctttgatgc ggcgacatgc    3180
catcagtggt ggctacagtt ggcaaagatg tgtgaaccga acagatagt ccatattcca    3240 tcattgatga tgcatttgcc tgcaagagcg ttgatttcgg atgattttga gtcgctgaaa    3300
gataaagaag atttactgcc atcaggagtg agcattgagg cagcacctca tggtgtatgt    3360
cgttggcgct ggccgttgcc agcgcaattg ccattggttt cagtgattat ccctactaga    3420
aatggtattg ctcatttacg cccttgtatc gaaagcctga tacaaaagac gcaatatgcc    3480
aatatggaag tcatagtgat ggataatcag agcgatgagg aggagacgct tgcttatctt    3540
gctcatatcg aacaggttta tggcgttagg gtgatttctt atgatcaacc gtttaactat    3600
tcagccatca acaatctggc agtgagaaac gcacatggag atatgatatg tttgctgaat    3660
aatgatactc aggtaatcag tattgactgg ctggatgaaa tggtttctca tttattacgc    3720
cccggcgtgg gtgtggtagg agcaaagctg tattacggaa atggcttgat tcagcatgca    3780
ggcgatgctg tcggccctgg cggttgtgca gatcattttc ataatggttt gtcagctaac    3840
gatcctggat atcagcgtag ggctgttagt gcccaagagc tgtcagctgt gactgcagct    3900
tgtttattga ctcataaaga gttatatctg gcgctcggag gacttgatga aacgaatttg    3960
ccgatagctt ttaatgacgt rgattattgt ctcagagttc gagatgctgg ctggagagta    4020
atctggactc ccttcgctga attgtatcat catgagtcta tttcccgtgg taaagatgta    4080
tcaaaacaac agcagatacg agcgaaatct gagttcgct atatgaaaaa acgatgggca    4140
tgtgcactta aacacgatcc agcctacaac caaaatttga gttatgaacg tcctgatttc    4200
tctttaagta gagctcctaa tatagtattg ccatggatga attaattcgc aggaaactat    4260
ttaagcctta tcgtaaatta aataaacaga gttatagaag tccgcaaagc tctgagatta    4320
actttgaacg attgtttata ttacatgagg gaaaatcacc tacattagcc tattttgaat    4380
cggctattat aagtcggttt cctgatgcag aatgtcattt tatcgacaca ttagcatcca    4440
ctgatatatt tattcctaga ggatctgccc ttgtcgtcat tagattcatc tccccaaaat    4500
ggcaacagca catagaaaga tataacgaca ggttttctcg aattgtttat tttatggatg    4560
acgacctgtt tgacccgact gcactatcta cgttaccaaa agagtatcgt accaagataa    4620
taaggaggtc ggcggctcag catcgatgga ttacgcaata ttgtgataac atttgggttt    4680
caactgccta tttggctaat aaatatgcac atcttaaccc ggagattgtt tctgctaaac    4740
cgtcactggc actcattgaa acacatcgat cagtaaaaat cgcttatcat ggctcaagtt    4800
ctcatcggga agaaaaatat tggttgagac aaatc    4835
```

<210> SEQ ID NO 59
<211> LENGTH: 1746

```
<212> TYPE: DNA
<213> ORGANISM: Escherichia coli
<220> FEATURE:
<221> NAME/KEY: misc_feature
<222> LOCATION: (9)..(9)
<223> OTHER INFORMATION: n equals a, t, g, or c
<221> NAME/KEY: misc_feature
<222> LOCATION: (35)..(35)
<223> OTHER INFORMATION: n equals a, t, g, or c
<221> NAME/KEY: misc_feature
<222> LOCATION: (877)..(877)
<223> OTHER INFORMATION: n equals a, t, g, or c
<221> NAME/KEY: misc_feature
<222> LOCATION: (1746)..(1746)
<223> OTHER INFORMATION: n equals a, t, g, or c

<400> SEQUENCE: 59
```

| | | | | | |
|---|---|---|---|---|---|
| gaaaaatgnc | ataaccgcat | tccatcaagc | ccgtnaatat | cccggacttt | catttatttc | 60 |
| tgaggcgtac | agggaagcaa | taactgctgg | tcagatattg | ctgtctccgg | tacatttacc | 120 |
| tgacactgta | tttttccatc | ccagtttacc | gacagggttt | cccccggcgt | cacgccactc | 180 |
| agccaggcaa | ggccttcgtc | ggccaccatg | cccagttccc | ggcctttttc | actggttaca | 240 |
| ctggcaccaa | acgggggctg | agagccatca | gcaagacgca | gtattgcaaa | cagacgtttc | 300 |
| cctttaagca | cgctgaattt | ccggtaacca | atggcacctt | ctgtcagcgc | cgattccaca | 360 |
| acagaacggg | ttgcttccac | atcatccggt | aagcgcttca | ggtcaacaga | ggttgtattc | 420 |
| cggtaataac | tgctgatgtc | agtcaccacg | cccgttcccc | agcgatttgt | caccacctgc | 480 |
| ccgccatcaa | ccggtacacc | tcccacacca | tccgtgtcaa | caagaagacg | tgttccaccg | 540 |
| gacattcccc | ctgcatgtaa | cgccgcacct | tttccggtaa | ttgttgcccc | accggaagca | 600 |
| ctgacgccga | aagacgtata | tcctttctgc | agggatgcaa | tattcgcgga | caaatttgcc | 660 |
| agcggactac | gatgactgta | ataggcatta | atctgacgtt | gcgatgtcag | tccaccgcca | 720 |
| ctgttaaggc | cggcgttcag | gctgtagctg | tccagaccgt | cattgaacgt | gwcagtgtag | 780 |
| ccggccatat | tcacataacg | gtcattactc | atactgccac | tgtagctcgc | tgtccccgtc | 840 |
| ccccagcggc | acggatatac | gcaggtaagc | agaatcntta | tcacgcccca | gatatttaga | 900 |
| ccttgaggct | gacaatccaa | ccgccacacc | ctgcagtccg | aaaacattaa | agtagcggtt | 960 |
| gacgctcacc | gtataatagt | ccgttttccg | tatgtcccag | tatgtctgac | ggctgtactg | 1020 |
| caggttaaaa | gaggtgttcc | agtccgccac | gttttattc | agcgtaacgg | tatacatctc | 1080 |
| tttttcccga | ctgctgtaat | cattacggta | gcgggcgttc | aggtactgct | ccatggtcat | 1140 |
| atagtttcgc | tctgagaaac | gatacccggc | gaacgtaatg | tcggcatccg | cattatcaaa | 1200 |
| ccgtttggag | tagctcagac | gccaggattt | ccctgaaac | gttctctctc | cctcaatacg | 1260 |
| ggctactgac | tgcgtgatat | cagcggaaag | ggtccccggc | acacccaggt | cccagccggc | 1320 |
| accggctgcc | agtgcattat | aatcaccggc | aagcacagcc | ccgccataca | gcgaccactg | 1380 |
| gttactgagc | ccccaggatg | cctctccggt | cgcaaataca | ggcccttcgg | tctcatgccc | 1440 |
| gtatccacgg | gaacgaccgg | agacaagttt | gtaccggacc | tgtcccggac | gcgtcagata | 1500 |
| aggaaccgag | gccgtatcga | cctgaaagtt | ttcttccgtc | cgttctgttc | aataacctca | 1560 |
| acatcaagac | gtccgcgaac | tgaactgtcc | aggtcctgaa | tactgaatgg | ccctgcgggg | 1620 |
| accatcgagt | cgtacagcac | ccgtccctgc | tgcgacacca | caacgggc | attagtctcc | 1680 |
| gcaatcccgg | taatctgcgg | tgcataagcc | ttcgcattct | tggggcggca | cattccgggt | 1740 |
| cagcgn | | | | | | 1746 |

-continued

```
<210> SEQ ID NO 60
<211> LENGTH: 723
<212> TYPE: DNA
<213> ORGANISM: Escherichia coli
<220> FEATURE:
<221> NAME/KEY: misc_feature
<222> LOCATION: (473)..(473)
<223> OTHER INFORMATION: n equals a, t, g, or c
<221> NAME/KEY: misc_feature
<222> LOCATION: (636)..(636)
<223> OTHER INFORMATION: n equals a, t, g, or c

<400> SEQUENCE: 60
tgtactgagc acggcgaata tccagtgttc aaattccact tgcagcgac  tgcatgatgt    60
ctgcggcgcg gtaacaatca gggcattact gtgtttgctg gcggcgatgg agacaacctc   120
acgcccgcta ccgaccgtgc cttccgcctc ttctttagcc gccgtgagcg tgccgctgac   180
ctgcttcagc acatcgacca gatcttcggc tttgctgtat ttgagataga aaacctggct   240
gttgccgctg cgttccattt ctgagtccag ccgacggatc aggcggcgca ttttgtcccg   300
cgtggccggg tcaccactga caatcacact gttggtgcgt cgtcggcga  caatttgaga   360
tttcagcgtc gcaggctggt tctcgccgct gtttttagtc aggctttcca gcacgcgggc   420
gatttccgaa gcagaggcgt tatccagcgg gatcacctct tcagtgcgat tanccgcgtg   480
atccacacgc tggatcactt ccgtcagccg ctccacgacg gaggcgcgcc cggtgagcat   540
aatcacgttg gagggatcgt aattaacaac gttgcctgag cctgcgctgt cgatcatctg   600
gcgcagaatc ggtgccagtt cgcgtaccga aacatnacgt accggcacga ctttggtgac   660
catttcatcg cccgcgtatt gtcgctgcct tcaccaacca gcggcagggc tcgactttcg   720
cgg                                                                723

<210> SEQ ID NO 61
<211> LENGTH: 2556
<212> TYPE: DNA
<213> ORGANISM: Escherichia coli

<400> SEQUENCE: 61
tagaggatcc ccggcgttgc gatcgtcacg aacatagacc cacakccgtc cggtaggtat    60
ttaccctgac ccggytccag tacatttacc ggcgtgtcat cggcatgcac tttacccggc   120
atcagcacat agtgcttcag ttcatcatac agcgggcgaa gctgctctcc catgatgtca   180
acccagcgcc ccatcgtatt gcagtgcagc tccacgccct ggcgggcata gatttccgac   240
tgacggtaca gcggcagatg ctcggcgaac ttagccatga ttatgcgggc cagcagagcc   300
ggactggcgt aactgcgctc gatgggtttt ggtggctgcg gagcctgaac tatacagtcg   360
caccggctgc aggccagttt tgggcgaacc gtttcgatta ccctgaacgc ggtgttgatg   420
atatccagtt gttcagagat gctttctccc agcggtttca gtttgccgct gcagacgggg   480
cattcggttt ctgccgggga gataacctgc ctgtcacggg gaagtgttgc cggaagtgct   540
ttgcggacgg gagagtctga tgttttcggc gctgtctctc cggccattga ggtgagttgc   600
aactgcgcct caccaagcct gttctggagc tcggttatac gcgtttctgc ccgtgcgatc   660
ttctttttcta tcttctcgcg gcttttctcg ctgctgcgac cgaacaacat tctctgtagt   720
ttagcgacca gcgctctgag tgagctgatc tcgcggcata gccggttatt tcaccagaca   780
gacggacgat aacagcctgc tgtgcgatca gcagggcctt cagttgctcg atgtcgtcgg   840
ggagtgtgtt gttcattccc ctgttttatc acgggttata tccggatgcc aggccgttct   900
gtccgtttgg gatgttgcca cgcgatcccc tccagtagca tggataactg agctggcgtc   960
```

-continued

```
aggtgcactt tcccttcccg ggttaccggc cagacgaagc ggccccgttc caggcgtttg    1020
gcgaacaggc ataacccgtc acgatcggcc cacagtattt tcaccatttt gccactgcgg    1080
ccccggaaga cgaagatatg cccggagaac gggtcatctt tcagcgtgtt ctgcaccttc    1140
gaagccaggc cgttgaagcc acaacgcata tctgtgatgc cagcgatgat ccagattctg    1200
gtaccggttg gcagcgttat catcgggtac ctccttttat ttcgcggatt agcgcccgta    1260
acatttccgg agtgagaggg tcaaacagtt ttaccacacc tgatttaaga tgcagctcgc    1320
accgtgggac gtttccggga tcacactcag ggcactcatc aggcttgtta cgccagaagg    1380
gatttgtaac tggtctggtc ggctctggcg tatcagtcag agccaccggg acaggcatgc    1440
attcctgtat gtcatcatcg ctcagtaagc cgtcctcgta ctggcttttc catttaaaca    1500
gcaggttatc attgataccg tgctctctgg cgatccgggc aacaacagca ccgggctgta    1560
atgcctgctt agccagacgg accttaaatt cacggctgta gctggctcgc cgttcttttc    1620
gccatgtgcc ttcgctgatt tgaggctctg ttaattcctt ctttctgttg gcataaagga    1680
tggcgtcaag ctgagctaat gaaactgaat cgggcaatgg ccatgcgata ccggatgcaa    1740
taaatcgctg aaaaagcgta tgtattgtgg aatgactgag acctagacgc tgagcgatgg    1800
cccggatggt cagtttatct tcaaatctta acgcagagc atcaggcaaa taagaacgga     1860
agcagggaat atcttttttt gtctgggaat tcatcgttcg tgtccatcta tatagatggg    1920
cgcgattgtt gccagacagg acaattttca caagacgtcg cagatggggc gcttaccaga    1980
aatgcgcggg tacgacagtg actcgtcaaa tctcagttgt agcacacgcg ggatcaattc    2040
cggattgtct gccagtaccg cctttcgtgc attcatctta aatgtcccctt tactgcaaaa    2100 atggacatta gtatcggaaa caggaaaggg aggcgaaaga cggtttaaat gagacggtta    2160
ccattgtgtc gggctgtgta cgttctcccc ggacagacag cctcagttcg tagaatctat    2220
aaattactgc tactgatgct gccggggaaa ggcgtaacga aaaaacagcc tccgttaccg    2280
gacagcaagg aggctgaatg gagtttacag gatttgcttt tttataatgt ctggccatgc    2340
agtaaaaccg gacaggtttt attatcatgt gaggtattct gacataaaat gctggatttt    2400
tattttgtga cgaatgctgc aaaattgcat ctgcactctg atgtagcttt tatctgtttc    2460
agtgaagcat gcccacaaac tgagttatta agttgtggaa gaacagtttt gtcccgcctg    2520
catctctcct ttcaaaaacc agtatgtcgc catgcc                              2556
```

<210> SEQ ID NO 62
<211> LENGTH: 790
<212> TYPE: DNA
<213> ORGANISM: Escherichia coli
<220> FEATURE:
<221> NAME/KEY: misc_feature
<222> LOCATION: (19)..(19)
<223> OTHER INFORMATION: n equals a, t, g, or c
<221> NAME/KEY: misc_feature
<222> LOCATION: (29)..(29)
<223> OTHER INFORMATION: n equals a, t, g, or c
<221> NAME/KEY: misc_feature
<222> LOCATION: (57)..(57)
<223> OTHER INFORMATION: n equals a, t, g, or c
<221> NAME/KEY: misc_feature
<222> LOCATION: (765)..(765)
<223> OTHER INFORMATION: n equals a, t, g, or c

<400> SEQUENCE: 62

```
cagttagtgt taaaaaatnt cctctgctnc agaaattaca cccaccaata tacaatnatt      60
aataaatttt cggttgggtt aggtaatggc tgggattcga taatatctct tgatgggtt     120
```

```
gaacagagtg aggaaatatt acgctggtac acagccggct caaaaacagt aaagattgag      180
agcaggttgt atggtgaaga gggaaagaga aaacccgggg agctatctgg ttctatgact      240
atggttctga gtttcccctg aataagatga tggattatct gactggctgt tcatcagtcg      300
gataatgatg aaaactgatg agcaacaggt tgtgcgggca atgtgcagga tccgtcacca      360
aagggtggaa gttgcgggcg actcagataa acgggttaca tgagctattt ctggagtttg      420
acgaagccgt ctggaaggga gaagaggcga ttccattgat gtctctggaa acatctgtc       480 agtcgtgctg ctggaaatat tgatagagca atgggaatgg ttatccaaca ttgatgaaca      540
tattgtatat ttacagaaat ttttaaaaac aggactcagc aggttaaatc gtgtaaaaat      600
tactcatgaa taccattatg gcttacaaa gcgatgtggt taagcagatc ttattcaggc       660
ctgtgcagcg taggattaca ataggatcga ataacgccat acaggggaat gggagatagg      720
ctgattcatc ctgtggctat aaccaggagc atatcgggaa tcmantatgt tacccccagat    780 ggaacaccat                                                              790

<210> SEQ ID NO 63
<211> LENGTH: 10906
<212> TYPE: DNA
<213> ORGANISM: Escherichia coli
<220> FEATURE:
<221> NAME/KEY: misc_feature
<222> LOCATION: (856)..(856)
<223> OTHER INFORMATION: n equals a, t, g, or c
<221> NAME/KEY: misc_feature
<222> LOCATION: (4922)..(4922)
<223> OTHER INFORMATION: n equals a, t, g, or c
<221> NAME/KEY: misc_feature
<222> LOCATION: (6875)..(6875)
<223> OTHER INFORMATION: n equals a, t, g, or c
<221> NAME/KEY: misc_feature
<222> LOCATION: (8094)..(8094)
<223> OTHER INFORMATION: n equals a, t, g, or c
<221> NAME/KEY: misc_feature
<222> LOCATION: (10800)..(10800)
<223> OTHER INFORMATION: n equals a, t, g, or c
<221> NAME/KEY: misc_feature
<222> LOCATION: (10849)..(10849)
<223> OTHER INFORMATION: n equals a, t, g, or c

<400> SEQUENCE: 63
gcggccgcag tactggatct ctttgcggca tgacgatgag ggggagagaa ataaacttaa       60
cccagtcatg gcagatgaag aacaggctta cgtaaaaggg ttatatgaag ggattatgct      120
gattggtaat ataatcaata agcctgaaga agctaaagcc ttaatcaagg caactgaaaa      180
tggctgcaga atggtgagta accggctgca acttctaccc gaagagcagc gtgttcgtgc      240
ctatatggcg aatcctgaat tgaccactta tggttccgga aaatatacag gattaatgat      300
gaaacatgct ggcgcagtaa acgtcgccgc ttccaccatt aaaggtttca acaggtctc      360 gatagagcaa gtcattgaat ggaatcctca ggtaattttt gtgcagaatc gttatcctgc      420
tgtagtgaat gaaatacagt caagcccaca gtggcaggta atagatgctg tcaaaaatca      480
tcgtgtttat ttgatgccag agtatgccaa agcatgggc tatccgatgc ccgaggctat      540
ggggattggg gaattgtgga tggcgaaaaa gctgtatcca gaaaaattca atgatgttga      600
tatgcataaa atagtcaatg actggtatag aacgttttac cgtactgatt atcagggtga      660
agactaatgc gagtgcttgc tgcgggcagt ttacgccggg tatggaaatc acttgtgtca      720
gagtatcagg ccgataatat acagtgtgat tttggaccag cgggtatatt aagggagcgt      780
attgaggtgg gtgaggcatg cgattttttt gcatcagcca atatgactca cccacagata      840
```

-continued

```
ttaatgtccg caggangagc attgtgtatt aaacctttg ccagaaatcg tttgtgtttg      900
tatgttcggg cgaataaatt caatgagaat gacgactggt attctttatt aaatcgggaa      960
acattgcgaa tcggaacatc aacggcggga tgtgatccat ctggtgatta cactcaggaa     1020
ctgtttgaaa atatggggag tgtcggtgaa aaataaggc aacgggctgt agcattagtt     1080
gggcgggagg cattcgtttc ctcttccagg aaatgcgata gcagcgcagt ggttaattga     1140
aaatgattat actgatctgt tcatcggtta tgccaattac gctcctggct tgcaatcaat     1200
tgattcagta aaagttatag aaataccgga accttataat ccgattgcta tctatggatt     1260
tgcctgtctg accgataatg ccctgccact tgccgacttt ttagtttcac ctgttgccag     1320
aggtatactt gaacagcatg ggtttatgcc tccaggtacg ttatagcccc ctgtcttaca     1380
gctgtctctt gatcagatct cctgatcaag agacttcatc accaggtaac cctcaaccat     1440
atcctgcata tcctgaagtc tgaaccagcc atcccacata actacccaac cggggcggcc     1500
tgtgcgtttg ctgtcatgcc atcgcccag tttcgccagt tcagacagg cccatttcag     1560
tgtcggcgtc tgtgacggaa gcggttttcc ttccagctta acccacagca gtttccactc     1620
tgtcggcgtc agtattttct tacagctgtc attttgtgtt tcttcactga tacctccctg     1680
ccgcaggcca gcacccgtac cgcgataaac gccttgataa ccaccatgcg ctcaaggtta     1740
tcccgggtct gcattcgcag cgattccaca catgtaccac cactttcca cgccttgtgg     1800
tattcctcta tcagccagcg tcgctcgtaa tggctgacga tacgtcgcgc atcggcggca     1860
ctcgccactt tttctgacgt cagcagatgc agcaggcac cgtcctctgc ctgctcccgg     1920
caacagacat acgtgagcgg gagcgcctgg ccgctgttgt cgggattttt tatgctgact     1980
tcgttgtaac tgatgaacat ccgggcctgg cgggctgccc gcccgccttt ttgcatcaca     2040
ttcagcgtgt ggcttcccgc ggttgccagg acttccggca gttcgaagag cttgccgggt     2100
gcttcttcca gccggcgatt ctgtcagca cgcaccacga agcgctgtcc gtggctgact     2160
ttataatgca ggtaatgcta gatatccgct tcccggtcac agacagtgat tacccgttc     2220
tgtatctccc ccagccgttc ggccatacgc tccgaagcct gctgccagcg gtaactttct     2280
ttttcttcat agggacgttc ttttcgctgg tgcttaacac cataggtgtc cgtgacccga     2340
ctccagcgct gctgttcgat aagaccgact ggcaggcgc tgtcggggc gtacatcagg     2400
acagagtgag ccagcagccc gcgcgtcttc gggttagtgg tggtattccc caggtcatca     2460
gatgccgtac tgtggctgaa gttaatggtg gtggtgtctt ccagtgcgag gagcagcgga     2520
tgagcctcac atgcccttac agtggcggta atccggcctt cggcaatggc ttgcggggac     2580
acagacgggt tacgtatcag gcggtacgca ccttcaacct gagcagtgga ctgggatgat     2640
ttcacaatag aaagacctgc atgctgagcg agagaagagg tcagtgacac aaggcgtcgt     2700
gtacgacgcg gatcaccgag acgggcatgt ccaaactgct cgttagccca tgaataacaa     2760
tcagaaagta ccataacaga gtcgaataaa atgaaatata agagaagatc aacgggtgaa     2820
gaaaagttc aaaaaatggc taccggggag gaaggaaagt accggatgga aagagccccc     2880
ctaaagcaga ctgacagaca tcacaaatcc ccggggggga cttgtgtata agagacaggt     2940
cttacagggg gagcgtccgt ctttttatca acatcaggca atgacataac attatgaaca     3000
agctcacaag tctgatggtt aaattttata atgctcctta ctaagaccgt atttttcat     3060
tctgagatag agttttttcc gcgggatttg taaatattca gcaacctcat tgatacgccc     3120
ctgatggata ttaagtgcct ctgtgattat ctgtcgctca gcgtcctcca ctcgtctgtc     3180
```

```
aagcggtgtc ggggttccga cgtgcatcaa cggatttgct gtttctgcca gcggtaatac    3240
tcctacagta aatagttctg ctgcattggc cagctctcgc acattatttg gccacatgcg    3300
gcgcatcatc tctttgagca tctcttttcc cacttccgga acaggatggt taagccgttg    3360
acatgcttta caaaggtaat ggcgaaacag tggttcaata tcatcggggc gttgagttaa    3420
tggcaggcaa gcgatttgtg tcattgcaaa gcagtaatag agctccgcga tgatatggtt    3480
gctggcggcc agctcgacca gcgaagtgtc tccaatacca atcaggcgaa aaggtcggtg    3540
ttcctggctt tgtaactgaa ccagatggta ctgctgttca cgcgtcaggt gttcaggatg    3600
gctgagcact aatgttcccc cctgagccag cgcaatgaaa tcattaagct gtggtgcatt    3660
gtctggtgtc agctcgcggt agataaattc gccttgtgca ttacgtccaa attggtgcag    3720
ataacgtgca ccggtcatcc gtcctgtgcc tggggcaccg tagagccaga cggcaatatc    3780
tgtttcagac aactgctgta aacgtcgccg atactgattt atccattcac ttctccctat    3840
caactccacc tgcaacgtct gttggcaata ctgacgacgc gcaatgattg attgacgctg    3900
gcgtagcgcc tcttcaacca gagaaagcaa tttgccggga tcaaccggtt tttgcaaaaa    3960
atcccacgcg cctttttta ccgcatcaac tgccattggc acgtcgccgt gcccggtaat    4020
aagcagaatg gggatctgtt gatcatcctg gtgaaataac atcatcaaat cgataccaga    4080
gcagccaggc atacacacat cacttagcac aatacctggc cagtctggtt gtatccacgt    4140
ctgcgcctca aaaggattgt tacaggcaaa aacccgatag cctgactgtt caagtaactg    4200
tgtgtaggcg tccagcacgt cagcatcatc atcaatcagc agaatcgaat attcactact    4260
tagcatcttc cacatccgtt agtctgaatt gcagtaccac acaggcattc ctggtcatcg    4320
ttgatgccag ccgtaattca cctttcattt gctccatcaa cgacacacaa attgaaagac    4380
caatacccag tcctacttct ttactggtgg taaacggctt caataacgaa ggcaacaatg    4440
cctcaggcca gcccgggcca ttatcgccaa tgaatacgtt cagcgtttta ccctgcattt    4500
gccagttaac ggtaatgaca gcgccttgcc cacaaacatc aagcgcattc gccagtacgt    4560
taaccagtac ctgctgggtt ctgacctcat cgcctgaaac tgtggctgta ccttgcggca    4620
gaacaagcgt agcttgcaaa gggcgatgac gcatggccag aagttcccag gccgcactga    4680
acatctgtgc taaatcaacg gaatggagtg atatttccag ttcggcgcgc cgggtaaact    4740
gccgtagtga acggataatg gcgtcaatgc gaccaatcac cccttcggct ttaccaagca    4800
tcatgctggc ctgttctgtc tgggtctgtt caatgcctgc gggctgtaaa cagatacatc    4860
gacagcgcat ttagcggctg attgatctcg tgggccagcg tggtcatcgt ttgcccgact    4920
anccgcagct tcgctgtctg aatcagttcg tcctgggtgg ctcgcagatc ggcttctatc    4980
acctttcgat cggtaatttc ttgttcaagt tgctgttttt gcacattgag ctgcccgaga    5040
gtatggcgta ataatcctgc aattctcccc agttcatcat tcccataaac aggaatagcc    5100
gtttccgtgc ctcccagacc aatttgcaca acggcctgat tcagtagggt aaagcgtttc    5160
accaaccgtg agcggataaa ataatggttg aatacccatg ccagcagtaa cgccagtgct    5220
gtcgccacca ggatcagccc accgctaacg cgaacaattt gttccattcg ttgattaaac    5280
atctgcattt gttgatgagt actgccaagt gcgcttccag taacgttctg aagcgaccca    5340
gtgtcgcttc cctggtgcga ctggcatcct ctaaggcttt tgggcggtg acatattcac    5400 gcatcgtagc cggcatttg tttttacga ttcccatatc cagcaattca tcgatagtct    5460
gcctcagggt aatggtgcca ggccagtcat ccagcatacg tatattttca tctgccgttt    5520
ttttcagatt ttcaaaataa cggagatgag tttccacctg tgtgtcgtca tcacgtcctg    5580
```

```
atttgagttc attgagtctg tcacgcagat cgtcaacaat ctgattttca atgcgtgcca    5640
gggtataaac ctgctgctgt tcattttgca cttcacgaga tcgcttcagg tattgcgccg    5700
tatcgccytg tcgggaggcg atttgatcca gcagcgttcc ctgctgccag gtgaaatcct    5760
gcactaaaga attaagctcg gtagtaaaat catcgtgtaa ccagtcaatc ctcgctgata    5820
gctcactcac cttttcccgt agtaaaaaca tgttgtaaag cgcacgatcc aactcggata    5880
acagtgatcg actgtcctgc aaaatgaccg tcagttgttg gcgttcccgg atgacagcc    5940
cccgactaag ccgttctatg gtgtcgagat gctgaataat ctgggtacga agttgcaatc    6000
gcaccgtggt gttgggagcc tgcaaaaatt catttagctg gtctaccacc agattcaggt    6060
tcccttcaat aaggaaagca gagtgaatac ggggaaaata ctcatccagc gagtaacgaa    6120
tttgtgagct tgttcatgc catgaataca gactgacact actgacaatc agggtcagaa    6180
gtgccccat cagaaatgcg caacgtaagc tggtactgat actgacctgt cttaaacgct    6240
gccacagcgt tatgttttc atttcagctc ttccagtttt tttatcgcca ggcgctggtt    6300
attcagaaac cagagttgcc attccatcat ttgctgctcg gcaaagctttt tgttatcgaa    6360
ctgtgccagc cagacgggat cttcactgct ggccgctgca acgggcactt gtgttaacag    6420
tgcacgtatt tctggtaatg gtttcttcag acgtgcctcg gtactgtgca gcgctcgcca    6480
ggcatctttt agctgtgcta accgaaagct aattgccgta tcaaacaagc gctgcaccag    6540
acgctgacgt ttcaggataa ggtgataatt cagcgggggt tgattcatca ggagctgttg    6600
ttgcgttgcc cgcggattgt ctgcggcaag tggtgtcacc ggatatttc ctgtattggc    6660
atcggccaga atacgctgtc ctttcggact taacaggtag tgaataaagc gacgggctgc    6720
atcgacgtgt gggcttttcc tgagaattgc aacgtaggtg ggggataccg cagaccgggg    6780
gaaataggta aaagagagat gggggtcatt taacagtaaa ttagcatagt tatcgataac    6840
ggggccggca acgccgagtc cgcttttat tttantcgct acgccaaaac tgcgggagga    6900
gattgtcacc aggtttcctg cacttgtcag caacgtttcc catcctttca cccagccttt    6960
ttgctgtagt aatgactcaa ccattaaatg gttagtatct gaacgcgacg gactactcat    7020
caataaagcg tcctgataga tcggcaaagc aagatcgtcc cagtcagcag gggcaggaag    7080
gtgttttaca gaaagcgccg gacgattaat gagcagacca aaacctgata ttgctactgc    7140
aacggaggtt gcacggatcg actccggcac caggttttgg ctttctgcgg gtgcatcatc    7200
aaacggggcc agtttctggt gctcctgaag gtgctggagc agcattggtg atgaagtcag    7260
gataagatcg acgttttcta cgttggccgt atcaagcaac tgttccagtg aggcactggt    7320
gcggttaagc gtacggatca ttaccgactc aggctctgtt tgccagcgct gtattatcca    7380
cgcggtagct ccgggtgaga atgtggtggc catcaccagt tcatttcgtt gagccctgac    7440
ggccccggcg tccatcagca acagtaaaag aatcatggtt ttgatgccga tttcgcacca    7500
gctaaaaaat cggtttgtga tccaggtcat aaatattaat acaccgcaaa atcgcattg    7560
agacaaaaat tacccgtttc agacattcgt ctgataacac gtctgctcaa agagaccgtt    7620
aatatattaa tcagagatta cccgataatc agcatgagat ttgttaatat ccgcacatgc    7680
taacaacaaa ccagataaag cataaatcta ccttgtctat gcatcaataa aatgggtcaa    7740
aaacaggctt tgatttttatt attttgtgtc aattgtgaca cattttttca gtttgatgtt    7800
tcatytcaat tatatgactc tcattgtcag aatactcctg atgttcatat caatataaaa    7860
tacaggtgaa gacatgttat caatatttaa aacggggcaa tcggcggata gtgttccggt    7920
```

```
ggagaaaatt caggtgacat atcgtcgcta tcgtatgcag gcgttactta gcgtatttct   7980
ggggtatctt gcatactata tcgtgcgtaa taatttcact ttatcgacgc cttatcttaa   8040
agagcaatta gatctcagcg ccacacaaat tggcgtactg agtagctgta tgcntatcgc   8100
ctatggtatc agcaaaggag tgatgagtag ccttgccgat aaagccagtc cgaaagtctt   8160
tatggcgtgt gggctggtgt tatgtgccat cgttaacgtt ggcctgggat tcagcactgc   8220
attctggatt tttgcggcat tggttgttct gaatggtctt ttccagggaa tgggcgttgg   8280
tccttctttc atcactattg ctaactggtt ccctcgccgg gagcgtggtc gggttggtgc   8340
tttctggaat atctctcata acgtcggtgg tggtattgtt gcccctattg ttggtgccgc   8400
ttttgcccta ctcggcagcg agcactggca aggtgcgagc tatatcgttc cggcctgcgt   8460
ggctatcgtt tttgcggtaa ttgtgctgat tctcggtaaa ggttccccac gtcaggaagg   8520
tctaccctct ctggaagaga tgatgccgga agaaaaagtc gtcctgaata cccgacagac   8580
ggtaaaagca ccagaaaaca tgagcgcctt tcagattttc tgcacttatg tattacgcaa   8640
caaaaatgcc tggtatgtct cactggttga cgtatttgta tacatggtgc gcttcgggat   8700
gattagctgg ttgcctattt acctgctgac ggtgaaacat ttttctaaag aacaaatgag   8760
cgtcgcgttt ttatttttttg aatgggccgc aatcccttcc acgctacttg ccggttggtt   8820
gtcagacaaa ctgtttaaag gcgtcgtat gccattggcg atgatttgta tggcgctgat   8880
tttcatttgc ctgattggct actggaaaag tgaatcgctg tttatggtga caattttttgc   8940 tgccattgtt ggttgcctga tttacgttcc acaatttctg gcttccgttc agactatgga   9000
gatcgttccc agctttgctg ttggttctgc agtaggctta cgcggtttta tgagctatat   9060
cttcggtgcg tctctgggca ccagcctgtt tggtattatg gtcgatcata ttggctggca   9120
tggcggattt tatcttcttg gctgcggtat tatttgttgc atcattttct gctggttatc   9180
acatcgtggt gcaattgaac ttgaacgtca cagagccgca tatataaaag aacactgatt   9240
accttcccca gggccgtctc cctggggagt ggagtatatt atgatttata agatatctgg   9300
aaatcagaga ttaatatgga aattttataa gactgattac aataaatgga gatggtattg   9360
tcatgagaaa aatggatatc ttttgtctca atcagataac gcatataatt cgcaattgtt   9420
atgcattgaa aatgctaaaa acagggata ctcagacgaa tcggtcttgc cacttttttct   9480 acatatttcc tatattcagg aaaaaggctg gaaatggtat caatgttatg attgtggata   9540
tattgtaaaa gaaacctctg ttttttttttc gacataccag gaatgtgtca atgatgttaa   9600
aaggaatata ctagcatcta tgtgtagtgg ttgtagtggc acagtaaatt tggccacctg   9660
attaaaggtg atattctcac cacaacataa aacaacaaga aaacaaagcg taccttctct   9720
cctgagttta aactggaatg cgcccaactt atcgttgata acggttactc ataccgggaa   9780
gctactgaag ctatgaatgt tggtttctct actctggagg catgggtacg tcagctcaga   9840
cgggaacgtc aggagatcac gccttctgct gcagcaccac tcacatcaga gcagcaacgt   9900
attcgtgagc tggaaaagca ggtgcgtcgt ctggaggaac aaaatacgat attaaaaaag   9960
gctaccgcgc tcttgatatc agacttcctg aatagttacc gataatcggg aaactcagag  10020
cgcattatcc ggtggtcaca ctctgccatg tgttcagggt tcatcgcagt agctacagat  10080
actgaaaaaa ccgtcctgaa aaccagatg ggctgtatta cacagtcagg tacttgagct  10140
acatggcatc agccacggtt cggccggagc aagaagcatc gccacaatgg caacccggag  10200
aggctaccag atgggacgct ggcttgctgg caggctcatg aaagagctgg ggttggtcag  10260
ctgtcagcag ccgactcacc ggtataaacg tggtggtcat gaacatgttg ctatccctaa  10320
```

-continued

```
aagcaacagc aaacagcgac cactggggag ccctgcattg cgggattgta ttgttcagcg      10380
ggccatgctg atggcgatgg ggccgaggag agtgattttc atacgctctc atatggtttt      10440
cgacttgtgc gaaatgtcca ctacgcgatc cgcacggtga aactgcaact caccgacttc      10500
aggggaaact cggggccgct gggtaatctc acataaaagt tcttcggtgt cataaacaac      10560
gagagtattt gattccttta tggtggcctg gtgcagagct gcccttccc aggacctcca       10620 tataatttt gtagcggcag tcagtggcac actcagttaa ctactttcac ttcagtgact        10680
ttgaatgagt cagggctgcc gttaaaggtg ttaatgaagg cttgtatttt ccacttctgg      10740
cctggttcaa gattggatgc tgtgtcgatt gtttgaccga taacgactcc atcttttaan      10800
agattaaatt ttacataagc attttgaca acagagtttg atttatttnc agcataaccc        10860
acaattgcct tcgtcccact tggggtgttt tccacatgaa ggttag                    10906
```

<210> SEQ ID NO 64
<211> LENGTH: 7430
<212> TYPE: DNA
<213> ORGANISM: Escherichia coli
<220> FEATURE:
<221> NAME/KEY: misc_feature
<222> LOCATION: (3651)..(3651)
<223> OTHER INFORMATION: n equals a, t, g, or c

<400> SEQUENCE: 64

```
atggttattt ttatttcctg caccttgctt catttgaaat aaaaacatat gcatacgacg         60
ctgccattga gcagaaaaat acaggaatta atgttatgag ttaaccataa tacctgtgtt        120
atgaatatct gacataaaca agaacaattc atatcttctg tattcagcag aataataaaa       180
gttcgtctgc cattctcaaa cttattcttc ggaatacgtt gtttcatgaa agaaggggcc        240
ggaataaaag ctggtcaccg taatgctaat attaatgcag actaccgcct tctggaatta       300
acagtcatca accagcacaa accattagca atcaaacaaa ttttaattaa caaaattta        360 gctaatacaa ttactgcatt aaccactctg cagtttgcct tctcaataag ttacagatgc       420
caaacaatac tcttttatat gttataacat aacacaaaca ataataaag aacagacggc         480 actccatttc tccacgtaag tgagccatca gaatcgctta tgaatgtgta cggcagacgt       540
atactcgtgt tttactgcag caaccggagc aaaagttgca cttccacagc ctgggttaag       600 ttttcatgc ttgtgggctc gtcctccctc catttccacc gcgggcaaac aaggccatct        660
tttgtctggc cacacagcag atggagagtc gaattatgct gtctgacgac accgggaaca       720
aatatgccat gccttcgcac aatgaacccg ggcatcatcg ttttatcttt ataatcgaga        780
caggtatgag ggaaagtcgg atgataagca gatagtgagt gaggcgctgg aacatggcgc       840
tctggcaaga gaagtgtcac aggttacctg atgatatggg gcaacctgat atctacttac       900
ttttttgcct actctcttac ttcatgccag cagcgaggt atcgacattg tgtttgaacg        960
ctgccgtgta ggtagcagcg aggccgctac tgtcggtaag tgcttccgga taaagctctc      1020
ctcccgcttg tgcaccactg gcattggcga tttgtttcac caaacgggga tctgtctggt      1080
tttcgataaa gtacaatttt acgtgctctc tcttaatttg attaatcagt ttcgccacat      1140
ttttactgct agcttccgac tcagtggagt accccactgg cgacagaaag cgaacccgt       1200 aggcggcagc gaaatacccca aacgcatcat gactggtcag tactttacgt ttttctcttg    1260
gaatagcagc aaacgtctgc gtggcgtaat tatccagttg cttcaactgc tggatatagc      1320
tgtcaccctg ttttcgataa tcgctggcgt gctccgggtc tgctttgctc aggccattga     1380
```

```
caatgttgtg agcatagaca ataccgtttt tcatgctgtt ccaggcgtgc ggatcagtga    1440
tggtgatccc atcctctttc attttcagtg tatctattcc gttagacgcg gtaattacct    1500
cacctctgta gccagaggct ttcaccgac ggtccagcca tccctccagt cccaatccat     1560
tgacaaagac aacatccgcc tgtgccagcg ttttgctgtc tttcgkcgac ggttcaaatt    1620
catgtggatc accatccggt tgcaccagat cagtgacatg aacgtatggg ccgccaatct    1680
ggctgaccat atcgcccagt accgagaaac ttgccaccac attcaactct tttgcaatca    1740
ccagtgggct cactagtagg ctggacagtg ccacaaccaa aatggaccgt ttcatctttc    1800
ctccttcatc tcgttgctat gtgtaaaaac acttcttgtc agcgacatct gcataacatg    1860
ccgccattag agccaaacag aactgaaaag cagaaaaaca gagtgctcgt gaggatgact    1920
gcaggacctg caggcaaatc agcgtaataa gaccagatca gtccaaccag actggcgcag    1980
gtaccaatac ccactgcagc taacaacatg atggacagac gttgactcca gaaacgcgcg    2040
ctggcagccg gtaacatcat aataccgact gtcatcaggg tgccaagtag ctggaaacct    2100
gccaccagat tgagtaccac cattgacaaa acaggcagt ggatcagcgc ccgcgaccga    2160
cgtgacagaa ctttcaggaa agtgacatca aacgactcaa tcaccagcac ccggtagatc    2220
aacgccagta ccagaaccga accggaacta attatgccga tagtgatcag agcattggcg    2280
tcaatagcca gaatggaacc gaacagcaca tgcagcaggt cgacactgga gccacgcaaa    2340
gagaccaggg tgacgccaag tgccagcgag ccgaggtaaa acccggcgaa actggcgtct    2400
tctctcaatc cagtgcggcg gctgaccaca ccagacaaca tcgccacaga cagcccggca    2460
atgaagccac cgactcccat cgcaaccagc gacatgcccg ataccaggta gccaattgct    2520
actcccggca acaccgcatg ggacagtgca tcaccgatca ggctcatacg gcgcagtagc    2580
aaaaaacagc caagtggcgc ggcgctcagg gtcaacgcca gacatccgac cagcgcccga    2640
cgcataaaac cgaaatcgcc aaatggctcg cacaacaggt gcagtaacat catggcagca    2700
gcccctgctg cggtggcgtg gctgcagccg tgagggaatg gagtatatcg gcacttctcc    2760
cccatcggtg gccttccgca ctgagcatca gtacatgagg aaagtatttt tctacctgtt    2820
ccatgtcatg caacaccgca agaattgtac gtccttccag atgtagctgc cgaataacaa    2880
ccagcagagt acggatagtc tgaatatcaa tgccagtaaa tggttcatcc agcagaataa    2940
ccgacggctg catcaccagc agtcgtgcga acagtacgcg ctgtaactga ccaccggaaa    3000
gtgtgccgat gtgcatcggc gaaaattctg tcataccgac ggtatccagc gcttcgatag    3060
ctttttttcg ccatagaccg gaaatacgac cgaacatccc gctgtgtgga atacatccca    3120
tcagcaccag atcgttaaca ctcagtggaa actggcgatc aaattcagtc aattggggca    3180
aataacctaa ctggcgttgc ccctgcggtg ccatgcagaa gcaaccaccc agaggtggca    3240
gcagaccggc caacgtttta agcaaggtgg atttacctgt gccattcgct ccgataatgg    3300
cagtcagtga accggtgtca aaacatccat tcagcgtacc cagcgggtgc tgtcccgaat    3360
agccaaatgc cagtgaatgt aatgcgatca tgtcagtacc accgcccagg aaataagagt    3420
ccataacagt accagcagca caccgacgat acccagtcgg gctattgcgg aaaaagcata    3480
aagactgacc acagtatccc ccatcaaaat tgttatagta taacattatt gctttatggg    3540
tgccgatgat aggtaagaaa atgtgtcatg gcttctgcag cgtaagcata cagcgagagc    3600
agtattgaca gggatgcgtt agtcatttag cagtgtaatg cgctaaatag ntgcgcggaa    3660
tagtagatca ctttgagggt actcagcccg gattgtgcgc tctgatcaat cgccaaatca    3720
aaacaaatca ccaaccgaac tgagcaatgc cgatcatagc accaatttcc cgtgacgaac    3780
```

```
gacaccggat gcagaaagcc atccataaaa cacacgataa aaattatgcc cgcagactga   3840
ctgccatgct gatgctgcac cggggcaacc gtatcaacga cgttgccaga acgctctgct   3900
gcacccgttc atctgttgga tgctggatta actggttact aaaatcattc cctgccgggc   3960
gtgcccatcg ctggccattt gagcatatct gcacactgtt acgtgagctg gtaaaacatt   4020
ctcccgacga ctttggctac aagcgttcac gctggaatac agaactgctg gcaataaaaa   4080
atcaatgaga taaccggttg cctgttaaat gccggaaccg ttcgccgttg gttgccgtct   4140
gcggggatag tgtggctaag ggttgtgcca gctctgcgta tccgtgaccc gcataaagat   4200
gaaaagatgg cagcaatcca taaggcactg gacgaatgca gcacagagca tccggtcttt   4260
tatgaagatg aagtggatat ccatcttaat cccaaaatcg cgctgactg gcagttacgc    4320
ggacagcaaa acgggtgatc acgccgggac agaatgaaaa atattatctg gccggagcgc   4380
tgcactgcag gacaggttaa agtcagccat gtgggcggca accgcaaaaa ttcggtgctg   4440
ttcatcagtc tgctgaagcg gcttaaagcg acatactgtc gagcgaaaac cagcacgctg   4500
atcgtgggca acaacattat ccacaaaagc cgggaaacac agcgctggct gaaggagaac   4560
ccgaagttca ggggcatttta tcagccggtt tactcgccat gsgtgaacca tgttgaacgg   4620
ctatggcaga cacttctcga cacaataatg tgtaatcatc agtaccgctc aatgtggcaa   4680
ctggtgaaaa aagttcgcca ttttatggaa accgtcagcc cattcccgta ggggaacatg   4740
ggctggcaaa agtgtagcgg tattaggagc agctatttag gagaacagct cgctgacccg   4800
gttgactatg actcaagccc atgacgaaga tagctttctg gatcaacatc gttcagtctg   4860
cacgtcccaa tccagccacc agccaccagc caccagccac cagccaccag ccaccagcca   4920
ccagccaggc tacagtgcca tcccgacctc cccacgtaaa cccagggaca ggctaaaggc   4980
agaaaatggg gaaggcagta tgactctccg tgacacagat gcgggtacct gatgggagtg   5040
agatcatctt cccctcccgg tcagttcccg gatcaacacc gtgagcagct ctggcgaagg   5100
ttttttccagc gtcattttac cgtaacgaaa ttcaacctta caggaactgg cacagactgt   5160
gcactaagtg gcagtggata aaagcggagt aagagccgcc acaggctctt tctgctcatc   5220
aggcattatc tcaacaggta ataattcaac gccagcgcca aagaggttg ttaccggaag    5280
acgccgcgcc cccttcgtt cagccagagc ctgagccatt tgaccaggag gttatcattg    5340
atatcgtgtt cctggtcaat acgggcaaca gaggtgccta cgacgttttt tcagttcggt   5400
tatctattga cttaactctt tggccagtaa tgctgcagcc cccgtgccat gaataaacga   5460
gtggtcgcag accacgcaac atgcaacatc attcagatcc cccgctaata ttacaggtaa   5520
ttcagaatca gcaatacttt tcccgaccat taaaagttct gagtcacgat cagttgactc   5580
atcactttca gtcgggctcg gtggaacagg atgaagacaa tgtaatctta ttctcaaacc   5640
ttctggcata tgaactatca tattcatgga gggaatttcc ttgtccacta aatactgtat   5700
ttctgcatca cttaaaatca tccaggaata tacatgcatg ccatataaat tttctttcgg   5760
gcatttcagg gagtatggaa acacttcatc cagaggtgat agtttctgtt cccaccataa   5820
gtttgtttca agaagaacaa gtatatcagg ttttcttta ttttaagtt caagaatggg    5880
tatatatttt ttattggtca taagaacatt gaataccagt atacttaaac ccagaaatcc   5940
atcagagtcc tttatttcct ttacctgctt cttgccaatt actgtataag gaattatcca   6000
taccaactgg taagcgacac aaattaaact tattatccca acaaacaact ctgtaaataa   6060
gtcaagaaaa acaacagaca gaaaaacatt caaagtacac agcaaaagta tctgtagtcg   6120
```

```
gggaaaatcc catccccga caacccatga tgtattaccg gaaacaggga taaaagttat      6180
gactgccaga aggatagcag taaaaataaa aacacaagtt atcacaaatc gctccttgtt      6240
ctgaaccgga acacaaaact gtcatatacg tttcaaaagt aaaaatacac tgctgccaca      6300
agatttacag cgtaaccgga cagcatatcc tgattacgga caatccatga aaccgcctca      6360
ccagaagcgt ccatcacatc cgttttttcc ctgttttata ttccccgaaa cattttattt      6420
tcaggaatct ccgggccttt atcccgcatc attgcaaaat ggcatctgaa tcgatcatga      6480
tttggcatcc atctccgatc acagtttggc atcacaatcg atcacgattt ggcatgcttc      6540
cgatcattga ttagcatcct gccagtcact ccgggaatta actcttttcg ccacagtctt      6600
cattgccgtg tttaaaccaa tggagacggc aatgtccaaa agagaatat  ccaggagcac      6660 tatggatacc tgtttttaaga tccttcagct caagttcgac cagaagctgg ctaaccgttg      6720
tatcggactt gcaaaacacc aatggggatt gatctctatt ttgcgacaca gacgcattat      6780
caatacatcg atggtgcgat caaataccct cagtggtctca ccgtggatca aatccagcaa      6840
ttgctcacag attaagactc gtcgggagtt ttgagccaac accagcagta acccatattc      6900
accttgagtg aaatctacag gctgttgatg agcatcaacc agcacgtaac ggtccgggat      6960
caagtgtcca gccgttaaaa aaaccactct actaccctgc tcgacctaag cctcggcgtt      7020
cagccgcctg aacgggtatg gcaagggtga aaagaaacag catccccaca gtaccgacca      7080
gacgacagga tgatgctgga acagaaagca ttcgcacctc tcttagaatt agacagtgcg      7140
tacaggatac gtaagacagg gtgacggggc ggcgataaac tctatttaca aagctgaaaa      7200
ttttctgacg atgaaaaact attcaacaag gttatctgag gcgttaaaat aaccagctcg      7260
attaacgact aacttgaggt gaatatgaat ttaaaaaata taattttaag tactgtttta      7320
tcaatcgcta gttgtcatgc cctggctgta ggtaattctc caaatagcgc tatctaacct      7380
tcatgtgggr aaacaccccc agtggggacs aaggscaatt ggtggggtta                7430
```

<210> SEQ ID NO 65  
<211> LENGTH: 6681  
<212> TYPE: DNA  
<213> ORGANISM: Escherichia coli

<400> SEQUENCE: 65

```
agattattct ggctcagatt cattttcat cagtcgcttt ccctataaa ccgtaaggtt         60 ccatagtgtc gacgctctcg cttaattccc atatcgtcga tagtcttatt agccgcttct       120
gtcaggtcag aaaagtatc acgcttcttt gggagttcaa gtcagatttc tcgccgtcgg       180
gcgatgcgct caaatgttt gtctgtatgg ggtcgcttca tcacgtcaag ccatcgcgct       240
gccgctctcc gccagagtac aagctcttcc agttgttctg cttttatct tatctgtggc       300 gatgcagtat cctcctccgt ttgtgtaaat cgttgagtgg tgaatcacgc aaagggctt       360 cttttttctg atctatcccc atattcttta gcgttctggt cgcagcatct ctgatgtcgc      420
agacactgaa cctttgtatt ttccatgatc ttgtggagtt ttcgatacat ctgctccgat      480
gctgggttat aaagatccgc tctttatcat ccttggcttg tgtaagcaat tctccccaac      540
gttctgctgc acgccgccat aactctcttc tttccagttc ctcagctttt tcatcatgta      600
ccattcgtgt atcccgtttt atccagtctg aaccgcaccg ggtttcctgg agaatgtttt     660
ctctgtgaac tcaggctgcc agatcatcgt ttccgatgga agcataataa gctttttctg     720
cttctgccgg argaatatgg cccagctttt ccagcaatcg tcgattgtca taccagtcca     780
cccacgttag tgtggccagc tccacttctg tccgtttttt ccagctctta cggttattac     840
```

-continued

```
ctccgttttg taaagaccat tgatgctctc cgccattgcg tcgtcatacg agtcgcctgt    900
actccctgtt gatgccagta atccggcttc cttaagccgt tgcggacaca taatgagagc    960
ctttatcgct gtaattgtca acgacggatg aaaagtgatc cacttatatc tccaccaacg   1020
gcccaatatt gatccaccgt tttactcagg attagcttct gctataaccc cggcctttcg   1080
tttctgtctg agtcgatagc tttctccttt gatttgaacg acatgtgagt ggtgtaagat   1140
acggtccagc atcgctgagg tcagtgctgc atcaccggcg aacgtttgat cccactgccc   1200
gaacggcaga ttggatgtca ggatcattgc gctcttttcg taacgtttag cgatgacctg   1260
gaagaacagc tttgcttctt cctgactgaa cggcagatag cctatttcat caatgatgag   1320
caggcggggg gccattactc cacgctgaag cgtcgtttta taacgccct gacgttgtgc    1380 cgtagataac tgaagtaaca gatctgctgc tgttgtgaag cgaactttga tacctgcacg   1440
gactgcttca tagcccatcg ctattgccag atgggttttc cccacacctg atggccccag   1500
taatacgata ttttcattac gttctatgaa gctgagtgag cgtaacgact ggagttgctt   1560
ctgcggtgct ccggtggcga atgtgaagtc atactcttcg aacgttttca ccgccgggaa   1620
ggctgccatt cgggtataca tcgcctgttt acgttgatga cgtgccagtt tttcttcatg   1680
aagcagatgc tccaggaagt ccatataact ccattcctgg tctactgcct gttgtgacag   1740
cgcaggcgct gcgcttataa ggctttccag ttgcaactgc ccggcgagcg ccatcagtcg   1800
ttgatgttgc agttccatca tcacgccact cctctgcaga atgagtcgta gatggagagt   1860
ggatgatgca gggggtgttt gtcgaagttc accagatttt catcaagatg cacgtcatac   1920
tcttttttct ccggagcagt gccagcatgg actgctgtct tcgagccagc gatcgcaggg   1980
acgggcctgg attgtttcat gctttcgttg gttagcgaca tcgtgcagcc agcgcagacc   2040
gtggcggttg gctgtttcaa catcgacagt gatccccatc gggcgcaggc gagtcattag   2100
tgggatgtaa aaactgttac gggtgtactg caccatccgt tccaccttac ctttagtctg   2160
tgccctgaag gggcgacaca gtcggggaga aagcccatc tccttgccga actgccacag    2220
cgaaggatgg aaccggtgct gaccggtctg atatgcgtca cgttgcagaa ccacagtttt   2280
catattgtca tacaacactt cgcgcggcac accaccaaag aagcggaacg cattacgatg   2340
gcaggtctcc agcgtgtcat aacgcatatt gtcagtgaat tcgatgtaca gcattcggct   2400
gtatccgaga acagcaacga acacgtgaag cggtgagcga ccattacgca tagtgcccca   2460
gtcaacctgc atctgtcgtc cgggttcagt ttcgaaccga acggcaggct cctgctcctg   2520
aggaaccgag agagaacgaa tgaatgccct gagaatggtc attccgccac gatatccctg   2580
gtctctgatc tcgcgagcga ttaccgttgc cgggattttg taaggatgag catcggcgat   2640
gcgttgacga atataatccc ggtattcatc caggagtgaa gcaacagcag gtcgcggcgt   2700 atatttggc ggctcagatt ttgcctgcaa ataacgttta accgtattgc gggagatccc    2760
cagttctctg gcaatcgccc ggctactcat tccctgcttg tgcaggattt taatttccat   2820
aactgtctca aaagtgacca taaactctcc tgaatcagga gagcagatta cccctggat    2880 ctgatttcag gcgttgggtg tggatcacta ttgcaccgtt cgtgacagta atggattgtg   2940
tcagacggac gacgggccca taacgcctgc tccagtgcat ccagcacgaa tgttgtttcc   3000
atggacgatg agactcgcca tcccacgatg tatccggcga acacatcaat gatgaacgcc   3060
acataaacaa agccccgcca tgtgcttatc ccggtaaaat cagctaccca caactggtcc   3120
gggcgttctg cgatgaactg acggtttaca ccgttgcatg cggcaacagc tttccggctg   3180
```

-continued

```
attgtcatgc gaacctttg caaaccccat atatttcaga cgataccgtt caacggtagt      3240
gaacccacca tcaccgctcc cggtatcccg ctcatgctgg tatacccaga catgcagggg      3300
ttccagcgta cagccaatct ttggggcaat ggaacaaatt gacgcccact acgagtcata      3360
cgactttcca gaacaatacg gagcgcccgc tgacggacca ccaaagagcc gccattattc      3420
ttattacctt taactaataa tgccaattca gacccaaaca cggcatcatt cgcttcagcc      3480
tctgcgccat taattaatgc caggacttgg tcaagaaagc gttgcgcttc gtttacatct      3540
gttgcttgtc gcaggtaata aggtattcgt tcaacaaact cggaacgtga taaaggctga      3600
tgctccagca aaacctcaag cattgcgggc cgcaacaaac gacgctcagc atcaacattg      3660
ggaaacttaa cctcaatggc atatgtggca aaatacttaa gttgctcctt aagccccaaa      3720
ttaggcataa gagaatcaat tgagccagac gccactgcag cgcttgattc aattgtttct      3780
acatactcgt aggaaggtac aacaacatct ggagccaatg ttttaagctc atggagttga      3840
cggataatcg gggatagaac ctcatcagga ttactgaacc aatcagtgga ccaaatacgg      3900
ctaattctcc accccaaacg ctccaaaacc tcttgacgca aacgatcacg ggcagattta      3960
gctgaatgat aagccgcacc atcgcactct atacccatta gtaacaacc cggatcttct      4020
accgacagat caataaagaa tcctgcaacc ccacctgagg ttcacactca aacccagcgt      4080
gattgagtgc ttccattata gcaacctcaa agtcactatc cggagccctg cccgtatacg      4140
tcgtgaggga atctaatttg ccactttcgg caaactgtaa aaaacctttc aacgaaataa      4200
caccaaattt actggtttca ctcgtcaata catcttcaga acgcattgaa ctaaacacat      4260
gcatccgttt cttgatcga gttaaaagca cattcaagcg gcgccagcma acatcggaat      4320
tgacaggccc aaagcgttaa taaacctttc caccatgctc agaaggtcca caggtaaagg      4380
aaataaagat tacatcacgc tcatcacctt gaacgttctc aagttttttc acaaaaagtg      4440
gctcttccat ggcatataag ccatcaattg catcgttaaa ttcagtgcga tttcggcgca      4500
attcatcaat agcgcgctca atctgatcgc gttgcctgga actcatggcc actacccaa      4560
gagattcatc cagccggtgt tgcgcatgat gaagtacagc ctcagcaact gcttgggctt      4620
cttcaatatt gtgttgatta gagcaacgac cttttgatac ataagtaaat ttgattccat      4680
actctggaga ctcagcattt ggagaaggga atatccaccaa atcactgtta taaaaatggc      4740
ggttagagta tgcaattaac ttttcgtgtc gtgaacgata gtgccaatgc aaacgtctca      4800
taggaaacag tggcaaagca gcatccaaaa tgccgtcagt atcacttaaa gccgcgacat      4860
catcgtcatc ttctccggcg gaacttcgat ctgaagtggc acactgaatt tggccacctg      4920
aacagaggtg atatgctcac ctcagaacaa cacaggtgct ccaatgaaaa aaaggaattt      4980
cagcgcagag tttaaacgcg aatccgctca actggttgtt gaccagaact acacggtggc      5040
agatgccgcc aaagctatgg atatcggcct ttccacaatg acaagatggg tcaaacaact      5100
gcgtgatgag cgtcagggca aaacaccaaa agcctctccg ataacaccag aacaaatcga      5160
aatacgtgag ctgaggaaaa agctacaacg cattgaaatg gagaatgaaa tattaaaaaa      5220
ggctaccgcg ctcttgatgt cagactccct gaacagttct cgataatcgg gaaactcaga      5280
gcgcattatc ctgtggtcac actctgccat gtgttcgggg ttcatcgcag cagctacaga      5340
tactggaaaa accgtcctga aaaccagac ggcagacggg ctgtattacg cagtcaggta      5400
cttgagttgc ataacatcag ccatggttct gccggggcaa gaagcatcgc cacaatggca      5460
acccggagag gctaccagat ggggcgctgg cttgccggca ggctcatgaa agaactggga      5520
ctggtcagtt gccagcagcc tgcgcaccgt tataaacgag gtggtcgtga acatgtcact      5580
```

-continued

| | |
|---|---|
| atcccgaatc accttgggcg gcagttcgca gtgacagagc caaatcaggt atggtgcggc | 5640 |
| gacgtgacgt acatctggac ggggaaacgt tgggcatacc ttgccgttgt tctcgacctg | 5700 |
| tttgcaagga aaccggtagg ttgggcaatg tcgttctctc cggacagcag actgaccatc | 5760 |
| aaagcgctga aaatggccta ggaaatccgc agtaaaccag ccggggtaat gttccacagc | 5820 |
| gatagtaata atgccggtat cagtttttat catcactctg tttgctgttt aaccagactg | 5880 |
| gtgtgattac tgatgcagtg aagaccttcc cgcatcctga ctcacacagc gatcgaccct | 5940 |
| ttgtgtcctg ccctggacct gtcggttgcc ggaagcgcct tcatgcgagg cgtctcctca | 6000 |
| ccgatgcgcg tgactcaaga agggcctgac ggtttgtctc gttactgtcc tgtccgggtt | 6060 |
| atctgtctgg agattcaact ctgtttcctc acaggagctc tgttatggca ggtaaagtta | 6120 |
| cggaaaccgc tgttgtgggt ggcgtggata cacataaaga tctgcacgtt gccgctgtcg | 6180 |
| tagatcagaa caataaagtt ctggggaccc agttttctc cacaatacgg caaggttacc | 6240 |
| ggcagatgct ggcatggatg acttcgtttg gggcattaaa gcgaattggt gttgagtgta | 6300 |
| ctggcaccta tggatcaggt ctgcttcgct atttacagaa tgccgggtta gacgttcttg | 6360 |
| aggtgactgc gccagatcgg atggagcgac gcaaacgggg taaaagtgac acgattgatg | 6420 |
| ctgaatgtgc cgctcacgcc gcattctccc gaataagaac cgtcacaccc aaaacgcgca | 6480 |
| atggcatgat tgagtctctg cgggtattaa aaacttgccg aaaaacagca atatcagccc | 6540 |
| gcagagtcgc tctccagatt atccattcca atattatctc tgccccggat gaattacgtg | 6600 |
| aacagctcag aaatatgacg cgcatgcagc tcatcaggac tctgggatcc tggcggcctg | 6660 |
| atgccagtga ataccgcaat g | 6681 |

<210> SEQ ID NO 66
<211> LENGTH: 1342
<212> TYPE: DNA
<213> ORGANISM: Escherichia coli
<220> FEATURE:
<221> NAME/KEY: misc_feature
<222> LOCATION: (1238)..(1238)
<223> OTHER INFORMATION: n equals a, t, g, or c

<400> SEQUENCE: 66

| | |
|---|---|
| tattcgcgca tacgcgttgc acatgttctt ttggcgaacg atcatcggca atacagagtt | 60 |
| cccaatgggg atagctttga gccaggacag aatccagaca ggcacgcamg tagatctccg | 120 |
| ctggattata acaggaatc acaatagata taactggagg gtgagtcata ctggcaagca | 180 |
| tcagactcac cwcttckttg ccaggcaacg aaggtaattc caccgtttct atccattcct | 240 |
| cataaccgac agaagacggg gtaacgctga acgtytcgtt atagaatgct tgcaggcgct | 300 |
| ctattgacat atcgccattg tscatcaata tggattttwt gattttttct agcggcatgt | 360 |
| cacgatagct ttggtgttct ttttgaatgc gagccaatag tgcagactcg actactttca | 420 |
| catcaacagc cgctatttca aactgattaa ttgcaaattt tgctgcctgt tctaatggat | 480 |
| caaatcgtaa tgcacaagag gcgattccag atagaacaac gactgacgct gaccgctcgt | 540 |
| ttatatggca acgttactgt ttcaaactca ttgaacccct tacctgtatc caaatrtaac | 600 |
| ttagctaatc cttgctttgg ttgggcaatt aatagagata ttaaattgat accatccctt | 660 |
| gctaatattt gagagctgct ccaaatcaat aatgaaaaat ggatcatttc cctctgcaac | 720 |
| ccaactttgt gaattatcta tatctatcga gagctgattt gttgccagat agggcagcac | 780 |
| aactgtattt tgcattttac tcactgcagg agaaacgtcc catgcttcgc atggtttcct | 840 |

| | |
|---|---|
| accaagtaac atcccataac gcttaaaatg ttctcttgct gacaacccgg tctgtttcac | 900 |
| atccaaatag ttatgcagat accaatgttc atcaaagtga gctagcaact cgtcttggtg | 960 |
| attttaacc atcacttta ttctcccta ttgacaggca ggcaactgcg ctgctcaaac | 1020 |
| ttcccataca taatgtaatg aagcagcgga ttaatgcctc cttgggccac atccggatag | 1080 |
| gtttgcaaat accagcgagt atcaaactgc tcactagggc tataacctt atccgcccc | 1140 |
| acgctaataa aatgctcaag agctgagagc ccagtgtctg caacctctgg gtagcgatgt | 1200 |
| tgataccaga gttcatcaaa caatcctgaa gcggcaanta ctccgcggca ctctctgtag | 1260 |
| ctgttgttct ggatggagtc tcctccttaa atgttctgcc aagagcacga actggggctg | 1320 |
| taatcttcca agagacggtt ct | 1342 |

<210> SEQ ID NO 67
<211> LENGTH: 1580
<212> TYPE: DNA
<213> ORGANISM: Escherichia coli
<220> FEATURE:
<221> NAME/KEY: misc_feature
<222> LOCATION: (14)..(14)
<223> OTHER INFORMATION: n equals a, t, g, or c
<221> NAME/KEY: misc_feature
<222> LOCATION: (18)..(18)
<223> OTHER INFORMATION: n equals a, t, g, or c

<400> SEQUENCE: 67

| | |
|---|---|
| cgaaggaagc agtntgcngc ctgcgctggc ggagttgcgc ctgttcccac cgatgatgct | 60 |
| gtacatgaat cctccggcga acagagcggt gaactggaaa ccatgcttga acaggccgcg | 120 |
| gtcaatcagg aacgggaatt tgatacccag gtggggctgg cgttagggct gttgagccg | 180 |
| gcgctggtgg tgatgatggc gggcgtggtg ctgttatcg tcatcgccat cctcgagccg | 240 |
| atgctgcaac tgaacaatat ggttggaatg taatttacgg agttatcaca tgaattcgtt | 300 |
| atcccgcaca caaaaaccac gggcaggttt tacccctgctg gaagtgatgg tggtgattgt | 360 |
| tattcttggc gtcctggcaa gtctggtggt gcctaacctg ttgggcaaca aagagaaarc | 420 |
| cgatcggcaa aaagccatca gcgatatcgt ggcgctggag aatgcgctgg atatgtaccg | 480 |
| actggataac gggcgttatc cgaccactga gcagggcttg aggcgctga tccagcaacc | 540 |
| ggccaatatg gcggattccc gtaactaccg taccggtgga tacattaaac gactgccaaa | 600 |
| ggatccgtgg ggcaatgatt atcagtatct cagcccgggt gaaaagggc tgtttgatgt | 660 |
| ttatacccctg ggggcagatg gtcaggaaaa tggggagggc gctggcgcag atatcggtaa | 720 |
| ctggaatttg caggagttc agtaatcagt gcctgaacgc ggattcacac ttctggaaat | 780 |
| catgctggtg attttcctta tcggccttgc cagtgcgggc gtgatacaga cgtttgcgac | 840 |
| cgcttcagag ccgcctgcga aaaagcggc gcaggatttt ctgactcgct ttgcgcagtt | 900 |
| taaggacagg gcagtgatcg aagggcaaac actcggtgtg ctaatcgacc cgcctggcta | 960 |
| tcagtttatg cagcgtcgtc acggacagtg gctacccgtt tctgcgaccc gcttatcgac | 1020 |
| acaggttacg gtgccaaaac aggtgcagat gctgttacaa cccggcagtg atatctggca | 1080 |
| gaaggagtat gcgctggagc tgcaacgtcg tcgcctgacg ctgcacgata ttgaactgga | 1140 |
| gttgcaaaaa gaggcgaaaa agaagacgcc acagatccgt tttcgccttt tgaacccgc | 1200 |
| cacgccgttt acgctgcgct tctactcagc ggcgcaaaac gcatgttggg cggtaaaact | 1260 |
| ggcacacgat ggcgcgttat ccctcagtca atgtgatgag aggatgccat gaagcgtgga | 1320 |
| tttaccttgc tggaagtgat gctcgcgctg gcgattttg cgctggctgc cacggcggtg | 1380 |

| | |
|---|---|
| ttacagattg ccagcggcgc gctgagtaat cagcacgttc ttgaggaaaa aacggtagcg | 1440 |
| ggctgggtag ctgaaaacca gaccgcactg ctctacctga tgacccgcga caacgggcg | 1500 |
| gtcaggcacc agggcgagag cgatatggca ggaagccgct ggktctggcg aaccacacca | 1560 |
| ctgaataccg gtaatgcgct | 1580 |

<210> SEQ ID NO 68
<211> LENGTH: 3241
<212> TYPE: DNA
<213> ORGANISM: Escherichia coli

<400> SEQUENCE: 68

| | |
|---|---|
| cttaaccatt acccagcatt tggtagttaa atagtcgtta aaagcataaa acatggacat | 60 |
| tgtgccatcc cagctaaagc atccattacc gcctgacagg gataaaaata aaaaagcagg | 120 |
| gaaccatttt ttcatcagaa atcacttccg taattacagt tattcattta ggtatgactc | 180 |
| agttataaat catgctcata ctggccgtgg tctggraatc cccgccattc agtatcccgc | 240 |
| tgccattacg aaagggcact gaagtaaagg tgaacgttga acgtgctgtg tccagacctg | 300 |
| ctgtcactcc gtaaccatt cctgaaccat tacctaatat aagaggtgtt gacattcctt | 360 |
| ttccctgata cagcgctata ccaaaatgag ttatatttgt tgccagtaca ttattctgac | 420 |
| ctcctcccat agtatttccc gtaacttta tccagagaga gccactctta tacggacagg | 480 |
| atatgcttat ggttttttgtg acttcaccac gtgagttgtc cacgtgctca ggattaatat | 540 |
| tcccaaaatc aacaacaata ttctgcccgt tattaatggt gcatgggggg atataaacat | 600 |
| tcccctgat gttaatctgc acatcagcca gtacagcgac cgatgtcaga agcaacgata | 660 |
| taaataatga taaacgaatc attccctcc ggagagcggg acagaaaaca ttttatttta | 720 |
| cgagatataa aattaacgta ttttagttga tactattacg aatatgatgc aaccagcgtt | 780 |
| gctgttgcag agaaaggacc ggctatcaaa ttctgcatat tccctttata tccaagtttg | 840 |
| gcatgaagtg atatagtttt atctgcatta ttacctgtga tttttccggg cgtaaatgga | 900 |
| gtccctaaag ttatcgcagt cccaatattt cctgcattac tgtttataaag ataaacgagt | 960 |
| aacccatcag aagatgtgtt tgatgtattc tgaactaaaa tagcattgtt ataagtgttt | 1020 |
| gttgccgtta tcgtaacctt cattgttccc agattatagg gacaccgcat attcacagta | 1080 |
| aactctttt cgtgatttcc atttgactc agggtctgaa tctctacatc ctgccagtca | 1140 |
| acagttgtgt tgcttacagt acaggcagga ataatcagtt ttcctctgaa ggtcagatta | 1200 |
| tcaactgcat gtacatgctg agacattaac actgccccca gcattaccgg aagacacaaa | 1260 |
| cctcttatct ttttcatctg aaatatcctg tacaaaaatt ttgctaacga tatgtcaatt | 1320 |
| caaacgtggc tgttgcttca taatcaccgg gtaccacact cttcgtccgc aggcttccgg | 1380 |
| cgttgccaca acatacgcgc cgaaaggaag ctcaagactg tttccggtaa cctttttcccc | 1440 |
| ctggcctttg ttatgggagg tgccgggttt cagcagactg ctgccatcgg tgtccagcag | 1500 |
| tgcaatgcct aaccggccag cattcactcc ggttaccttc agatggcccg ggagggcgcc | 1560 |
| tcttccgtcc ccttaaaggt cagggtcaca attttgccaa ctgctgttgc atggcagttt | 1620 |
| tccagcctga tgacaaacga ctctgtcggc gaacgtccgg gcggatacca gaaatccctg | 1680 |
| gacgcccggg ttttgaagac gacatgttta ttcagactgt caccgacac atggcagggt | 1740 |
| ctgtcaagca gattacccct gaatgccaca tctgaggcta ttgcctgtcc ggcagacagt | 1800 |
| gcggcaaaca gtaaagagc gcctgtgctt tttatcatca cattcccctta ctcatatttt | 1860 |
| atgctcagac gcagcatggc cggattgctc ctggcatcag aatactcacc ctcctgtgtc | 1920 |

```
gcccttttcc tccaggcggc cagcatctcc tcctgccgcc ggtcaggccg gcacagtaaa    1980
aaggtatcac catcgtgtat aacaagatgg tcacagccgg atagcttacg gtcaggaagt    2040
aaagcacttc cgcttccggg accggttacc agtgagccgg agactgtcat cgcaacgccc    2100
cgttttccgg gctgaagtgc accaccgtcc ccacatcctg ccagcctcag catcagaggt    2160
gctccggctg ccgcagagtg attttccggc cggaggytta acggcacctc attactcacc    2220
agcgtgcagg gtgaggacag cagtgcacca ctgacggtca ggcttccggt gcgtcccccc    2280
cgttcattta tccggtaatg acgcaactca tctgcagtaa agacgtcatc gtatataccc    2340
cgctcttcag cccgcaggaa agtatggatg aaaccactca gcgacagtgc aataagatac    2400
agtactgctg ttgttttatt cacaaccata atatcccacc cgcatttaac cgttattgcg    2460
gtacattatt tctctttttt cacagagcaa cggctaccat tacagataaa cgacagtacc    2520
gggcgaccac catagtcatt aatataagac agataagggg tattataatt tgccgatttt    2580
actgtctgct ctgaacgggg agacagcatc acggtttcaa actcaccttc ctctgcctgc    2640
ttttcacttc ctcccagacc aataacagtg acataatagg gcgttgggtt ttcaatacga    2700
tacccaccgc tgactttgtt cagaattaac tggtcctgcc atacttcatt tggtctggtt    2760
ttaattgctg ccgggcgata aaaaagcttt attttggtct gtaaggctat ctgcagtaca    2820
ttggcctttt cactcctcgg cggtatttcc ctgagattaa aataaaacag tgattccctg    2880
tcctgaggaa gtttactgat atccggtgtg gtactcagcc tgaccatgct tttcgcaccc    2940
ggctcaaggc gctgaaccgg aggggtggca ataaccggcc ctgtaataat tttttcctga    3000
ttttcatttt ctatccatgc ctgagcaaga tagggcagtt gtttgttatc attggagata    3060
tcaagcgtca ttgacttctc actcccgtca acaccgcgc gggttctgtc cagcgaaaca    3120
gcagcgtctg ccccggatat aacaaacagg gggatggcag ccatcagaat cttttttcga    3180
atcatactta atttccacat tctgtaattt cacctggtcc ggaaaatggc ataaccgcat    3240
t                                                                   3241
```

<210> SEQ ID NO 69
<211> LENGTH: 398
<212> TYPE: DNA
<213> ORGANISM: Escherichia coli

<400> SEQUENCE: 69

```
aacgtggatc tccagctgat cggtgccgta ttccaggtcg taagtttcac tgatggtttc     60
acgcggcagt ttgcccggtt tacggaccgg tacaaagcca acgcccagac ccagagctac    120
cggagcgcca aacaagaagc cacgcgcttc ggtgccgaca actttggtaa tgcccgcatt    180
tttgtaacgc tcaaccagca agtcgatgct gagagcgtaa ttttcgggtc ttccagtaag    240
ctggtgacat cgcggaaaag aatgccgggt tttgggtagt cctgaatgct tttgatgcta    300 ttttttgagat actcaagctg ctgtgcatcg cgggkcataa gtgtatgcct gcttgttacg    360
gtggtactca cggcgcgttt ttaaacgtat caaaagtt                             398
```

<210> SEQ ID NO 70
<211> LENGTH: 17710
<212> TYPE: DNA
<213> ORGANISM: Escherichia coli
<220> FEATURE:
<221> NAME/KEY: misc_feature
<222> LOCATION: (6)..(6)
<223> OTHER INFORMATION: n equals a, t, g, or c
<221> NAME/KEY: misc_feature

```
<222> LOCATION: (8)..(8)
<223> OTHER INFORMATION: n equals a, t, g, or c
<221> NAME/KEY: misc_feature
<222> LOCATION: (4490)..(4490)
<223> OTHER INFORMATION: n equals a, t, g, or c
<221> NAME/KEY: misc_feature
<222> LOCATION: (4661)..(4661)
<223> OTHER INFORMATION: n equals a, t, g, or c
<221> NAME/KEY: misc_feature
<222> LOCATION: (7318)..(7318)
<223> OTHER INFORMATION: n equals a, t, g, or c
<221> NAME/KEY: misc_feature
<222> LOCATION: (11186)..(11186)
<223> OTHER INFORMATION: n equals a, t, g, or c
<221> NAME/KEY: misc_feature
<222> LOCATION: (17685)..(17685)
<223> OTHER INFORMATION: n equals a, t, g, or c

<400> SEQUENCE: 70
cagttncngt tctcatagac agattgataa atcgtaaac agccctagc attcccgttt      60
cctttgcaca catattcagg cacgggata agtataaag aatgtcgtac tgctgctacc    120
agagcaatat tcccccctga tggccgtatc agagatagta tgccggtatt ttgcgggtgg    180
ttcccgtcag gttatcgtgt acctccacgt tcgtagtcac caccggcatt ccggcytttc    240
tcagcctcaa acatcagct gcaatacgct gactgccgaa ccagaacagg ccgtccagtg     300
cagtcaccag caaccccgcc tccagcgcat gcttcagccg ttcacggggc gctttcactt    360
cccgggcaat ctgctggtat ggcgatgatg tgttttcatt cccaatcacc ggcgaatac     420
gatgagacag atgataccgg tatgtatccg gcacaccgga aaggctggcc ttcaggctgt    480
acacgcagcc aaatcgttta tcattgaaca ccacattttt ctggctgatg ccccattctt    540
cacgcagcgc ggcaatcagt tgtggtgtac gggtaagcaa caagcgaaaa ggcagttcaa    600
aactggtgac ataatccaca ttcaacaggg caatgcgaag tcgttcttct ggtccggctt    660
ctgtctgccg gcactcctcc aggacatcct gccactgcag gcgaagacgg gaagactcat    720
tcagttctgt aaagcagtat ttatccgcca gatagtcaat tcgtgtatgc atactgaaga    780
gtattccgta taagattca gctggcaaa ctttatcagt ctgtaaaaac taacggaaga     840
gtcgatattt ctcccgacaa tcaccggatg attgttgcaa tacctcgtgg catcagagac    900
tgaacagcag tttttaacgc aacgtattgc tctgatgtat caggccggac aacccgaaaa    960
cagccttcca cccggcattg tccgccagcg cttatcaccg gccaggtctg ttgcagtaaa   1020
tccgccactt gcgaacatgc ttcatcaact gtgacactgg cccgcggatg gcaaatgctc   1080
gtctggctga gcagcaacag gcatcgcatt gttgctcctc tatgttgttc ccgcaaccag   1140
cgtaatacca ccggcgagga tggacaggca gtgtgattac gctccgtaat acgttcgtgc   1200
acccgtcggt gaaggaact acagaatgtc tgaatctgtt gcccgttgat gtatccttct   1260
gtcgaatgaa gtgtgaagtg gattgccagc agatgcggcc agtgatccac cgcctgctga   1320
acaaaacgcc ggatttcccc cggctctgaa agtaaggctt cggttatttg cactatttta   1380
tctctgttga atttggttaa gtcggtgcag acgcatcaac acaagtacgg ttcgatgcaa   1440
acagctgtga ctggcaatat gaaaggaatg atgaatcagt caggatgaca aagtgccggc   1500
tgaccggagg ggacgcagga agattcacgg ggggaccagc accagggaac agcgccacaa   1560
taccagcgct gacacgttga acattgccag cgtaccggta tcacaacacg tttcatactt   1620
ctgcccccgt gattcttcga ttcgttactg tatctactgt gacacttcgc ttttatacct   1680
gcggctggat cggcccggct tgatgaatct tcactgatca gcttataaaa ccctctgtcg   1740
gtcataccgg tgaaactggt gatatagttc atgtcaatca gggaattatc ggcacgcaga   1800
```

```
aatacgctgt cgtggcttgt tgtagtcaac atggtcagaa tgtcctctgt gagatttatg   1860
aagattgtgc gaatgcgggg aatctactga gctgtgcttt cagaactggc ctgttacggg   1920
akrscaggga ttaccggcgg ggtaacgggc ttccggatca tacacaccac gattatcgcg   1980
gacaaaatca ctgaacgccc atatcacctc tttaagtatg tcttcgcagc ccggtacatg   2040
acgatccagc gccacatccc gagtggtact actttgatgc gcccggtgac acaaagcccg   2100
gattgttcca gacatcctga atcaaacgcc ccagattagg ggcgtcgaaa tatgcctctc   2160
tgaccattat attccggtgt acaggtagca ggtcagaagt gacaatgcgt cacctgacgt   2220
taaaagtcac tacacccaag atgacgttca acagcaccat gcgattcaat gtaagcccgg   2280
gctgtctgtt ccagtacacc aggctcagcg ttgtatgtgt tagctgcatc aaataccaac   2340
gacagcactt caggatacac aaccagatgt gtaatggagt tatcttcacc caatactttt   2400
ccccacgcct gctcaatcag atttctgaga accaccacct cacgactctt acaccagaca   2460
tcgttattaa gtagcagcac cataagataa ggagtggtat cgttagtcac agcctcccta   2520
ctccagagat aatataaagg ggtgggctca acagatttat cttacgtcg cttacactgc   2580 aaatattcag aaatgagtct atgcagttca ccagtaaaat ccgccatcag agagggaatg   2640
gccttattaa taccagggca aggtattaat ttaaattgta ataatttaat ttcaggatgt   2700
gtggctgcag cccgatacag agttgcaagg acacactttt gccagagggc gttactggaa   2760
agcttaacgt ttgattctgt atacataata aatcacctta cagttacaac aggtcaaaaa   2820
ccgctgtagc cagagttacg ctggcctgat gctttagtac cgggcttcgt cagataatcc   2880
agacgctcca ataagcgctg atactgctca gggaaatcag gatcatgaat atcctggatg   2940
tcacgtccat tagcagggaa atgaataacg cagcccctg gattaacaat gcagaaatcg   3000
tcctgaggta ctgatcaata cggagaggac tctcgcgtgt ggtttattga caccacagtg   3060
cagattcggc gaatccgcga tcacggtgcg atttcgttcc acagcacaca atcatgaccc   3120
cgggttttat tcaggtaagc aggattgcgg atatccggtg tcgcgccttt ctgtcacgaa   3180
cggggtaggt gcgaaacacc ggataaaatg caggctggca atacctctga acgccctgcg   3240
cagagcggat attttggatt aagtactcgc acctccgcag tcctgaaaca agtctggctg   3300
gtagctgtaa acagacttcg tacatgttgc tctggaatag atccccgtgc cacaggcttc   3360
gcagaacttt ttcccgggaa aatgctgccc gcacatcaca caatgccact ccagcacgac   3420
cggtaatggc gatagaaaca tcgccatatc ctcaatgtaa gggtgggact tttccggatt   3480
cagcaccacg caggccgcct tctgttgcgc gctcagggca tgtaaatcgt gctcaaacca   3540 cgcccctga gcatctgtct gcaaaatcaa ccgaccacga caggaaaggc agaaacaatg   3600
cctgatattt ctgctaaggc tgaggccgca ctgataatgt gttcacccgg cgtgatcccc   3660
agccccgttt ttataccgtt cattcagcca ctccctcctc actgaagtgc cctgtatggc   3720
agtgagtgca gtaccgctcc ccataataat cgtggtgaca ttgtctgcag tgccagctgg   3780
ctttacgcac cacgggtaag gcatccggta cgaatttctg cagacgctta atcagttgta   3840
tttctctgcg ctccggtctg acataagggc actgttgacc gtgctccgtc agcccgtcgt   3900
cagtgtgttc aaaccaggga agttcagtgt cgtattgcgg atggtatctg agcgcactgc   3960
cgcaaaggtg gcaggtgtag cggtcgtaag gtgcagtctg tgcggtacgg gcagcggtca   4020
gacgtccgtt gccatcaaat gcgagaaaag attttgcgta catagtatat gttccttacc   4080
gccagacgac acgcaggcgt cagcgtccct ttacgggcag cgtgggcagg gtgtgaatgg   4140
```

```
cggtacagtt aagggggggg tggaaaatgg gcgggctgtt gttacagcac tgtggatgtc    4200
acatcatggc gtaccaacgt aaaaaataat cagcaggccc ggatacatcg ttgtcgccgg    4260
acatcagccc gtcctgctgg ttttgccggg ctcagcccg actgcagccg aaattacgct    4320
caccagtggc gtgagctttg gtatgttcct tcgccagata gtcagcacgt tccagcacct    4380
gctgaaagcc agtgtcatca ccgcgttcca gccacaccgc cggcgtgtca ggaaaatgcg    4440
ccaacgtggc ataaggcccg gcatccaccc ccagggcact gcaccaggcn tgwttaatca    4500
tcccggccag tgaccccgga tcgcggtaat cgccggcacg acaccaggta tcccggttga    4560
ccagcagcag gaggtgatag tgttttttgc ccctgagtac cccgaactcc cgggcccagg    4620
cgtaatgcag ggtggtggga tgcacgcgtt taccttcacg ncgttacgct tctggtaagc    4680
gtcgattcgg gctttcaggg cattgatgaa gcgggatatc acagccgcgt ccgtagctgc    4740
cggtacatcc gggagacgca gatcaacccg aagtgccgtc aggcgggat gaacattcag    4800 tgcgtgccgc accgtctcac gaatacgttg ctgccagaag gggttgtatt tgtaggtcat    4860
ggttaaatct ccgtatggtt catacggaat agccacgtcg taaaaaatgc gcagagcccc    4920
tgacgtggcc accgacagaa cacggcctca ggcgcgttgt gataacccag ctatcgtttc    4980
cggactgacg gttgaatttc ctgcgttgtt ttcttaatgt aaaaaacctg ctacgggtaa    5040
ggctgtgagg aggaagtgat ggtgatacgc aaaaagaagt gcagggactg cggagaagcg    5100
acagagcata acacggtatg ttgcccacac tgcggttctg tcgatcccttt cggctattac    5160 cgcaatacag acagaatatt caccctcctg atggtcctgc tggttgtggt tctgctgatg    5220
acggctgcgg tcagcgtgta tgtgctgtgg tagtcggagg ggcagggagc agacgatgac    5280
gtaaaatatc tccggtgctc agatatcacg gccggtcaga ccgcaaacca acggttaatc    5340
gtaaccggat caggcaaatg tgtgattagc ccctggcgc tcatacccgc accgcagacc    5400
accttaagta cttcccgccc gacaccattc cctgctcccg gataatttgt tgtcgctata    5460
ccgcttaaca tcaccgatac cacaccggcg cagatagcac cggattcatt gtagagatga    5520
cttaaggttc agtaacata tttccagaca gaagcgggaa cacgatcgta agtttgttc    5580 atggtcagtt ctgccagccg gtgatcaacc gcagagttga aatttccag ctccgccggg    5640 gtgagtttat accgtgcgtg ggaaatcact ttttccagtg tctcccggga tgaacaacga    5700
cggaactgat acagccagtc ttctttggtt tttacttcca ttcgtctctc gttactttat    5760
gctgcggtta acaggatgcc gtcagtatac cgcatgcaga cactctcccg ctcccccgct    5820
tgctgcgata caacttaacg tttcaggaat ccagtcatcg caccgggaaa ggctttctgg    5880
tgacaggaaa cgtcaggaac aggagtttct cagactccca ctcatcggat caggctcaga    5940
caggattatt aatacgctca gttcatgtgt catatacagg gcatcgggga tgaatatatg    6000
ggtataactc agagcctgta ctacagcttt cactgctgac tgattttacg tatcagcgtt    6060
catgtatctg cactctgata tagaatactt ctaccgagc tactcttacg ttagctcact    6120
ctcacatcag gcaacatcac ttattcagct cacttacctc ttaccactca ctacttcttt    6180
atatttataa tatcaatcag acagcctat ccccccggta atatctgttg ccttcccgcc    6240
agccacaggc ttattcacca caaccacctc cgataacaac tctgcaatta tcagaacgcc    6300
tgcttctctc cctgtcctca cgaaaactat ccctcttta tcgcgcgtgc gtgcggaagc    6360
atcttttcgc aacaaccacc cgggattccg ctacggctct gccatcgcaa tcccccgtt    6420 tatctccgga cagccacatt cccgattatt ttttacgttt ctccccggtt gttatgccgg    6480
tgaaggtggt gcgtcgtttt catcaccaca ccggttgcga ttaacaacat ccggaggaac    6540
```

```
attctcatga ccacacccctt ttcactgatg gatgaccaga tggtcgacat ggcgtttatc   6600
actcaactga ccggcctgag cgataagtgg ttttacaaac tcatccagga cggagccttt   6660
ccggccccca tcaaactggg ccgcagctcc cgctggctga aaagtgaagt ggaagcctgg   6720
ctgcaggcgc gtattacaca gtcccgtccg taatttctgc cccttatccg ttcacccgca   6780
gcagacgcct ccccggcctg ccgttgacat tctgctgcct gttttatccc cgtgaggaat   6840
atgaaaatga acaacagta ccagacccgc tacgaatggc tccacgaaag ctaccagaaa   6900
tggctgaccg gcttcamccg gcacgccgta tcctggggcg tgtgtcatcc gaatatctac   6960
tatttccata atctgacgcc cgggtgggtg tcattcaacg gcgaacagtc ggagattgcc   7020
attgttcccg gcagtctgca ccggctgatt tatggtcatg acaaacgggc catgccgccc   7080
ctggatgatg atctggtggt gaatttatgc accagtgaga atctgctggt tcatcatccg   7140
atgctggaag gcattctgct gtctgagtgc acgcgcctgc ataaaaaatc actggcgaac   7200
aaactgatca gtatattccg tcagtttgac ggcacggagc tgcgtctcaa actggtctgg   7260
cttttgctgg ttgatttaat gaccggaaac tgccttgacg actggacgga gaacctgnaa   7320
cggaaatcag aaaaagagct ggagaaatgg atcattgagc gccagaaccg gaacgcaccg   7380
ctgacgaatc tgatggatca gtacgtgctc ctggcattcc gcacaacggt tgacgatagc   7440
cgcaactgat gtctgcatgc tgccsgctga agccatattc acggggcagg gacgcccctg   7500
cttccgcaac aatccggggt aatggcgacg tacgcctgca gagtgtgttc atcgttgtca   7560
cagccggaca aggtgaatac cgttgatgat gcggggatga acctgctggt ccaccgcgct   7620
gtcactcaga cgcgtcagcg tgtatggacg ccccgatcga atggttcttc cgccagagtg   7680
cacagaaatg aggcacggaa cgttacctga agggtgaccg gcacggactg caacttgttg   7740
ccattgatgg cgcacaagtc acatacagca gaatgtcgtg accgcacctt accggtgaag   7800
cgaaacggtg ctgcccccact ccaccaccat cccggataac gccattacgc tgtctgataa   7860
gcgcttttac agcgcaaatc tggtgcagaa aagcgtaaag ctgacctgcc ggagcaggat   7920
gtgggcatgt tgcgggctta caacctgata cggcatgagg cactaaaagc agcatcagaa   7980
atcagcctga gttcgcgttc cggtttatcc cgacagagag gacagtgccg gcaacacgg    8040 tgtcaccggg gagcatcccg aaacgaccgg agcatctgcg ggatgctctg taagtggtgt   8100
taaggtgggc ggttaaggta tcaaaaaaat cgttatcctg tgaaagacag tgcgctctgc   8160
tgaagtgaac gtcactgccg ggaagcatcg ggtttcgcta ccggacagtc gcggtaacgc   8220
gtttaccggc atctgtctgt gtggcaggga tggctgatat tgtcggttat accagcggca   8280
ggtgcgtcct gttatctgta aaatcagggc gtgccggtac acaacgcctc gttgatgccg   8340
gtcactgaac gaatcatcct ctgacgaaaa caaccgtcga tacaacgccg gcgtaaaaag   8400
aaaaccggaa accatcttgt gcacgacagg tactcagggg ggtataacgc ctgcgcacca   8460
tcacatccgg gaacagggct gctcctcagt gtcttcgtgt ggcgaagcat ctgcaaccgg   8520
acggtactgc cctcagagca atctccctgc tgcagtgcac agagtaagcc ggaaagctgg   8580
tgaatgccgc catgacacac tgcgacgtgg agaaacaaac gacacactcc gtccgcagta   8640
acactgaagg tagtcccgca aacctcgac ttcttcctgc acgttatcag cggactgaac    8700
cccggtcagc cacttaaacc tgctaatcgt gttgctgcat acccgcccgg ccggaaggtg   8760
ttatgaagcc cgccaccgga gcgcttctgc aaatatccgg ggagataaaa ttttcgtgac   8820
aggatgacgg tcgtgctgca gacgtaaagc cgcaggagcg gacacgacag acagtgttca   8880
```

```
ctgtggcgtc ctttgccgtc ggtatcgtgc tcacgctgag gtcccggggg tacacctgac   8940
gacaaatacc tgcgattccc gggacggtct gttctccgta aaataaagaa aatgcgggat   9000
gcctcccgga ctgcagagaa gagggattga cagacagtgt atattgcgta cgattacagg   9060
ggaaaaacac agtaaatatg gaggtcaggt ccgaaaacaa cctacgaaat ttctatgaaa   9120
aacgattgaa aaaatcatca aattcagttc gtttttctat ggtaattttt aaacactccc   9180
gatgataacc tgttgtatgt gcatgtgggg aacgcaccga aaacatcaga atcatctgaa   9240
aaaaacaacg aacacaccag aaaaacagga gcaaccataa cgaagcaaca tattgatttt   9300
aaacagaatt taaggttaac agacaaaaaa cactttcaac tgaaggagaa atatacactg   9360
gcgacagtgc agggttttc atgcaaaaaa aatgagcttt tatctccggc gcatactgac    9420
cgggatgcag ccatgacaga gcaaaaacca ttaaatatca ggaggttaaa cacacaaaaa   9480
gctgacatgc atcagggagc aatccctcac aacagaggct gagcggcaac gcttcctcac   9540
aggacggcat tcctgaaagg acaggcagcc acggcttttt actgcccgta tccggtatat   9600
ttatctgccg tgacgtgcag aggatttgt gtttccggaa atcaggaaaa caggagaacc    9660
gcggagata tgatggaaaa agaaccggat gatatctgcg cagactgtcc gaatattgat    9720
gcaataaaac ggcacaaaca acaggccgga gccatcaggg aatacactga gtggttaaaa   9780
aaacaaccgc gtgcttctta ctttttttctc ttccggttgt acgcatacct tcagaatgaa   9840
gtgatatccc gaaaacaaaa acattcgctc accagcgata acagccatcc cccggaatct   9900
gatgtcaccc ctccggattt aaccctteee cgtcgctact actgtgatta cggttacacg   9960
ccctacccca tgatgggcgg acagatgtct gttttttgcca caacgtcaga aaccaccagt   10020
tcgacgaatg cagtccccgg aaacgcagtt accgggaatg agactgaaaa gcatgaaaac   10080
gcggtaccgg cgacattccc cgtcagccgt tctgcaatgc ccccggaacc tctgcggttt   10140
gccacgggtt ttccatcgca accactgctt gccggtcccc gggaaaagcc gatgcgcacc   10200
gtgcatcctg acatccacag cgaaattata tggttctgct ccacttacct gctgaaatcc   10260
ggaccacaga ttacgaagac gattatcaac tcagtattct ctgaatgggc ccgcatcagc   10320
aatgattacc cctcccccttt ttcgtgggtg dacagcaggg acagtgaaca gtgtgactgg   10380
ttatggaacg ccatgcagct ccggtgtgtg ggaaccccgc tgaatcccct accccggag    10440
cagaaatact ggtttgcctg cgccacgttt gataactggg agggctggaa tgagcaacag   10500
atacagtttt tactgaaaag taatcccaga cgaaacagag cgaagtttac ggtcaccttc   10560
ggccctccct ggattcagca taaagccatt cttcttgatg agctgaagag tgcccgggag   10620
caacaaaaaa ggcgcgatga acgcgctgat ggttccgtcc cgctgaaact gtccggaaaa   10680
atccacaaac accttgaaag tattgcccgg agtcgtggta tccccccaaa aaaactgctg   10740
aatgaaatga ttgagcaggc gtaccaggac tcagtggtga acagccggaa taaaccactg   10800
atttaaaata atttcagaca gatattatct ccgtgaatcc cccgccacct ttccggtgcg   10860
cggggtttg tctttttca ccgggaatac atgtatgaat ccgtctgatg ccattgaggc     10920
aattgaaaaa ccgctctcct ccctgcctta ctcgctttcc cgtcacatcc tggaacatct   10980
gcgcaaactc acccgtcacg aacccgtgat tggcattatg ggtaaaagcg gggccggtaa   11040
atcctcactc tgtaatgcac tgtttcaggg ggaggtcacc ccggtcagtg atgttcacgc   11100
cggcacccgg gaagtgcggc gcttccgtct gagtggccat ggtcacaaca tggttatcac   11160
tgacctgccc ggggtgggcg agagcngga caggatgca gagtatgaag ccctgtaccg    11220
tgacattctg cctgaactgg acctggtact gtggctgatt aaagccgatg accgtgccct   11280
```

-continued

```
gtctgtggat gagtatttct ggcgacacat cctgcaacgc ggacatcagc aggtgctgtt    11340
tgtggtgacg caggccgaca aaacggagcc ctgccatgaa tgggatatgg ccggcattca    11400
gccctctccc gcacaggcac agaacattcg cgaaaaaacg gaggcggtat tccgtctgtt    11460
ccggcctgta catccggttg tggccgtatc ggcccgcacc ggctgggaac tggatacgct    11520
ggtcagtgca ctcatgacag cgcttcccga ccatgccgcc agtccctga tgacccgact     11580 gcaggacgag ctgcgcacgg agtctgtccg cgctcaggcc cgtgaacagt ttaccggtgc    11640 ggtgaccga atatttgaca cagcggagag cgtctgtgtt gcctctgttg tccgtacggc     11700
cctgcgcgct gttcgtgaca ccgtggtctc tgttgcccgc gcggtatgga actggatctt    11760
cttctgaacc tgttgtggat gatgtcctcc ctgcctctga gtctgctcac aaaagcgctg    11820
ttttcgttac tgtctctctt gtccgtgcaa tagctcaata atagaataaa gcgatcgata    11880
actatttcat cgatcgttta tatcgatcga tatgctaata ataaccttta ttaccaacat    11940
gcgcagatac gcacagacag acattcaggg gacgacagaa caacacttca gaaactcccg    12000
tcagccggac ctccggcact gtaacccttt acctgccggt atccacatct gtggataccg    12060 gctttttttat tcaccctcac tctgattaag gaaatgctga tgaaacgaca tctgaatacc    12120
tgctacaggc tggtatggaa tcacattacg ggcgctttcg tggttgcctc cgaactggcc    12180
cgcgcacggg gtaaacgtgg cggtgtggcg gttgcactgt ctcttgccgc ggtcacgtca    12240
ctcccggtgc tggctgctga catcgttgtg cacccgggtg aaacagtgaa tggcggaaca    12300
ctggtaaacc atgacaacca gtttgtatcc ggaacagctg atggcgtgac tgtcagtacc    12360
gggcttgagc tggggccgga cagtgacgaa acaccggcg ggcaatggat aaaagcgggt     12420
ggcacaggca gaaacaccac tgtcaccgca atggtcgtc agattgtgca ggcaggagga     12480
actgccagtg atacggttat tcgtgatggc ggagggcaga gccttaacgg actggcggtg    12540
aacaccacgc tggataacag aggtgagcag tgggtacacg gggagggaa agcagacggt     12600 acaattatta accaggatgg ttaccagacc ataaaacatg gcggactggc aaccggaacc    12660
atcgtcaaca ccggtgcaga aggtggtccg gagtctgaaa atgtgtccag cggtcagatg    12720
gtcggaggga cggctgaatc caccaccatc aacaaaaatg gccggcaggt tatctggtct    12780
tcggggatgg cacgggacac cctcatttgc gctggtggtg accagacggt acacggagag    12840
gcacataaca cccgactgga gggaggtaac cagtatgtac acaacggtgg cacggcaaca    12900
gagacgctga taaccgtga tggctggcag gtgattaagg aaggaggaac tgccgcgcat     12960
accaccatca accagaaagg aaagctgcag gtgaatgccg gcggtaaagc gtctgatgtc    13020
acccagaaca cgggcggagc actggttacc agcactgctg caaccgtcac cggcacaaac    13080
cgcctgggag cattctctgt tgtggagggt aaagctgata atgtcgtact ggaaaatggc    13140
ggccgtctgg atgtgctgac cggacacaca gccaccagaa cccgtgtgga tgatggcgga    13200
acgctggatg tccgcaacgg tggcaccgcc accaccgtat ccatggggga tggcggtata    13260
ctgctggccg attccggtgc cgctgtcagt ggtaccccgga gcgacggaac ggcattccgt    13320 atcggggcg gtcaggcgga tgccctgatg ctgggaaaag gcagttcatt cacgctgaac     13380
gccggtgata cggccacgga taccacggta aatggcggac tgttcaccgc cagagggggc    13440
acgctggcgg gcaccaccac actgaataac ggtgccacgc ttacccttc cgggaaaacg     13500 gtgaataacg ataccctgac catccgtgaa ggtgatgcac tcctgcaggg aggcgctctt    13560
accggtaacg gcagggtgga aaaatcagga agtggcacac tcactgtcag caacaccaca    13620
```

```
ctcacccaga aaaccgtcaa cctgaatgaa ggcacgctga cgctgaacga cagtaccgtc    13680
accacggata tcatcgctca tcgcggcacg gccctgaagc tgaccggcag caccgtgctg    13740
aacggtgcca ttgaccccac gaatgtcacc ctcgcctccg gtgccatctg gaatatcccc    13800
gataacgccc cggttcagtc agtagtggat gacctcagcc atgccggaca gattcatttc    13860
acctccgccc gcacagggaa gttcgtaccg gcaactctgc aggtgaaaaa cctgaacgga    13920
cagaatggca ccatcagcct gcgtgtacgc ccggatatgg cgcagaacaa tgctgacaga    13980
ctggtcattg acggtggcag ggcaaccgga aaaaccatcc tgaatctggt gaacgccggc    14040
aacagtgcgt cggggctggc gaccaccggt aaggggattg aggtggttga agccattaac    14100
ggtgccacca cggaggaagg ggcctttgtc caggggaata tgctgcaggc cggggccttt    14160
aactacaccc tcaaccggga cagtgatgag agctggtatc tgcgcagtga agaacgttat    14220
cgtgctgaag tccccctgta tgcctccatg ctgacacagg caatggacta tgaccggatt    14280
ctggcaggct cccgcagcca tcagaccggt gtaagcggtg aaaataacag cgtccgtctc    14340
agcattcagg gcggtcatct cgggcacgat aacaacggtg gtattgcccg tggggccacg    14400
ccggaaagca gcggcagcta tggcttcgtc cgtctggagg gtgacctgct cagaacagag    14460
gttgccggta tgtctgtgac cgcgggggta tatggtgctg ctggccattc ttccgttgat    14520
gttaaggatt atgacggttc ccgcgccggc acggtccggg atgatgccgg cagcctgggc    14580
ggatacctga atctggtaca cacctcctcc ggcctgtggg ctgacattgt ggcacaggga    14640
acccgccaca gtatgaaagc gtcatcggac aataacgact tccgcgcacg gggccggggc    14700
tggctgggct cactggaaac cggtctgccc ttcagtatca ctgacaatct gatgctggag    14760
ccacgactgc agtacacctg gcaggggctc tccctggatg acggtaagga caacgccggt    14820
tatgtgaagt tcgggcatgg cagtgcacaa catgtgcgtg ccggtttccg tctgggcagc    14880
cacaacgata tgacctttgg tgaaggcacc tcatcccgtg acaccctgcg tgacagtgca    14940
aaacacagtg tgcgtgaact gccggtgaac gggtgggtac agccttctgt tatccgcacc    15000
ttcagctccc ggggagacat gagcatgggt acagccgcag ccggcagtaa catgacgttc    15060
tcaccgtccc ggaatggcac gtcactggag ctgcaggccg gactggaagc ccgtgtccgg    15120
gaaaatatca ccctgggcgt tcaggccggt tatgcccaca gcgtcagcgg cagcagcgct    15180
gaaggttata acgccaagc cacactgaat gtgaccttct gataattcgg cattgtctct    15240
ctgtggtccc ggtcatcatg accgggaccc ggacaggtgc aaacgcttca gtgccacatt    15300
cactggcatt cacaataaca tgatattcat cacggagtga ctatgttaca gatagtcggt    15360
gcgctgattc tgctgatcgc aggatttgcc attcttcgcc ttttgttcag agcattaacc    15420
agcacagcgt ctgcgctggc agggttcata ttgctgtgtc tgttcggccc ggctttactg    15480
gctggctata tcactgaacg cataacccgg ttattccata ttcgctggct ggcaggcgta    15540
tttctgacga ttgccggaat ggtcatcagc ttcatgtggg acttgatgg taaacatatc    15600
gcactggagg ctcataccTt tgactctgta aaatttattc tgaccaccgc tctcgccgct    15660
ggtctgctgg ctcttcccgt gcagataaga accattcagc agaacgggct cacaccagaa    15720
gatatcagca aggaaattaa cgggtattac tgctgttttt atactgcttt tttccttatg    15780
gcgtgttctg catacgcacc attgatcgca ttgcagttcg atatttcacc ctcactgatg    15840
tggtggggcg ggttgttgta ctggctggct gcattagtga cgctgctatg ggcggccagc    15900
cagatccagg cgctgaaaaa actgaccagt gccatcagcc agacactgga agaacaaccg    15960
gtgctcaaca gtaaatcgtg gctgaccagt ttgcaaaacg attacagcct tcctgactca    16020
```

```
ctgacggagc gcatctggct cacgctcatt tcacaacgga tttcccgggg agaactgagg    16080
gaatttgaac tggcagacgg aaactggcta ctggacaatg cctggtatga agaaacatg    16140 gcgggtttca acgaaaagct gagagagagc ctgtcattta cccctgatga actgaaaacc    16200
ctcttccgga accgcctgaa tttatcaccg gaagcgaatg acgattttct cgatcgttgc    16260
ctggacggcg gtgactggta ccccttttca gaaggccgcc gttttgtatc attccaccac    16320
gtggatgagc ttcgtatctg tgcctcctgc gggctgacag aagtacatca tgccccggaa    16380
aatcataagc cggatccgga atggtactgc tcctctcttt gtcgcgaaac agaaacactg    16440
tgtcaggaca tttatgaacg ttcttacacc ggttttattt ccgatgcaac ggcgaatggt    16500
ctgattctca tgaaactgcc ggaaacctgg agtacaaatg agaaaatgtt tgcttccgga    16560
gggcagggac atgggtttgc cgctgaacgg ggaaaccata ttgtcgacag agtccgtctg    16620
aaaaacgcac ggatcctcgg tgataataat gccaaaaatg gagcagacag actggtcagc    16680
ggaacagaaa tccagacgaa atattgttca actgcagccc gtagcgtcgg tgcggcattc    16740
gacggacaga acggacagta tcgttacatg gaaatcatg gtcccatgca actggaagtc    16800
cccgtgatca gtatgccggc gctgtggaaa ccatgaagaa taagatccgc gaaggtaaag    16860
tacccggtgt aaccgatccc gaagaagcgt cccggctgat tcgtcgggga catctgactt    16920
atacccaggc ccgtaatatc acccggttcg ggaccatcga atcggtcact tatgatattg    16980
ccgaggggtc ggttgtcagt ctggcggccg gagggatcag ttttgccctg acggcatcgg    17040
tcttctggct cagcaccggc gatcgcgatg ctgccctgca gacagctgct gtccaggcag    17100
gaaaaacctt cacccgcaca ctggctgtct acgtcacaac ccagcaactt caccggctca    17160
gtgttgttca gggtatgctg aagcatattg attttcgac ggccagcccg actgtccggc    17220
aggcgcttca gaaggggacc ggtgcaggaa atatcagtgc cctgaacaaa gtgatgaagg    17280
ggtcgctggt gacatctctg gcactggtag ctgtcacaac cggccctgac atgatcaaaa    17340
tgttgcgggg acggatctcc ggtgcgcagt tcatcaggaa tcttgccgtg gcatcttcct    17400
gtgtggcagg tggtgctgtc gggtcagtgg cgggcgggat attgttcagt ccactgggac    17460
catttggtgc actgacaggg cgtgtggttg gcggtgttct ggggggaatg attgcctccg    17520
ctgtatcagg aaaaattgcc ggagcgctgg ttgaagaaga tcgcgtcaaa attctggcaa    17580
tgattcagga gcaggtgaca tggcttgccg gcagtttcct gctgaccgga catgagattg    17640
aaaatctgaa cgcgaatctg gcccgtgtta tcgatcagaa tgctnctgga gatcattttc    17700
gccgccggta                                                           17710
```

<210> SEQ ID NO 71
<211> LENGTH: 1803
<212> TYPE: DNA
<213> ORGANISM: Escherichia coli

<400> SEQUENCE: 71

```
aataaccaat agatgcttaa gtttacgata tgcctcaacc cgcgtctgct ctaagctgat     60
aaggccagtt ttgtagagat ccgctgccaa ggttgcctgc gtttgcacat ccatgtaacc    120
ggcggtgatt tcattcatgg catcgttatc ttgaccagtc agcttagcac gctcctgttc    180
aagctgcttg gttagggcgt caactcggct ctgtaatgag actacggccg gtgcggtttc    240
cttcatatag ctgcgcagtt gttttagctc cgcctgttga cgcaccagct ctccttcaat    300
ctggctgacc actcccaagc gtgcgctgct ggtagattca gggctgagaa gttggtggct    360
```

```
attctgaaat gctaatactt tagctttttc atcctgtaag cgttgatatg ctctatttac      420 ttcttttca acaaaggcca attgttcgag cgcaacctga tgacctaatt tgttaataaa      480
acgctccgat tctttgagca ttaactcaac aactcgctga ccgtattggg gatcaaatgt      540
ctgcaactca acggtaagta ctcctgataa ttcatcaagg tgtaacgtca aatgtttgcg      600
gtaataatca agaaaatctt ccctactgac tcccttatgc aaccgcgaga ataatctgc       660 actatcactc tggaaatgtg ctttaagtgc aagttctttg tccaacttgg ccagcatatc      720
ccatgacttc atataatcct gaacgagtaa tatatcctga tgattactac cacctatccc      780
taacattgat aacgcatcag gcaacatttt aacttgatcg gcttgtttaa tcattaattc      840
agcccggstc ataacgat cggaagcaat gaagccaaaa tagagcactg cgatagaaaa        900
gcagataact acccaaagaa aactgcctag ctgtaaactt tcttccacg agcggtgtac       960 aatttgatat cctctcgaat caatcaaaaa tagttttgga ttattgctca gttttcttaa     1020
ctttcgcgta aggcgagata ttgaggatga agaattcgga gatgtcataa tcagttgctg     1080
ctcaaagtga ctggtaaatt ttgatggcat catcaatatt atcaaaaact tctaatttac     1140
catcacgtaa caagatgccc atatcgcatt gttgtcgtag attttcata tcatgcgaaa      1200 ccataatcaa actagctgtt tctcgctttt tgttaaatac atcaatacat tttgtttaa      1260 aacgtgcatc acctactgag gtaatttcat cggtaagata tatatcaaaa tcaaaagcca    1320
tactaacagc aaaagaaaat tttgatttca tgccgctaga gtatgtttta ataggcagct    1380
cataatgttg tccaatttca gaaaactctt taacccactc ttctacgggg cttgtatcgc     1440
gtacaccatg aatgcggcaa acaaatcgcg tgttttcacg accagtcata ctaccttgaa    1500
atcccccagc tagtgctaga ggccaagata ctcggcagag acgagttact ttccccctgt    1560
taggcgtatc catccctcct aacaaacgta acaaagtaga tttyckgct ccatkgatac     1620 ctagaatacc tatattacgg tcccttggta gctcaatatt tacattcctc aggacataat    1680
ttcgtccaaa tttagttgga taatatttg atacattatc aagaataatc attttctta    1740 acgctaacta gcaatcaatt ggcgatgccg taatcggtaa caactcatag caaaagtgag   1800
caa                                                                   1803

<210> SEQ ID NO 72
<211> LENGTH: 1283
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n equals a, t, g, or c
<221> NAME/KEY: misc_feature
<222> LOCATION: (19)..(19)
<223> OTHER INFORMATION: n equals a, t, g, or c
<221> NAME/KEY: misc_feature
<222> LOCATION: (101)..(101)
<223> OTHER INFORMATION: n equals a, t, g, or c

<400> SEQUENCE: 72
nggacccaag gtaaaaacng gtaaaaaaaa cmattgaccg attaaacttt atttctctgc      60
ccgcattagt ctggagagag gatggatgtc attttaattt nactaaagtc agtaaagaag    120
caaacagata tcttattttt gatctggagc agcgaaatcc ccgtgttctc gaacagtctg    180
agtttgaggc gttatatcag gggcatatta ttcttattgc ttcccgttct tctgttaccg    240
ggaaactggc aaaatttgac tttacctggt ttattcctgc cattataaaa tacaggaaaa    300
tatttattga aacccttgtt gtatctgttt ttttacaatt atttgcatta ataacccccc    360
```

```
tttttttttca ggtggttatg gacaaagtat tagtacacag ggggttttca acccttaatg      420
ttattactgt cgcattatct gttgtggtgg tgtttgagat tatactcagc ggtttaagaa      480
cttacatttt tgcacatagt acaagtcgga ttgatgttga gttgggtgcc aaactcttcc      540
ggcatttact ggcgctaccg atctcttatt ttgagagtcg tcgtgttggt gatactgttg      600
ccagggtaag agaattagac cagatccgta atttcctgac aggacaggca ttaacatctg      660
ttctggactt attattttca ttcatatttt ttgcggtaat gtggtattac agcccaaagc      720
ttactctggt gatcttattt tcgctgccct gttatgctgc atggtctgtt tttattagcc      780 ccatttgcg acgtcgcctt gatgataagt tttcacggaa tgcggataat caatctttcc      840
tggtggaatc agtcacggcg attaacacta taaaagctat ggcagtctca cctcagatga      900
cgaacatatg ggacaaacaa ttggcaggat atgttgctgc aggctttaaa gtgacagtat      960
tagccaccat tggtcaacaa ggaatacagt taatacaaaa gactgttatg atcatcaacc     1020
tgtgggttgg ggtgcacacc tggttatttc cggggattta agtattggtc agttaattgc     1080
ttttaatatg cttgcaggtc agattgttgc accggttatt cgccttgcac aaatctggca     1140
ggatttccag caggttggta tatcagttac ccgccttggt gatgtgctta actctccaac     1200
tgaarttcat catgggaaac tggsattacc ggraattaaw ggtgatatca cttttcgtaa     1260
tatccggttt cgctataagc ctg                                             1283

<210> SEQ ID NO 73
<211> LENGTH: 6836
<212> TYPE: DNA
<213> ORGANISM: Escherichia coli
<220> FEATURE:
<221> NAME/KEY: misc_feature
<222> LOCATION: (2934)..(2938)
<223> OTHER INFORMATION: n equals a, t, g, or c

<400> SEQUENCE: 73
tcaacctgac caaccactag aatcaactca cgtccgtcgt tagggggctc atattcttgt       60
gtactcccca cattgtattt actgactcgt gatgattgta attgcgctaa taatgactct      120
gcgcgtgctt cttctttcgc atctaaaacg tacgtagtga gtaactgctc aagcttactc      180
ggacggcggc tatcaaaata gattccaacg gggtcaatcg agagtgatga aggtcgacat      240
aaattagacc ccaatccgtt ggagcggata aaaccatctt caatccggat cactgattgc      300
agttcaggat aacggtttcc ccacaccaac acctgttcat catcttttaa ctgtgagggc      360
acagtacgaa caaaacaaag ttcatctgcc aaatacgcac aaaatgtgcg tataaaagca      420
cgcttccaca gagaaaaacc aacgagataa agacgacgcc aaggtttggg ctctacctgc      480
tgctgagcca aaatcgctac aacatcttct acctcacaac gttttcccaa tataggatct      540
aaataacgcg gataacggat caacgccgcc gcaactaagc ggggcaatga aatagatgaa      600
acgccttcgg ctgacattgc ttcttcacgg cgtatacaac gtttactgtc atgcgttaac      660
ccccacccag cataaaatgg cataccgaag caatatacag gtttgcccaa cagcaacgct      720
tccaaagcca acctgcgatg aaactgtgta caccgcatcc accatacgaa ttattctatg      780
cggatggcaa gttcactcac cacctcaaca tcagccagtc gaggatcacg ccccactaaa      840
cgtgctaaca cgccgctttt tttgctaaag cgtgtatctg ggtgtgttcg caacaataga      900
cgcgcattag ggtgattacg gcgagcctcg accaccatag aaacaaaatc agcttcgcaa      960
gcaagagccc cagaaattga caagtctccc gctacttgat ccacaagcaa aatacgcggt     1020
```

-continued

```
cttggatcat ccagtaaacg tgctaagttt gaatgagccg tgaggtgaat aactcaggtt    1080
gtatatgtgt cggtaaatct aaagaaggcc cgtcagtagc acgggacaga gccattaaat    1140
gtatgctcag tgctattggg tatagcagtt atacttggtg attcctaaac gcaaaatatc    1200
mgagatcaga tgctccagcg cgcgcaaagt aaagccgtat ccaacaggtt ccaataataa    1260
gctgttctaa ttgactcgtc tgatgtgcat cataatatat ccccagaggg tcagcaataa    1320
gagaaaccgc ctttcctcct tttgctgggt gcccgatata gccaataaaa ccatcttcaa    1380
gttgccaata agatattcct aactcttgag ctttctgttt aatctgctta gtattagatt    1440
tttttcccca gccaactaaa acgtcatttt tagaaaagc ctcgtctcct ttcatataaa     1500
gcaatgggtg accaagcata ggctcaatat tattttytct ggcaagaatc cctttcgatc    1560
ccgtatataa atacatgttg tctctgtgaa ctgaagattc tctacaatgg tgtataaagt    1620
gtgatttaga tgaacagctc tgcgctctct aatgactttg caatactatc ttttgctgaa    1680
gtgagaatgt ccgcctttaa ctcgggccac ctaataccaa ttgtaggatc attccatgca    1740
atgcctctat cactggcagg gcataataa ttagttgttt tatacaaaaa ttcggccgat     1800
tcagtcagtg ttacaaaacc atgggcaaat ccttccggaa tccataatgt cgtttgtttt    1860
cccctgaaag atgaacgcca acccattgtc cgragctcgg tgagcttttg cgaatatcta    1920
ccgcaacatc aaacacttca ccggctacac aacgcactaa cttgccctgg gcatggggag    1980
gtaactgata gtgcaagcca cgcagtaccc ctttagaaga ttttgagtga ttatcctgca    2040
caaaggtaac tggatatcct acagcctctt caaacaactt gtgattaaaa ctctcaaaga    2100
aaaaaccacg ctcatctcca aatactttg gctcaaaaat aagcacacca ggaattgctg     2160
tcttgattac attcatctat atgcccacat ttaattaaat atttttaggg gaagcatatt    2220
ccctccccct tctcaattac atcacgcctt atcaatcatt tttaataaat attgcccata    2280 ggcgttttt gccaacggag cagcaagytc acgaacctgg tcggcactaa taaacttctg     2340
gcgataagca atctcttccg gacaagccac tttcaatccc tgacgcgtct cgatggtctg    2400
aataaagtta ctcgcttcaa ttaggctttc gtgggtaccg gtatcaagcc aggcataacc    2460
acgccccatc attgccaccg atagattgcc ttgctccagg taaatacggt tcacatcggt    2520
gatttccaac tcaccacgcg gcgatggctt gagaccctttg caacgtcca caacgctgtt    2580 gtcgtagaaa tagaggccgg tgactgcgta stactcttag gctccagtgg ttttttcttcc   2640 agtgaaatag cggtaccttg attatcaaat tcgaccactc cataacgttc cgggtcgtgc    2700
acatgatagg caaatacagt agcaccggtc tctttggccg cggctgcctc caactgtttc    2760
tgtaggtcat gaccgtagaa gatgttatcc cccagcacca gtgcacacgg ggctgaacca    2820
atgaattctt cacctagaat aaaagcttgt gccaacccgt ctgggcttgg ctgaacctca    2880
tattgtaaat tcagtcccca gtggctgcca tcacccagca atcgctgaaa ggaggagta    2940 tcttgtggag tgctaatgat caaaatatcg cgaattccag ccagcatcag ggtgctcagc    3000
ggccgcagta ctggatcatc ggcttgtcat agatgggcaa caactgcttg ctcaccgcca    3060
tagtaaccgg atagagacgt gtaccagatc caccggccaa taataacct ttacgtttag     3120 tcatgatgct tgtttcttat ttttaaatta cataagaata aagtggcttg agccgcgcct    3180
ttctgtttta tcctcacctg tggtttactt ccccatgatc tcagtcaaca tccgctcaac    3240
accgactgac cagtccggca aaaccagatc aaatgtacgc tggaattttt tagtatcaag    3300
tcgggaatta tgagggcgtt tcgccggggt cggaaaggcg cctgtcggca ctgcattaag    3360
ctgtgtgact gccagttcaa ctcctgcgtc tctggctttg tcaaacacca accgggcgta    3420
```

-continued

```
gtcaaaccaa gtggtagtac cggaggcagc caaatggtac agcccggcaa cgtcgggttt    3480
gctctgtgca actcggattg catgggcggt acaatcggcc agcaactcag ctccagttgg    3540
agcgccaaac tgatcattaa tgaccgatat ctcgcgacgc tctttgccaa gacgcagcat    3600
agttttggcg aagttggcac cgcgcgcagc ataaacccaa ctggtacgaa agataaggtg    3660
acgtgagcag agtgccgcac cgtgttcccc tgccagcttg gtttcgccat agacgttgag    3720
cggggaaatc acatcggttt ccacccaagg acgttcacca cttccatcga aaacatagtc    3780
ggtggaataa tgtactagcc acgcacctaa tgcttcagct tctttggcaa taaccgccac    3840
actagttgca ttgagtaact cggcaaattc ccgctcactc tccgctttgt cgactgcagt    3900
atgggccgct gcgttaacaa tcacatccgg cttgacgaga cgtaccgttt cagccacccc    3960
tgcagaattg ctaaaatcac cgcaatagtc ggtggagtca aaatcaacgg cagtgatgtg    4020
ccccagaggc gccaatgcac gctgcagccc ccatccactt tctggccaca ccagactcgc    4080
cagcaaaaaa gtgagtgctg tcaataactc aaccagcgga taacgcttgc tgattttcgc    4140
ctgacagtcg cggcagcgcc ctttgagcat caaccatgag agcagcggaa tattgtcacg    4200
aacgcggatg gtctgctggc aatgcggaca gtgcgaacgc ggtagcgcaa ggcttatttt    4260
tgactgcgca ctcggcattt caccatgaaa ctccgccatt tgttggcgca gcatgatggg    4320
gtaacgccaa atcaccacat tcaaaaaact gccgatgatc aatcctccga cggttgccag    4380
tatgggcatc gccgcggggt attgctgaaa acatcaaaaa agcatggtta aaggttattt    4440
gttgtaactt gccggatgcg ggcctgcggg tgtatgccat acggctttcc ttcaggcccg    4500
atgcgcctta tttcatgccg gatgcggcgc gagcgcctta tccggcatac aggcttactc    4560
agctgacatc ttatgctcgg taacctgatt aatggtttcc ggcccttgct gcggtttcgg    4620
cagattaagc gccgccagtg tctcgtaagc cgactggctc acaccgccct cgaagttcat    4680
ctcgctcgct cccggcaact ggtaagcatt gcgcccgga ttccatttct aaagaactc     4740
cgaaagatcc gtctgggcga cccaggatgc acacagcatc agcttgtcgg cagcgttacc    4800
gttggattcg gcacagtaat ttcttttcgcc aaacttggtt ttgccaacct catcgccgcg    4860
tgctttacgg tgcatcaact ggaacaggtt ccagcctttc atcccttcac gatcgctgta    4920
gaacttaggc aggtcacctt ctggatacca ctgtttgata tcaaagtttt tctctgccca    4980
ctctttcagc tgtgcgtaca tcagcagacg gtcacccgca ccgccgcgcg cccatgcctg    5040
accgttgctc tcctccagat attccggcgc gacggtaatg tcgtcagcga cacggttcat    5100
cttgccgaga tagcgatcct gcatgtacag cgccagcacg ttgttcgcta cttcagttgc    5160
gccaggaaca gtcagcggcg tttcggcggc gttgtgacca acttcgtgcc agatcagcca    5220
gtcgttcagc ggcgtcgtcg gcagcgtggt gctgttcgtc gagaagctgc tgttcattac    5280
cggataacca gagtgcgcat caccgatgga gatctgcaca tcgttggtga acgatgctt     5340
gtggcccgtc aagtttttat aggtaaacat ccggtgctta ccgtcttcat cattacgacc    5400
gtagaagtca ttcatcgagc tggcaaaggt atccagatct ttagcgaatt ctgctacgcc    5460
accagtgaaa ttgctggcct caaggttctt cttcggcgtg gtgtagacga aagcgtctga    5520
ctccagctcg cccaacggcg caggggagtt cagagcgttt ttccatgcgc catctttata    5580
gaacggcgct ttcaccacac cagtaaaggt gaattcggct gactcattct gtgggctgtt    5640
gcccttgata taaatcagac caccgtaagg aaccgtaaac ttcacctcac cattggcttt    5700
cagctcatag gttttcgtca cttttggcgg acggttcaga gcgacttcat gcttctcacg    5760
```

-continued

```
tccggtaagg tcgtcggcca gcgccacggt gacagtcaca ggaactgatg cagaagactc    5820
aatggtgacc tctttctgag ccggagccca caggccagta gactgcatgt tacccgcaaa    5880
ccatttggtc ggattcgagt acaggctgat ggtttcagta accttctcac cttctgccga    5940
taccgctccc ggatacttct cgacatcaac tttgatgttc agatcccacc aggaacgacc    6000
cagcatcagg cgcgtcagcg gttttttccat atagttgagc ggatagctcg ggttcatcat    6060
gcccgcttta ttaacgctct tctcgccgta gatcatgttg ttatcgacca gcgatttttt    6120
cagctcatca gaaacactgc gtgccgccag tataggcatc gttggcgtag cagttcagga    6180
actcggtgaa cgttttaaag cccagctcgt catccttgtc gttttcatag cgatattcaa    6240
ttttattcca cagccagacc gacatgttct ggtacagacg ttccagatcg acgctgctca    6300
gacgctcacc tttgcgacca ttggtccgga agtagagctc atgctgatac agacgctgaa    6360
tgttggtgcc taaatccgca gcctgcacca tcgcttttgc cgtgtcggcg ttaaggctta    6420
gttgcgtata ctgtgcaaca tacatgccac cagtaaccgg aacccccgtg ccaggacgat    6480
attccagaca gttgacctcg tagtggtaag ttgggtcctt acactccttt aatccaggaa    6540
acttctcaaa gattttgcc ttcgcagcct tcagagaatc ctctgttta tgatcggcct    6600 catcaataaa ggcataacgc gtttcctgtt tgccatctac atcttccagc cagctggcaa    6660
cttccagctt cggtttgtca tcaggtttgt tttctacctg atatttccac ttaacttccc    6720
ctgtcttact atcgatggtg tacggcagcg caccatctac ggcaggataa cgttcataga    6780
cccaaatgcc cgttgcgcgc tgctgacgaa cgcggttcgg ataccttgc ggatcc        6836
```

<210> SEQ ID NO 74
<211> LENGTH: 1332
<212> TYPE: DNA
<213> ORGANISM: Escherichia coli
<220> FEATURE:
<221> NAME/KEY: misc_feature
<222> LOCATION: (9)..(9)
<223> OTHER INFORMATION: n equals a, t, g, or c
<221> NAME/KEY: misc_feature
<222> LOCATION: (44)..(44)
<223> OTHER INFORMATION: n equals a, t, g, or c
<221> NAME/KEY: misc_feature
<222> LOCATION: (343)..(343)
<223> OTHER INFORMATION: n equals a, t, g, or c

<400> SEQUENCE: 74

```
ggaaaaacnc gccgtatatt agcccgcgcg gaaaaagccc cgtnacgggc aaacgcagca     60 aggtttatc ccagcgcagg cgcatggcag gatttttgag tagccgttgc cccagcacca    120
gaagccccag caatcccgcc agccagtaaa cgccgctggt ctgtaacgtg tcgctcatgg    180
cgatgagcgt gcgggtggag gcgggcagcg cgtgtccgga atgatcaaac tgttcgatga    240
tttttggcac cactgccgtc agcaaaatag tgaccacgcc cgttgccacc accagcagta    300
ccagcgggta gagcatggcc tgcagcaggc gtgaatttcc agnacctgcc gctgttacgg    360
tgtaacccgc caggcgattg agcaccacgt cgagatgtcc ggattttct ccggcagcaa    420 ccatcgaaca aaacagggaa tcaaagacgc ggggatgttc cgcaggctg tccgacaggk    480 tgtaacyttc ctgaatccgc tgcgcagcgc cattccgagg cttttacat gcagtttttc    540 actttgctca ctgaccgcct gtaagcaggt ttccagcggc attgctgcct gtaccagcgt    600
tgccagttgg cgcgtgaaca gcgcaagatc tgccgccgcc acgcgacgat gtgcgtgccg    660
ccgacgctgc aacatccccc ctgacgaagt attcatccgg gcttcaatat gcacgggat    720 aagctcttta ccgcgcaaca actggcgggc atgacgcgcg gaatccgcct caatcatacc    780
```

| | |
|---|---|
| tttggttttg cgaccattac gctccagcgc ctgatagtaa aacagtgcca ttacgcctcc | 840 |
| atggttaccc gcagaacttc atcgagagag gtttctccgg cgagcacttt ctcaatgccg | 900 |
| ttgctgcgga tacccgcaga gtgttgtcgg acataacgtt ccagctccag ctccccggcc | 960 |
| tgacggtgga tcaaatcacg caatgtggca tccaccacga tcagctcatg gatggcagtc | 1020 |
| cgtccgcgaa aacctttgtg attacaggcg ggacagccct gtggatggta cagagtgacg | 1080 |
| gtacgggcgt cggtaattcc cagcaggcgt ttttcttcgt cggtggcagg cgcggcctga | 1140 |
| cggcagtcgg agcacagcgt gcggaccagt cgctgcgcca tcacgcccgt cagactggaa | 1200 |
| gagagcagga aaggctccac gcccatatcc tgcaaacgtg tgatcgcccc caccgctgtg | 1260 |
| ttggtatgca gcgtggaaag taccaggtgt ccggtcagtg aagcctgaac agcgatttct | 1320 |
| gcggtttcgg ta | 1332 |

<210> SEQ ID NO 75
<211> LENGTH: 4407
<212> TYPE: DNA
<213> ORGANISM: Escherichia coli
<220> FEATURE:
<221> NAME/KEY: misc_feature
<222> LOCATION: (2638)..(2638)
<223> OTHER INFORMATION: n equals a, t, g, or c
<221> NAME/KEY: misc_feature
<222> LOCATION: (3425)..(3425)
<223> OTHER INFORMATION: n equals a, t, g, or c
<221> NAME/KEY: misc_feature
<222> LOCATION: (4227)..(4227)
<223> OTHER INFORMATION: n equals a, t, g, or c
<221> NAME/KEY: misc_feature
<222> LOCATION: (4256)..(4256)
<223> OTHER INFORMATION: n equals a, t, g, or c
<221> NAME/KEY: misc_feature
<222> LOCATION: (4300)..(4300)
<223> OTHER INFORMATION: n equals a, t, g, or c

<400> SEQUENCE: 75

| | |
|---|---|
| cccaacgttt atcgtatttc attaaagtcc cttgcccgat gctatctcga gttacatgac | 60 |
| gaaatcgctg atttggatgt catgattgcg gcaattgtcg atgarctggc gcctgaactg | 120 |
| attaaacgta atgctattgg atacgaaagc sttcgcagtt gctgatcacg gcaggagaca | 180 |
| atccccaacg attaagatca gaatcaggtt ttgcggcact gtgtggtgtc agccctgttc | 240 |
| ccgtatcttc aggaaaaacg aatcgttatc gacttaaccg gggtggagat cgtgctgcaa | 300 |
| atagtgcact tcacatcatt gccatcggac gtttgcgaac tgacgataaa acgaaggaat | 360 |
| atgtcgccag acgagtagcg gaagggcata caaaaatgga agcaatacgc tgcctgaagc | 420 |
| gctatatctc acgcgaagtt tatacattac tgcgtaatca aaacaggcag ctcaacagca | 480 |
| tcccgataac ggcttgactc ttagaagggc gtccagggca gccactatac aagcaggcag | 540 |
| ttccggcagt tactgtggcg ttaccagatc aaacagagtc tgagtcgacg aggaaattgc | 600 |
| tgggataaca gcccgatgga gcgcttcttc aggagtctga aaaacgagtg gataccggtg | 660 |
| acgggttaca tgaacttcag cgatgctgcc catgaaataa cggactatat cgttgggtat | 720 |
| tacaacgcgc tcaggccgca cgaatataac ggtgggttgc caccaaatga atcggaaaac | 780 |
| cgatactgga aaaactctaa agcggtggcc agttttttgtt gaccactaca tttagtgcga | 840 |
| cacgggaagc gcgatatgaa cgatacgata catcaatggt ttattgcggt gataacctga | 900 |
| agggtgagat tgaggctatt tataatagtc ttgagaggcg tcaggtttag agcaggaatg | 960 |
| ctgagtagcc atcttatcga ttgttttcga gcgtaagatg gctgaatgga atggctatta | 1020 |

```
ttgcacagtc cttaattata acattcatac cgacatgatt atcttctgtc cggaagaatc    1080
agaggctgcg gtttcagact gtctgccggt acattcctct ctccgttaaa aaccataacg    1140
ggttcattat cttcgtctgt cagcagattg aatggcggta tattttcagt acgaatgccg    1200
gtcagccact gaaaaatacc tgcgaaatga cgggcactga ttttctgct gacggactga    1260 tgagacgtga tgtcactggc ggtaataatc aggggaacgc tgtagcctcc ctgcacatga    1320
ccatcatgat gaacaggatt agcactgtcg ctgaccgaca gaccatggtc agaaaagtaa    1380
agcatggcaa aatgacggga atgccggcga aggataccat caagctgccc gagaaagtta    1440
tcccagttta ctgatgctgg cgaggtaaca ggcaattttt cggggatact gccccaggta    1500
atgattcggc caggagttaa gccggtcaca cgggttcgga tgagacccca tcatgtgcag    1560
gaatatcact tcgagagga tttatccgcc agtgcacgtt ctgtttcctg taacaacaac    1620
atgtcatccg ttttacggga agcaaagctg cctttcttga ggaaaacggt atgctccgca    1680
tcagaagcaa taacagagat gcgtgtatca tgctccccca gctttccctg attggatatc    1740
caccatgtgc tgtatcctgc ttttgctgcc agcgccacca cgttgttgcc ggagtcaggg    1800
ttctgctcat agtcataaat cagtgtccgg ctcaggaag gtacggtact ggctgctgcc    1860
gatgtatagc cgtcaataaa taaaccggga gcagtattca gccacggtgt ggttggcacg    1920
ggatagccat ataccgacat ataatccctg cgcacactct caccagtgac gataacaatc    1980
gtgtcataca acggtacacc cggcaggatt ttccagttgt cagccccgtg ctgattcagt    2040
tgtttataac gctgcatttc acgcaatgtg tcagttgtcc ccacaacagt tcctttaacc    2100
atccgcaacg gccagctgtt tactgagcat aatacgaaca gcagcagtgc cagccagtta    2160
cggtgaccgc ggtggtgtgt tcgccagaaa atcaccatga ataccagaat cgcggcactg    2220
accagaaaat gataaacagg aatcatcccg gtaaactccg ctgcctcatc agttgtggtc    2280
tgcagcaacg caacaataaa actgttgttg attttaccgt acgtcatacc ggcaggcgca    2340
tacagtgcac aacagaacag aaataacagc gctgtaatgg atgtgagggt atttctgtgt    2400
gcaagaagca gaagaaagaa cagcagcaac acattcccgg tggtattctt ctcagtgtat    2460
ccgcatgcaa ttgtggttat gacagaaaca acaaaaaaga ataaaaacaa tataatcctg    2520
agagtgttgc ccggacaaaa cagttttctg tatattcatcg gagtatatcg acaacattat    2580
tatgaagaga acaggataat aaaaatcaga agttatctgt gaaacagata acagacancc    2640
ctgcagtata atattactgc agggtgttcc ttttttaatta cagaaatacg taattatctt    2700
aattgcagaa atatgcgcaa ttatcgttca gaagcagtgt cgtcagaagt tataagtcac    2760
accaagcagg atgtcatgac ttttaacatc aacctctgat ttatatttat cccccttctgt    2820 atccttgtaa tacagggagg atttaccagc atccagatag cgatagctga ggtcaagagc    2880
gatatccggg gttacgtcat agcgaacacc ggccccaatg ctccatgcga agttgtcagc    2940
agagcctgag cgtgatatag aataacgcac tcgctcaccg tagccataat cccaactacc    3000
gctacctgtt gattcctgat gaattctggc gtaaccaatt ccggcagaca cccatggcgt    3060
aaatgcactg tcgtttctga aatcatagta cgcattcagc atcaggctgt tgactgacac    3120
ctcattcttc aggtcactat gtcccgcgtg gtccttatag aggttgtatg ttgtgtcagc    3180
ttttccacgg gcgtaaaact ccagttctgt acgcacagga atactgaact gcggatgcaa    3240
gtcataacca aacgctatac ctccactgaa taccgtgtta tggccatccc cccctatac    3300 tttgatgttt cctctcttatt ttcggacagg aaactctggt cagaaagaga tactgctgaa    3360
gtacctgctt taccggtcag ataaaaaccg ctttacctt cctcagcacc cgcatttgct    3420
```

```
gcaancatac aggcagcggt aactgctgaa acagcaaaaa cttttttcat ttcaattaac      3480
tccattattt cactattttt gtaaatagca ctcctaatat tttaaaacca gtcaaaagat      3540
agtatcaagc aaattattca tgtctaatga acagataaaa tcgactatgt gtcggcaaga      3600
ctctgctcca ccgatattcc tcttatttcc gcctcgatga ataccccccg ttaccttatt      3660 tgtaccccctt ataatgggat gttggccagc cagacccggc atgattagtt ctccctgtcg     3720
actatgctcc gggagggatg tcaccgggtc tggtgaggcg cggataaccg ctaataggggg     3780 aaggtcaggt attttacacc gggaccgtca gggcaagata acgaaagcca gctccccgca      3840
tgaactgacg ccagatagtt tctgtccatt gctgcttttc tcatcttacg tcttaaccct      3900
gccttgaata ccttatctct cgtcaaaata ttaatagcga tatgccgtat ccctgaaaat      3960
aatcccgctg cgtttcctct tcttacttgc agtcgtcttc attcattacc acgtccagac      4020
gccatgcagc ttattctcca cgtgccagta atttcggatc gctgtgacga acttctctgc      4080
ggttaaatca gcagaactga tataatatct gaccattatt tctgactctt gcttttgttc      4140
tgctattatt gaccgaaagg agactgccag gcatatttt tcagcccttt ccattcaaac       4200
gtgaattcaa tcagctcatc agggacntcg ccaaaccata tgaagacggg atcctnctct      4260
gccgtgactc ttgtcactaa ttgcgtaaca gtcatgctcn gggataatta aatctttcag      4320
cggaaataaa aagattatca gatatgggga tgacaccaca gcaccgctga ggccagtatg      4380
gataaaccat gtaccttatt aaccaaa                                          4407

<210> SEQ ID NO 76
<211> LENGTH: 824
<212> TYPE: DNA
<213> ORGANISM: Escherichia coli
<220> FEATURE:
<221> NAME/KEY: misc_feature
<222> LOCATION: (687)..(687)
<223> OTHER INFORMATION: n equals a, t, g, or c
<221> NAME/KEY: misc_feature
<222> LOCATION: (807)..(807)
<223> OTHER INFORMATION: n equals a, t, g, or c

<400> SEQUENCE: 76 tttttttgcaa gagaatttcc ctgaacctga agctcatcat cgccatctcc gccgttcagg     60
taattattac ctgctccccc aattaactta tcgttgccat caccgccata gagctggtca     120
tctccgtttc caccactcag tgtgtcatta cctttatcac catataagcg gtcattcccg      180
tcatttcctt ctatatggtc atcaccatcc gcgccatgga agatatcagc aaatttactg      240
ccaaaaaact tgtcggcacg cgtggtccca ataagttctt ccacggaata taagttatca      300
gtctctgtta aattttttacc attgatatga gtgaattcat aactccgata ttgcgttttt     360
tcagttcttt ttccaactga aacctcctgc tccttcacaa cttcctgtaa aaccttaaca     420
tcaccaccaa gtacacgtgt taccgtgtaa ttacccgctt cggttgcttt tgtgccatca     480
atggtcagat aaccggtgtc tgttttatca taataaacaa catcatgtcc tttacctgcg      540
tagatattgg ctgagccggc agataaaaag accttatcat cccgtctctcc caggtgtgac    600 tcaatacgaa tttcccgata ctggttatta ccgactgatg catgctgaat caggttagag     660
taatcatata cagacccctt gtcctgnaac ccccttcacc gtccatttat caacacccctt    720 gactaataac tcggtaatat attcatattt tccggactgc ctcctttcac gaatttcctc     780
accgggagtt taacaatggg cgtaacnaat ttgcaataac gtgg                       824
```

<210> SEQ ID NO 77
<211> LENGTH: 550
<212> TYPE: DNA
<213> ORGANISM: Escherichia coli
<220> FEATURE:
<221> NAME/KEY: misc_feature
<222> LOCATION: (2)..(2)
<223> OTHER INFORMATION: n equals a, t, g, or c

<400> SEQUENCE: 77

| gnggccgcag | tactggatca | tcaccgaagt | ttcgcgcgga | aaagcgttag | agaaagatct | 60 |
| aatgcttcat | gatggtgatg | gacttttcct | gatggtgaaa | tccagcggga | aatgctctgg | 120 |
| cgtttccgtt | atcaacattc | gacaacaaag | cagcggacaa | tgatgggact | cggtgtcttt | 180 |
| tccacacttt | cacttgctga | tacccgaggg | ctaagagtgg | attatatttc | cttattagcc | 240 |
| aacagaatcg | acccgcaaat | tcaagctaaa | gccgtagacg | aagagcaata | tttgaaaagg | 300 |
| tgggcaccta | cgttaccaat | actggcttaa | tggctacata | cggcggtcag | ggtcagttta | 360 |
| cgcttacaaa | atataaaaca | atttgataca | aaatattcct | cttattctaa | ataaaagtat | 420 |
| cttgaaaacc | ttccaactgg | aaggtagatt | gaatttatgc | taaacataaa | gaggaattgc | 480 |
| ttatgaatta | cgttatccgc | actaccaccg | tcgtctttag | tctcatgctg | ggcaggttac | 540 |
| gcaactgctg | | | | | | 550 |

<210> SEQ ID NO 78
<211> LENGTH: 382
<212> TYPE: DNA
<213> ORGANISM: Escherichia coli

<400> SEQUENCE: 78

| cactaaaggc | cctggatgtt | tttcgctcat | tagtagacat | ctcgctgata | acggcgctct | 60 |
| acgcgcactc | acttaaaaat | tcatccgccg | cttcggtgtc | catgccacca | aattcggcaa | 120 |
| tcacttccag | aagtgcctgc | tcaacgtctt | tcgccatgcg | attagcgtcg | ccgcagacat | 180 |
| aaatgtgggc | accatcattg | atccagcgcc | acagctccgc | gccctgttcg | cgcagtttgt | 240 |
| cttgtacgta | aacttttttct | ttttgatcgc | gcgaccaggc | aagatcgata | cgtgtcagca | 300 |
| cgccatcttt | gacgtagcgc | tgccamtcca | mctggtacag | gaagtcttcc | gtaaagtgcg | 360 |
| gattaccaaa | gaacagccag | tt | | | | 382 |

<210> SEQ ID NO 79
<211> LENGTH: 3576
<212> TYPE: DNA
<213> ORGANISM: Escherichia coli
<220> FEATURE:
<221> NAME/KEY: misc_feature
<222> LOCATION: (1528)..(1528)
<223> OTHER INFORMATION: n equals a, t, g, or c
<221> NAME/KEY: misc_feature
<222> LOCATION: (2618)..(2618)
<223> OTHER INFORMATION: n equals a, t, g, or c

<400> SEQUENCE: 79

| taaatcagca | gaactgatat | aatatctgac | cattatttct | gactcttgct | tttgttctgc | 60 |
| tattattgac | cgaaaggaga | ctgccaggca | tattttttca | gccctttcca | ttcaaacgtg | 120 |
| aattcaatca | gctcatcagg | aacatcgcaa | acaatatgaa | gacggatttc | ttctctgccg | 180 |
| tgactcttgt | cactaattgc | gtaacagtca | tgctctggat | tatttaattc | tttcagcgaa | 240 |
| aataaaagat | tatcagatat | gggatgacac | acagcaccgc | tgagcaagta | tgtataacca | 300 |
| tgtacttata | acaaaaggag | acgtaagaag | gggaacgggt | atcagagggc | caatcaaagc | 360 |

```
aggtataatg aacgccagta taattgtccg caacccagaa atatattatt gaactggtta    420
tctcctgcga atgcatatac tgcaacggcc gttaaaatag cattatatcc ataaagcccg    480
gcagagattt tatcaggaga aagctcagga atacagaatg ataccaccac actcagaaac    540
gaagcgacaa ccgtaatcat cagtagtttc cggctccctg caagtagtcc cagcataaca    600
agaataccgc cgacagcatc aggaaacata aaaatctcca taaagctacc agacaatgcc    660
accggatagt ttttcagcaa aacagaacct gcacttcgcc cgaaggtact gacatatcat    720
gaggcattat tccggaatgt aataaccacg tagcgataat aaaggggggcg gtcaatacgg    780 gtaaccctct gagcactgac gacaacaggg gagtaaacaa acaataccaa agagttccga    840
cgataagtac agcaattccg gagactgaca cagggacaag catgccacag gctatgccat    900
acagaacagc attatatccc catataccttt cattaatctc ctcatcagga taccgcaaac    960
accaggcaaa gaacgagaaa agtgctgcac tgatggctga gaaatacagt atttcggggt   1020
gccccatatt aaaagaggct attccagtcg ccaaaaaaaa gaacaagcca gaaacaacat   1080
tgttctgtaa taatacctgt gaataccccct tactaaaggc ggttatcacc tgttttactc   1140
tcatgtaaaa tgtcacacac acctcataca taaaccattc tccgcttctg cgggacagta   1200
ccgcccctga ctccacctca cagcggattg tgtatttttta aacaatcaca gtcttctcat   1260
atactttcca ttctgaagct tatctcttcc tccgtgataa gcttccgtcg cgggatgtgt   1320
tatacgccct gtaagacagt tataaaggac atcaatgcca tagttaatga ytaccgaatt   1380
ccggtggata gtcagtactg gtttgccaca aaacagtgca gtcacacatg acaggagaag   1440
atatgagccg gataccgctg ctctgagact taacgctcat gtaaactttc tgttacagat   1500
tcttccaggg actaagaaga taactgantt acgttcgcat tccagtstttt atttctgcag   1560 tgacagccat acccgagctt aatggaatgt gcttattccc ggttgacaaa tcattctctt   1620
caacagaaac aatgacatta aaaacgagtc ccagtttctg gtcttctatt gcatctaaat   1680
ttatattttt taccttaccc accagataac catatcgggt gtaaggaaaa gcctccactt   1740
taatgatggc attctgcccg acgttaataa aaccaatatc tttatttttgt accagagcag   1800 taacctccag cgtgtcatct tccggaacga tgaccatcag tgtttccgct gttgtaacaa   1860
ccccaccttc agtatgaacc ttcagttgct gaacttttcc cgaaacaggg gccctgatta   1920
ctgaagcctg ttgacgctct tcattttttct ctaactccag agttaataac tcaatgctgt   1980
ctgttgtttg tcttagcttg tctaaaattt catttttaaa aagctgcgtg acaagctgat   2040
attcttcttt tgcagacaat atctcactct caatttgctc cagttgcgat ttataaaccc   2100
gtaattcatt tgctgcctca acatatttat tctcctgctc aagtacagca tgttttgcaa   2160
ttgcctgttt atgcaacagg ctcctgaaat catccagacg gctttttttca accctcgata   2220 catttttcata acgtttata cgggcaagta ttgttaawcg ctctgctctt ttcttatcca   2280
gattcagttc tttttgatac ttctgatttt gccatgtgga aaactgttct tttatcaaag   2340
aagttaaacg cagtacttcc tcttcagata cattctgaaa ataaggctca tcaggaagtt   2400
tcagttcagg aagtttattt aattcaattg accggctcag aatttgatac cgaatttgtt   2460
ccagcctggc ctgtaacagt gatgactgcg ttttttaacgt atcagcttca gctcccagcg   2520
ctgtaagctt taataacaca tccccttttcc ggactgactc tccttctttt acgayaattt   2580
ctttaactat cgagtttttca ataggtttaa tttcttttnta cgcccactga gtgttaatttt   2640 cccatttgca gtggcaacaa tttccacctg gcctaaaaca gataaaatga aagcaataac   2700
```

-continued

```
cagaaacccc ataataaaat aagcaaccag acgcggccgt ctggataccg gcgtttcaat    2760
taattccaga tgagcgggta agaattcatt ttcgtccttt tcacgtaccg gagtatctaa    2820
ctgcttccgg attttccatg tttcactcca gacaagttta tagcgcaaca ggaactcgct    2880 gaacccatt aaccatgttt tcatattctt ctgttctttc tgttagtctg actgtaactg     2940
atataagtaa ctgtataaac tttccggttc agaaagcagc tccttatgtt taccctgttc    3000
aacaattttc ccttttcca tgacaataat gcggtctgca tttttactg tagacagacg      3060 atgagcaatg attataaccg ttctgcccctt acatattttg tgcatattgc gcatgatgac   3120
atgctccgac tcataatcca gagcactggt tgcttcatca agatgagta ttttagggtt     3180 gttcaccagc gcccttgcaa ttgcgatgcg ttgacgttga cctccggata atcctgcccc    3240
ctgttccccg acaatggtgt tataccctc acgcaattca gaaataaaat catgagcacc     3300
tgstaatttc gctgcataaa taactttttc gacggacatg ccaggattag ccagtgaaat    3360
attatcaata atactgcgat taagcagcac attgtcctgc aacacaaccc ccacctgacg    3420
acgtaaccag ttaggatcgg ccaacgcaag atcatgtcca tcaattaaga cctggccatt    3480
ttcaggaata taaaaacgtt gaattaattt agtaatgtg cttttttcctg aaccagaacg    3540 tccgacaata ccaataacct cccctgctt aatact                               3576
```

<210> SEQ ID NO 80
<211> LENGTH: 3541
<212> TYPE: DNA
<213> ORGANISM: Escherichia coli
<220> FEATURE:
<221> NAME/KEY: misc_feature
<222> LOCATION: (1758)..(1758)
<223> OTHER INFORMATION: n equals a, t, g, or c
<221> NAME/KEY: misc_feature
<222> LOCATION: (2529)..(2529)
<223> OTHER INFORMATION: n equals a, t, g, or c
<221> NAME/KEY: misc_feature
<222> LOCATION: (3392)..(3392)
<223> OTHER INFORMATION: n equals a, t, g, or c
<221> NAME/KEY: misc_feature
<222> LOCATION: (3425)..(3425)
<223> OTHER INFORMATION: n equals a, t, g, or c
<221> NAME/KEY: misc_feature
<222> LOCATION: (3452)..(3452)
<223> OTHER INFORMATION: n equals a, t, g, or c
<221> NAME/KEY: misc_feature
<222> LOCATION: (3471)..(3471)
<223> OTHER INFORMATION: n equals a, t, g, or c

<400> SEQUENCE: 80

```
tcagcccggt gagcgggttt gacaattccg cactcaccat tgggctaagg gttatcaggt     60
ggggttaagg aaatggcaaa acctaccccc gtccaaactc cagtcgctgc acattcacca    120
tccctggctt ctcacctgcg ctgacatcaa tttgtgtcac ccgcagcgca tatttttcat    180
ccagtgcttt taaccagttc agcaggtcat taaacaccac aggttctatc cagacctgga    240
tattctcccc gcgctcggca atccgtttga tgaccaccga gtgcgcggaa gctgtcactg    300
atgacccgcg atacctgtgc tggcgttgtc gtgccggatt ttcgcgccgc aataatatcc    360
ggcgcggcgc tcttcagtcg cgcgttcatc gccaccagct gctgcaacat cgtctcctgt    420
tgctcaatcc gttcgctcaa cggctgccag atgagaacgt aatatccggc gctaaacagg    480
aacactaccg ctgccagtaa catgcctttt tcacgcggcg aacgccccgc caggtgttgt    540
gtcagccagt gttcgccacg gcttaactgg cgttcacgcc attgctgaaa atagtgaata    600
aatttatcgc gtaacatgtt atttcctccg caacgttacg ccgccggaaa ccgcatcacc    660
```

```
ctctttctgt aacgcgtcct gttgcacaac ataatctgcc gccagtgcgc tacgagttta    720
tcgaagctgg caaagttcgc agcccgtagc tggaggtgaa cgtctggcg tttttgatca     780
aaggtgaaac acgcatttcg atgtcggtaa gtgacgctga tttcagggta ctggcgatcg    840
ctgacaattc tgcgagcagc cgggtatcgt cggtctgtgg gcgatatttt ttcagcgcca    900
tcgtcacctg agagcgtaaa ttcacaatcc gcttctgctc cgggaatagc gttaagaact    960
gtttctccgc ctgggtgcgg ctttgcgcca cctgttcgct gacgctccat aacgtcacgc   1020
cccgttccac taccagcgca accagaatca acaatatcgg cagaatcatc acccgccagc   1080
gcgcccactg ttttcggtag ctgacacgag gctgccacgg ccctgttagc aggttccctt   1140
ccggttcgcc ataagtggta atggcgggca gagcgtaacg gtcagcgttc ggcgtctgca   1200
ccagcccatg cagacagttc ttccggtgca atgccgacca cggttagtga aagcggtaaa   1260
tcctgctcat tgagctgtgc tcggaacatg accggagcca gcgcccgccc ggcgctccat   1320
ccccggcatt catcgatgcg gmagataacc cgttgcgcat cgccagccat aaacccacaa   1380
ggaatggaca tccagtccgg cgcgacgata gcgcgggtga tgccgtttgc ctgcaaccac   1440
tgcgcaatgt tgcgcatatg ctgctggtga atcacagcta cggttgccag ttgctggtcg   1500
attttcaacg gggcgaaatg cagttcatcg atatcctggt tcagctcttc ttccagcaag   1560
gcgggcagaa tcgtcggtat ctgcttgcgg ggcacatcag gcagttcaac ctgccagacg   1620
ctgatccatt cgccgggaat gtagagtcga atcgcatcag tttgcagcca ttgctggaga   1680
cattcatcag caacgtcagg ccagatgccg cactccacgt cggcggtacg acgctgccaa   1740
cggatgggag cggaamgnca aagcgggaaa aaaatctcaa gcatggaact cactcacttt   1800
ctcctgtctg atgccagaga acagaaaagt gttgtgggcc catgcggaca attaacgaat   1860
tcatcgtcag ttcaatctca ttcacggtga tatctgaacg cagccagaag taattgctgt   1920
ccacgctcag gacggttttt agctgttttt tagtacgctc atcgacgtca gcaagtaacg   1980
gctgtgcaag aaactgatcg acatcttccc agcccttcgc atgacgttgt tgtaataacg   2040
ctcgcgcctg aacagggctt aaccacgggt caaacagcgc ctcaagaatc acactttgcg   2100
tgacgtctaa ggtattgatg ttgatttgct ggcgggtcat cggcagcgca cagaccagcg   2160
gtttcagttt ttgataaagc ccggcgtcca ttccctgcac cacgcgcatc tcgctgatat   2220
cagccagcgg ttgattagcg gcgtaaaacg gcaccgaacg ggcgagatac tcgctgtctt   2280
cacggcccag acgcgtctgc acgctgcggt cttcgtcaat aaactcccac aggctttcgg   2340
ctatcagttc ggcccgataa gcaggcacat ccaggcgcgt gatcagggca atcagttgtt   2400
gtaccgcgag cggacgcgac gccgtcgtcg gctgagcgag ggcattcagg ttaaagcaag   2460
cctgtgcgtc acgcagagtg acggcgattt gccctgcggc agtgggaaaa aacgcgggcc   2520
ggaagcccna cgtgcgccag atgcacgcgc ttttcatttt tcaggctcag actgagtgcg   2580
ctcaacgcca ggctttccgc actggcgctg taccacagcg cctgctggta ctcctgctgg   2640
tgcgcgttcg cccaagttgt ttctgcatcc gcccggaaag cgtgatggtc accagcatca   2700
taaccgccaa caataccagc accacgacca gtgccattcc gcgttttggt ggtgaggtga   2760
tcatgataat tgcggcccgc gtaacaacca gatgcgttca atttcgcccc attgtggcga   2820
atgcagggtt atgcgtactg ccacggggat cgcctgcact gatgaccagc tctcctgcca   2880
gcgcgtgccg tcgtagaact gcaaacggag cgaatccgcc gggattaatt tttgcgttgt   2940
tggcttcacg ctgcctgccg catcggtcag tggccaggct aaccgttcga gataaccacc   3000
atgaatgcgg taaccgacgg tgagcagatt actgcgcggc agacgcatca acggattaac   3060
```

-continued

```
cacgccgcca cgtacaaaac gcatcccttc actctcagac gccagcacgc cagcgcccgc    3120
cagtaacgct rgttcacgct ggccctgatc gcctcttacc ggacgcggca tcatttgtgt    3180
cagatcgtgg gtcagaaaac tcatcgtttg ctgcatgagg tttagttttt gatcgtgtcc    3240
ggcgacggcg ctattcacgc gtgtaacccg tttgtcacct gctgcgccat cattgccagt    3300
gaggcaaaaa tggctattgc caccagcatt tccagtaacg tgaaaccagc gcgagtcctt    3360
ctcactgttg gtctcccacg gcgctaaacc angcgcgtcg tgactgaatc actgacgaaa    3420
agtcntcatg aagactgact tcaatatcca cngcatggag cagcgcatta ncggtattca    3480
gtggtgttgg ttcgccagaa ccaagcggct ttcctgccat aatcgctctc ggccctgggt    3540
g                                                                    3541
```

<210> SEQ ID NO 81
<211> LENGTH: 1234
<212> TYPE: DNA
<213> ORGANISM: Escherichia coli
<220> FEATURE:
<221> NAME/KEY: misc_feature
<222> LOCATION: (1156)..(1156)
<223> OTHER INFORMATION: n equals a, t, g, or c

<400> SEQUENCE: 81

```
gtactggaca tctttgatga acaagctcct cagtgtaaat tgtacgtctc tgatcgtaat      60
cttcctgagg gcgttgaaca tctatccgct gaatttatac cctatactcc tgagtcggca     120
gattttctga ttcaacgttt tttctctgaa actatccata ttgaaagtgc aattgttgtt     180
acagcactta aaattgccaa tcagattgct ctatctcaaa atgagaccaa gaatgtgtat     240
ctgcttggat ttgattttac gataaagggg gggttcacta gcaagatccc ctgcgcagcc     300
ttgcatgccg aaccagaata tcaagagcga attatcagta gtcaagaaca gctattgcag     360
atgctccttg cagaaaaaac acgcctgaat atcaatatca atcatgttgg taataagcct     420
tacagcgtat attctgttga tgcatttaat caagtgttcg ctgcccgcca tcgtggagtc     480
gtgctgccca cacatgccca gatttccact acatcatcac aaaatggggt gaaggtgatc     540
gcagagatta ctactaatca ctttggtgat atggaccgat tgaagtcaat gattgtagcg     600
gccaagcagg caggggctga ctatatcaaa ctgcagaagc gtgatgttga aagtttctat     660
agcagggaga agctggagtc accgtacaac tctccttttg gcaccacctt tagggactat     720
cggcatggca ttgaactcaa tgaagagcaa ttttcctttg tcgactcttt ctgtaaagag     780
attggtatcg gctggtttgc ttctatttta gatatgccct cgtatgagtt cattcggcaa     840
tttgaaccag atatgatcaa gctaccatca actatatctg aacataaaga ttatttggct     900
gctgttgctt ctgattttac taaagatgta gtaatttcaa ctggttatac tgatgaggcc     960
tatgagcgtt ttaycctkga taactttacc aaggttagaa atatttatct gctgcaatgc    1020
acctcggctt atcccacacc gaatgaagat acccagctag gtgtgataag acattattat    1080
aatttggcga aaaaggatcc acgtattatt cctggttttt ccagccatga tattggtagc    1140
ctttgttcca tgatgntgtc gcagccggtg caaaaatgat tgaaaagcat gttaaatttg    1200
gcaatgtggc ttggtctcac tttgatgaag ttgc                                1234
```

<210> SEQ ID NO 82
<211> LENGTH: 6313
<212> TYPE: DNA
<213> ORGANISM: Escherichia coli

<400> SEQUENCE: 82

```
atgggacctt tcttcaatga tgttgccgag tggttagagt cattaggtcg taacgctgtg      60
aatgttgtat tcaatggagg agatcgtttt tactgccgtc atcgacacta tctggcttat     120
taccaaacgc cgaaagaatt tcctggttgg ttacgagata tccaccggca atttgacttt     180
gataccattc tctgttttgg tgactgccgt ccattgcaca agaagcaaa acgttgggcg      240
aagtctaaag ggatccgctt tctggcattt gaagaaggat atttacgtcc gcaatttatt     300
actgttgaag aggacggtgt aaacgcgtat tcatcgctgc cgcgcgatcc tgacttttat     360
cgtaaattac cagatatgcc tgcaccacat gttgagaact taaaaccctc gacgatgaaa     420
cgtattggtc atgcaatgtg gtattacctg atgggatggc attaccgaca tgaattcact     480
cgctaccgtc atcacaaatc attttctcct tggtatgagg ctcgttgctg ggggcgtgcg     540
tactggcgta actattttac aaaataatgc aacgtaatgt attggctcgg ttagtgaatg     600
atctggacca acgttactat cttgttattt tacaagttta taatgatagc caaattcgta     660
atcacagtaa ttataatgat gtgcgtgatt atattaacga agttgtatat tcattttcgc     720
ataaggcacc gaaagagagt tatttggtga tcaaacacca tccgatggat cgcggtcaca     780
gactctatcg accattaatt aagcggttga gtaaggaata tggcttaggc gagcgagtca     840
tatacgtaca cgatctccca atgccggaat tattacgcca tgcaaaagcg ttgtgacaa      900
ttaacagtac agtggggatc tctgcactga ttcataacaa accactcaaa gtgatgggta     960
atgctctgta cgacatcaag gggttgacgt atcaagggca tttgcaccaa ttctggcagg    1020
ccgattttaa accagatatg aaactgttta agaagtttcg tgaatattta ttgatgaaga    1080
cgcaaattaa tgctgtttat tatggtgtaa aatcaaaaag caatagaagg tccgcattcc    1140
taaacggtag cagatgatgg ttttcatggg cgtttcaggt tactcaatca gccaacaacc    1200
gcagcgaaaa ccctgctttc tcgaccagtt caggccggtt ttacctccaa tgctttccgt    1260
cagaactgag atttcagcca gttgccggat aagtgtgtcg atttgcagca gtatactttt    1320
tcgtacagcc agaatgtggc agactgaggt ggaatagata acgtccgtat gcccgctcac    1380
cacctccggg cgggagtgtg tggtatctga catcatcatt tttcctttct gtttataaat    1440
gaaaacgcca gccgtgttca ggctgacgtc agggaagtga atcgggtga gtgatcttca     1500
ctggttctgg tgcaaaagtt actgttggcg cagggtacgg atacctccc tggcctgttc     1560
gatacagggc aacagtgctg ccgaatctgt tttatcctca tcgttgtcga agataattcc    1620
cgattcgcag tcgatattgt cctgcagcca cgtaatcaga atatccagcg ctgtttccgt    1680
ggttaatgat tcatgttgt gaatttccgg attaccagtc gaaagtgggt aaacctggca     1740
gacatctggc actggcatcc agatgaatga gactgacacc ataacgccgg atgagtgtga    1800
cgaccagacg acggaacgta acagataacc ggtaccggta aaatgaatcc attctgattc    1860
accaaagtca ctggtctggt gtaacagcga gtacagccag gcgttgtcct tttccgtgat    1920
atgtgcggta ctgcagcgta tgccggaaag agtcgtaaac ggttgtggag tgcaggttga    1980
ctgttggtca gattcatcca ccacgcggag tgaataaccg ttttcagcga ccttgttaat    2040
cagttcagcg agattaatac catcgacgtc aacgacaatg cgccccatat tcagtgcctg    2100
tacgttaacg ctgtcggctt ccggcgtcag ggaaagtttc attgtttcac ctccgggtgc    2160
ttacccagga taatattatt taccgctctg taattgtcgc gggtcatcag gccggtcgcc    2220
ctgcgagccc ggaggatatc gatgctgttt attaactgag agcgggtaca ggcgctgaat    2280
cccggctggt cggtacgcac cagcgcgtat ttttccacga gaaagttcac cgcatcacac    2340
```

```
agtgaaatgc ctgcctcaat atgctgctcg atcacacgtt catcggcaaa cggtgtgtca      2400
ttcagtgtga ggccgtagtg ctggtccagc agtcgggaca gaagtatctg ccagatttca      2460
acaggagacg ggcgagaact ggccgcctgc ccgggtaata caggtaatgt tttcatactg      2520
aagattttcc tgatatgcag atataaaaat gggaaagtgg cgtggtgaaa acaccaggcc      2580
gtagcagaag gctattctgg agagttaatt tttcatttcg ggcgtcggat aaacagccag      2640
ataaacgtaa ccacaactgc tgagggtatc ggctttgcag gtcagcccct tgcatacag       2700 cgtgacggta tgctgatggc ggggattcag ttcaccgctg gtgagcatga gttccagttg      2760
tttcatcagc agcggaaagg cctggtccag gtggtacgca tctgcattgc tgtataggcc      2820
tctgataccg gcgcggtcgg caaggtaatg caaccggtta ccctcctgca ccagacgtgc      2880
cccgaaacag ggcgtcacgg tgcagggcag cccccaccag gggcggtcgt gattgtcgtc      2940
gggaagtgtt gtcccgggga gtgtgtctga cacgataaaa tccctacaga aaatcggcta     3000
agaatgctcc ggtattggcg ataattctgc tcatcagaat tcccactcag ttcagggtga      3060
cgctcatcag ccggacatac gggccaaaac tgtccttacg gcgttcagca aacacggcca      3120
gcacaccggg aatatcctgt acttcacgac cggtatacgc ctcagcactg ccgtgccagc      3180
ggtacttacc ggtgcagaac ggaaatagac gggatgcagg atgctgttgg tgaatacgca      3240
tggcttcacc acgggtgatg atttcataa tgggatacct ctgaagacag aagataaaag       3300
tgaaaacagg tgtgatgtgg ttgtgacggt gacgggttaa agcagaccgt gttccgcaaa      3360
ggagaaaacc tgactgccac caactatcag atggtccggt acccggatat ccaccagggc     3420
cagtgcctgt accagacgtt ccgtgataag gcggtctgcc ttactggggg tgacttcacc      3480
ggacgggtga ttgtgtgcca gtaccacggc ggcggcattg tggtacaggg cgcgtttaat      3540
cacttcccgg ggatggactt ccgtgcggtt gatggtgccg gtgaagaggg tttcaccggc      3600
aatcagctga ttctggttgt tcagatacag tacccggaac tcttcacgct ccagtcccgc      3660
catcttcaga atcagccatt cccgtgccgc acgggtggag gtgaaggcca cgccgggttc      3720
atgaagatgg cggtccaggg ttttcagggc ccgcagaatg agactgcgct cgccgggcgt      3780
catctctccg ggcagaaagg aaagttgttg cattgtgctt ctctccattc agtcgatgat      3840
gcgcataatg gcgctgcatt ccggatgctg cagggcgtaa tcccgcaacc ggtaataatg      3900
gatcgtcatg gcataacact ccgtacgaca ggcatgatga ctgtacgtca tcagacaggc      3960
ggcaatgccg gcggcttccg ggctcatttc agcgcggtta ccgttcatgg cattgaacag      4020
tacccagttt tcgtcatcat cgtcatccgg ttcgggtgcc ataaatgccc cgccgttgtt      4080
cagggtgtac agattccaga taccaccgca gtagtcttcg cacagacggt ccatccagcc      4140
gaagacacgg ggctccaggg tcacccactg tggaatgagg ccaaagtgct gcggccagaa      4200
gctgatcgcc tgttcatcag ggactatggt ggcaaccagc tgaggctggt cattccctga      4260
tgcagcggtt acggaaacag aaggagtggt ggaattatgc aagacggttg tcatgagatt      4320
attccttata aaagtaaat gaatggaaga acccccgggg gaagggacag acgtgagtca      4380
gaactgcgct ttcagggaaa cggcatcagc gcatactctc cagcagcgtt tcagccatca      4440
cccacaatgc gcggttgagc ttaatgtcgg tgtcgatgct gtgaatggca cgggtatgga      4500
tacgttttcc tctggcactg cgaccggaaa ttccgccttt cagcatattc tcctgaatgg      4560
tctgataagc actccacagg tccttaccgt aatcctcccg cgtcgtggt gtcagaatgt       4620 cggcggtggt gacgggctga tgttcgtcac cataacggta agtcagtgcc gcctgtgcca      4680
```

-continued

```
gcgcctggcg tgccggtggc ggcagaatca gcgactgcat ggcatcacgc ttttcctcaa    4740
tccggtcaaa aaccccccacc acctcgtaag ccccttcaat aactttctcc accacatttc    4800
cccggtgcgg aacacgcact tcccccagag actgaccaca gacgcatccg ttctggcaga    4860
cgaacctgaa gtaacccggc agcatctggt agctggaggt accgtcatga gagttgagca    4920
gaataatttc agggacatgt tctccgttta tctctccggc ccgccgcaga cgcagcatgt    4980
gtttggtgta ttcccggcgg tccgggtcac gtacgcgggc tggcaggcg aagaatggct    5040 gaaagccttc ccgctgcagg ctttccagta cggtgatggt ggggatgtac gtatagcgtt    5100
cactgcggga ggtatgccgg tcttcaccga aaatacccgg tacatggtgc atcagttctt    5160
cgtgtgtcag cggacggtca cggcgtatct ggttcgcata accaaaacga ctggctagtc    5220
gcataatttg ctccttatcg gtggttaaga tttactggtg taataaatga aaaagccacg    5280
tctcccggag aagacgcggc ctgacagatg aaatgaatga cgtttattgt ctgagaagcc    5340
cttaactggc gagctgagta ttaagctgtg ttccggcatc accagcgcaa ctgaccttca    5400
gcattacgga taaccagccg ggaatatgtt ccctggtcat cttcagtaaa cacattgcgg    5460
taagctgtta tgacagcaac cgcctgcccg tatgagaaag atccttcagc caggacatac    5520
tctgtgtgta acccggcata tctggtttct cctgataaat agcctctgcc atacgttgtg    5580
gcagaggctg aagcatgaaa ctgacttcag ggatcagtta acatttttc cggaaacggt    5640 aatcagcagt ggatggtagt cctggggatc gaaaaccgat aacggcagac tgacacgatg    5700
gccgttactt tcttcagttg ctttaatgat ttcggttgtg cgacattttt ccacgcactc    5760
cgtttccaga aatgcgtctg tggttcgcgt ggcattactg tcaccaaagg cttccgtttc    5820 cattttctg gtcaccagcg tctgaccata tttgtctttg agttcagag tgatggtgag    5880 ggggccaaat ccttcatcgt ttccgccatt atccagccgg aactggtaag cacaaatatt    5940
tcccgggagc catatcgtat ctgtattgcg tatactgatg taacgttgat cctgtgcccg    6000
gagtggggca gaccacgtta accccagaat gaaggcggta atcatgcagg ttttgaacag    6060
gtgaatcatg gtatttacct ctctgagtca tgacgattac actgacaaat caggtgataa    6120
aacgtaaaag gcgcagaata gccgttatgc cggtaactcc ggggggtaatg tttcttccag    6180 tcggttaacc atattgccga gatgggatgc atcatattcc atgacggggc gttgcctgat    6240
gatactgacc accagtggtt tgattaacat gttggtcgcg gcccgttgtt gtataccggc    6300
ggcgaaaatg atc    6313
```

<210> SEQ ID NO 83
<211> LENGTH: 432
<212> TYPE: DNA
<213> ORGANISM: Escherichia coli

<400> SEQUENCE: 83

```
cgttggccgc ttgcgcagat aaaagcgcgg atattcagac gccagcaccg gctgcaaata     60
cgtctatttc agcaacacaa caaccagcta tccagcaacc gaatgtctcc ggtaccgtct    120
ggatccgtca gaaagtcgca ctgccgcctg atgctgtgct gaccgtgaca ctttctgacg    180
cgtcgttagc cgatgcaccg tcaaaagtgt ggcgcagaaa gcggtgcgta ctgaaggtaa    240
acagtcacca ttcagctttg ttctgtcatt taacccggca gatgttcagc gaacgcgcg    300 tattctgttg agtgcggcga ttaccgtgaa tgacaaactg gtatttatca ccgataccgt    360
tcagccggtg atcaaccagg gcggaactaa agccgacctg acattggtgc cggtacagca    420
aaccgccgtg cc    432
```

<210> SEQ ID NO 84
<211> LENGTH: 3494
<212> TYPE: DNA
<213> ORGANISM: Escherichia coli
<220> FEATURE:
<221> NAME/KEY: misc_feature
<222> LOCATION: (3394)..(3394)
<223> OTHER INFORMATION: n equals a, t, g, or c

<400> SEQUENCE: 84

| | | | | | |
|---|---|---|---|---|---|
| gggctgatta | cgattttatc | aatctgtcta | tagaacatga | actgaatgaa | ggaatagctg | 60 |
| gcagagagag | gttatgccgg | actggcggat | aaccggaacc | ggttggcaga | ggtggttacc | 120 |
| cgtaaattgc | aggacagctt | ttatatgaac | tttcctggga | tgcgctgaac | acggcataca | 180 |
| gtgaacaccc | agagtggttt | tccgggcttg | tctccgggga | tgagaattaa | aaagtggatt | 240 |
| atgctgctat | agcgcggcgt | gatttcctgc | agggatttcc | atttataaga | atacgccgct | 300 |
| tcggggaatc | tccggttctc | ctgagagtta | cgattgtttt | tttactcaaa | tccacaacac | 360 |
| ctgaactgga | acttgtgttg | catccctgat | tgttactctg | caggaaacat | ctttttacc | 420 |
| atcaaaggat | gactgttttc | ctttctcccc | tccgtaaaac | acaacttcga | tcacatttct | 480 |
| gacatttttt | ccagatttta | cataacagga | ttgtttctgt | atgttttta | tctggtgtaa | 540 |
| atttcagcac | tgacattccg | cttacgttaa | tttactga | atacccacg | aggagaatat | 600 |
| gcagcaccgg | caggataact | tactggcgag | cagaacgtcg | ttgcctggta | tggtttccgg | 660 |
| tcagtgcgca | tttaagctcc | gcactttctc | tccggtggca | cgctattttt | ccctcctccc | 720 |
| ctgcctttgt | attctttcgt | tttcgtctcc | ggcagccatg | ctgtctccgg | gtgaccgcag | 780 |
| tgcaattcag | cagcaacagc | aacagttgct | ggatgaaaac | cagcgccagc | gtgatgcgct | 840 |
| gaagcgcagt | gcgccgctga | ctgtcatacc | gtctccggaa | atgtctgccg | gtactgaagg | 900 |
| tccctgcttt | acggtgtcac | gcattgttgt | ccgtggggcc | acccgactga | cgtctgcaga | 960 |
| aaccgacaga | ctggtggcac | cgtgggtgaa | tcagtgtctg | aatatcacgg | ggctgaccgc | 1020 |
| ggtcacggat | gccgtgacgg | acagctatat | acgccgggga | tatatcacca | gccgggcctt | 1080 |
| tctgacagag | caggaccttt | caggggggcgt | actgcacata | acggtcatgg | aaggcaggct | 1140 |
| gcagcaaatc | cgggcggaag | gcgctgacct | tcctgcccgc | accctgaaga | tggttttccc | 1200 |
| gggaatggag | gggaaggttc | tgaacctgcg | ggatattgag | cagggatgg | agcagattaa | 1260 |
| tcgtctgcgt | acggagccgg | tacagattga | aatatcgccc | ggtgaccgtg | agggatggtc | 1320 |
| ggtggtgaca | ctgacggcat | tgccggaatg | gcctgtcaca | gggagtgtgg | gcatcgacaa | 1380 |
| cagcgggcag | aagaataccg | gtacgggca | gttaaatggt | gtcctttcct | ttaataatcc | 1440 |
| tctgggggctg | gctgacaact | ggtttgtcag | cggggggacgg | agcagtgact | tttcggtgtc | 1500 |
| acatgatgcg | aggaattttg | ccgccggtgt | cagtctgccg | tatggctata | ccctggtgga | 1560 |
| ttacacgtat | tcatggagtg | actatctcag | caccattgat | aaccggggct | ggcggtggcg | 1620 |
| ttccacggga | gacctgcaga | ctcaccggct | gggactgtcg | catgtcctgt | tccgtaacgg | 1680 |
| ggacatgaag | acagcactga | ccggagctgc | agcaccgcat | tattcacaat | tatctggatg | 1740 |
| atgttctgct | tcaggcagc | agccgtaaac | tcacttcatt | ttctgtcggg | ctgaatcaca | 1800 |
| cacacaagtt | tctgggggt | gtcggaacac | tgaatccggt | attcacacgg | gggatgccct | 1860 |
| ggttcggcgc | agaaagcgac | cacgggaaaa | ggggagacct | gcccgtaaat | cagttccgga | 1920 |
| aatggtcggt | gagtgccagt | tttcagcgcc | ccgtcacgga | cagggtgtgg | tggctgacca | 1980 |

-continued

```
gcgcttatgc ccagtggtca ccggaccgtc ttcatggtgt ggaacaactg agcctcgggg    2040
gcgagagttc agtgcgtggc tttaaggagc agtatatctc cggtaataac ggtggttatc    2100
tgcgaaatga gctgtcctgg tctctgttct ccctgccata tgtgggaact gtccgtgcag    2160
tgactgcact ggacggtggc tggctgcact ctgacagaga tgacccgtac tcgtccggca    2220
cgctgtgggg tgctgctgcc gggctcagca ccaccagtgg ccatgtttcc ggttcgttca    2280
ctgccggact gcctcttgtt tacccggact ggcttgcccc tgaccatctc acggtttact    2340
ggcgcgttgc cgtcgcgttt taagggatta ttaccatgca tcagcctccc gttcgcttca    2400
cttaccgcct gctgagttac cttatcagta cgattatcgc cgggcagccg ttgttaccgg    2460 ctgtggggc cgtcatcacc ccacaaaacg gggccggaat ggataaagcg gcaaatggtg    2520
tgccggtcgt gaacattgcc acgccgaacg gggccgggat ttcgcataac cggtttacgg    2580
attacaacgt cgggaaggaa gggctgattc tcaataatgc caccggtaag cttaatccga    2640
cgcagcttgg tggactgata cagaataacc cgaacctgaa agcgggcggg aagcgaagg    2700 gtatcatcaa cgaagtgacc ggcggtaacc gttcactgct gcagggctat acggaagtgg    2760
ccggcaaagc ggcgaatgtg atggttgcca acccgtatgg tatcacctgt gacggctgtg    2820
gttttatcaa cacgccgcac gcgacgctca ccacaggcag acctgtgatg aatgccgacg    2880
gcagcctgca ggcgctggag gtgactgaag gcagtatcac catcaatggc gcgggcctgg    2940
acggcacccg gagcgatgcc gtatccatta ttgcccgtgc aacggaagtg aatgccgcgc    3000
ttcatgcgaa ggatttaact gtcactgcag gcgctaaccg gataactgca gatggtcgcg    3060
tcagtgccct gaagggcgaa ggtgatgtgc cgaaagttgc cgttgatacc ggcgcgctcg    3120
gtggaatgta cgccaggcgt attcatctga cctccactga agtggtgtc ggggttaatc    3180 ttggtaacct ttatgcccgc gatggcgata tcaccctgga tgccagcggc agactgactg    3240
tcaacaacag tctcgccacg ggggccgtca ctgcaaaagg tcagggcgtc accttaaccg    3300
gcgaccataa agcgggaggt aacctgagcg tcacagccgg agcgatatcg ttctcagcaa    3360
tggaacgctt aacagcgaca aggacctcag cctngaccgc cggcggcaga aattcactca    3420
acagaatgaa aaactgactg ccggccggga tgtaacgctt ccgcgaaaa aacatcacac    3480 agggttaccg gcca                                                      3494
```

<210> SEQ ID NO 85
<211> LENGTH: 9319
<212> TYPE: DNA
<213> ORGANISM: Escherichia coli
<220> FEATURE:
<221> NAME/KEY: misc_feature
<222> LOCATION: (2)..(2)
<223> OTHER INFORMATION: n equals a, t, g, or c

<400> SEQUENCE: 85

```
gncccaagct taggttcgcg gccgcagtac tggatctatt gccagcttca ccgccagact     60
gtcagtcagt acatcaccgt atttctgctg gcaggttgcc gggcggctgc acagtcactg    120
atcagttgct tctgctgtgc cgtactcaac tcttcgtact ttttgataat accgccgcag    180
tcaccgcctt tcgcctgaca ggacttcatt tcagcagagc aggcatctat ctgcttattg    240
ctcaggtagt tattctcaac aacaaccaca ggggattaga agcctttag cctgaaatat    300 tttgcgagag cacatccaat accaataaat gagccaatca cacatccgat aaacaaaaca    360
tgccgaatct ctttcaaact aatatttaaa ttacctgtta tcaaccactc caccaaagaa    420
aaaaacacat caatacatag gaatgacacc actatagaaa gaaatgcgat tataaaaata    480
```

```
ataaacaatt ctgataagtg ctgagaattg ccgctcattt tttcacctcc ggaatgtaag    540
actcaatctt tttaccttca tactcagaag caaaagaagc cgacacatcc ccagctatac    600
caggaatcct actgggtgtc atttcttttg atagccccaa ttctcctttta atatcggtat   660 atttttgaag tgttggatta aatttcgggt cccagccgtc ttttaaccag ttagcaccac    720
tattaatgcc ccatgaaagg cctttaccaa tgccatatcc aatagcagaa ccagcaccat    780
tgatcaacgc accagatgtt ggggcttttc cttcgagcca gtttcctaat gctcctccag    840
ttgcattcca gccaactgtg cctacaactc cattccctgc actaatcaca ttaacccaac    900
caccgataat cgctgttgta ggatctatag ttccatccgt cagatagcta acacctgcat    960
tagctcctgc ccctaatccc cacatggcct gagcaccgcc agtaagagag ctacactacc   1020
agtggccaac gctccggcat acgctttatt gactgcttct cctcgcttac aggcttcacc   1080
gcctggggca tcgttacagg aaagtacatc tgcgccatgc gtctgagcag ctttgctctg   1140
ctcggactct gtgccaccaa ccaggttatt ctcagcaatg ttcttcccga caccagcccc   1200
agcagccgcg ccagccacat cgccactggc aatgccgcca ccatacccg ctgacagcgt    1260 tgccagcgtg cttacggttt gcttctgatc ttctgtcagt ttcgacggat ctacgtccgg   1320
atagaggctt ttcgcaatgg ctgacgagat cacttcacca gtacccgcac caattgcgcc   1380
tgctgccgca ctgttgccct gaagggctgc tgtcacacca ccgagaatgg catgggcaat   1440
ggcttttgcc gctgtattgt catcaatacc cgcgtgatga ccgatgatgt tcgccagctc   1500
cggcgccgaa gctccggcca gagcacctgc taaattaccc cccgccagcc cctgaagtgc   1560
agccgttgca gcctggatac cgcgctgcat atcgctgccg gtaccatact tttcctgttc   1620 cttttttgtat tccggcgtat cacgcagttt tgccagatat gcctgccgct gttcttccgt   1680
cgcatccgcc ggaacaggcc catatttatc ctgcgcagct tcaacgcatt cagttccccc   1740
tgcgtccgcg caatatccgc cacctgactg cctatgtcac tgataagccc cactgtctgc   1800
agacgcctct gctccttctc cttgtcaaat atcgggctga tactgtcatt agcgtgcgca   1860
gggtcacggc tcaggttcgc cagattctgc ttctgattgc ccctgtcccg gatggtgata   1920
gtgccttctg ccactgcggc ctgagtcgtt ccttccgcat gtccgctgtg acctccggcg   1980
gatatcatgc caccccggcat gttaccctga aatttatccc cgaagctgcc accaccgctc   2040
agactgattc cactgtgact gactttataa tccgcttcgt tgtgaaggtc actgaaccccc  2100 agcgttccgg tatccaggtg gtttttatcc ggtgtggcag tggaggcaat caccgcacca   2160
tccagttggg tatgtttacc cactgtgatg tcgaagccgc cgtcaccggc aaacattccg   2220
gtttgttcag caacggagtc aaagcggctc ttcatcttat cccgggaggc agcgatgtaa   2280
cctgagccgg tcatggagcc aaaggtaaaa ctgccgccgg casccacgct ggtctgttta   2340
ctgtcgtact tactggtgtc ctgctggctg cttatcagca ggtcgtggcc cacatcggcg   2400
ataatcctgt tgccgttgac ctgagcaccg ttcagtaccg tatcccgacc actgttgatg   2460
gtgacggttt taccgctgtc tgttgtggtt tcagtccact cagtaccgtt acctttctcg   2520
ctgccttttg ccgcattaac gctggcaaag acactgatac cggcaccttt acctgcaccg   2580
atactgacac ccacgccacc gccactgctg ctgttcctgc ccgttgtttt ttgtgtgttt   2640
gccgcgccac tcaacagaac atcattcgca gcatccaggt ttgtgttacc accggcctta   2700
agctggcttc cggcaatcac aatatctccg cggttatcgc ccctgttttt accggttgcg   2760
acaacagaca gattattccc ggcattcagc gtactgccgg atactgtgtc actttcagaa   2820
```

```
tgttgttgtg atttcgattt ctgggtggtg agcgacaggc tgactcccgt cgcattcggg   2880
tcaccggttg cggaggccat tgccgcagcc tgtccggcct gcacaccaga cagcgctgtc   2940
tttgtagcct gcagggtttt cagacggctg tcactgctct ccttcgtctc ctgtgcactg   3000
gtgaccgcat tattgatggc actgcccact gtgccggaaa gggcaaccgt cagcccgctt   3060
ttcttctgct caaatttttc gtccacagta cgacggtcat gccccgggtc aaccaccaca   3120
ctgtcaccgg taatgctgat atcccggttc gcaatcacat ccgaaccgct gatatgagcc   3180
tgtttgcccg cggtaatact gacattaccg gcagtggagc cgatggtact ggcactctga   3240
ctctgcgttg tcccggcctc gcggcggtcg tgcgttgtct tactgctgcc aatggtgaag   3300
ccaataccgc cggtacccat cagaccggat tcttcgtttt ccttaaagcg ccaggacgta   3360
tctgtactgg tggcagcaag aacatcaaca tggttacccg ccgccagtga cacatcccgg   3420
tcagccacca catccgaacc ctctaccgtc aggttatcac cggcgttaac ggtcacgcgg   3480
ttccccgaca gcagggaacc tgyttcacgg gaggcactgt cctcactgat ggtgtgggtg   3540
gttttcttac tgagaaaacc tccgcttttt ttcttcgttt ccagatagtg atagtcactt   3600
tctgtcgccg tggtcagggc aacatcacga ccggcattca cgctgatatt gccggttgcg   3660
gtaacggatg acgcaacagc ggtgatatcc cgtcctgcgg tgacggtggt gtcaccacck   3720
ctggcgattt ccgttccctg ctgacggact gtctcgttaa tctctttctt tttcttcgac   3780
gtatagctgt cgcctgcgcc ggcagactct gccaccaggt tcacatcacg tccgccccgg   3840
atgaccacgt tattttccgc agccataccg gcagcctgac tggcaatatc acgaccggca   3900
acaaggagga ggttatcgcc cgccgtcacc gtggacacag ctgcgtggct ttcatgactt   3960
tctgacctgc cgttgcgact gttttttgctt tccctgactg cattcagact caggtcgtta   4020
cctgcagaaa gcagggcgct gtgcccggca gaaacagagg atgctgtgac atccagatta   4080
tggcctgcag ccatcgccag gttaccgccg gcgctgatgc tgctgccctg tgaggtggtg   4140
gatgatgaac tgttgtcatc agtgtgccag aaaccggact gacttttgct cccgcttatc   4200
aggtttacgg caatgttgat gtcattaccc gcagacattc caaggtctcc accgacgag    4260 accgttgccc cggtaatatc aatgtttttc cctgcatcca gtgaaagtga atcagtgcct   4320
ttaatggtcg caaccggacc ggtgtccgta ccgctgagat gcacaccacc atatcggctg   4380
tcactgcccg cattccattg ctgacgccgg gtgatattgc tgatgttgcc actcacgctt   4440
tccagttgta cggttttacc gctgatgact gagctgatat tgctgatatc cccgatggcg   4500
ctcaggtcca ggctaccgcc cgcgcttatc agccctgcat tcaggttgtc gatatagccg   4560
gtactgtcga gcgaaaggtc gttctgtgcg ttgatgctgc cgccgctgtt ggtgatattg   4620
ccgtccgcaa gctgcacgtt gttcccgctg ataacgctgc cgttatgcag ggtgatatct   4680
tccggcgaca gatacagttt cgggaccatg actgtctgtc cgttgatggt gactgactcc   4740
caccacagca tgctgccgtc aagctgagca atctgttcag ctgtcagcgc cacaccaaac   4800
tctaatccca gtcctttctg ttgtctggcc gcgttatcca tcagataccg catctgttcc   4860
gtgtctgaac ccagtccgtt gagataacgt gaacccgtcc ggctcagcac cgcgttactg   4920
acataccggg tatcaaagac cgcatccccc aggaaacgat aatctttttc cggtttcagc   4980
ccgaggcggt caagaaaata cgatgagccc agaaactgtt tttcatcggt atacgacgga   5040
gccgtttcac gtggcgcctg acccggtttc gctccaagaa gctcatacag tccggcaaac   5100
aaatggctgt ccacctgtcc gagaccatcc agtttcgggt tcaccgtaat cagatacgga   5160
ctgtccgggt ccgtggacgg aaccaggtat ccattgttgc cggaaggcag tggccagtca   5220
```

-continued

```
tcactgatac cggtctgacc ggtcagtggc gaacctccgg caatattttt cagggcacct    5280
gccagttcat cgtgccattg cggagagcca accaccaccg gctcatactg ctgcagcgct    5340
gtctgtgtca gactgtctcc gccggtctgc tgacttaacg tattcagtac aggtgcagag    5400
accaccggac tgacactacc tgcatgtgca gtggttgttc cgttattgat actgctggta    5460
aaacgggtct taacatcccc gcccgcctga ataacggaat aatacgtctt accgggcgtg    5520
taatcttttt cccggccatc cagtgaaaat ctgatggtat tgttttcaaa ttccggtgac    5580
agcaggggca gtttatccag agagcctgtt gcatagctac cgtaaaacgt tttcgggtcg    5640
tagcggtata ccagatattc attctctgtc cccgtctgcc agctctgatt gcttaactct    5700
ctgcccgaga gtgcgatatc cccattcgcc aggataaatg acgcccggtt ttccagtcgt    5760
tcagcctcag cagaaagatt acgccctgac gcaatgcggc ctgccggatt atcagcaccg    5820
gttactgttg tgatgttctg gctgctgaga agcgctgtg tggcactgtc agcaaacgga    5880
gcgtaataat aaagcgtatc cattgtgata ttgcatgccc cgtgcccgtt gcagggcgta    5940
ccgtgctgat tttcaacttc acgggtgaaa tagccatagc tgccgtcagg aagaagggaa    6000
aggggaatat caaccagagc atttcccatt ccctgaatgg atgaggggtt agtccgggtt    6060
gttgttgtgg cagaaaatcc ctcccgctgg ttcagaagat gcccggttct tacaacaata    6120
tcgccctgat gcgtctcaat attccggaaa gtattgataa tctctgtgtt tgcaccgccg    6180
gaagcatcct tctgtaccca cagactgttg ccggccagga tatcaccatg ctggttatgc    6240
agacggtctg taaacagctt caggttattc cccgcataaa tcagcgcact gttcagcagg    6300
gtaccggcca cattcattgt cagactgcct gccgtgccgg taaaaccact gatggtgata    6360
tcactccggc tgttcagact cacatcgcca ccggcctgaa gtgaacccgg tgcgttaagg    6420
aaaagacgct gtgcgctgaa aacactgttg cctttaccgg cagtcagcgt tccattgttg    6480
gtgaatgcct ctccggcacc gagcaccatg gcatcaccct gcatgacacc gccgttggtg    6540
atggcatttt gcgacgtgac ggaaagggtt ttccctgcgg ccagggtacc gtaattcgtg    6600
agggcagcaa tcagtttcag tgtgacatca ccggtggcca ccacctgccc ctgaccactg    6660
aagtcctgag cgtcaagcag caggttgcct gcactgtaca gccgccctgt accattttgc    6720
agcagtgaac tgcccttgac gccaagcccg gaggttccca gcagggtacc gctgttgctg    6780
aatgtgtggt aattcaccag caggtccgca ccctgaagcg taccggtatt attcagcgtg    6840
gttcctttaa cgtcggcact gccggtggca agtacgcgtc cgccgttgac agtattcacc    6900
acatccagca gcagggtggc agcctgtacc agtccgctgc cggtgttcgc cagcacctgc    6960
gccgtcagcg tgaggttact gccggagagg attttgccgt cgttctgcag acggtcagtg    7020
gcgttcaggg aaaccccgcc accaccctgt atcgtgccct ggttactcag ggtcgcagta    7080
ctgacattca gtgcattccg gctcatcaga acaccaccgg aacggttgtt cacgccaccg    7140
gaggcggcca gcgtcagcgt ttcgccctgc agatgcccgc cgtttgtgag ttgtcctgcc    7200
gtgatggtgg tggcatttcc ctgtaattgc ccgtcgtttg tgacactgtc tgccttcagc    7260
gtcagcacac ctgcactgag cagttttccg ctcgcgtgat tgtgcagcgt ctgattcacc    7320
gtgagcgtga gagcatccac accggtgatg tcacccgcac tggtcagtga gttcgccttc    7380
agggtcagat tttttgcaat ccattgtccg ctgttgctta aattcagtgc actgagcgcc    7440
atttcaccgt tcgaggtgac tttgctgcct gctgtgctga cgagctcacc cgtcagacgt    7500
gcagtcaggc tgtcagccgc ctggatcgcc ccgctgtttg ccagactgtc tgcggtgatc    7560
```

```
agcacccgtt tgccctgcca gtgtccggaa ctggtaatac tgcctgcggt gattgtcaga    7620
tcgccgctgg tcagcaatga acctccgtta ttcatcagcg caggttgagg ggatgccata    7680
cgggcggcaa gcgtcagcgc ggctatcccg gtgagcgtgc cactgttggt gacactgttc    7740
tggcgaatcg tgacatggtt accctggaca gtgccgctgt tatccagtga gtttccatca    7800
agggagagcg tgccggccga aagcagactg ccccggttgt ccatggtggc tgctttcagc    7860
gtggtgtcac cctggctcat gatatcgccg gtactggtca actgaccggt tgccgaagca    7920
gtaaggttac cggttgccag cacggaacca ctgttcgccc agttgtcccg cytgcacggt    7980
gagattctgt ccctgcgtgg tcctgcgta tgcagtgttt taccccggag ggtgaggtcg    8040
cccgccgtca gccagcgccc gttactaccc tgtgagaggg tgtcgccagc aagcgccagt    8100
gcaccggcgc cctgcaacag gccgtcacca tccagcgtgg tcgccctgac gctcagcgtg    8160
tcagcgatga ttttccccgg attgctgagg gagacagcat ttaacattaa accattatca    8220
ccggtgataa gcccgctgtt gcggatgtcc ggtatatcca gcgtcaggtc tgcagcactg    8280
tacagcgtgc cgttctgctg attatcaagc ctctgtgtgt taacggtaag tgaggcctcc    8340
ccctgcaaca gaccgctgtt ggtcagggtc tgtgactgtg tattcagggc ggaaccaaca    8400
agtacgccgc tgctggtcag ttccggcgca ctgaggctga gcgacggggc actgcttttc    8460
ccgctgtggg tgagcttttc actggcgttc accaccatgg tctgttgtgc tgcctgcgta    8520
cctgcaagac gtgcatctct ggcgttgatg ctgagatttt taccgctctg aagctgtgcg    8580
cccgctgcgg tactcagttt gtctgcctga acccggaggg tgtcaccggc actgttttcc    8640
ccgtccagcg ccactgttgt cacattcagc gtcatcgcag catcgctgtg ggtgaccgat    8700
tttttaccgg agctcagcgc ctgcgcactg accgtcagcc ctttgccgcc ggacagcaca    8760
ccgttctgtg tcacatcctg cgccttcagc accagtacat catcgctcac cagcgaacct    8820
gtactggtca gtttcccact ggccgtgata tccactttgc ccttcgcgcc agtgcggccg    8880
ctctgggtaa agtcgcgggt attcacggtc aggggaccgc cactgagcag ggagccactg    8940
ttgctgagcg ttgtactgcc gagcgtcagg gaagcccccct gaacagcacc actgttattc    9000
agcgtgccgg catcgagtcc cgcatgacct ttcgccagca atattccgtc ctgtgtcagc    9060
gtggtggcgc tggccgtgag attctgcccg gcggttatct gtcccctgtgt tgtcagcgtg    9120
tcactggcga cagtcacgat atcgcgggcc gcgttaatct ggctggcggt atcctgtgtg    9180
atgttttttcg cggcaagcgt tacatcccgg ccggcagtca gttttcatt ctgttgagtg    9240
attctgccgc cggcggtcag gctgaggtcc ttgtcgctgt taagcgttcc attgctgaga    9300
acgataatcg ctccgggct                                                 9319
```

<210> SEQ ID NO 86
<211> LENGTH: 551
<212> TYPE: DNA
<213> ORGANISM: Escherichia coli

<400> SEQUENCE: 86

```
atgaggcgat taaagcaaca ttgggcagtg ataatgcccc cacccagcca cctaacgcag      60
cgaagagtaa tacatcgccc atgcctaatg cttctttacg cagaactatt ccggctatcc     120
agcgsaggga gtaaaaagtg ataaatccca ccagtacgcc ggtaactgcg tcttgtagcg     180
ttaacggact ctgttgcgcc catgctgcaa tcagcccggt ccacaatacg ccctgagtaa     240
aaacatcggg cagccattgg ttgtcgaggt caatgacgct cgcggcaatc agccaggcgg     300
ataatatcat caccgccagc ccccatccac tttctggcca caccagactc gccagcaaaa     360
```

-continued

```
aagtgagtgc tgtcaataac tcaaccagcg gataacgttg ctgattttcg cctgacagtc     420
gcggcagccc tttgagcatc aaccatgaga gcagcggaat attgtcacga acgcggatgg     480
tctgctggca atgcgggaca gttgcgaacc gggttagcca agggctttat tttttggact     540
gcggcactcg g                                                          551
```

<210> SEQ ID NO 87
<211> LENGTH: 595
<212> TYPE: DNA
<213> ORGANISM: Escherichia coli
<220> FEATURE:
<221> NAME/KEY: misc_feature
<222> LOCATION: (342)..(342)
<223> OTHER INFORMATION: n equals a, t, g, or c
<221> NAME/KEY: misc_feature
<222> LOCATION: (590)..(590)
<223> OTHER INFORMATION: n equals a, t, g, or c

<400> SEQUENCE: 87

```
catttaccaa accccgttcg aatatcttat ctattgccca tctcatatta aatataaccg     60 ataaatttggt ggatactaat agtaattacc ttgttattga aaatataatt attgttattt    120
ttagcctcat taattaaatt gaaaaatcct ctctaatttt tgtcagatta gggctgtaga    180
aaggatcgag ttcaagatgt ttaccccatt tgcttttcat aaagtccact tccctggcaa     240
atctggctag tttctccggt gaatcttcgg ctcctcgact aatcgattca tagtggtaaa     300
gctcggcata aggtgtccag agattacgat accccgcttc gngtactttc agacagaagt     360
ccacatcatt aaaagcaaca tgcagattct cttcatccaa cccggcaact tcctcataaa     420
tatctttgcg aataagcagg caagccgccg tgacggccga gagagtttgt gtcaacaaca     480
aacggctgaa atagcccgga tggtggcgag gataatgttt atgggagtgt ccagctacac     540
caccaatacc gagaatcact ccgccatgtt gtaaaagtat cattactgtn atagg          595
```

<210> SEQ ID NO 88
<211> LENGTH: 399
<212> TYPE: DNA
<213> ORGANISM: Escherichia coli
<220> FEATURE:
<221> NAME/KEY: misc_feature
<222> LOCATION: (76)..(76)
<223> OTHER INFORMATION: n equals a, t, g, or c
<221> NAME/KEY: misc_feature
<222> LOCATION: (115)..(115)
<223> OTHER INFORMATION: n equals a, t, g, or c
<221> NAME/KEY: misc_feature
<222> LOCATION: (379)..(379)
<223> OTHER INFORMATION: n equals a, t, g, or c

<400> SEQUENCE: 88

```
tggcagttga acagattttc acatcagcaa cagattagcg aacgggactt ggcattagcc     60
gagcgtttta gtgaangttt agctctaaca cgtctattag aagagcgcac gcagnattat    120
cactgaacta gagattgaaa acaattgct taccaccaag ttgtctggcg tagagcagca     180
gttaagggct gagcaagagt cgcttcagca ggcccagtct gcattgctct cagcagcaaa    240
agaaaagcaa catcaacttg atgagttgga atcggtgctc aatgagcggt acagtgagat    300
tgcaacctta acccgttggc tggaagaacg tgatcaggca ctccttagtg cagcaagtga    360
acaacaacag accaatgana ccatatagag ctcagccag                            399
```

<210> SEQ ID NO 89
<211> LENGTH: 1013

```
<212> TYPE: DNA
<213> ORGANISM: Escherichia coli
<220> FEATURE:
<221> NAME/KEY: misc_feature
<222> LOCATION: (943)..(943)
<223> OTHER INFORMATION: n equals a, t, g, or c
<221> NAME/KEY: misc_feature
<222> LOCATION: (974)..(974)
<223> OTHER INFORMATION: n equals a, t, g, or c
<221> NAME/KEY: misc_feature
<222> LOCATION: (1013)..(1013)
<223> OTHER INFORMATION: n equals a, t, g, or c

<400> SEQUENCE: 89
```

| | | | | | |
|---|---|---|---|---|---|
| atactctgct | tgttgagcag | ccattacgtc | gctttgtgac | gcaatattag | actcgtgcac | 60 |
| tgctattagt | tgagtcagtt | catcacattg | tttagaagcc | gcagccaaag | caagagtttg | 120 |
| ctcatctatg | ctttgctgca | atgtttgttg | cacaagttgc | ccttcttcca | gctgttgctg | 180 |
| tagatttgca | cttacctttt | tcagtgcatc | atattccaag | cctaacgtat | cgtgctgtgc | 240 |
| ttccagtaat | ccataagcat | gctgcaactg | gttttttagtt | tgctgctcac | cgtcaagctg | 300 |
| ttgctgcaat | gcattagcct | gctgttgcaa | caagttcacc | atattgtctc | gctcggccag | 360 |
| tgtacgaacc | tgtgtatcct | ggatatgtag | cgcttgttcc | aactgaagct | gtaattcggt | 420 |
| aatttgccgc | gaatgttcgc | tcaatgctct | gttgctcttg | ctgagcgcga | gagtaaggtg | 480 |
| agatgcacgc | tgtgtttctt | cactcaattg | taacgtcagg | gtattgacct | gttgctccag | 540 |
| ttgatggcga | gcttgctcct | ggctcgtgat | gcgactctgt | tgctgctcta | gttgatgcag | 600 |
| agctgtatgc | aactcatcgt | tggcttgtat | tcgctcctgc | gaccatacac | tcaagtttgt | 660 |
| ttgggcctca | ttgagctgtt | cttgcaataa | tgccacctca | gatgtcagcg | aattgatatg | 720 |
| ttgctgggca | aaagatagct | catcagattg | cacttgagca | tgtgcaagct | gcttttccat | 780 |
| ttctaatatg | ctgttatgtt | gtgcagtaat | gcgctcggca | agacgccccc | tttccaatgc | 840 |
| ctgctgttct | accaatagct | gccgttcagc | ctgaatgtca | tcttgttgtg | tagacaactg | 900 |
| acgttttaac | tgggaattct | cccaactctc | gctacaagat | ttnccccaaac | gacaaaagat | 960 |
| gtcttggact | tgtntgggtt | acacgagcat | tttctgagga | ttttataccca | atn | 1013 |

```
<210> SEQ ID NO 90
<211> LENGTH: 689
<212> TYPE: DNA
<213> ORGANISM: Escherichia coli
<220> FEATURE:
<221> NAME/KEY: misc_feature
<222> LOCATION: (643)..(643)
<223> OTHER INFORMATION: n equals a, t, g, or c
<221> NAME/KEY: misc_feature
<222> LOCATION: (650)..(650)
<223> OTHER INFORMATION: n equals a, t, g, or c
<221> NAME/KEY: misc_feature
<222> LOCATION: (658)..(658)
<223> OTHER INFORMATION: n equals a, t, g, or c

<400> SEQUENCE: 90
```

| | | | | | |
|---|---|---|---|---|---|
| gatatccaca | tcgagacgtt | tgaaaagagt | ctggtgatcc | gttttcgtgt | tgacggcaca | 60 |
| ttacatgaaa | tgctgcgtcc | ggggcgcaaa | ctggcctcgc | tgctggtgtc | gcgtatcaag | 120 |
| gtgatggcgc | ggctggacat | tgccgaaaag | cgcgtgccgc | agsatggacg | tattgcgctg | 180 |
| ttgctgggcg | gccgggcgat | tgacgtgcgt | gtatcaacca | tgccttccgc | ctgggggaa | 240 |
| cgggtggtgc | tgcgactgct | ggacaaaaac | caggctcgcc | tgacgctgga | gcgtctgggt | 300 |
| ttaagtctcg | aactgactgc | gcagttgcgc | cactgttaca | caaaccgcac | ggcatttttc | 360 |

-continued

| | |
|---|---|
| tggtgacggg gccgaccggt tccggcaaaa gcaccacgct gtacgctgga ttgcaggagc | 420 |
| tgaacaacca ctcgcgtaac attctcacgg ttgaagaccc tatcgaatac atgattgaag | 480 |
| ggatcggtca gacgcaggtt aacacccgcg tcggcatgac attcgcccgt ggcctgcgcg | 540 |
| caatttgcg tcaggacccg gatgtggtga tggtcsgtga atccgcgat accgaaaccg | 600 |
| cagaaatcgc tgttcaggct tcaactggac cggacacctg ggnactttcn acgctggnat | 660 |
| accaaaaaaa agggtgggg ggattatac | 689 |

<210> SEQ ID NO 91
<211> LENGTH: 1281
<212> TYPE: DNA
<213> ORGANISM: Escherichia coli
<220> FEATURE:
<221> NAME/KEY: misc_feature
<222> LOCATION: (46)..(46)
<223> OTHER INFORMATION: n equals a, t, g, or c

<400> SEQUENCE: 91

| | |
|---|---|
| ctcagcagaa ccgagatctt ccatcagctg gcgggcctcg aagantccc gctgccagac | 60 |
| cgcattcagc cgctgttcaa attcggcctc gtcgatttgc ctcagcgtaa agggcgcgtt | 120 |
| cagcccccgt tgcagctcct gcaaaacaga gagcgacaac ggatgcacat ggaggatctc | 180 |
| cagcgacgct tcgcaccatg ccaccaggct aaaccgacgg ctgaaactat agggcagacg | 240 |
| cacggtgtta gcggtggttt cctgtgctac aggcaccatt aacgcgttct cccggcatta | 300 |
| aggaacgcac gaacttctgg cggtaaggcc tgattttgcg caggcaatat cgctgcgcag | 360 |
| tgtgcggcat caggcttaag ccctgctcat cgcggtagat ttgctcggcg cgcatgtagt | 420 |
| tatatttgcg ctgcgacaca ccgtctgccg ccataccgtc acgcagaatg gtcgggcgga | 480 |
| taaacaccat caggttacgt ttttcttttt tatccgccgt cgatttaaac aggttaccaa | 540 |
| tcaacgggat atcgcccagc agcggcactt ctcgccacgc tttctcccgc ctggtcgtcc | 600 |
| atcagaccgc caagcacaat tagctcacca tcgttagcca acacggtggt tttcagtttg | 660 |
| cgctcaccaa acaccacgtc gaggctggtc tgtccttcca ccttcgacac ttcctgctca | 720 |
| atcaccatct gtaccgcgtt tccttcgtta atctgcggcg tgactttcag catgatgccg | 780 |
| acttttttcc tctctaccgt gttgaaagga ttgctgttat tggagccaac ggtagatcca | 840 |
| gttaataccg gaacgtcctg gcccaccatg aagaaggctt cctggttgtc cagcgtggtg | 900 |
| atgctcggcg tggagagcac gttcgagctg gagtcgtttt tgaccgcctg taccagcgcc | 960 |
| atccagtcgc ctttcamcac gccaaccgcc gtaccgctaa agccagaaag aagctgagca | 1020 |
| agcgtggaga gatcgccgtt agtatccgga tttatggtgg tagcgccgtt ttcactgatc | 1080 |
| accgtggagc ctttctgcgg ttttgcytga gaaatcgtgc gcccagcgta ccaataggga | 1140 |
| tctgcgtacc gttagcaaac tgcattaatc cggcatcttt cgacgcccac tgcacgccga | 1200 |
| aattgataat tcaccttcgg caacttccac gatcaacgcc tcgacatgta cctgagcacg | 1260 |
| gcgaatatcc agttgttcaa t | 1281 |

<210> SEQ ID NO 92
<211> LENGTH: 421
<212> TYPE: DNA
<213> ORGANISM: Escherichia coli

<400> SEQUENCE: 92

| | |
|---|---|
| caatattagc gcacggcacc aaaggtgatg aatgagcagg ctgraatatt attttcccgc | 60 |
| ggtgcagaaa tccttgttct tggttgtaca gaaattccgg ttattctggc gcaacgttaa | 120 |

-continued

```
agagcagcct tcccgctata ttgactcacg gcgtcactcg ttcgtgccgg aataaaatgg      180
tacgaaaatc gtgtcggtaa acattatctt ttaacccaat aatcatttaa atcgcagcca      240
gaaagttatt cgcttttaac tgaattatat ttataacgga gaacattatg gtttggctgg      300
aaattatcgt agtacttggt gcaatakttt ttggtattcg ccagggggga atcggtattg      360
gtttatgtgg cgggcttggg cttgccattc tgactctggg acttggtctg cctatggggg      420
g                                                                     421
```

<210> SEQ ID NO 93
<211> LENGTH: 1018
<212> TYPE: DNA
<213> ORGANISM: Escherichia coli
<220> FEATURE:
<221> NAME/KEY: misc_feature
<222> LOCATION: (781)..(781)
<223> OTHER INFORMATION: n equals a, t, g, or c
<221> NAME/KEY: misc_feature
<222> LOCATION: (990)..(990)
<223> OTHER INFORMATION: n equals a, t, g, or c
<221> NAME/KEY: misc_feature
<222> LOCATION: (993)..(993)
<223> OTHER INFORMATION: n equals a, t, g, or c

<400> SEQUENCE: 93

```
gttaacaatg gcgtaacaaa tttcaataac gtagaagatt tgctgtcaga aaggtcaata       60
tttcctttca atgggtcaaa gacttgcttc tggaattcat ccggtttttt ctccagacgt      120
tttccttctt cataatagtc aatataactt ttaccactga gtgttttgkc yccatttctg      180
gtgacaccag ctaactcacc tatcagcgta tcccmatgtt gctgggtaat gaggactgat      240 cttttcaacag aatactcttt attatactga gataatattt taaagttatc ttctaaaaat      300
gcagcatggc gggcatcata tcccattttc aaagtaattt tgccgtgtt ttttctccca       360 ttcagcaata acatcggcca ttttactggc gacatgttca acattgcct gttttgaagc       420 ctcaaggatg cctgaaatta tccccgtaac agcccctacc agcgcgctta ccggtgcacc      480
aaccagagat gtcgttgcag cagcactaat acctgaagat actgaagcca gaacagtgct      540
tatcgttgtt aacgatgcat caatagctcc tgtttctttg tggaaagcag caagtaaact      600
gtcaccatcg tatccaagtt ttttgaatcg ttgtgaatac tcctctattt tattggcacg      660
tttaaactta tcggcaatgg acaggaatga gaggggacta attgccagtg tcacaacaga      720
agcaattaaa ccggcagcag cagcagatgt agataacccc tgtgctgcac gctgtgcgay      780
naatatattg agaaatacct tttccaacat tacccagtac tttcgttgtt aattcaacac      840
ctgctgcagc tttagttccg gtatctgcat ctgcattgct cagaatgaaa cttgctgaaa      900
tcgcagataa aatacccgat acagtatcta accctgcacc gatattatca aggttaggta      960
aattctgtaa cttattacca acaccgttcn ggnctgttgg tattgggata atacactt      1018
```

<210> SEQ ID NO 94
<211> LENGTH: 400
<212> TYPE: DNA
<213> ORGANISM: Escherichia coli

<400> SEQUENCE: 94

```
ggcaatgttc aaatcgatat tgtgcagcac ctgggttggg ccaaagtgct tggagacgtt       60
tttaaattca atcacaggat tttcatcctt ctttccagac gacgcagaat aaagctcagc      120
accagggtaa taatcagata gaacaccgcc acggcgctcc agatctcaag ggcgcggaag      180
```

```
ttaccggcaa taatttcttg cccctgacgg gtcagttccg ccacgccgat cacaataaac      240
agcgaggtgt ctttaatgct gatgatccac tggttacccg gcggcggcag catacgacgc      300
gtgccagcgg taaaatgacg tagcgaatgg tttcccmacg tgaaagaccg agcgccagtc      360
ctgcttcacg aaaacctttg tggatagaca gcaccgcacc                            400
```

<210> SEQ ID NO 95
<211> LENGTH: 1857
<212> TYPE: DNA
<213> ORGANISM: Escherichia coli
<220> FEATURE:
<221> NAME/KEY: misc_feature
<222> LOCATION: (16)..(16)
<223> OTHER INFORMATION: n equals a, t, g, or c
<221> NAME/KEY: misc_feature
<222> LOCATION: (1465)..(1465)
<223> OTHER INFORMATION: n equals a, t, g, or c

<400> SEQUENCE: 95

```
cgtgttcccc tggccngctt ggtttcgcca tagacgttga gcggggaaat cacatcggtt       60
tccacccaag gacgttcacc acttccatcg aaaacatagt cggtggaata atgtactagc      120
cacgcaccta atgcttcagc ttctttggca ataaccgcca cactagttgc attgagtaac      180
tcggcaaatt cccgctcact ctccgctttg tcgactgcag tatgggccgc tgcgttaaca      240
atcacatccg gcttgacgag acgtaccgtt tcagccaccc ctgcagaatt gctaaaatca      300
ccgcaatagt cggtggagtc aaaatcaacg gcagtgatgt gccccagagg cgccaatgca      360
cgctgcagct cccatcctac ctgaccattt ttgccaaaca acagaatatg catcaggtac      420
gctccctata gttttgttca atccaggatt ggtaggcacc actcttgacg ttgttaatcc      480
attgttgatt atccagatac cactgcacgg tcttgcgaat accagactca aaagtctcct      540
ctggctgcca atccaacgca gcgctcatct tgcaagcatc aatcgcatat cggcgatcgt      600
gtccggggcg atccgccaca taagtaattt gatcgcgata agagccagct ttcggtacca      660
tctcgtcaag cagatcacaa atagtatgta ctacatccag gttctgcttc tcgttgtgac      720
cgcctatgtt ataagtctcc ccgaccaagc cagtggtcac taccttgtag agtgctcgtg      780
catgatcttc cacatacaac cagtcacgaa tttggtcacc tttaccataa accggcagcg      840
gcttgccatc cagcgcattg aggatacact gcgggatcag cttctcggga aagtggtaag      900
ggccatagtt gttggagcag ttagtgacaa tggttggcag gccgtacgta cggtaccaag      960
cacgcaccag atgatcgctg gaagccttgg aggcagaata gggactgcta ggagcgtagg     1020
aggtagtttc ggtaaagagc ggcaatgcct caccggaggc tacttcatcc ggatggggca     1080
gatcgccata tacttcatcg gtagaaatat ggtggaagcg aaaggccgcc ttgctcaact     1140
cgcccagact gctccaatag gcgcgagccg cttccagcaa tgtataggtg cctacgatat     1200
tggtttcgat aaagtcggct ggccctgtga tagaacgatc aacatggctt tcagcagcca     1260
gatgcatcac ggcatctggc tggtgcagag caaacacccg atccaactca gcacgattac     1320
agatatcaac ttgttcaaac gaataacgct cacttgacga tacactggcc aaagattcca     1380
aattgccagc ataggtgagt ttatccagat tgataacgga gtctccagta tcactaatga     1440
tatgacgcac cacggcagag ccganaaaac cagcaccgcc agtaacgaga atcttcatat     1500
atttcgctct cttattttac aattaatagc tattaaaaat aaacttgttg actccgatat     1560
attagaaata tcgggatacc gaactaaata ttttttatatg cttttgccaa gcagactcta     1620 tatccacccct gtatcactat gctttctggc atacaatatc ccatcattga cacaatgata     1680
```

| | |
|---|---|
| aacatataaa taaagaaaat tttaaatcat ataaccaaat tactttcatt tattatcaat | 1740 |
| aagtattttg ataagaatac ctataccaca gggagccccc tgaaacataa tattagcgaa | 1800 |
| gaatgataac tgatagttac catcttagag ataaaaactt atttgtgtgg cgggatg | 1857 |

<210> SEQ ID NO 96
<211> LENGTH: 1128
<212> TYPE: DNA
<213> ORGANISM: Escherichia coli

<400> SEQUENCE: 96

| | |
|---|---|
| agctctttcg tgtaaaataa aatacagcat atcctatata gcttacaatc attaaatgaa | 60 |
| gtcgccaata tttatatgtt ttatcaatat cagcttgact cattgttatt tctttgtcag | 120 |
| gagactctga aaatatggac atatataacc tcttttatta tgaaatattt tcaataataa | 180 |
| taatccgtta gtaatcctat cataggggtaa tgtctcatca tgttaaaatg atcacattta | 240 |
| taatcatgtc aaaagaaca acagaaaaaa tcatataaaa tcaattaaat ataattgcca | 300 |
| catattgttg ttattwaaac attggtggtg aatttaaagc gagaacagtt tgtaacagtg | 360 |
| actccttgca gactaagtta gagtctcctt ctaaaattag acggwkttct attgatggat | 420 |
| aatagtaagc gcaccgtgaa kgacgtgggg taaaaattag tttacagatt gagtgacatt | 480 |
| ccagggcaac aactctttca cgcggttggc aggccaggtg ttgattacac tgatcacgtg | 540 |
| gcgtacatta ccggactcga ttccgttaag tttgcagcta ccgatcaggc tgtacatcac | 600 |
| tgccgcactc tcgcctccac catcagagcc gaagaacatg tagttacgcc gccccagtgc | 660 |
| aatacccgga ggcgttttca cacaggttat tgtcgatctc cacccagcca ttgcggcagt | 720 |
| attcgttcag agcgtcccat tgcttcagca gataggtgaa cgctttcgct gtatccgagt | 780 |
| ggcgcgacag tgctcatctg cccctggagc cactcataca acgactgcat tagcggtacc | 840 |
| gttctggctt ttctgaccgc cagtcgctct tctgccggac tgccgcggat ctcagcctcg | 900 |
| atagcgtaca gttcaccgat acgctgcagg gcttccgtgg tgatgtcagg tggcgctctt | 960 |
| gcatgcacat cgtggatttt tctccgggca tgggccatac aagccgcttc ggttacctga | 1020 |
| ccgctttcgt aaagagcatt gtaacccgca tatgcatcgg cctgcaggat acctctgtag | 1080 |
| tccgccagat gttgctgtgg gtggatgcct ttgcggtcgg gagagtat | 1128 |

<210> SEQ ID NO 97
<211> LENGTH: 439
<212> TYPE: DNA
<213> ORGANISM: Escherichia coli
<220> FEATURE:
<221> NAME/KEY: misc_feature
<222> LOCATION: (401)..(401)
<223> OTHER INFORMATION: n equals a, t, g, or c

<400> SEQUENCE: 97

| | |
|---|---|
| gtttgcttac gaaccgtgaa atatgacggt cccatataac tgcctgatac ttgtatatca | 60 |
| tatacttgtg catgcatgtc atcattaaaa agtactttgt caccgtcttt aagttgaaga | 120 |
| cgtgtaaaat ctttatacgg caagtagacg gaaaacgggc gctttccctg tcgccaatca | 180 |
| caccgacatg actgactttt gcgagaggaa gtgcataatt caccaattca gagcctaatg | 240 |
| cattgcgctg ggtaagctca aatcggaatg ggtttcgaac ctttcccgca acattgatca | 300 |
| ttggaccttg ttgctcaact gaaaatcaca tcttgatctt ttaatgccag cttcgggagt | 360 |
| ttccccatacc gtatgaaatc ataaagatca atttgckgtg nttactgcta ttttgtgcgt | 420 |
| gaacacctta atttttgcg | 439 |

-continued

<210> SEQ ID NO 98
<211> LENGTH: 906
<212> TYPE: DNA
<213> ORGANISM: Escherichia coli

<400> SEQUENCE: 98

| | | | | | |
|---|---|---|---|---|---|
| tattcgtaat | tagttataaa | cagatgatgt | aaacaccagt | tgactagagt | caatcttata | 60 |
| ctggcaacat | ctatgattaa | tttgtgtggt | tataattta | aatatcttat | atttatgggc | 120 |
| tattattgat | atctgtcaga | gtatcaataa | tagaaggtaa | ttgttttaca | tactatcaac | 180 |
| ttttggataa | cgttttaaaa | tgcaccttgc | acatcgtatt | ttattatttt | cactaatctt | 240 |
| ttttataacg | gcctgcgcac | atgatccaaa | acaagttgaa | gcctctcgtc | cattggtaac | 300 |
| agcgattaat | tcttcttatt | ctcttattcc | tgaagatttg | caggcaccat | aaataacca | 360 |
| agatcaaggc | acgacattca | acaaaaatgg | cgtaatttat | actattgagg | aaaggtatat | 420 |
| atcggcttta | ggttctcaat | gcataaagtt | aagttatgcg | atgaataaaa | attattcaaa | 480 |
| gcgaagtgtt | gtatgtaaag | agaataacaa | gtggtatcaa | gtacctcagt | tggaacaaac | 540 |
| atcagttagc | actttgctta | tgaagaata | aagttgaagg | tagacggtta | gaaaataatg | 600 |
| aaaatttcgc | aacttagcac | tcttctcttt | cttatttctg | catcagcatt | cgccgcaata | 660 |
| gagcaaaatc | aatctaatgg | ttcacattta | gattatgatc | ttgctgcctc | gacaggagag | 720 |
| tctcggaaaa | tgctagcaga | catcactgga | cagcctaata | caacctccac | aacaggaagc | 780 |
| ttcacacaac | agaatcgtaa | tgggatgttg | cttccaggag | agtcagatgt | acgaaaatta | 840 |
| ctgccgcaat | ctgaagcagg | cttacctcct | ccgtatggtg | ctaatttatt | tgccggaggc | 900 |
| tatgaa | | | | | | 906 |

<210> SEQ ID NO 99
<211> LENGTH: 1395
<212> TYPE: DNA
<213> ORGANISM: Escherichia coli
<220> FEATURE:
<221> NAME/KEY: misc_feature
<222> LOCATION: (1121)..(1121)
<223> OTHER INFORMATION: n equals a, t, g, or c
<221> NAME/KEY: misc_feature
<222> LOCATION: (1264)..(1264)
<223> OTHER INFORMATION: n equals a, t, g, or c

<400> SEQUENCE: 99

| | | | | | |
|---|---|---|---|---|---|
| gcggcctgat | atatgccgtt | attacaaaaa | gaggatcaac | cacactgcct | tttggaccgt | 60 |
| gtttaagtct | gggcggtata | gcaacacttt | atctacaggc | attgttttaa | tgataaccac | 120 |
| gtcattatca | aagtgacatt | ttaactctta | ttaataacct | tagagattat | ttaccatgtc | 180 |
| gataaaacaa | atgccaggga | gggtattaat | atcgctattg | ttgagcgtta | caggattatt | 240 |
| aagtggctgt | gccagccata | atgaaaatgc | cagtttactg | gcgaaaaaac | aggcgcaaaa | 300 |
| tatcagccaa | aacctgccga | ttaaatctgc | gggatatacc | ttagtgctgg | cgcaaagtag | 360 |
| tggcacgacg | gtaaaaatga | ccattatcag | cgaatcgggt | actcgagacc | cgcagacacc | 420 |
| tgacgccttt | ttaaccagct | atcaacgaca | aatgtgcgct | gacccaacgg | tgaaattaat | 480 |
| gatcaccgag | ggaattaatt | acagcataac | gattaatgat | acacgtacag | gtaaccagta | 540 |
| tcagcggaaa | ctggatcgta | ccacctgtgg | aatagtcaaa | gcataacgtc | gggtagatat | 600 |
| aaattggcgc | gggttgtttt | tcgtgacgca | cgaatttatc | tcattcaatg | gctgacaaaa | 660 |
| attcgtcaca | ctcttaacca | gagacaatct | cttaatacag | acaaagagca | tctgcgcaaa | 720 |

```
attgcacgcg ggatgttctg gctgatgctg cttattattt ctgcaaaagt ggcgcattca    780
ctctggcgct atttctcctt ttctgcggaa tatacggcgg tttccccatc ggcgaataaa    840
ccgctccgtg cgratgcaaa agcgttcgat aaaaatgacg tgcaattaat cagccagcaa    900
aactggtttg gcaaatatca gcccgtcgcc acgccggtaa acaacccga acctgcacct    960 gtggccgaaa cgcgtcttrr tgtggtgttg cgtgggatcg cctttggtgc cagacccggc   1020
gcggttattg aagaaggtgg taaacagcag gtctatttgc agggtgaacg cttggctcgc   1080
acaacgcagt gattgaggaa atcaaccgcg accatgtgat ntgcgctatc agggaaaaat   1140
agagcgcctg agcctggctg aagaggagcg ttccaccgtt gccgcgacca caaaaaagc    1200 tgtcagtgac gaagcaaagc aagctgttgc tgaacctgct gtcagtgcgc cagttgagat   1260
cccngctgcc gtgcgtcagg cactggcgaa agatccgcag aaaattttta actatatcca   1320
gcttacgcct gtgcgtaagg aagggattgt cggttatgca gtgaaaccgg gggcagatcg   1380
ttctctgttc gatgc                                                   1395

<210> SEQ ID NO 100
<211> LENGTH: 380
<212> TYPE: DNA
<213> ORGANISM: Escherichia coli

<400> SEQUENCE: 100
cacttgaata aaactgacac cgtttacctc cataatagtg agcatagccg ccattgcggc     60
ctgatcggcg aaccggaaat cgcaacctgc gaacgacaac cgaaccggca agcgtgcggg    120
aaggacggat accggactct ttcgccactt cagcaatcac cggcagcgtg gaaaaaacaa    180
taaacccagt accggccata atggtcatag accaggtgat aatcggcgcg attatgttga    240
tatatttcgg gttacgccgc ataaaattac cagcgacggt accagataat ccattcccct    300
gcggcctgta aggctgaggc cgccacaaca acggtcataa taatcaggat cacgtcgact    360
ggcggcgacc ccataggcag                                                380

<210> SEQ ID NO 101
<211> LENGTH: 995
<212> TYPE: DNA
<213> ORGANISM: Escherichia coli
<220> FEATURE:
<221> NAME/KEY: misc_feature
<222> LOCATION: (22)..(22)
<223> OTHER INFORMATION: n equals a, t, g, or c
<221> NAME/KEY: misc_feature
<222> LOCATION: (35)..(35)
<223> OTHER INFORMATION: n equals a, t, g, or c

<400> SEQUENCE: 101
ctttacggtt taataggga angccgactg gatgnaaaaa tggaatctgg agcccagaat      60
aaatctgaat ttaatgtgga ctggatatgc tccataacc ccggcaggga gtcatctgtg     120
cgaagatatt tgcgttatgc tgtaatataa taattcaatg tatttcagga acagtaatat    180
actacagttt ctactttctt gtatttaata aattgttccg catcgctaaa gcaggtctt    240 tcagaagcca caagaattct gtggtcccag tattttagt tatcctattt ttatatctaa    300
cttgtaatac ttcagcatt ttcattcatc ctaatgaag gctgtaataa tctttgagct     360
tagaaacatc aaaattatgc atctcattaa ttttgtcagt cacacgacct ctggtaaaaa    420 taaaccccc agaaatatgc catttctagg ggggcgtaa gaatcaatat attttagtgt     480
tgttacattt agctcttagc tcttagctct tagctcttag ctcttagctc ttagcgtttg    540
```

-continued

```
tagtttcatc gcaatgagta aaaggacaac aagaataagt gataacgtta agagaagagc    600
atagaaacca ttccagtggt atatttctat tattttagac aatggatagc cagccgcgga    660
cgcaccaaga tatgcgaata aactaacaaa accagtagaa gcaccagatg catatttatg    720
tgagttttca gcagctgcca ttgcgatcag aaattgtggc ccaaagataa agaagccagt    780
gatgaaaaat aataacgaaa aaacatattt actatcaata gaaaccaacc atagacatgc    840
agaagcaatg attataccaa ttgtataaat aacattcatt tgagagcgat tgcccttaaa    900
cagaatatct gatccccatc cagctacgat agcaccaaaa aagcctccaa cctcaaacat    960
cattactgtt gcatttgctg ttagcaagtc atatt                               995
```

<210> SEQ ID NO 102
<211> LENGTH: 817
<212> TYPE: DNA
<213> ORGANISM: Escherichia coli

<400> SEQUENCE: 102

```
taaaagcgac tccatgtgaa atttctgttt gtcgttttt ccccgttgta gcggctctgc      60
tcctggcttc cctgatagtc agcccgcagg cgccagggcc ccagattccc ccccacagtc    120
ccgttataac tgaactgatg agagtctcct ccctgataat tacgggaaac cgtcccgttg    180
aggttataat ccagcatcag tccgggaatg ccgtcgtccc agcgtgaggg aggcagccag    240
gtggcatcag aatactcaag ccaggcctgc ggcatattga tgcgtaatac gcccgctccg    300
gtatcaggac gaatatccac tcccggcaac ccatgaaaat ccgcacactg accatcatgc    360
cagtaaacaa ctttatccag agattctgct gttaaccccca tcagtctgac catatctgat    420
gtcagacagc tgcggcaatt ttttttctgc cttatctcct gacaacgcag gttcaacaaa    480
tgamatctgt aacgatgcgg gagaaatact ttgcccgtta acaatcacat ccagaagata    540
ttgccccggc agaacatagc cggcttctga aaaacgggtg aagtcaatat ttttcttgtc    600
cgctgcgtca agtacatctg tattaaactc aacggcactg gctgcgttac aaaacagaga    660
caacaatatc acacaggtaa tattgttgac tgcaaaggt attctgtctt tcattccacg     720
catcaccaga ttcacaaaaa agataaataa ccggacatct caccggagtg actcactcat    780
aatcgacccg gaatcccagc acagcaaaat aatttcc                             817
```

<210> SEQ ID NO 103
<211> LENGTH: 709
<212> TYPE: DNA
<213> ORGANISM: Escherichia coli

<400> SEQUENCE: 103

```
tttttgtcag agcgttcact ctctggctgg atgatttcgg ctcgggaaat gcaggcttaa     60
tgtggggact gtcggggatg tttgaacggg taaaaataag tcatgagttt tttcattatg    120
tcctgaaaaa cgggtgtgca atgccacttc tccgtgctgt ggcagacact gttgcctgtc    180
acaacagagg cgtgatactc gaaggtgttg aaaatgaagc gttgttccgt attgccagag    240
acatgaatgt ccagggctgt cagggatggc tctacaggcg tgtgggggtt gatgaattat    300
ccgcgcttat tcagcagtat gaataatcct ttttcacaga ctggtcagct gtcaacattt    360 atgtttttt atctgcggga atttatccgt ctgcctgtcg ggactactct gtcatacaga    420
aatcaggcca gaataaattg ttgtggaaag gtgagattta ccggatgact gatgtgctct    480
tgtgcacagg tatacaggca gtgtgtttcc agtatatgga aaatgattaa atgaataaca    540
```

| | |
|---|---|
| cagacttatt agaaaaaatc atcaggcatc aacaaaacaa agatcctgca tatcctttcc | 600 |
| gggaacatct tttgatgcaa ctctgtatcc gtgtaaacaa aaaaatacag aacagtacat | 660 |
| ctgagttttt tggtgcatat ggtataaatc actcagtata tatggttct | 709 |

<210> SEQ ID NO 104
<211> LENGTH: 485
<212> TYPE: DNA
<213> ORGANISM: Escherichia coli
<220> FEATURE:
<221> NAME/KEY: misc_feature
<222> LOCATION: (477)..(477)
<223> OTHER INFORMATION: n equals a, t, g, or c

<400> SEQUENCE: 104

| | |
|---|---|
| tcatcaaggg acgggcata tctggatgcg acagggcaaa ccaaccactg agaatccaac | 60 |
| ctgccaaagc ctgaccagga agtccgacgt taaagaaacc agctcgactg caacggcaa | 120 |
| aaccaagacc aatcaagacc agaggaccca tagcacggaa gatttctcca atcccacgca | 180 |
| gactgccaaa ggctgtatag aacaattctt cgtagcccca aatagcatca taaccgaaga | 240 |
| tccacatgac aatggctccg agtaaaaattc ctaggaatac agaaatcaag ggaaccgaaa | 300 |
| tttgttgtaa ttttttagac atcactcttc tcctttccca agttyccacc agccatcaag | 360 |
| acaccaagtt cttgtttatt ggttgtttct ggtgatacaa taccttgaat cttaccatcg | 420 |
| tggataacgg caatacggtc tgagacgttt aaaatctcat ccaattcaaa gctgacnaca | 480 |
| aggac | 485 |

<210> SEQ ID NO 105
<211> LENGTH: 459
<212> TYPE: DNA
<213> ORGANISM: Escherichia coli
<220> FEATURE:
<221> NAME/KEY: misc_feature
<222> LOCATION: (436)..(436)
<223> OTHER INFORMATION: n equals a, t, g, or c
<221> NAME/KEY: misc_feature
<222> LOCATION: (449)..(449)
<223> OTHER INFORMATION: n equals a, t, g, or c

<400> SEQUENCE: 105

| | |
|---|---|
| agcagaatag gcaacatcac cacgccgaca aacagcgaga agagaatgac gccagccgcc | 60 |
| aggaacacca gctcatagcg cgccgggaag acgttaccat ccggcaagag cagcgggata | 120 |
| gagagcacac cggccagagt gatcgcccca cgcaccccgg cgaaagacgc gatcaggatt | 180 |
| tctcgtgtgg tccacgaacc aaactccatc ggcttcttct tcaggaagcg gttgctgaac | 240 |
| tttttcatcg tccacagcca gccgaaacgg accagcatca gcgccgcata tatcagaata | 300 |
| atattggtaa acagcatcca gatttcgacg ttagggtcga tttcttgctg gccatcagcg | 360 |
| gacgtcttcc agrattaccc ggcagctgca gaccttaaca gcagggaaca ccatggccgt | 420 |
| tttaaggaca atttcnagca tcggcccang tgctgtttt | 459 |

<210> SEQ ID NO 106
<211> LENGTH: 908
<212> TYPE: DNA
<213> ORGANISM: Escherichia coli

<400> SEQUENCE: 106

| | |
|---|---|
| ttaatagcac taatactgtc ctgctctatt ccgctgacat tttcagtcag ctgctgtatg | 60 |
| ggatgggtta cccaaaacca gaccagcata cctgacaaga gaccgcatat cactaccaga | 120 |

```
aacagcgacc agtacagtgc attccatagt gcctttgtcc aggctgtatc agtaagagca      180
ttaagttcct ctccctgtaa aataatatac agatatcctt tcggttcatc actctggtaa      240
agcggtgcgg tactgaaaac ttttttgctta tttacacttc ggggatcatc accatatacg     300
ggccagacac tgccggagag aaatttttttc aacggtgcaa tattgatata ccggcgtttg    360
agatgacccg gagggcggcc tccacaagca gtcgcccttc cggtgaaacc atatacagct     420
ccacactggg attaagcgtc atcagacgct caaacagact cgttaatgtc cggtgttacc     480
agacaaaaca agcatcgcaa gacgccacaa acggtgcgct tacttaaata agccggttac     540
aggtgaaaaa tcacgtcctg atattcaaat gttttttcag gtcatatttt agcaggacac    600
taccagcacc taacagcagc acatcttttta taacaaaact gtcaactttc cccagttgtg   660
gtaacaggct gagcgtggtt attcctgtaa caataacgat aatatctccc agtacaccag    720
cagcaggcct gaagaaaccg ataatcaatg ccagaaatgt gatagtttcc actatgccga    780
ggaaatagct ccctccatga ataccaaata taatatacag gatattcagc caggtgggat     840
atatcagggg cttgagagcc ataacttcaa aatcaaacca tttataagtc ccaaaaagca    900
taaatatt                                                              908

<210> SEQ ID NO 107
<211> LENGTH: 1057
<212> TYPE: DNA
<213> ORGANISM: Escherichia coli
<220> FEATURE:
<221> NAME/KEY: misc_feature
<222> LOCATION: (88)..(88)
<223> OTHER INFORMATION: n equals a, t, g, or c
<221> NAME/KEY: misc_feature
<222> LOCATION: (1019)..(1019)
<223> OTHER INFORMATION: n equals a, t, g, or c

<400> SEQUENCE: 107
cgggctaacc caatatgctt tattaacccg ggataattac cctgttgcat attgtagttg       60
ggctaattta agtttagaaa atgaaatnaa atatcttaat gatgttactt cattagtcgc     120
agaagactgg acttctggtg atcgtaaatg gttcattgac tggattgctc ctttcgggga    180
taacggtgcc ctgtacaaat atatgcgaaa aaaattccct gatgaactat tcagagccat    240
cagggtggat cccaaaactc atgttggtaa agtatcagaa tttcacggag gtaaaattga    300
taaacagtta gcgaataaaa ttttttaaaca atatcaccac gagttaataa ctgaagtaaa   360
aaacaagtca gatttcaatt tttcattaac aggttaagag gtaattaaat gccaacaata    420
accgctgcac aaattaaaag cacactgcag tctgcaaagc aatccgctgc aaataaattg    480
cactcagcag gacaaagcac gaaagatgca ttaaaaaaag cagcagagca aacccgcaat   540
gcggaaaaca gactcatttt acttatccct aaagattata aagggcaggg ttcaagcctt   600
aatgaccttg tcaggacggc agatgaactg ggaattgaag tccagtatga tgaaaagaat   660
ggcacggcaa ttactaaaca ggtattcggc acagcagaga aactcattgg cctcaccgaa   720
cggggagtga ctatctttgc accacaatta gacaaattac tgcaaaagta tcaaaaagcg   780
ggtaataaat taggcggcag tgctgaaaat ataggtgata acttaggaaa ggcaggcagt    840
gtactgtcaa cgtttcaaaa ttttctgggt actgcacttt cctcaatgaa aatagacgaa    900
ctgataaaga aacaaaaatc tggtggcaat gtcagttctt ctgaactggg caaaagcgag    960
tattgagcta atcaaccaac tcgtgggaca cagctggcca gcctttaata ataatgttna   1020
actcattttc tcaacaactc aataagctgg ggaagtg                              1057
```

<210> SEQ ID NO 108
<211> LENGTH: 752
<212> TYPE: DNA
<213> ORGANISM: Escherichia coli
<220> FEATURE:
<221> NAME/KEY: misc_feature
<222> LOCATION: (714)..(714)
<223> OTHER INFORMATION: n equals a, t, g, or c
<221> NAME/KEY: misc_feature
<222> LOCATION: (719)..(719)
<223> OTHER INFORMATION: n equals a, t, g, or c

<400> SEQUENCE: 108

```
taccgggccc cccctcgagg tcgacggtat cgataagctt gatatcgaat tcctgcagcc    60
cgggggatcc actagttcta gagcggccgc caccgcggtg gagctccagc ttttgttccc   120
tttagtgagg gttaatttcg agcttggcgt aatcatggtc atagctgttt cctgtgtgaa   180
attgttatcc gctcacaatt ccacacaaca tacgagccgg aagcataaag tgtaaagcct   240
ggggtgccta atgagtgagc taactcacat taattgcgtt gcgctcactg cccgctttcc   300
agtcgggaaa cctgtcgtgc cagctgcatt aatgaatcgg ccaacgcgcg gggagaggcg   360
gtttgcgtat tgggcgctct tccgcttcct cgctcactga ctcgctgcgc tcggtcgttc   420
ggctgcggcg agcggtatca gctcactcaa aggcggtaat acggttatcc acagaatcag   480
gggataacgc aggaaagaac atgtgagcaa aaggccagca aaaggccagg aaccgtaaaa   540
aggccgcgtt gctggcgttt ttccataggc tccgcccccct gacgagcatc acaaaaatcg   600
acgctcaagt cagaggtggc gaaacccgac aggactataa agataccagg cgtttccccc   660
tggaagctcc ctcgtgcgct ctcctgtttc cgaccctgcc gctttaccgg atanctgtnc   720
ggctttctcc cttcgggaag cgtggcgctt tc                                 752
```

<210> SEQ ID NO 109
<211> LENGTH: 486
<212> TYPE: DNA
<213> ORGANISM: Escherichia coli
<220> FEATURE:
<221> NAME/KEY: misc_feature
<222> LOCATION: (11)..(11)
<223> OTHER INFORMATION: n equals a, t, g, or c
<221> NAME/KEY: misc_feature
<222> LOCATION: (477)..(477)
<223> OTHER INFORMATION: n equals a, t, g, or c

<400> SEQUENCE: 109

```
cttgggtaat ngacctcata tccctccgcc aaaaaaggat ctacatgcga ttttgcgaag    60
ccagcgttga ttgtaggcga gagaatggtt ctgttgtttt ggtacatttc agttgtcatg   120
gatttcacaa atgtagcatg acctttcacc tgtccaagag actgcaacac catctgtcca   180
aaacaataaa taggaatcaa acaggctacc aacatcaaca gtatcccaa taaggctcgt    240
agtttagtcc ttgacatgac gccccctccaa ttgcttttct agtcctttga caatccgtcg   300
attacgatac acgcgataca gcaagagaag gatgaccgcc atcgctccta gtaataacca   360
caaccagaat tgcccacgct ctctcaccgc tcgattccgc tctgcaattg gtgccgtata   420
cggaatccgc ttcccacgta ccaacagacg atgactgtta atcctatacg gtgtacnagt   480
caacca                                                              486
```

<210> SEQ ID NO 110
<211> LENGTH: 313
<212> TYPE: DNA
<213> ORGANISM: Escherichia coli

```
<220> FEATURE:
<221> NAME/KEY: misc_feature
<222> LOCATION: (7)..(7)
<223> OTHER INFORMATION: n equals a, t, g, or c

<400> SEQUENCE: 110
ttacgcnttc aaccaggtct tctggtttac caacgcccat caggtaacgc ggtttgtctg      60
ccggaatttg cgggcataca tgctccagaa tgcggtgcat atctgctttc ggctcaccca     120
cagccagacc gccgacagcg taccatcaaa accgatatct accagacctt aacagaaat     180 atcacgtaaa tcttcgtaaa cgctgccctg gatgatacca aacagcgcat ttttgtttcc    240
gagactgtca aaacgctcac ggctacgtcg cccaacgcag agacatctcc atggagcgtt    300
ttgcgtaatc cca                                                        313

<210> SEQ ID NO 111
<211> LENGTH: 1613
<212> TYPE: DNA
<213> ORGANISM: Escherichia coli
<220> FEATURE:
<221> NAME/KEY: misc_feature
<222> LOCATION: (27)..(27)
<223> OTHER INFORMATION: n equals a, t, g, or c
<221> NAME/KEY: misc_feature
<222> LOCATION: (40)..(40)
<223> OTHER INFORMATION: n equals a, t, g, or c
<221> NAME/KEY: misc_feature
<222> LOCATION: (168)..(168)
<223> OTHER INFORMATION: n equals a, t, g, or c

<400> SEQUENCE: 111
cggaaatccc agtaattcca tcctcanata ttccactcan cctcactgta acaaagtttc      60
ttcgaataat aaaaatcatg ctttctgtta tcaacggaaa ggtattttta ttctctgtgt    120
ttgctttatt tgtgaaattt agtgaatttg cttttttgttg gctttatntg atgtgtgtca    180
cattttgtgt gttattttc tgtgaaaaga agtccgtaa aaatgcattt agacgatctt      240
ttatgctgta aattcaattc accatgatgt ttttatctga gtgcattctt tttgttggtg    300
ttttattcta gtttgatttt gttttgtggg ttaaaagatc gtttaaatca atatttacaa    360
cataaaammc taaatttaac ttattgcgtg aagagtattt ccgggccgga agcatatatc    420
caggggcccg acagaagggg gaaacatggc gcatcatgaa gtcatcagtc ggtcaggaaa    480 tgcgttttg ctgaatatac gcgagagcgt actgttgccc ggctctatgt ctgaaatgca    540
ttttttttta ctgataggta tttcttctat tcacagtgac agggtcattc tggctatgaa    600
ggactatctg gtaggtgggc atcccgtaag gaggtctgcg agaaatacca gatgaataat    660
gggtatttca gtacaacact ggggagactt atacggctga atgctcttgc agcaaggctt    720
gcaccttatt atacagatga gtcgtcggca tttgactaaa ttatggcatt ccggagtttc    780
tggaagataa aaaagaagc ccttatcaga aagcagacag gttatatcag tattctgtcg    840
ataaataacc tgccctgaaa atacgagaat attatttgta ttgatctggt tattaaaggt    900
aatcgggtca ttttaaattg ccagatatct ctggtgtgtt cagtaatgaa aaagaggttg    960
ttatttatga ttaagtcggt tattgccggt gcggtrctat ggcagtggtg tcttttggtg   1020
taaatgctgc tccaactatt ccacaggggc agggtaaagt aacttttaac ggaactgttg   1080
ttgatgctcc atgcagcatt tctcagaaat cagctgatca gtctattgat tttggacagc   1140
tttcaaaaag cttccttgag gcaggaggtg tatccaaacc aatggactta gatattgaat   1200
tggttaattg tgatattact gcctttaaag gtggtaatgg cgccaaaaaa gggactgtta   1260
```

```
agctggcttt tactggcccg atagttaatg gacattctga tgagctagat acaaatggtg      1320
gtacgggcac agctatcgta gttcaggggg caggtaaaaa cgttgtcttc gatggctccg      1380
aagtgatgct aatacgctga aagatggtga aaacgtgctg cattatactg ctgttgttaa      1440
gaagtcgtca gccgttggtg ccgctgttac tgaaggtgcc ttctcagcag ttgcgaattt      1500
caacctgact tatcagtaat actgataatc cggtcggtaa acagcggaaa tattccgctg      1560
tttatttctc agggtattta tcatgagact gcgattctct gttccacttt tct            1613
```

<210> SEQ ID NO 112
<211> LENGTH: 930
<212> TYPE: DNA
<213> ORGANISM: Escherichia coli
<220> FEATURE:
<221> NAME/KEY: misc_feature
<222> LOCATION: (1)..(1)
<223> OTHER INFORMATION: n equals a, t, g, or c
<221> NAME/KEY: misc_feature
<222> LOCATION: (26)..(26)
<223> OTHER INFORMATION: n equals a, t, g, or c
<221> NAME/KEY: misc_feature
<222> LOCATION: (126)..(126)
<223> OTHER INFORMATION: n equals a, t, g, or c
<221> NAME/KEY: misc_feature
<222> LOCATION: (540)..(540)
<223> OTHER INFORMATION: n equals a, t, g, or c

<400> SEQUENCE: 112

```
ntagtccatg gccccatgga gcgaantcca aagtgtggat attgtcgttt taattcatcc       60
caaaagctga aatacgccaa acccacgtt ccctaacatt ggtatcatgc ataatgacca      120
cagccnttca gaaagctttg gcaaccagct ttcaaaatca tgggtaccgc ttcaaacgta      180
tgcaaaccat caatatgaag cagatcaatg ctaccttgtg aaaaatgctc taacgcttgg      240
tcaaatgtac tgcgaatgag agtagaaaaa cctgaatagt gctgttgatt atattctgat      300
acttgcctgt aaacttcttc gccatacagc cccgcatgtt catctccccc ccaggtatca      360
acggcaaagc agcatgtttc taaatctagt ttagagactg cttggcaaaa tgagaaataa      420
gaacttccat aatgagttcc cagctcaaca atatttcttg gccgcagtgt gtcaactaac      480
cagaaagcaa aaggaatgtg ttctagccaa gcagattgtg caaggtatgt aggacaccan      540
aaaagagatg gtttgaaaat gaaattcaat tccctgccaa tatcagtgat gggatataac      600
tcacgattct ctactaactg actaattttt tgactatcca ttgaggaaaa ctcacatgta      660
tttatagaat taaatcaaga aacctgaaaa tacctatagt gcggtaactt attaactaac      720
atttaaatat taacaataca cttggaaata ttagttaaaa ataaatcatt atgatttctc      780
atcaatcctg gtgctcacgc aaagttgcca gccccataat aataagacca tagaacaagc      840
aaagtaatac acccacagtc gcaagattat agaatcgccg tggatattcg gcatcttccg      900
ctaaagttgg ttgggtaata accaatagat                                      930
```

<210> SEQ ID NO 113
<211> LENGTH: 659
<212> TYPE: DNA
<213> ORGANISM: Escherichia coli
<220> FEATURE:
<221> NAME/KEY: misc_feature
<222> LOCATION: (238)..(239)
<223> OTHER INFORMATION: n equals a, t, g, or c

<400> SEQUENCE: 113

```
acgatatccc ccctctgctt ttgagaggca atctgctttta atacatgatt catcacaaca       60
```

```
cctcttgctg cgctttgatc ttaattttat attttttgggt agggaaaagt aattgcccct      120
gatacggctc accatttacc aacgtttcac agctatgttc cagagctaaa ttaagacctg      180
gtagaatatc ccagcaattc accccttga cattttcaaa gctgtcataa gcaccggnna      240 aggggggggcc aacatgttat acatggagca gccaatgata cgatattcaa agccctcttc    300
cagttgcatc agatcctgct tggtaasgga ggaagagagg ccacgaatac gagagcgatg      360
atgtgtaatc ggcatacctg tgatatgaag atcattcaat tcaggtaaga agatgcagga     420
ctcttgatgt ttcccctcgg tgtaaatgct gataccaatg ccccactctt tgagcccaga      480
gacaaagttt tctgtgccat caattggatc tagaacaatg taagaacctt tgggattcca     540
ctcaatatct cctaaagggg ctaattcctc tgaaattagc acatgccctg gtagatgctt     600
tctacagagt tcgaaaacta tatcttgaac ttttagatcc agtactgcgg ccgcgatcc     659
```

<210> SEQ ID NO 114
<211> LENGTH: 556
<212> TYPE: DNA
<213> ORGANISM: Escherichia coli

<400> SEQUENCE: 114

```
cccggatata catcaggaga aattggagca gcaattggat gcgccattaa tgcctggtta       60 gggatcccg catgtgggca cgcaaatggc tcagaatatg atcgaccttc accagataaa      120
ccaaatctga gcgaaccatt tatcccaaga cccacgtatg acgcttcact tcattcctgg     180
catggcggat actgagtaaa tcatcctgaa tcattatgtt caacatcatc aattctccgg    240
acttgttgtc agatgtccgg agaatattaa ccttttcttc agaaacagaw tgatcaagaa     300
tcacactcct tctttaagag gattttatcc agaaaactga ctttcttcta tcaaaatmac    360
agtatcctgt tttatcagga ataatcttta cctccggtat cattcccata atcagatatc    420
agaaaaatgt gccagtaatt ttttactgat gacttcaaac atttcacatt catcacacgt    480
cagattactc caaagttctt tcagatatgt gttctgcgcc agagtgagtc tctgaataaa     540
aaacatacct tcagac                                                      556
```

<210> SEQ ID NO 115
<211> LENGTH: 503
<212> TYPE: DNA
<213> ORGANISM: Escherichia coli
<220> FEATURE:
<221> NAME/KEY: misc_feature
<222> LOCATION: (60)..(60)
<223> OTHER INFORMATION: n equals a, t, g, or c
<221> NAME/KEY: misc_feature
<222> LOCATION: (65)..(65)
<223> OTHER INFORMATION: n equals a, t, g, or c
<221> NAME/KEY: misc_feature
<222> LOCATION: (90)..(90)
<223> OTHER INFORMATION: n equals a, t, g, or c
<221> NAME/KEY: misc_feature
<222> LOCATION: (460)..(460)
<223> OTHER INFORMATION: n equals a, t, g, or c
<221> NAME/KEY: misc_feature
<222> LOCATION: (496)..(496)
<223> OTHER INFORMATION: n equals a, t, g, or c

<400> SEQUENCE: 115

```
tacctgtttg tggaatttga cccagaagtg attcatacca cgactatcaa cgcgacccgn       60
gtgtncagcc acttcgtgcg ctttggcgtn cgcagcgata gtcccatcgg cggttattca     120
tcagctatcg gtatataaac cgaaagacat tgtcgattcc ggcaaccct tatccgggtg     180 ataaggtgat tattaccgaa gcgcgttcga aggctttcag gccatttttca ccgaacccga   240
```

```
tggtgaggct cgctccatgc tattgcttaa tcttattaat aaagagatta agcacagtgt      300
gaagaatacc gagttccgca aactctaaaa cgcaatccca aacagtgttt tgacattagc      360
atccgtggtg gcagccagcc atgcggcatc ttctccacgc cagtgcgcaa tacgttgcaa      420
aatatggggc agatgggctg gctcgttgcg ccgggatgan ggctttggcg tgagatcgcg      480
agggagcaga tacggngcat cag                                              503

<210> SEQ ID NO 116
<211> LENGTH: 433
<212> TYPE: DNA
<213> ORGANISM: Escherichia coli
<220> FEATURE:
<221> NAME/KEY: misc_feature
<222> LOCATION: (138)..(138)
<223> OTHER INFORMATION: n equals a, t, g, or c

<400> SEQUENCE: 116
tttaacatca aaattacctg cagctgaaat gattttgctg atttcattaa ttaatggatt      60
aagattaccc tgacttccat aggctaatgc atcattccca tacacataac ttgccttatt      120
attactctgt tgatactnaa gtgcctttt aagggaatct ggtgtgatta ccctgccgtc       180
tttatcaaaa atctgctcta tctggtgatt agagatatca cctgactctt tttcaaacca      240 gttttttaaat gtaataccat ttttgtggcc aatggaaaga acattacctt cagctttata    300
catgatgagg tcattacctt ctcgcctgaa ggccacatcc cggaaatcaa tatcagccaa      360
actgagttta tcgtctttcc ccccatcatc gtcaataata tgatggccat atcctgaaag      420
ataacgataa ata                                                        433

<210> SEQ ID NO 117
<211> LENGTH: 302
<212> TYPE: DNA
<213> ORGANISM: Escherichia coli
<220> FEATURE:
<221> NAME/KEY: misc_feature
<222> LOCATION: (280)..(280)
<223> OTHER INFORMATION: n equals a, t, g, or c
<221> NAME/KEY: misc_feature
<222> LOCATION: (299)..(299)
<223> OTHER INFORMATION: n equals a, t, g, or c

<400> SEQUENCE: 117
gcgctctgtt cccgttcctg ttcatcacca tcgcctgtgg tgcggtatct ggcttccacg      60
cgctgatctc ttccggtacg acgccaaaac tgctggctaa tgaaaccgac gcgcgtttca    120
tcggctacgg cgcaatgctg atggagtcct tcgtggcgat tatggcgctg gttgctgcgt    180
ccatcatcga accgggtctt tacttcgcga tgaacacccc gcctgctggc cttggcatca    240
ccatgcctaa cctgcatgaa atggggtggc gagaacgcgn cggattcatc atggcgcant    300
ga                                                                    302

<210> SEQ ID NO 118
<211> LENGTH: 656
<212> TYPE: DNA
<213> ORGANISM: Escherichia coli
<220> FEATURE:
<221> NAME/KEY: misc_feature
<222> LOCATION: (628)..(628)
<223> OTHER INFORMATION: n equals a, t, g, or c

<400> SEQUENCE: 118
aattaataag ccaaatacta catcacgtaa tacttgcaaa gaagtgcgtg gagtttgact      60
```

```
aataatgggt tgtccatta atacttaccc aaataatcgg ctcattatag caacgagcct      120
ccgattaaaa tttaaaatac tcaatcattt aatagcaacg ttagcagcta cagcgatttg      180
ataaataatt tgtgtgatat ctttaaatga ttgcatggtt ttgctatcaa cctgaggtag      240
aaccaatatc tgatcccccg gttgtacttt accttgccct ttaaattcta caagaccatt      300
tgcatgtaca atagcaattc gcttgtcgtt agctcgctca gtaaaacctc cggcccatgc      360
aacataatca tccaaattag catcggcatt atatactact gcttgtggca tcaacacttc      420 acccccccact tgaataagat cagtcttatt tggaataact atttgatcgc cttgttctaa     480
ttggatawtg gcaataacac ctttatctgc aactactact ttaccaagcg gtkgaacttt      540
acgagccttt ycaacaaact gcatcactaa ctctgcttct ttagcacgta tattcgcctc      600
accatcagat cgcgcgggtg tggtaaantt catacgttcc aagcggttta gagatt          656
```

<210> SEQ ID NO 119
<211> LENGTH: 436
<212> TYPE: DNA
<213> ORGANISM: Escherichia coli

<400> SEQUENCE: 119

```
atatgttatc tggatccaga taaagagcgt tcttgacccg ctatatccag acaggtcagt       60
tacaccctgt ccggaaaaac tgatcggaat aacaacagta tattttctaa tacactggca     120
aatggtgccg gcggtgtggg gattcagctt ctggatagcg ctggtaatgc ggttgctgct     180
ggacagaaga aatatctggg acaggtagga ccatcaacat ctctcaatat tggattaagg     240
gcatcttatg cactgaccaa tggacagact ccacctactc ccggacgagt tcaggcgtta     300
gttgatgtta ccttcgagta taattaggaa tgtcggggat gggctatccc cgatattatt     360
gcaggattag tctgtgatac agatatacag cccatatgaa caactgtttg catatataaa     420
aatgatgata atttta                                                      436
```

<210> SEQ ID NO 120
<211> LENGTH: 559
<212> TYPE: DNA
<213> ORGANISM: Escherichia coli
<220> FEATURE:
<221> NAME/KEY: misc_feature
<222> LOCATION: (463)..(463)
<223> OTHER INFORMATION: n equals a, t, g, or c
<221> NAME/KEY: misc_feature
<222> LOCATION: (499)..(499)
<223> OTHER INFORMATION: n equals a, t, g, or c
<221> NAME/KEY: misc_feature
<222> LOCATION: (552)..(552)
<223> OTHER INFORMATION: n equals a, t, g, or c

<400> SEQUENCE: 120

```
aataattaaa tttggaggga tcagttttct gataatgttc tgttattaaa acattatccc       60 atgggcgta gttatatcaa ttagcaggat cttatgagtt aactaacatc agttttgaat      120
ttttaatggg ggtaatttat cttttactaa aaatatttta actattaata tagcatcatg     180
gttgttacgg tttgttttaa ttctatttta taatgtgcta tatattgtat ttttgtgctt     240 agataaaatat gttttttcat tactttagtg atgttaatat tttgcgtgta gtaaaaatca     300
ttgttataac aaatgtcact gttgctatac tttgctgaac tgtttatcgg tcattttgat     360
tcaatcactg gttctatatt ttttaataac cgttctgtag cgattaatat attgctctcc     420
agaggataca ctatatgaaa tatattaaaa gtcattaatt ttnattccaat gttgtttaga     480
```

```
gttatgttca gtgtttggna ataggatgtg tttctaaacc gtcttgggtt ctataataaa      540
ttctattctt anaggtttt                                                   559

<210> SEQ ID NO 121
<211> LENGTH: 481
<212> TYPE: DNA
<213> ORGANISM: Escherichia coli

<400> SEQUENCE: 121
catgtccctt cctgaatact ggggagaaga gcacgtatgg tgggacggca gggctgcttt       60
tcatggtgag gttgtcagac ctgcctgtac tctggcgatg gaagacgcct ggcagattat      120
tgatatgggg gaaaccccgg tacggattta cagaatggtt tctccggacc tgaaagaaaa      180
ttcagcctcc ggctcaggaa ttgtgaattt aacagtcagg gtgggaacct tttctctgat      240
tcccggataa gggtgacttt cgatggcgtc cggggtgaaa cgccggataa gtttaattta      300
tccggtcagg caaaaggcat taatctgcag atagctgatg tcaggggaaa tattgcccgg      360
gcaggaaaag taatgcctgc aataccattg acgggtaatg aagaagcgct ggattacacc      420
ctcagaattg tgagaacgga aaaaaacttg aagccggaaa ttattttgct gtctgggatt      480
a                                                                     481

<210> SEQ ID NO 122
<211> LENGTH: 535
<212> TYPE: DNA
<213> ORGANISM: Escherichia coli

<400> SEQUENCE: 122
ccatatagtg acttcattga acaaaatgta aatggaatct tgctggagaa tgacccacat       60
atatggataa aagctctttc attacttgtt agtgcagatc ataaacgtag cgagttggcg      120
ttcaatgcta aaaatatagc ttgtaaaatt gtaggtgtcg agtaaaaaga tatttttatt      180
taattggtgc tattgaatgt ttaaaaatcg aactgattgg tgttttaata ttaatcatag      240
gttatgatgc aaaaatatat taggcattgc ctgcttcaat taacttgaga gtgtaagttg      300
aattgaaata tggttatatg ataaagcaat atatgttaat acatatgtca accgaaaatg      360
ccattatgtg ttttttactt tatctgtaac gacacaatat ataaataag gctaataatc       420 aaaacgcttt ttaatttgat tgtttttgaat caagtgacta agaaattctc ttgctgcaaa     480
taactccctt agtgattttt tttgagtcta ttttattctc tgggcatggt catgc           535

<210> SEQ ID NO 123
<211> LENGTH: 412
<212> TYPE: DNA
<213> ORGANISM: Escherichia coli

<400> SEQUENCE: 123
ccggccccat aatgatggtt ttattaaggt tagcgccgac ggtttcgatg aacgatttca       60
ggtcggtatc tttaaaatta gcggtgaaag tggcttcttc cgcccagacc ggtgaactgc      120
ataatgccgc tgccagcacc agcggcagta acgcttttt tgttttgagg ccagttgtct       180
tcttacgcca gaccgacaac gtcatatcac gccaaaacac gatgaatgat tctcctggat      240
taaatgcggt tagcgcagcg cgatggaaat gtcgtggcgc gcacccttgc gtaaaaccgt      300
aagttgaatg gaatccattg aaggtaactg ccgcatcaga gcaatcattg ctcgtggatc      360
agtgaaatcc tgctgattta gcgcaaatgc gatatcgcct tccttaaaac cg              412
```

<210> SEQ ID NO 124
<211> LENGTH: 576
<212> TYPE: DNA
<213> ORGANISM: Escherichia coli

<400> SEQUENCE: 124

```
tagcctgttc agcgtatatt tgggatgaga agccaaagtg gctttggtgg tgtcccagcc      60
caggttttta ttactgctgg ttatttacct ttcatgtttt tcaataaagt tgtgactcag     120
ttgaaatctg ctgtcaatgc taatatggga cttttttgtt atagacaagt gactcctttt     180
gcaactttta tagcacgttt tatgctagaa acaatggtgg gcatgattgt cggtataatc     240
ctagtactag gattattgtg gtttggcttt gatgcaatac ctgcggatcc attgcaagtg     300
atccttggtt attctcttct gatgctgttt tctttttctc ttggtattgt attttgtgtt     360
atttgtaatt krgcgaraga ggcagataaa tttcttagct tgttaatgat gcctttgatg     420
tttatctctt gtgttatgtt tcctcttgct actattcccc ctcaatatca gcattgggtt     480
tttatggaat ccacttgtgc atgctgtaga actaatccga agggcatggg atatctgggt     540
tatcgtagtc ctgatgtaag ttgggcgtat ctgtcg                               576
```

<210> SEQ ID NO 125
<211> LENGTH: 132
<212> TYPE: DNA
<213> ORGANISM: Escherichia coli

<400> SEQUENCE: 125

```
ttaccaagca ggatctgatg caactggaag aaggctttga atatcgtatc attggctgct      60
ccatgtataa catgttggcc gccgtacgcg gtgcctatga cagctttgaa aatgtcaaag     120
gggtgaattg ct                                                          132
```

<210> SEQ ID NO 126
<211> LENGTH: 542
<212> TYPE: DNA
<213> ORGANISM: Escherichia coli

<400> SEQUENCE: 126

```
gattagggt cactcaggat tataaaaaag cggcagaata ctataaaaaa ggtgataaaa       60
ataatgatat tacagcacaa taccgtctgg caaaacttta tgaacaaggt aacgtgtaa      120
aacgtgatta tcaacaagcg ataaaccttt accttaaaca tatcaacaga atggatcaca     180
tcactgcccc cagttttgtg gctctgggtg atatctattc tctggattgs ggggtagaga     240
aaaacccaca actggctgaa aaatggtatc aaaaagcgat agatgcagct aatacacaac     300
ataaccagga aataaatcat taaacgacaa cacttaatac catattgtga agatgttcag     360
acatggcgga attcccctat tctttgttgg cgcttacaac agactatatt ccgccatatc     420
tgtctttatt gtgtataaac catcgatact gatgtttgat agtgctaaat aatcattggc     480
gcaatcacaa agcctaatgc cactccagca ataattcccc ccaacccagg cagcataaat     540
gg                                                                    542
```

<210> SEQ ID NO 127
<211> LENGTH: 382
<212> TYPE: DNA
<213> ORGANISM: Escherichia coli

<400> SEQUENCE: 127

```
gaaccactta gcggcagcta tcgggaatcg cctgctgaaa gacggtcaga cagtgattgt      60
```

```
ggttaccgtg gctgatgtta tgagtgccct gcacgccagc tatgacgatg ggcagtcagg      120
cgaaaaattt ttgcgggaac tgtgcgaagt ggatctgctg gttcttgatg aaattggcat      180
tcagcgcgag acgaaaaacg aagcaggtgg tactgcacca gattgttgat cgccggacag      240
cgtcgatgcg cacgtgggga trctgacaaa cctgaactat gaggccatga aaacattgct      300
cggcgarcgg attatggatc rcatgaccat gaacggcggg cgatgggtga attttaactg      360
ggagactggc gtccgaatgt cg                                                382

<210> SEQ ID NO 128
<211> LENGTH: 126
<212> TYPE: DNA
<213> ORGANISM: Escherichia coli

<400> SEQUENCE: 128
cgtcccgcac ccggaaatgg tcagcgaacc aatcagcagg gtcatcgcta gaaatcatcc       60
ttagcgaaag ctaaggattt tttttatctg aattctagcc agatcccgc tgatttatgc       120 tggtta                                                                  126

<210> SEQ ID NO 129
<211> LENGTH: 258
<212> TYPE: DNA
<213> ORGANISM: Escherichia coli
<220> FEATURE:
<221> NAME/KEY: misc_feature
<222> LOCATION: (142)..(142)
<223> OTHER INFORMATION: n equals a, t, g, or c
<221> NAME/KEY: misc_feature
<222> LOCATION: (205)..(205)
<223> OTHER INFORMATION: n equals a, t, g, or c

<400> SEQUENCE: 129 accccccagcc tagctggggg ttttctgtgc acaaaaaatc ccggcataat ggccgggatt       60
tgcgagcttt cccactattt cttgattcct aaacggaaca tatcagttgg gaataaaggt      120
tgtattatca cttcatcatt anaaatgaat aatttgggcg ataaagctgt tacgtcatag      180
atattttcag cgattaatct taganttgac ctaaaaactg gaatacttgc atcatctgca      240
aagacaaaca tgtcatcg                                                    258

<210> SEQ ID NO 130
<211> LENGTH: 399
<212> TYPE: DNA
<213> ORGANISM: Escherichia coli

<400> SEQUENCE: 130
aaccagcggt tcgcatcatc tcatcccact gactctccgc ttttgacaga tctgcatatc       60
ctcgggccaa cttatccagt actccgtagt ttgccgattt attcacccgc cagaacaccg      120
cctcacctgc atcggcaagc cggggggaaa actgatacc cagtagccag aacagaccga      180
aaataatatc gctgctaccc gcagtgtctg tcatgatttc aactggattc agccctgtct      240
gctgctcaag aagtccttcc agtacaaaaa tcgaatcccg taatgtaccg ggtaccacaa      300
tgccatggaa cccagagtac tgatcagata cgaattatac caggtgatgc ctcgtccaga      360
accaaaatat ttctgttag atcctgagtt gatggtctt                              399

<210> SEQ ID NO 131
<211> LENGTH: 745
<212> TYPE: DNA
<213> ORGANISM: Escherichia coli
<220> FEATURE:
```

```
<221> NAME/KEY: misc_feature
<222> LOCATION: (297)..(297)
<223> OTHER INFORMATION: n equals a, t, g, or c
<221> NAME/KEY: misc_feature
<222> LOCATION: (323)..(323)
<223> OTHER INFORMATION: n equals a, t, g, or c
<221> NAME/KEY: misc_feature
<222> LOCATION: (330)..(330)
<223> OTHER INFORMATION: n equals a, t, g, or c
<221> NAME/KEY: misc_feature
<222> LOCATION: (335)..(335)
<223> OTHER INFORMATION: n equals a, t, g, or c
<221> NAME/KEY: misc_feature
<222> LOCATION: (715)..(715)
<223> OTHER INFORMATION: n equals a, t, g, or c

<400> SEQUENCE: 131
aaataacatc aacatacatt tgactcgcgg gggaaacgtt tacggagtct tcatactggc      60
acttttttat gctgctgact actcttcgtc atcgccatca acatgcgcac gaatcagcgc     120
cataaacggt tgccaaagc gttccagctt gcgcatccca acgccgttaa cgctgagcat     180
ttcgctggcg gtgatcggca tctgttcagc catctcaatc aaggttgcgt cgttaaacac     240
cacgtacggc gggacattac tttcatcggc tatcgattta cgcagtttgc gtaattnggc     300
gaacagtttg cgatcatagt tgncgccgan cgatntctgc atcgctttcg gtttgagcgc     360
cacgatacgc ggcacggcaa ttgcaaagag gattcgccgc gcagcaccgg gcgcgcggcc     420
tctgtcagtt gtagggcaga atgctgggca atattttgcg tcaccaggcc gaggtgaatc     480
agctggcgga tcacgctcac ccaatgttca tggcttttat cacggcccat gccatagact     540
ttcagtttgt catgaccata gtcgcggata cgctggttat tagcaccacg aatcacttcc     600
accacataac ccatcccaaa ccgctgattc acacgaccaa tggtggaaag ggcaatctga     660
gcatcggttg aaccgtcgta ctgtttcggc ggatcgaggc agatatcgca gttnccgca     720 cggctcctga cgcccttcgc caaaa                                            745

<210> SEQ ID NO 132
<211> LENGTH: 439
<212> TYPE: DNA
<213> ORGANISM: Escherichia coli
<220> FEATURE:
<221> NAME/KEY: misc_feature
<222> LOCATION: (108)..(108)
<223> OTHER INFORMATION: n equals a, t, g, or c

<400> SEQUENCE: 132
agaatggcgg cttcttgccc ccctttgccc cggtcctgac tagcatggct ggagtccagt      60
gtccaggcca cgaccatgct catcatggaa gcagcttttg tagtacantc gcagcttatt     120
ttcctggaac gaaatgtctg gcatcgtggt gcataacata accccaatg cccagcagat     180 gcacagaagg ttctagaatc gcccactgat atcccataca aaatttacca aaacgtgttc     240
gtatttctcg tataaataat gtctctatgg tgacgttcta gacttcaaac ccactttttg     300
aatttgatga tgtgctccta atctcttcag gaatgtaacg cccttggttt acagctacca     360
atacactgga ggtatactta tctgcaactg gatgaactag atgtacttga gcaaacattt     420
cataagctcg acgacagtt                                                  439

<210> SEQ ID NO 133
<211> LENGTH: 350
<212> TYPE: DNA
<213> ORGANISM: Escherichia coli
<220> FEATURE:
<221> NAME/KEY: misc_feature
```

```
<222> LOCATION: (97)..(97)
<223> OTHER INFORMATION: n equals a, t, g, or c
<221> NAME/KEY: misc_feature
<222> LOCATION: (208)..(208)
<223> OTHER INFORMATION: n equals a, t, g, or c
<221> NAME/KEY: misc_feature
<222> LOCATION: (335)..(335)
<223> OTHER INFORMATION: n equals a, t, g, or c

<400> SEQUENCE: 133
ctggaaagcg acgttgatgg attaatgcag tcggtaaaac tgaacgctgc tcaggcaagg      60
cagcaacttc ctgatgacgc gacgctgcgc caccaantca tggaacgttt gatcatggat     120
caamtcatcc tgcagatggg gcagaaaatg ggagtgaaaa tctccgatga gcagctggat     180
caggcgattg ctaacatcgc gaaacagnac aacatgacgc tggatcagat gcgcaccgtc     240
tggcttacga tggactgaac tacaacacct atcgtaacca gatccgcaaa gagatgatta     300
tctctgaagt gcgtaacaac gaggtgcgtc gtcgnatcac catcctgccg               350

<210> SEQ ID NO 134
<211> LENGTH: 400
<212> TYPE: DNA
<213> ORGANISM: Escherichia coli
<220> FEATURE:
<221> NAME/KEY: misc_feature
<222> LOCATION: (256)..(256)
<223> OTHER INFORMATION:
<221> NAME/KEY: misc_feature
<222> LOCATION: (256)..(256)
<223> OTHER INFORMATION: n equals a, t, g, or c

<400> SEQUENCE: 134
ccccaagatt gctaacaaat gcgcgttgtt catgccggat gcggcgtgac cgccttatcc      60
ggcctacgaa accgcaagaa ttcaatatat tgcaggagcg gtgtaggcct gataagcgta     120
gcgawtcagg cagttttgcg tttgcccgca accttagggg acatttagcg acccccattta    180 tttctcactt ttccgcctca tcatcgcgcg ttaatttctt tcatgaatca cgctttacaa     240
tatccagcgc gcgcanaacg gtactggcag ggatctgaat tttcctccag cagcacaatc     300
aaatcgacag ccagtttgac atcgtcaagg ggcattttcc cagtgacata atctctccat     360
tgctaagcgg gttaaaacgc gctaacctgt ttcgattttt                           400

<210> SEQ ID NO 135
<211> LENGTH: 463
<212> TYPE: DNA
<213> ORGANISM: Escherichia coli
<220> FEATURE:
<221> NAME/KEY: misc_feature
<222> LOCATION: (25)..(25)
<223> OTHER INFORMATION: n equals a, t, g, or c
<221> NAME/KEY: misc_feature
<222> LOCATION: (432)..(432)
<223> OTHER INFORMATION: n equals a, t, g, or c

<400> SEQUENCE: 135
ctatccttat gaccacccaa ctacntcatt tacacccaaa ccagcgatct gaataaagaa      60
gcgattgccc agttacgact gggcggaaaa tgcgcgtaag gatgaagtaa agtttcagtt     120
gagcctggca tttccctgtg gcgtgggatt ttaggcccga actcggtgtt gggtgcgtct     180
tatacgcaaa aatcctggtg gcaactgtcc aatagcgaag agtcttcacc gtttcgtgaa     240
accaactacg aaccgcaatt gttcctcggt tttgccaccg attaccgttt tgcaggttgg     300
actgcgcgat gtggagatgg ggtataacca cgactctaaa cgggcgttcc gacccgacct    360
```

```
cccgcagctg gaaccgcctt tatactcgcc tgatggcaga aaacggtaac tggctggtag    420
aagtgaagcc gnggtatgtg gtgggtaata ctgacgataa ccc                      463
```

<210> SEQ ID NO 136
<211> LENGTH: 584
<212> TYPE: DNA
<213> ORGANISM: Escherichia coli
<220> FEATURE:
<221> NAME/KEY: misc_feature
<222> LOCATION: (425)..(425)
<223> OTHER INFORMATION: n equals a, t, g, or c
<221> NAME/KEY: misc_feature
<222> LOCATION: (467)..(467)
<223> OTHER INFORMATION: n equals a, t, g, or c

<400> SEQUENCE: 136

```
ttggtcagcc gtacctgaat gggggctgat gcccggctgg ttaatggcag gtggtctgat     60
cgcctggttt gtcggttggc gcaaaacacg ctgatttttt catcgctcaa ggcgggccgt    120
gtaacgtata atgcggcttt gtttaatcat catctaccac agaggaacat gtatgggtgg    180
tatcagtatt tggcagttat tgattattgc cgtcatcgtt gtactgcttt ttggcaccaa    240
aaagctcggc tccatcggtt ccgatcttgg tgcgtcgatc aaaggcttta aaaaagcaat    300
gagcgatgat gaaccaaagc aggataaaac cagtcaggat gctgatttta ctgcgaaaac    360
tatcgccgat aagcaggcgg atacgaatca ggaacaggct aaaacagaag acgcgaagcc    420
tacgntaaag agcaggtgta atccgtgttt gatatcggtt ttagcgnact gctattggtg    480
ttcatcatcg gcctcgtcgt tctgggggcg caacgactgc ctgtggcggt aaaaacggta    540
gcgggctgga ttcgcgcgtt gcgttcactg gcgacaacgg tgca                    584
```

<210> SEQ ID NO 137
<211> LENGTH: 527
<212> TYPE: DNA
<213> ORGANISM: Escherichia coli
<220> FEATURE:
<221> NAME/KEY: misc_feature
<222> LOCATION: (108)..(108)
<223> OTHER INFORMATION: n equals a, t, g, or c
<221> NAME/KEY: misc_feature
<222> LOCATION: (191)..(191)
<223> OTHER INFORMATION: n equals a, t, g, or c
<221> NAME/KEY: misc_feature
<222> LOCATION: (510)..(510)
<223> OTHER INFORMATION: n equals a, t, g, or c
<221> NAME/KEY: misc_feature
<222> LOCATION: (513)..(513)
<223> OTHER INFORMATION: n equals a, t, g, or c
<221> NAME/KEY: misc_feature
<222> LOCATION: (525)..(525)
<223> OTHER INFORMATION: n equals a, t, g, or c

<400> SEQUENCE: 137

```
gcaggcagga ggaactgccc agtgatacgg ttattcgtga tggcggaggg cagagcctta     60
acggactggc gttgaacacc acgctggata acagagttga gcattggnta cacgggggag    120
ggaaagcaga cgttacaatt attaaccagg atgtttaccc agaccataaa acatggcgga    180
ttggcaaccg naaccatcgt caacaccgtt gcagaagktg gtccggagtc tgaaaatgtg    240
tccagcggtc agatggtcgg agggacggct gaatccacca ccatcaacaa aaatggccgg    300
cagttatctg gtcttcgggg atggcacggg acaccctcat ttgcgctggt ggtgaccaga    360
```

```
cggtacacgg agaggcacat aacacccgac tggagggagg ttaaccagta tgtacacaac        420
ggtggcacgg caacagagac gctgataaac cgtgatggct ggcaggtgat taaggaagga        480
gggaactgcc ggcgcattac caccatcaan ccngaaaagg gaaanct                     527

<210> SEQ ID NO 138
<211> LENGTH: 441
<212> TYPE: DNA
<213> ORGANISM: Escherichia coli
<220> FEATURE:
<221> NAME/KEY: misc_feature
<222> LOCATION: (440)..(440)
<223> OTHER INFORMATION: n equals a, t, g, or c

<400> SEQUENCE: 138
gtcagtctct gggggaagtg cgtgttccga ccggggaaat gtggtggaga aagttattga         60 agggcttac gaggtggtgg gggttttttga ccggattgag gaaaagcgtg atgccatgca        120
gtcgctgatt ctgccgccac cggacgccag gcgctggcac aggcggcact gacttaccgt        180
tatggtgacg aacmtcarcc cgtcaccacc gccgacattc tgacaccacg acgccgggar       240
gattacggta aggacctgtg gagtgcttat cagaccattc aggagaatat gctgaaaggc       300
ggaatttccg gtcgcagtgc cagaggaaaa cgtatccata cccgtgccat tcacagcatc       360
gacaccgaca ttaagctcaa ccgcgcattg tgggtgatgg ctgaaacgct gctggagagt       420
atgcgctgat gccgtttccn t                                                 441

<210> SEQ ID NO 139
<211> LENGTH: 398
<212> TYPE: DNA
<213> ORGANISM: Escherichia coli
<220> FEATURE:
<221> NAME/KEY: misc_feature
<222> LOCATION: (164)..(164)
<223> OTHER INFORMATION: n equals a, t, g, or c
<221> NAME/KEY: misc_feature
<222> LOCATION: (210)..(210)
<223> OTHER INFORMATION: n equals a, t, g, or c

<400> SEQUENCE: 139
cgagcgagat gaacttcgag ggcggtgtga gccagtcggc ttacgagaca ctggcggcgc         60
ttaatctgcc gaaaccgcag caagggccgg aaaccattaa tcaggttacc gagcataaga       120
tgtcagctga gtaagcctgt atgccggata aggcgctcgc gccnattccg atgaaataag       180
gcgcatcggg cctgaaggaa agccgtatgn atacacccgc agcccgcatc cggcaagtta       240
caacaaataa cctttaacca tgcttttttga tgttttttcag caatacccccg cggcgatgcc       300 catactggca accgtcggga gggattgatc atcggcagtt ttttgaatgt ggtgatttgg       360
gcgttacccc atcatgctgc gccaacaaat ggcggagt                               398

<210> SEQ ID NO 140
<211> LENGTH: 580
<212> TYPE: DNA
<213> ORGANISM: Escherichia coli
<220> FEATURE:
<221> NAME/KEY: misc_feature
<222> LOCATION: (566)..(566)
<223> OTHER INFORMATION: n equals a, t, g, or c

<400> SEQUENCE: 140
gccgaacaga cacagcaata tgaaccctgc cagcgcagac gcttgctgat taatgctctg         60
aacaaaaggc gaagaatggc aaatcctgcg atcagcaaag tcagcgcacc gactatctgt       120
```

| | |
|---|---:|
| aacatagtca ctccgtgatg aatatcatgt gtattgtgaa tgccagtgaa tgtggcactg | 180 |
| aagcgtttgc acctgtccgg gtcccggtca tgatgaccgs aacagagaga caatgccgaa | 240 |
| ttatcagaag gtcacattca gtgtggcttg gccgttataa ccttcagcgc tgctgccgct | 300 |
| gacgctgtgg gcataaccgg cctgaacgcc caggtgata tttccccgga cacgggcttc | 360 |
| cagtccggcc tgcagctcca gtgacgtgcc attccgggac ggtgagaacg tcatgttact | 420 |
| gccggctgcg gctgtaccca tgctcatgtc tccccgggag ctgaaggtgc ggataacaga | 480 |
| aggctgtacc cacccgttca ccggcagttc acgcacactg tgttttgcac tgtcacgcaa | 540 |
| ggtgtcacgg gatgaggtgc cttcancaaa aggtcatatt | 580 |

<210> SEQ ID NO 141
<211> LENGTH: 446
<212> TYPE: DNA
<213> ORGANISM: Escherichia coli
<220> FEATURE:
<221> NAME/KEY: misc_feature
<222> LOCATION: (388)..(388)
<223> OTHER INFORMATION: n equals a, t, g, or c
<221> NAME/KEY: misc_feature
<222> LOCATION: (399)..(399)
<223> OTHER INFORMATION: n equals a, t, g, or c
<221> NAME/KEY: misc_feature
<222> LOCATION: (415)..(415)
<223> OTHER INFORMATION: n equals a, t, g, or c

<400> SEQUENCE: 141

| | |
|---|---:|
| tgcggacatc cagcgttccg ccatcatcca cacgggttct ggtggctgtg tgtccggtca | 60 |
| gcacatccag acggccgcca ttttccagta cgacattatc agctttaccc tccacaacag | 120 |
| agaatgctcc caggcggttt gtgccggtga cggttgcagc agtgctggta accagtgctc | 180 |
| cgcccgtgtt ctgggtgaca tcagacgctt taccgccggc attcacctgc agctttcctt | 240 |
| tctggttgat ggtggtatgc gcggcagttc ctccttcctt aatcamctgc cagccatcac | 300 |
| ggtttatcag cgtctctgtt gccgtgccaa cgttgtgtac atactggtta mctccctcca | 360 |
| gtcgggtgtt awgtgsctct ccgtgtancg tctggtcanc aacaacgcaa atganggtgt | 420 |
| cccgtgccat ccccgaagac cagtaa | 446 |

<210> SEQ ID NO 142
<211> LENGTH: 327
<212> TYPE: DNA
<213> ORGANISM: Escherichia coli
<220> FEATURE:
<221> NAME/KEY: misc_feature
<222> LOCATION: (290)..(290)
<223> OTHER INFORMATION: n equals a, t, g, or c

<400> SEQUENCE: 142

| | |
|---|---:|
| tgaatacgtt aagtcagcag accggcggag acagtctgac acagacagcg ctgcagcagt | 60 |
| atgagccggt ggtggttggc tctccgcaat ggcacgatga actggcaggt gccctgaata | 120 |
| atattgccgg agttcgccac tgaccggtca gaccggtatc agtgatgact ggccactgcc | 180 |
| ttccgtcaac aatggatacc tggttccgtc cacggacccg gacagtccgt atctgattac | 240 |
| ggtgaacccg aaactggatr gtctcggaca ggtggacagc catttgtttn ccggactgta | 300 |
| tgagcttctt ggagcgaaac cgggtca | 327 |